US009790253B2

(12) United States Patent
Shair et al.

(10) Patent No.: US 9,790,253 B2
(45) Date of Patent: Oct. 17, 2017

(54) OSW-1 ANALOGS AND CONJUGATES, AND USES THEREOF

(75) Inventors: Matthew D. Shair, Lexington, MA (US); Anthony William George Burgett, Norman, OK (US)

(73) Assignee: President and Fellows of Harvard College, Cambridge, MA (US)

( * ) Notice: Subject to any disclaimer, the term of this patent is extended or adjusted under 35 U.S.C. 154(b) by 72 days.

(21) Appl. No.: 14/118,589

(22) PCT Filed: May 18, 2012

(86) PCT No.: PCT/US2012/038562
§ 371 (c)(1),
(2), (4) Date: Jan. 27, 2014

(87) PCT Pub. No.: WO2012/159027
PCT Pub. Date: Nov. 22, 2012

(65) Prior Publication Data
US 2014/0135279 A1    May 15, 2014

Related U.S. Application Data

(60) Provisional application No. 61/488,023, filed on May 19, 2011.

(51) Int. Cl.
| C07H 15/24 | (2006.01) |
| C07J 17/00 | (2006.01) |
| C07J 41/00 | (2006.01) |
| C07J 43/00 | (2006.01) |
| C07J 51/00 | (2006.01) |
| A61K 47/48 | (2006.01) |

(52) U.S. Cl.
CPC ....... *C07J 17/005* (2013.01); *A61K 47/48384* (2013.01); *A61K 47/48561* (2013.01); *C07H 15/24* (2013.01); *C07J 41/0055* (2013.01); *C07J 43/003* (2013.01); *C07J 51/00* (2013.01)

(58) Field of Classification Search
None
See application file for complete search history.

(56) References Cited

U.S. PATENT DOCUMENTS

| 5,708,164 A | 1/1998 | Winterfeldt et al. |
| 7,321,050 B2 | 1/2008 | Chen et al. |
| 7,659,241 B2 | 2/2010 | Senter et al. |
| 7,745,394 B2 | 6/2010 | Doronina et al. |
| 7,829,531 B2 | 11/2010 | Senter et al. |
| 7,851,437 B2 | 12/2010 | Senter et al. |
| 2003/0069214 A1 | 4/2003 | Jin et al. |
| 2005/0004044 A1 | 1/2005 | Huang et al. |
| 2008/0227852 A1 | 9/2008 | Wiemer et al. |
| 2011/0319352 A1* | 12/2011 | Shair .................. A61K 31/498 514/26 |

FOREIGN PATENT DOCUMENTS

| CN | 1844138 A | 10/2006 |
| JP | H94-8794 A | 2/1997 |
| WO | WO 2004/091484 A2 | 10/2004 |
| WO | WO 2010/068877 A2 | 6/2010 |

OTHER PUBLICATIONS

Kuroda et al., Journal of Natural Products, 2001, 64(1), pp. 88-91.*
Ma et al., Bioorganic and Medicinal Chemistry Letters, vol. 11(16), 2001, pp. 2153-2156.*
Kang et al., Bioorganic and Medicinal Chemistry Letters, vol. 19, 2009, pp. 5166-5168.*
International Preliminary Report on Patentability, mailed Nov. 28, 2013, for Application No. PCT/US2012/038562.
International Search Report and Written Opinion, mailed Nov. 30, 2012, for Application No. PCT/US2012/038562.
GenBank Submission;NIH/NCBI, Accession No. 567388. Xiong et al., Feb. 5, 1994. 1 page.
GenBank Submission;NIH/NCBI, Accession No. AF125185. Chuang et al., Mar. 25, 1999. 2 pages.
GenBank Submission;NIH/NCBI, Accession No. AAD21618. Chuang et al., Mar. 25, 1999. 2 pages.
GenBank Submission;NIH/NCBI, Accession No. NM_030758. Low et al., Feb. 26, 2014. 5 pages.
GenBank Submission;NIH/NCBI, Accession No. NP_110385. Low et al., Feb. 26, 2014. 3 pages.
GenBank Submission;NIH/NCBI, Accession No. NM_002556. Mesmin et al., Feb. 27, 2014. 6 pages.
GenBank Submission;NIH/NCBI, Accession No. NP_002547. Mesmin et al., Feb. 27, 2014. 4 pages.
Deng et al., First Total Synthesis of an Exceptionally Potent Antitumor Saponin, OSW-1. J Org Chem. Jan. 8, 1999;64(1):202-208.
Fairn et al., Emerging roles of the oxysterol-binding protein family in metabolism, transport, and signaling. Cell Mol Life Sci. Jan. 2008;65(2):228-36. Review.
Fernandez-Herrera et al., Side-chain opening of steroidal sapogenins to form 22-oxocholestanic skeletons. An approach to analogues of the aglycone of the potent anticancer agent OSW-1. J Mex Chem Soc. 2009;53(3):126-30.

(Continued)

*Primary Examiner* — Traviss C McIntosh, III
(74) *Attorney, Agent, or Firm* — Wolf, Greenfield & Sacks, P.C.

(57) ABSTRACT

Provided are a number of compounds structurally related to OSW-1, a natural compound that binds OSBPs. Also provided are pharmaceutical compositions comprising the OSW-1 analogs, as well as methods for use of these OSW-1 analogs, or pharmaceutically acceptable salts, enantiomers, or stereoisomers thereof in the treatment of atherosclerosis, Alzheimer's disease, and cancer, including p21-deficient cancer. Conjugates of OSW-1 analogs with monoclonal antibodies, including monoclonal antibodies targeted to cancer cells, are also provided. Also provided are pharmaceutical compositions comprising the conjugates, as well as methods for use of these conjugates, in the treatment of cancer, including p21-deficient cancer.

59 Claims, 14 Drawing Sheets

(56) References Cited

OTHER PUBLICATIONS

Fortner et al., Enantioselective synthesis of (+)-cephalostatin 1. J Am Chem Soc. Jan. 13, 2010;132(1):275-80. doi:10.1021/ja906996c.

Fournier et al., Identification of a gene encoding a human oxysterol-binding protein-homologue: A potential general molecular marker for blood dissemination of solid tumors. Cancer Res. Aug. 1, 1999;59(15):3748-53.

Garcia-Prieto et al., Effective killing of leukemia cells by the natural product OSW-1 through disruption of cellular calcium homeostasis. J Biol Chem. Feb. 1, 2013;288(5):3240-50. doi: 10.1074/jbc.M112.384776. Epub Dec. 17, 2012.

Im et al., Structural mechanism for sterol sensing and transport by OSBP-related proteins. Nature. Sep. 1, 2005;437:154-8.

Kasai et al., Analysis of antitumor active OSW-1 and its analogues by liquid chromatography coupled with electrospray and atmospheric pressure chemical ionization quadrupole mass spectrometry. Rapid Comm Mass Spectrom. 2007;21:1100-14.

Kubo et al., Acylated cholestane glycosides from the bulbs of *Ornithogalum saundersiae*. Phytochemistry. 1992;31(11):3969-73.

Laitinen et al., ORP2, a homolog of oxysterol binding protein, regulates cellular cholesterol metabolism. J Lipid Res. Feb. 2002;43(2):245-55.

Lehto et al., The osbp-related proteins: a novel protein family Involved in vesicle transport, cellular lipid metabolism, and cell signalling. Biochim biophys acta. Feb. 20, 2003;1631(1):1-11. Review.

Ma et al., Synthesis of OSW-1 analogues and a dimer and their antitumor activities. Biorg and Med Chem Lett. 2001;11:2153-6.

Matsuya et al., Synthesis and antiyumor activity of the estrange analogue of OSW-1. Eur J Org Chem. 2005:803-8. doi: 10.1002/ejoc.200400632.

Mei, Syntheses of natural products OSW-1, superstolide A and their derivatives. Dissertation. University of Iowa, 2009. ir.uiowa.edu/etd/255. 238 pages.

Morzycki et al., Synthesis of a highly potent antitumor saponin OSW-1 and its analogues. Phytochem Rev. 2005;4:259-277. doi: 10.1007/s11101-005-1233-6.

Shi et al., 23-Oxa-Analogues of OSW-1: Efficient Synthesis and Extremely Potent Antitumor Activity. Angewandte Chemie. Aug. 20, 2004;116(33):4424-4427. DOI: 10.1002/ange.200454237.

Tasdemir et al., Bioactive isomalabaricane triterpenes from the marine sponge Rhabdastrella globostellata. J Nat Prod. Feb. 2002;65(2):210-4.

Taylor et al., Use of oxygenated sterols to probe the regulation of 3-hydroxy-3-methylglutaryl-CoA reductase and sterologenesis. Methods Enzymol. 1985;110:9-19.

Tsubuki et al., A new synthesis of potent antitumor saponin OSW-1 via Wittig rearrangement. Tetrahedron Lett. Jan. 7, 2008;49(2):229-32.

Wojtkielewicz et al., New analogues of the potent cytotoxic saponin OSW-1. J Med Chem. Jul. 26, 2007;50(15):3667-73. Epub Jul. 3, 2007.

Wyles et al., Characterization of the sterol-binding domain of oxysterol-binding protein (OSBP)-related protein 4 reveals a novel role in vimentin organization. Exp Cell Res. Apr. 15, 2007;313(7):1426-37. Epub Feb. 6, 2007.

Xue et al., A total synthesis of OSW-1. J Org Chem. Jan. 4, 2008;73(1):157-61. Epub Dec. 8, 2008.

Yan et al., Characteristics of oxysterol binding proteins. Int Rev Cytol. 2008;265:253-85. doi: 10.1016/S0074-7696(07)65007-4. Review.

Yan et al., OSBP-related protein 8 (ORP8) suppresses ABCA1 expression and cholesterol efflux from macrophages. J Biol Chem. Jan. 4, 2008;283(1):332-40. Epub Nov. 8, 2007.

Yu et al., Total synthesis of the anticancer natural product OSW-1. J Am Chem Soc. Jun. 12, 2002;124(23):6576-83.

Zhou et al., OSW-1: A natural compound with potent anticancer activity and a novel mechanism of action. J Natl Cancer Inst. Dec. 7, 2005;97(23):1781-5.

Zhu et al., Apoptosis induced by a new member of saponin family is mediated through caspase-8-dependent cleavage of Bcl-2. Mol Pharmacol. Dec. 2005;68(6):1831-8. Epub Sep. 23, 2005.

Partial Supplementary Search Report for EP 12786278.7, mailed Jan. 19, 2015.

Burgett et al., Natural products reveal cancer cell dependence on oxysterol-binding proteins. Nat Chem Biol. Aug. 7, 2011;7(9):639-47. doi: 10.1038/nchembio.625.

Chemical Abstracts Service Accession No. 1997: 276067 (Japanese Patent No. H948794, Feb. 18, 1997).

Chemical Abstracts Service Accession No. 2006:1359285 (Mimaki et al., Structures and biological activities of plant glycosides: cholestane glycosides from Ornithogalum saundersiae, O. thyrosides and Galtonia candicans, and their cytotoxic and antitumor activites. Natural Product Communications. 2006;1(3):247-53).

Anderson, Target identification studies of the antiproliferative natural product OSW-1. Dissertation. Harvard University, May 2009. ProQuest Dissertations Publishing. 111 pages.

Kang et al., Synthesis of biotinylated OSW-1. NIH Public Access Author Manuscript. 2010:1-10.

Mimaki et al., Cholestane glycosides with potent cytostatic activities on various tumor cells from Ornithogalum saundersiae bulbs. Bioorg Med Chem Lett. 1997; 7:633-6.

Sakurai et al., Three-dimensional structures of OSW-1 and its congener. Org Lett. Dec. 17, 2010; 12(24):5732-5.

Shi et al., Preparation of 8-(arylsulfanyl)adenines with diazonium salts under mild, aerobic conditions. J Org Chem. Jan. 21, 2005; 70(2):717-20.

Tamura et al., Inhibitory effect of a new steroidal saponin, OSW-1, on ovarian functions in rats. Br J Pharmacol. Aug. 1997; 121(8):1796-802.

\* cited by examiner

|  | $K_d$ (nM) | $K_i$ (nM) | | |
|---|---|---|---|---|
|  | 25-OHC | ceph 1 | OSW-1 | schwf A |
| WT OSBP | 32±14 | 39±10 | 26±9 | 68±23 |
| OSBP(M446W) | 41±13 | 31±6 | 18±6 | 60±23 |
| OSBP(V582M) | 82±26 | 31±10 | 46±15 | 37±11 |
| WT ORP4 | 54±23 | 78±15 | 54±11 | 2600±570 |

OSW-1 ANALOGS AND CONJUGATES, AND USES THEREOF

RELATED APPLICATIONS

The present application is a national stage filing under 35 U.S.C §371 of international PCT application, PCT/US2012/038562, filed May 18, 2012, which claims priority under 35 U.S.C. §119(e) to U.S. provisional patent application, USSN 61/488,023, filed May 19, 2011, each of which is incorporated herein by reference.

BACKGROUND

In the early 1980s the hypothesis was advanced that cholesterol synthesis is regulated via an oxysterol binding protein, i.e., a cytosolic component that bound to oxysterols. Today two protein families have been described which are known to bind oxysterols: the liver X receptors (LXRs), and the protein family described as cytoplasmic oxysterol receptors, termed oxysterol binding proteins (OSBPs) or OSBP-related proteins (ORPs).

OSBP (oxysterol-binding protein) is a protein found in eukaryotes that was first identified based on its high affinity for oxysterols, especially 25-hydroxycholesterol ($K_d$=37 nM). It is the founding member of a family of evolutionarily conserved proteins; at least is twelve are now known in mammals, including OSBP (also referred to as OSBP1), ORP1L, ORP1S, ORP2, ORP3, ORP4L, ORP4S, ORP5, ORP6, ORP7, ORP8, ORP9L, ORP9S, ORP10, and ORP11. Lehto et al. (2003) *Biochim Biophys Acta* 1631:1-11; Yan et al. (2008) *Int Rev Cytol* 265:253-85; Fairn et al. (2008) *Cell Mol Life Sci* 65:228-36. OSBP1 is an 89 kD protein comprising a sterol-binding domain and several other domains involved in protein-protein and protein-lipid interactions. These domains include a pleckstrin homology (PH) domain, which localizes proteins to phosphatidylinositol-containing membranes, and an FFAT domain, which is an endoplasmic reticulum (ER)-localizing domain. OSBP1 does not exhibit enzymatic activity. Although an understanding of its cellular function remains incomplete, studies in the last few years have revealed that OSBP1 is a sterol sensor that can exert control over key signaling pathways.

In addition to OSBP1, mammals express at least eleven other OSBP-related proteins referred to as ORPs. Like OSBP1, each ORP contains a sterol-binding domain, although beyond that there is considerable variation in ORP configuration. Most ORPs include a PH domain in addition to the sterol-binding domain. The sterol-binding domain of OSBP/ORPs is conserved among the family of twelve proteins, but it is not similar to sterol-binding domains of other proteins such as LXR, Insig, or NPC-1. The ORPs are less well characterized than OSBP1, although they have been implicated in lipid metabolism, signaling, vesicular traffic, and non-vesicular sterol transport. Currently, their cellular functions are not well understood, although it is believed that they play important cellular roles since they are expressed ubiquitously and they are evolutionarily conserved. They have been implicated in atherosclerosis and possibly cancer. For instance, overexpression of ORP1L leads to atherosclerotic lesions in mice. Additionally, atherosclerotic lesions were found to contain up-regulated ORP8, and ORP9 has been identified as a therapeutic target in raising high-density lipoprotein (HDL) levels. Knockdown of OSBP1 or ORP8 led to enhanced levels of cholesterol efflux upon LXR agonism. Increased cholesterol efflux is a therapeutic approach in the treatment of atherosclerosis, suggesting that ORPs may be atherosclerosis drug targets. In yeast, there are 7 Osh proteins (ORP homologs). Interestingly, yeast can survive with any six of their seven Osh proteins deleted, but not all seven.

Cephalostatin 1 (1), OSW-1 (2), ritterazine B (3), schweinfurthin A (4), and (−)-stellettin E (5) (see FIG. 1) are natural products that are potently cytotoxic to selected human cancer cell lines with half-maximal growth inhibitory concentrations ($GI_{50}$) in the low nanomolar range. These molecules also have highly similar cytotoxicity patterns against the sixty cultured human cancer cell lines evaluated by the National Cancer Institute (NCI-60), strongly suggesting that they share a cellular target or act by similar mechanisms. Compounds with Pearson correlation coefficients (p values) greater than 0.6 (1.0 is a perfect match) by COMPARE analysis are considered mechanistically related. These compounds previously have been referred to as CRAMs (Cephalostatin and Related Antiproliferative Molecules).

WO 2010/068877 discloses that CRAMs and certain synthetic analogs thereof are high affinity ligands of oxysterol binding proteins (OSBPs) and OSBP-related proteins (ORPs), including OSBP1 and ORP4.

SUMMARY OF THE INVENTION

The invention relates in part to a number of compounds structurally related to OSW-1, a natural compound that binds OSBPs. Because OSBPs have been shown to be integral to atherosclerosis and Alzheimer's disease (AD), an aspect of the invention relates to the use of the OSW-1 analogs, or pharmaceutically acceptable salts, enantiomers, or stereoisomers thereof, in the treatment and/or prevention of atherosclerosis, Alzheimer's disease, and cancer, including p21-deficient cancer. Another aspect of the invention relates to conjugates of OSW-1 analogs with monoclonal antibodies, including monoclonal antibodies targeted to cancer cells. A further aspect of the invention relates to methods of treating cancer using the conjugates of the invention. Additional aspects of the invention relate to pharmaceutical compositions containing the compounds and conjugates of the invention.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION OF THE INVENTION

Figure 1A:
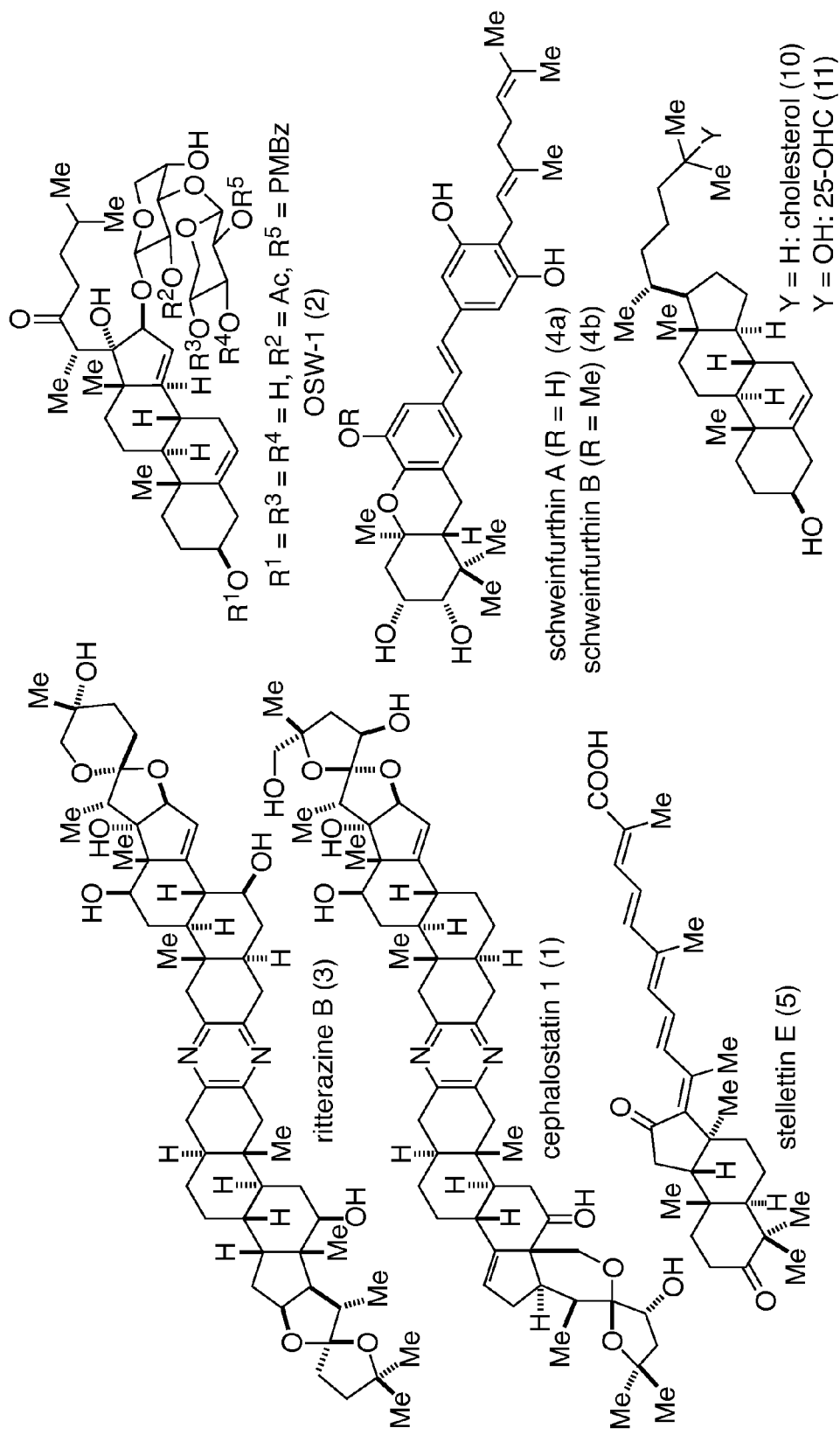
FIG. 1A depicts the chemical structures of cephalostatin (1), OSW-1 (2), ritterazine B (3), schweinfurthin A (4a), schweinfurthin B (4b), stellettin E (5), cholesterol (10), and 25-hydroxycholesterol (25-OHC; 11).

Human OSBP1 is an 807-amino acid protein with certain structural and functional characteristics described above. Nucleotide and amino acid sequences for human OSBP1 are publicly available as, for example, GenBank Accession Nos. NM_002556 and NP_002547, respectively. Corresponding nucleotide and amino acid sequences are also available for a number of other species, including mouse and rat.

OSBP1 is known to be involved in 25-hydroxycholesterol (25-OHC)-induced increase of sphingomyelin synthesis through activation of ceramide transfer protein (CERT). Sphingomyelin is a phospholipid component of cell membranes that is synthesized from ceramide and phosphatidylcholine. Some inducers of apoptosis, such as Fas ligands, do so by activating sphingomyelinase causing sphingomyelin hydrolysis and generation of ceramide, which is known to cause apoptosis. Binding of 25-OHC to OSBP1 causes, indirectly, an increase in transport of ceramide from the ER to the Golgi apparatus, where sphingomyelin synthase 1 is located. This leads to an increase of sphingomyelin synthesis. It is thought that OSBP1 and CERT work in concert to coordinate cholesterol and sphingomyelin levels in cells, which is important to maintain proper membrane structure. Importantly, an OSBP1 knockout mouse was reported to be embryonic lethal. This suggests although OSBP1 is required for animal development, cell lines can survive with OSBP1 expression ablated.

A second activity of OSBP1 was revealed when it was discovered that caveolae of the plasma membrane that were deprived of cholesterol or treated with 25-OHC caused differential phosphorylation states of ERK1/2 (extracellular signal-regulated kinase 1 and 2). OSBP1 was found to be the sterol receptor mediating this event. Upon binding cholesterol, OSBP1 forms a ternary complex with two phosphatases, PP2A (a serine/threonine phosphatase) and HePTP (a tyrosine phosphatase), which then inactivates ERK1/2 through dephosphorylation. Conversely, addition of 25-hydroxycholesterol (25-OHC) or depletion of cholesterol disassembles this complex, leading to ERK1/2 hyperphosphorylation. ERK1/2 is a component of the MAPK/ERK signaling pathway, which is responsible for linking growth factor signaling with cellular responses including cell division. The observation that OSBP1 can control ERK1/2 activation is notable since it shows that OSBP1 can link sterol binding to key signaling pathways in the cell.

It has also been reported that OSBP1 can control up-regulation of profilin-1 through activation of the JAK-STAT pathway in response to 25-OHC and 7-ketocholesterol. However, these effects have only been observed in specific endothelial cells that may not represent roles for OSBP1 in cancer cells.

Human ORP4, also known as OSBP2, is expressed in different isoforms as a consequence of alternative transcription start sites from the OSBP2 gene. Specifically, a long version (ORP4L) of 916 amino acids and a short version (ORP4S) of 461 amino acids have been characterized in humans. Nucleotide and amino acid sequences for human ORP4L are publicly available as, for example, GenBank Accession Nos. AF125185 and AAD21618, respectively. Nucleotide and amino acid sequences for human ORP4S are publicly available as, for example, GenBank Accession Nos. NM_030758 and NP_110385, respectively.

As the OSBP/ORP family has been implicated in lipid transport and metabolism, vesicle trafficking and cell signaling, this protein family contains attractive targets for the treatment of a range of disorders, including but not necessarily limited to cancer, atherosclerosis, and Alzheimer's disease.

ORPphilins

OSBP1 and ORP4L are targets of cephalostatin 1 (1), OSW-1 (2), ritterazine B (3), schweinfurthin A (4a), and (−)-stellettin E (5). These natural products, previously termed CRAMs (Cephalostatin and Related Antiproliferative Molecules), are referred to herein as ORPphilins. These compounds have previously been reported to exert anti-cancer effects. Compound 1 induces apoptosis through an atypical mechanism. Compound 2 is 30-150 fold more cytotoxic toward glioblastoma and leukemia cells compared to non-transformed astrocytes and lymphocytes, respectively. Compounds 4a and 5 are selectively growth inhibitory toward tumor cells deficient for tumor suppressors neurofibromatosis 1 (NF1) and p21, respectively. Repression of p21 expression and loss of NF1 are known to be important for the development of some cancers. Therefore, small molecules that selectively inhibit the growth of cancer cells with these genetic alterations are attractive candidates for cancer-specific therapeutics.

Cancer

Cancer is a well-known disease in mammals characterized by abnormal cell proliferation that is uncontrolled by external signals and, in many but not all instances, the capacity to invade tissues and metastasize to distant sites. Cancer causes significant morbidity and mortality through its disruption of normal cell and tissue function. A number of cancers are further characterized by somatic genetic mutations, loss of differentiation, and/or abnormal expression of any of a number of tumor suppressor genes including, for example, p53, p21, and neurofibromatosis 1 (NF1). Loss of expression of p53 and/or p21 results in loss of control of cell replication and is frequently a characteristic of cancers that are resistant to conventional anti-cancer therapies.

The p21 protein, also known as p21/WAF1 protein and as cyclin-dependent kinase (CDK) inhibitor 1, also referred to herein simply as p21, binds to and inhibits the activity of cyclin-CDK2 or -CDK4 complexes, and thus functions as a regulator of cell cycle progression at $G_1$. Normally the expression of this gene is tightly controlled by the tumor suppressor protein p53, through which this protein mediates the p53-dependent cell cycle $G_1$ phase arrest in response to a variety of stress stimuli.

The p21 protein is often not expressed in advanced tumors, indicating that ORPphilins, if lethal to cells lacking p21, may have an excellent therapeutic window in patients with late-stage, difficult-to-treat tumors. Since few small molecules have been reported to be highly selective towards isogenic cell lines lacking p21, this characteristic indicates that ORPphilins are compounds with uncommon cellular targets and mechanisms of action that could render them useful in the treatment of cancer.

Atherosclerosis

Atherosclerosis results from high serum cholesterol levels (hypercholesterolemia) which leads to the accumulation of cholesterol in arterial walls. The plaques that characterize atherosclerosis inhibit blood flow and promote clot formation, and can ultimately cause death or severe disability via thrombotic or ischemic myocardial infarction (heart attack) and/or stroke.

OSBPs may be useful in the treatment of atherosclerosis. For example, it is known that mammalian oxysterol-binding protein-1 (OSBP1) binds oxygenated derivatives of cholesterol and mediates sterol and phospholipid synthesis. In addition, it has been recently shown that mammalian oxysterol-binding protein-related protein 8 (ORP8) acts as a negative regulator of ABCA1 expression and macrophage cholesterol efflux, and thus may modulate the development of atherosclerosis. Yan et al. (2008) *J Biol Chem* 283:332-40.

Alzheimer's Disease

Alzheimer's disease is a common, chronic neurodegenerative disease that often leads to dementia and death, which is characterized by a progressive loss of memory and sometimes severe behavioral abnormalities, as well as an impairment of other cognitive functions. It ranks as the fourth leading cause of death in industrialized societies after heart disease, cancer, and stroke. The incidence of Alzheimer's disease is high, with an estimated 2.5 to 4 million patients affected in the United States and perhaps 17 to 25 million worldwide. Moreover, the number of sufferers is expected to grow as the population ages. A characteristic feature of Alzheimer's disease is the presence of large numbers of insoluble deposits, known as amyloid plaques, in the brains of those affected. Autopsies have shown that amyloid plaques are found in the brains of virtually all Alzheimer's patients and that the degree of amyloid plaque deposition often correlates with the degree of dementia. While some opinion holds that amyloid plaques are a late-stage by-product of the disease process, the majority view is that amyloid plaques and/or soluble aggregates of amyloid peptides are more likely to be intimately, and perhaps causally, involved in Alzheimer's disease. Because there is no cure for Alzheimer's disease, managing the disease usually involves medications to control symptoms, in combination with various non-drug strategies designed to ease the suffering of the person afflicted and that of his or her family and caregivers. Unfortunately, not all patients with Alzheimer's disease are responsive to the currently available therapies.

OSBP1 has been shown to modulate processing and trafficking of the amyloid precursor protein. Laitinen et al. (2002) *J Lipid Res* 43:245-55. These results suggest that OSBP1 could play a role in linking cholesterol metabolism with intracellular amyloid production, and, more importantly, indicate that OSBP1 could provide an alternative target for a directed therapeutic for human maladies including Alzheimer's disease and atherosclerosis.

Cephalostatin 1 and Ritterazine B

Cephalostatins are a group of complex steroidal pyrazine alkaloids which were first isolated from the sea worm *Cephalodiscus gilchristi*. They represent cytotoxins that are highly effective against the PS cell line ($ED_{50}$ of $10^{-7}$-$10^{-9}$ μg/mL) and are anti-tumor agents. They are natural marine products that occur rarely, however, and are available only in extremely small amounts. For example, only 139 mg of cephalostatin 1 and a total of 272 mg of other cephalostatins could be isolated from 166 kg of *Cephalodiscus gilchristi* (tubular worms 5 mm long). All of the cephalostatins (such as cephalostatin 1, cephalostatin 2, cephalostatin 3, cephalostatin 4, cephalostatin 5, cephalostatin 6, cephalostatin 7, 25'-epi-cephalostatin 7, 20-epi-cephalostatin 7, cephalostatin 8, cephalostatin 9, cephalostatin 10, cephalostatin 11, cephalostatin 12, cephalostatin 13, cephalostatin 14, cephalostatin 15, cephalostatin 16, cephalostatin 17, cephalostatin 18, and cephalostatin 19) are intended to be encompassed.

In addition to its unusual COMPARE profile, another indication that the cellular target and mechanism of cephalostatin 1 (1), and likely all ORPphilins, is unique was the report that cephalostatin 1 induces apoptosis without formation of the apoptosome and without release of cytochrome c from the mitochondria, both events that occur with most cytotoxic anti-cancer small molecules. Treatment of the J16 Jurkat cell line with cephalostatin 1 leads to activation of caspase-4 and caspase-2 as well as release of Smac (second mitochondria-derived activator of caspase) from the mitochondria. This specific sequence of events is rarely observed in small molecule-induced apoptosis, suggesting that studying the mechanism of cephalostatin 1 may uncover new apoptotic signaling mechanisms. Therefore, cephalostatin 1 may be useful in treating tumors that have become resistant to conventional cancer therapeutics.

It was shown that cephalostatin 1 also led to formation of the multi-protein complex known as the PIDDosome (comprising proteins PIDD, RAIDD, and caspase-2). The histone deacetylase inhibitor trichostatin A is the only other small molecule known to induce formation of the PIDDosome. Cephalostatin 1 was also shown to induce an ER stress response.

The highly similar structures of ritterazine B and cephalostatin I and their nearly identical COMPARE Pearson correlation coefficient (p=0.93) suggest these compounds likely share a cellular target(s).

A few synthetically produced cephalostatin analogues, synthetic methods for preparing the cephalostatin analogues, pharmaceutical compositions containing the analogues, and methods for using the analogues as active agent in pharmaceutical uses, are described in U.S. Pat. No. 5,708,164 (Winterfeldt, E. et al.); which is hereby incorporated by reference in its entirety, such as for the cephalostatin analogs, and their preparation, as described therein.

OSW-1

OSW-1 (2) is more abundant than cephalostatin 1, which has enabled some in vivo studies. The $GI_{50}$ of OSW-1, taken as an average against the NCI-60, is 0.78 nM. In vivo studies of OSW-1 have been limited, but nude mice subcutaneously implanted with P388 tumor cells demonstrated a 59% increased life span upon a single intraperitoneal (i.p.) treatment of 0.01 mg/kg OSW-1. OSW-1 also shows selectivity for malignant cell types over non-malignant cells. OSW-1 is 40 times more active in leukemia cells (HL-60, $GI_{50}$=0.04 nM) versus normal lymphocytes ($GI_{50}$=1.73 nM), and in malignant brain tumor cells, the selectivity increases to 150 fold (U87-MG, $GI_{50}$=0.047 nM versus normal astrocytes $GI_{50}$=7.13 nM). Finally, CLL (chronic lymphocytic leukemia) cells taken from patients that were refractory to fludarabine, a commonly used chemotherapeutic for treatment of CLL and other blood cancers, were highly sensitive to OSW-1 ($GI_{50}$=0.3 nM). These studies, albeit limited, demonstrate that OSW-1 is quite selective at inhibiting the growth of some tumors in vivo.

The use of OSW-1, and analogs thereof, for treating pancreatic cancers, leukemias, colon cancers, malignant gliomas and other brain tumors, and ovarian cancers is disclosed in US Patent Application Publication No. 2005/0004044 (Huang, P. et al.); which is hereby incorporated by reference in its entirety, such as for the preparation of OSW-1 analogs.

Schweinfurthins

The family of natural products known as the schweinfurthins currently includes four compounds isolated from the African plant Macaranga schweinfurthii Pax. Schweinfurthin A (4a) (average $GI_{50}$=360 nM vs. NCI-60) exhibits a similar cytotoxicity profile to cephalostatin 1 (p=0.59 with 1) and the other ORPphilins. Schweinfurthins B and D also display significant activity in the NCI's 60-cell-line anticancer assay with mean $GI_{50}$ values of less than 1 μM. Their biological activity has attracted interest because some central nervous system (CNS), renal, and breast cancer cell lines are among the types most sensitive to these compounds. Inspection of the spectrum of activity shows no correlation with any currently used agents and suggests that these compounds may be acting at a previously unrecognized target or through a novel mechanism.

Like cephalostatin 1, only small quantities of schweinfurthin A have been available to from natural sources, which has limited in vivo studies. Repeated attempts to isolate larger samples of the schweinfurthins from natural sources have not been fruitful. A synthesis of schweinfurthin A has not yet been achieved, although the Wiemer group has achieved total syntheses of schweinfurthin B, E and F. See also, US Patent Application Publication No. 2008/0227852 to Wiemer, D. et al.; hereby incorporated by reference in its entity. For the is preparation of some related stilbene derivatives, see U.S. Pat. No. 7,321,050 to Chen, G. et al.; hereby incorporated by reference in its entirety.

In a single reported mouse xenograft experiment with schweinfurthin A, i.p. administration of 9.3 mg/kg (Q2Dx4) led to "reduction in tumor volume compared to vehicle-treated controls without overt toxicity." Beutler et al. (2006) The schweinfurthins: Issues in development of a plant-derived anticancer lead, In: Bogers R J C, Craker L. E. Lange, D., eds. *Medicinal and Aromatic Plants*; Springer, Dordrecht, The Netherlands, p. 301-9.

(−)-Stellettin E (−)-Stellettin E (5) is a marine natural product also reported to have a cytotoxicity pattern similar to cephalostatin 1 (p not reported). (−)-Stellettin E is a light-sensitive compound only isolated in small quantities, prohibiting detailed cell-based studies and in vivo experiments. However, the cellular target of (−)-stellettin E (and by analogy ORPphilins) is made even more intriguing by the discovery that the compound is 117 times more cytotoxic to a HCT-116 colon cancer cell line engineered not to express the p21-CDKN1A (herein "p21") tumor suppressor, compared to the parental HCT-116 cell line ($GI_{50}$=39 nM in HCT-116 p21$^{-/-}$ versus $GI_{50}$=4.57 μM in HCT-116 p21$^{+/+}$). These results suggest that (−)-stellettin E (and possibly all ORPphilins) may be lethal to cells lacking p21.

Figure 5:
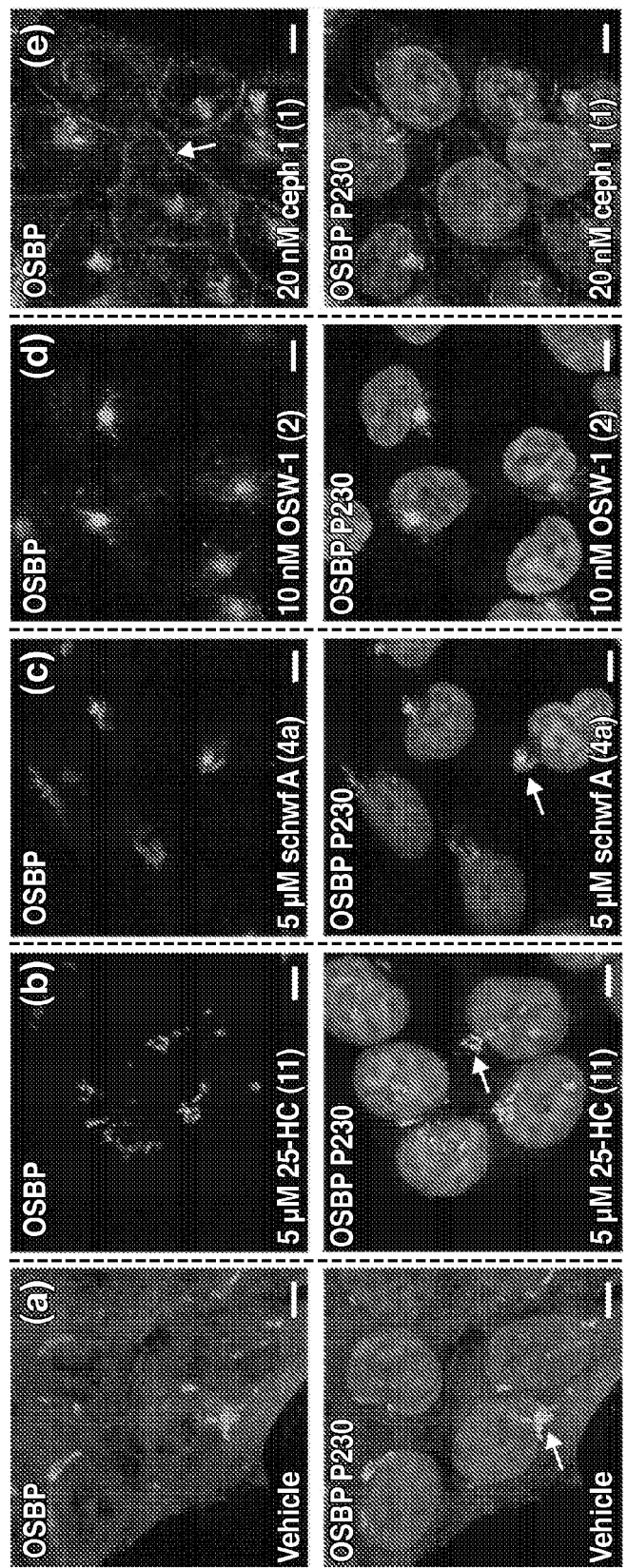
FIG. 5 is a panel of 10 immunofluorescence photomicrographs depicting ORPphilin-induced OSBP1 translocation in HCT-116 cells treated with the agents indicated in the lower left of each image and stained with fluorescently labeled antibodies for the antigen or antigens indicated in the upper left of each image.
Figure 6A:
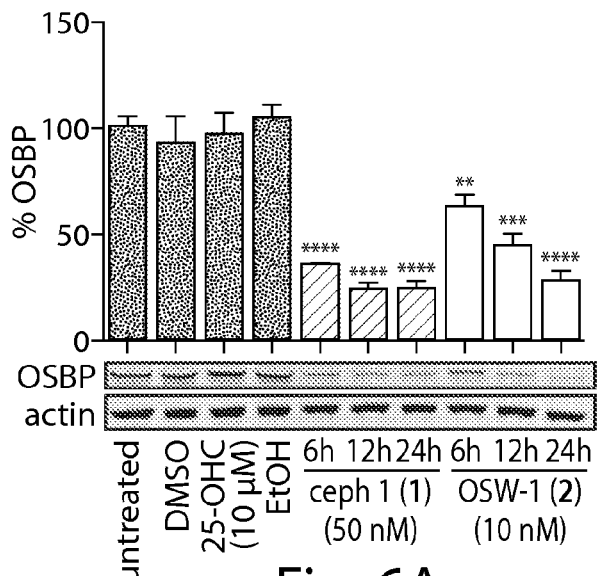
FIG. 6A is a bar graph and associated Western blots depicting a time-dependent to reduction in OSBP1 protein levels in HCT-116 cells upon treatment with indicated concentrations of the indicated agents.  P<0.01 (n=3); * P<0.001 (n=3); **** P<0.0001 (n=3) relative to vehicle-treated cells (two-tailed students t-test).
Figure 6B:
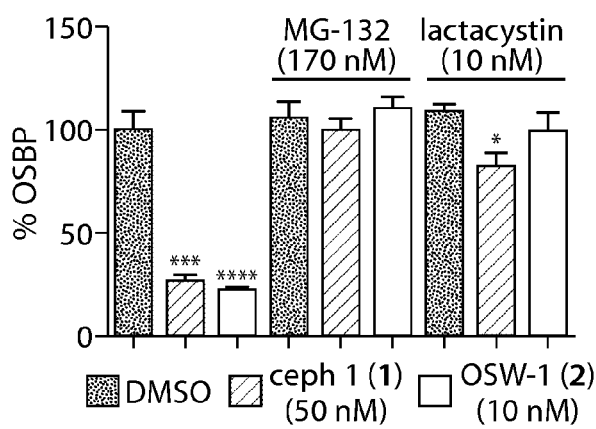
FIG. 6B is a bar graph depicting inhibition of reduction in OSBP1 protein levels (at 24 h time point) in the presence of indicated concentrations of the proteasome inhibitors MG-132 or lactacystin.
Figure 6C:
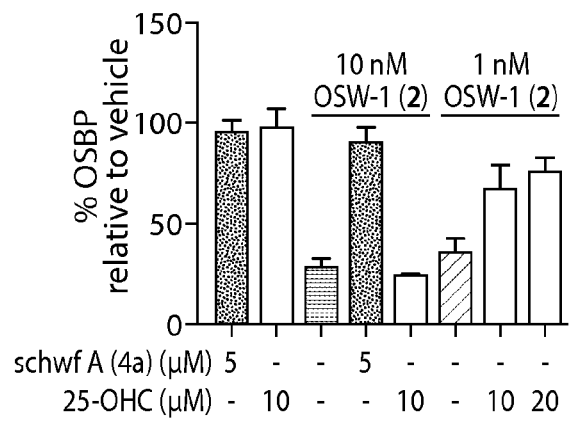
FIG. 6C is a bar graph depicting schweinfurthin A (4a) and 25-OHC at indicated concentrations do not induce reduction in OSBP1 levels after 24 h of treatment, but can block the reduction induced by OSW-1.
Figure 7:
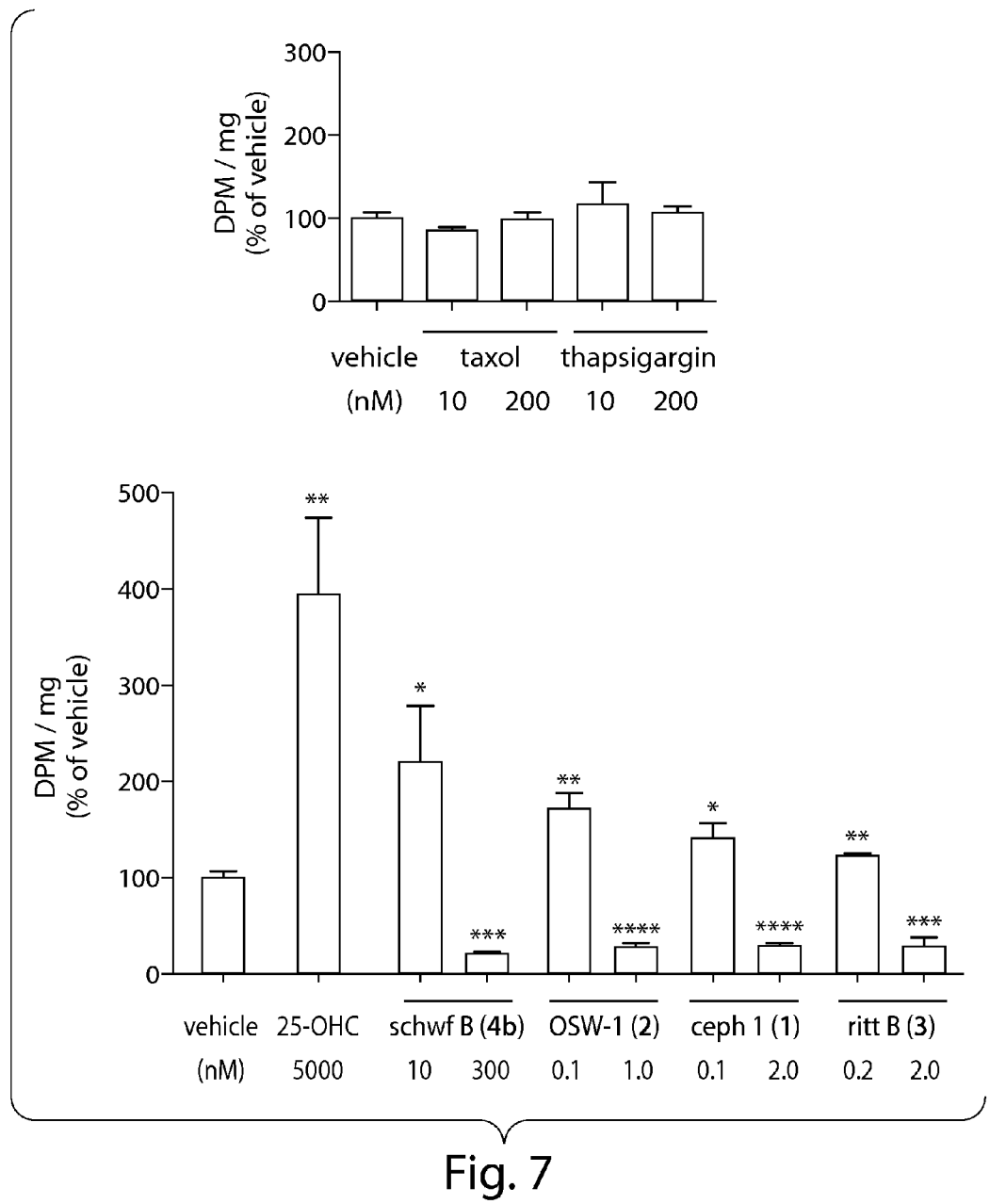
FIG. 7 is a graph depicting inhibition of sphingomyelin biosynthesis in CHO-K1 cells by indicated concentrations of indicated ORPphilins. Inset: negative controls. All data are mean±s.d. from three individual experiments. * P<0.05 (n=3);  P<0.01 (n=3). * P<0.001 (n=3), **** P<0.0001 (n=3) relative to vehicle-treated cells (two-tailed students t-test). DPM: decays per minute.

In accordance with the instant invention, the inventors have identified OSBP1 and its closest paralog ORP4L as high affinity receptors of cephalostatin 1 (1), OSW-1 (2), ritterazine B (3) and schweinfurthin A/B (4a/4b). These compounds are disclosed herein to alter several aspects of OSBP1 cellular activity, revealing new activities of the largely mysterious OSBP/ORP proteins. For instance, 1 induces partial localization of OSBP1 to the plasma membrane (FIG. 5E), 1 and 2 cause OSBP1 degradation (FIG. 6), and all ORPphilins studied induce a reduction in the rate of sphingomyelin biosynthesis (FIG. 7).

Prior to the instant invention, the function of OSBP1 and its paralogs, the ORPs, has not been well understood, due in part to a lack of reagents capable of altering the function of these proteins in cells. Small molecule perturbation of OSBP/ORPs by administration of 25-OHC or alteration of cellular cholesterol levels could affect many proteins beyond OSBP/ORPs. Further complicating its use, 25-OHC is a potent inhibitor of cholesterol biosynthesis in cells. Therefore, the effects of 25-OHC on OSBP1 activity could be due either to 25-OHC binding to OSBP1 or to cellular cholesterol depletion.

The identification of OSBP1 and ORP4L as targets of the ORPphilins offers new, high affinity small molecule probes of these proteins. Furthermore, ORPphilins are likely more specific for OSBP1 and ORP4L than 25-OHC, since results disclosed herein show that neither NPC-1 or Insig—two cellular receptors of 25-OHC—are involved in the activity of these compounds. All of the ORPphilins appear to compete with 25-OHC for binding to OSBP1 and ORP4L. The simplest explanation for this observation is that the ORPphilins displace 25-OHC from the highly conserved lipid-binding domain, which is present in the C-terminal end of all of the OSBP/ORP proteins. Crystal structures of Osh4, a yeast protein with homology to OSBP1, reveals that the lipid-binding domain is a large hydrophobic cavity comprising a partial β-barrel. Im et al. (2005) *Nature* 437:154-8. Such cavity could conceivably accommodate the ORPphilins.

Convergence of the ORPphilins on the same protein targets validates the indication, provided by their similar pattern of growth inhibition in NCI-60 cell line panel, that these compounds could have the same mechanism of action. Surprisingly, however, findings disclosed herein reveal that the ORPphilins have individually distinct activities in targeting OSBP1 and ORP4L. For example, cephalostatin 1 (1) and OSW-1 (2) induce OSBP1 degradation in cells, whereas schweinfurthin A (4a) does not. Immunofluorescence microscopy shows that the different ORPphilins affect OSBP1 localization and Golgi integrity in different ways. Further, 1 and 2 bind OSBP1 and ORP4L with only slight variations in affinity. Schweinfurthin A (4a), however, binds OSBP1 with approximately 40 times greater affinity than ORP4L, a surprising result given the high protein sequence homology of ORP4L to OSBP1. The lower affinity of schweinfurthin A (4a) for ORP4L versus OSBP1 could be the reason it is ~100-300 fold less cytotoxic than the other ORPphilins, and also the reason 4a falls off the ORP4L binding/cytotoxicity correlation. This large difference in schweinfurthin A's binding affinity for OSBP1 and ORP4L suggests that it is feasible to discover small molecules that selectively interact with individual members of, or subsets of, the OSBP/ORP superfamily.

Figure 3A:
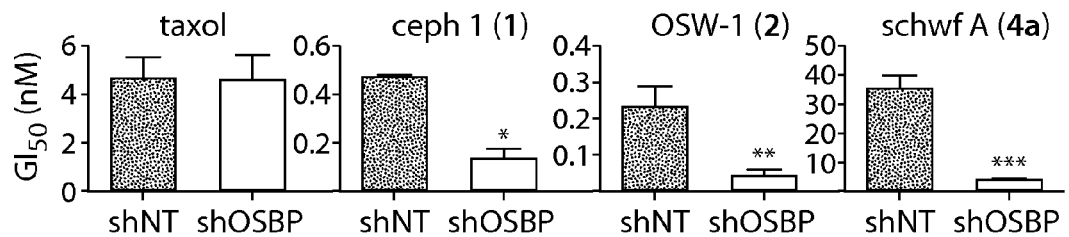
FIG. 3A is a series of four bar graphs depicting knockdown/dose-shift experiment in HCT-116 p21$^{-/-}$ cells stably transfected with either OSBP1-targeting shRNA (shOSBP1) or non-targeting shRNA (shNT). Bars represent s.d. of three or four individual experiments. * P=0.0002 (n=3);  P=0.0006 (n=4); * P=0.0003 (n=3) compared to shNT cells (two-tailed students t-test).
Figure 3B:
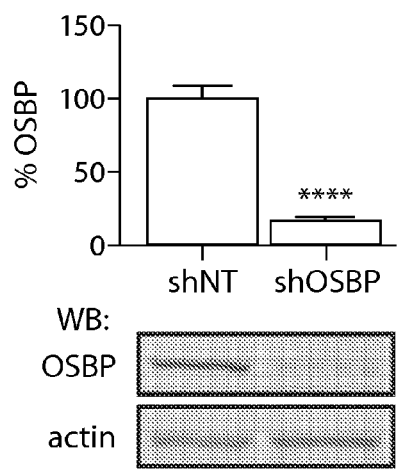
FIG. 3B is a bar graph and pair of corresponding Western blots depicting quantitation of OSBP1-levels in shNT and shOSBP1 cells. Mean±s.d. of seven individual experiments. **** P≤0.0001 (n=7) compared to shNT cells (two-tailed students t-test). WB: Western blot showing equal loading based on actin.
Figure 3C:
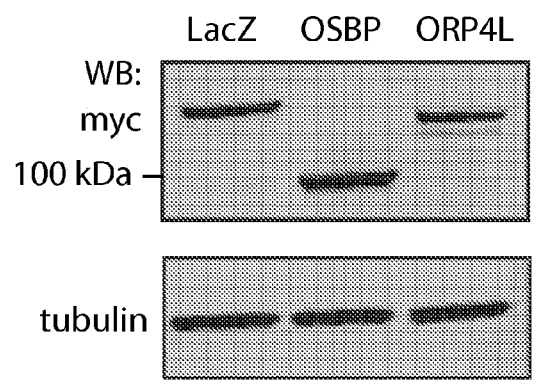
FIG. 3C is a pair of Western blots depicting HeLa cell lysates expressing lacZ-, OSBP1-, or ORP4L-myc-his.
Figure 3D:
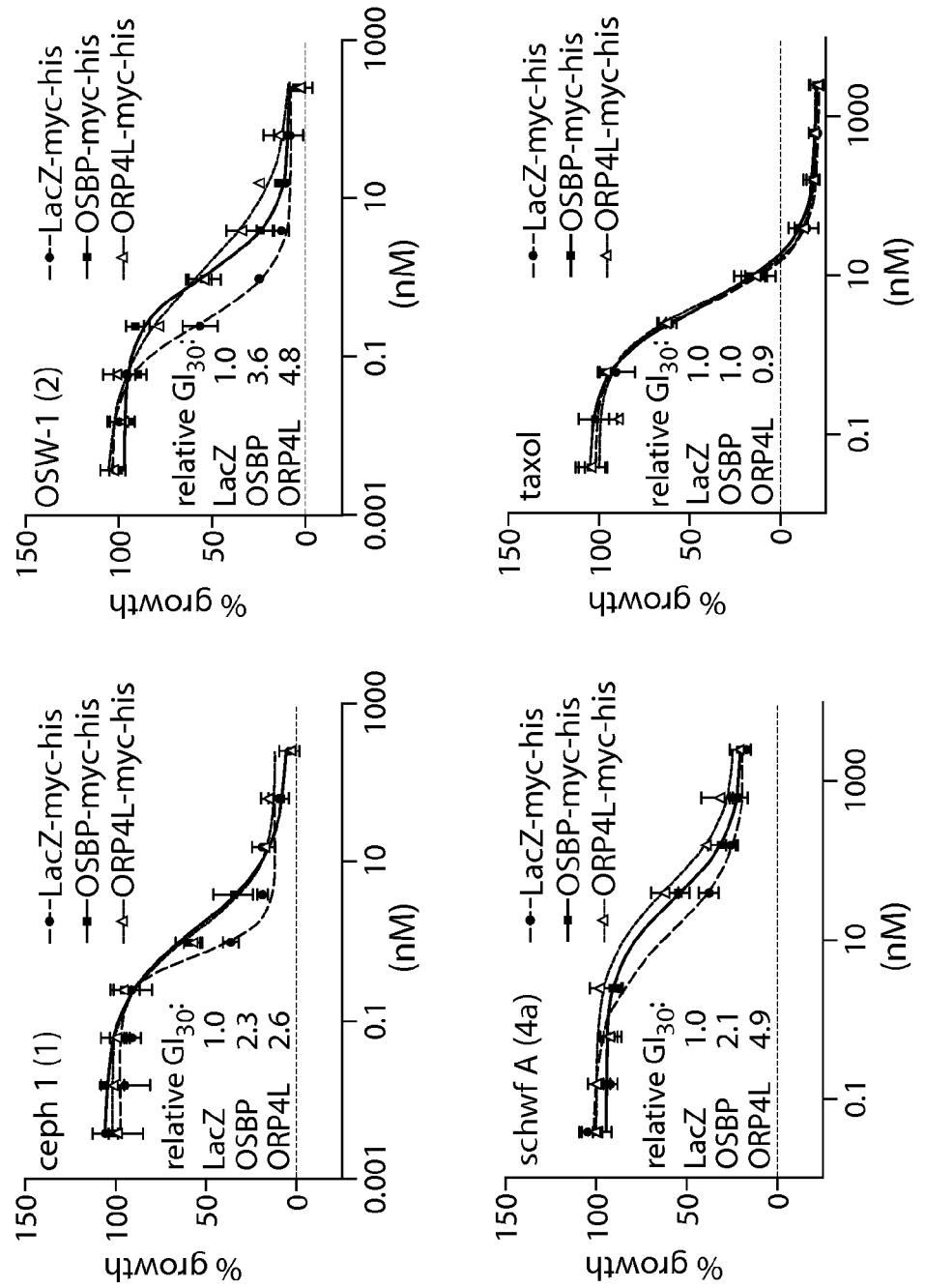
FIG. 3D is a group of four graphs depicting effect of overexpression of lacZ, OSBP1, or ORP4L on the growth inhibitory activity (48 h) of 1, 2, 4a, and Taxol® in HeLa cells.

Multiple lines of evidence indicate that OSBP1 and ORP4L mediate the antiproliferative activities of the ORPphilins. Verifying that OSBP1 and ORP4L mediate the antiproliferative activity of ORPphilins was made more challenging by the lack of enzymatic activity of these proteins as well as their poorly understood function. First, the Example below show that knockdown of OSBP1 levels sensitized cells to the ORPphilins (FIG. 3A), while overexpression of either OSBP1 or ORP4L desensitized cells to these compounds (FIG. 3D). These results are consistent with the ORPphilins inducing a loss-of-function for OSBP1 and ORP4L, which led to the observed antiproliferative effects. However, these results did not rule out the possibility that OSBP1 and ORP4L are "decoy proteins," namely, high affinity receptors that prevent the small molecules from reaching the actual efficacy targets that cause the antiproliferative effects.

Figure 3E:
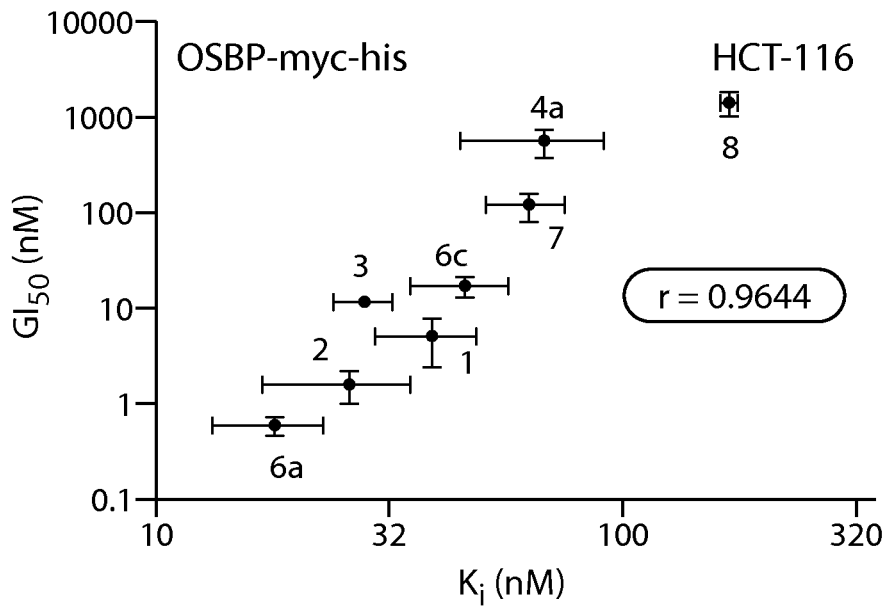
FIG. 3E is a graph depicting correlation between binding affinity ($K_i$) to OSBP1-myc-his and growth inhibition ($GI_{50}$) in HCT-116 cells.
Figure 3F:
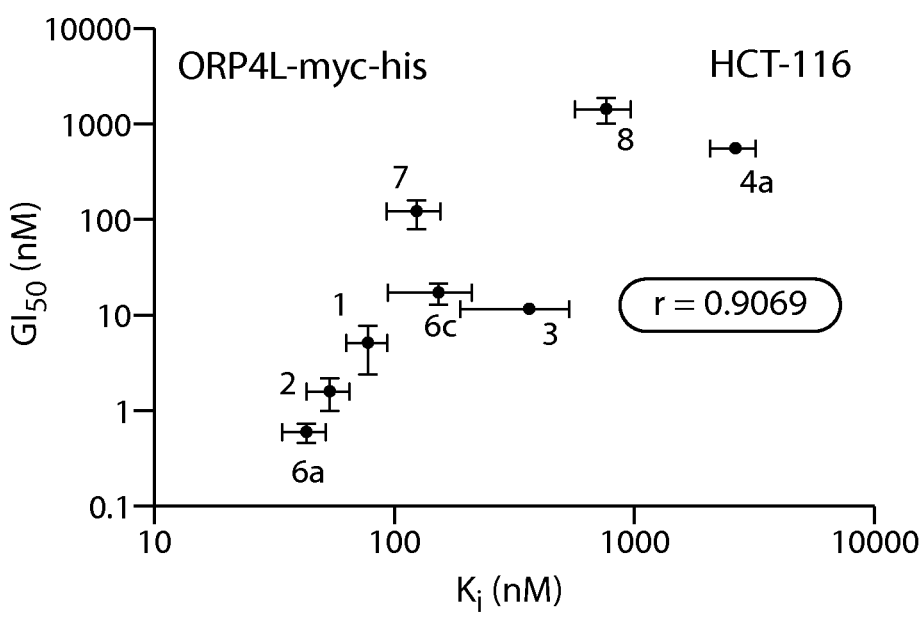
FIG. 3F is a graph depicting correlation between binding affinity ($K_i$) to ORP4L-myc-his and growth inhibition ($GI_{50}$) in HCT-116 cells.

Three lines of evidence were obtained that together strongly support OSBP1 and ORP4L as efficacy targets for the ORPphilins. First, it was determined that structure-activity relationship (SAR) for 1-4a and four analogs of 2 exhibited a positive and strong correlation between their affinity for OSBP1 and their potency of growth inhibition (FIG. 3E). With the exclusion of schweinfurthin A (4a), the same analysis using ORP4L provided a similarly strong correlation (FIG. 3F). Additionally, compound 9, an OSW-1 (2) analog that does not bind OSBP1 or ORP4L, was between 700 and 2100-fold less active than 2 at inhibiting cell growth when evaluated in three cell lines. These results are consistent with OSBP1 and ORP4L as efficacy targets. If instead OSBP1 and ORP4L were decoy proteins, an inverse correlation between $K_i$ and $GI_{50}$ would be expected.

Second, the growth inhibitory activity of the ORPphilins was significantly suppressed by co-incubation of cells with sub-lethal doses of 25-OHC, a known high-affinity ligand of OSBP1 and ORP4L. Independent evidence that 25-OHC competes with the ORPphilins for binding to OSBP1 in cells came from observation that 25-OHC suppressed OSBP1 degradation induced by OSW-1 (2). If OSBP1 and ORP4L were decoy targets, displacement of the ORPphilins by 25-OHC would free more compound to interact with the actual efficacy target. This would be expected to sensitize cells to ORPphilins, not desensitize cells as observed.

Finally, two dominant drug-resistant alleles of OSBP1 were identified. Over-expression of OSBP1 (M446W) desensitized cells to 1, 2 and 4a, and over-expression of OSBP1 (V582M) desensitized cells to 1. Interestingly, these mutants did not show altered binding to 1, 2, or 4a. One possible explanation for the desensitization of cells overexpressing these OSBP1 mutants is that these mutations affect protein-protein interactions, and that the interaction of OSBP1 and other proteins is involved in the antiproliferative activity of the ORPphilins. Mutants of the thyroid hormone β receptor provide a precedent for this possibility since known mutants in this protein suppress ligand-induced transactivation by disrupting protein-protein interactions rather than affecting ligand binding. Collingwood et al. (1997) *Proc. Natl. Acad. Sci. USA* 94:248-53. OSBP1 has several known interacting partners and has been reported to function as a sterol-sensing scaffolding protein, capable of making multi-protein complexes in a ligand binding-dependent fashion. Therefore it is reasonable to speculate that the activity of the ORPphilins is reliant on OSBP1 interacting with other proteins, and that mutations altering OSBP1 protein-protein interactions could modulate the activity of these compounds.

Taken as a whole, the aforementioned results strongly support OSBP1 and ORP4L as efficacy targets. However, it seemed curious that ORPphilins appear to cause a loss of function of OSBP1, yet OSBP1 shRNA knockdown did not on its own cause growth inhibition. One explanation for this is that a complete or nearly complete ablation of OSBP1 expression is required to inhibit cell growth, and the OSBP1 shRNA knockdown experiments only reduced OSBP1 levels by ~85%. In contrast, the ORPphilins, highlighting the power of small molecule effectors, are capable of inhibiting total OSBP1 function in the cell. This is especially true for cephalostatin 1 (1) and OSW-1 (2), which have a dual means of disrupting the functions of OSBP1. Namely, both compounds are high affinity ligands (low nM $K_i$) of OSBP1, and both compounds induce OSBP1 degradation.

A second explanation is that co-depletion of both OSBP1 and ORP4L is required to phenocopy the effects of compound treatment. With a lack of an effective ORP4L antibody, a simultaneous knockdown of both proteins was not performed.

Figure 4A:
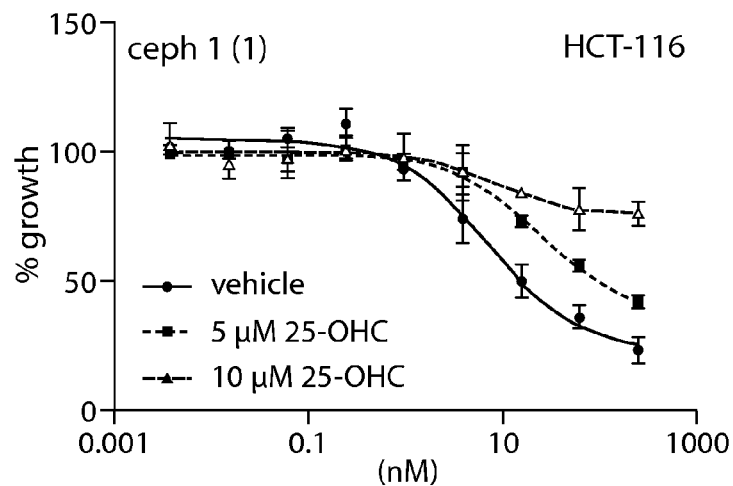
FIG. 4A is a pair of graphs depicting effect of 25-hydroxycholesterol co-administration on growth inhibitory activity (48 h) of cephalostatin 1 (1) (left) or OSW-2 (2) (right) in HCT-116 cells.
Figure 4A:
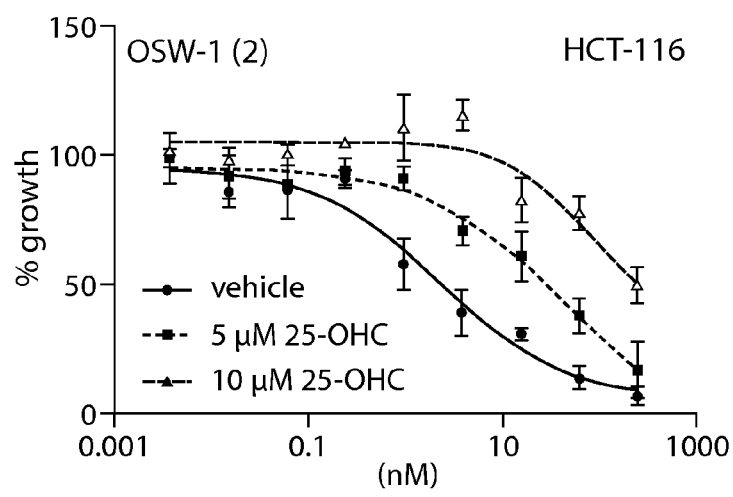

A third explanation is that the ORPphilins perturb the cellular functions of multiple members of the OSBP/ORP superfamily, beyond OSBP1 and ORP4L, and the inhibition of these other OSBP/ORPs contribute to the antiproliferative activity of the ORPphilins. This would be a likely possibility if there was a critical cellular function performed redundantly by multiple OSBP/ORPs, which would mirror the situation in yeast. Yeast possess 7 Osh proteins, which are the yeast homologs of the OSBP/ORPs. Yeast reportedly can survive the loss of any six of the seven Osh proteins, but not loss of all seven. Furthermore, the OSBP/ORPs exhibit significant sequence homology in the lipid-binding domain, and most have been shown to bind 25-OHC. Given that the ORPphilins compete with 25-OHC for binding to OSBP1 and ORP4L, other OSBP/ORPs may bind these compounds. The significant desensitization achieved by addition of 25-OHC (FIG. 4A) could be due to displacement of ORPphilins from other ORPs in addition to OSBP1 and ORP4L. Superfamily-wide inhibition of OSBP/ORPs, or inhibition of a subset of these proteins required for cell survival, would also explain the failure of genetic perturbation methods to uncover a role of the individual ORPs in cell proliferation, with the exception of the inducible expression of ORP9S, which is reported to be cytotoxic.

Since ORPphilins are selectively growth inhibitory to tumor cells lacking p21 (FIG. 2A), and 4a is selective toward tumor cells lacking NF1, results disclosed herein provide a strong indication that loss of these tumor suppressor proteins renders cells highly sensitive to perturbation of OSBP1 and ORP4L. Thus, findings disclosed herein indicate that OSBP1 and ORP4L are new targets for achieving synthetic lethality with NF1 and p21, which could result in tumor-selective cancer therapeutics.

ORP4L mRNA levels have been reported to be increased in metastatic breast cancer tumors compared to localized tumors, signifying a possible role for ORP4L in the early steps of the metastatic cascade. Fournier et al. (1999) *Cancer Res.* 59:3748-53. Therefore, ORPphilins will be useful reagents to further explore the role of ORP4L in cancer metastasis.

The discovery that cephalostatin 1 (1) and OSW-1 (2) induce a significant drop in OSBP1 levels will be useful in studies of their anti-tumor activities, since this effect could be used to determine whether the compounds have reached specific tissues. Moreover, compounds 1 and 2 could be used to lower OSBP1 protein levels in animal models of disease.

Various aspects of the invention concern OSW-1 analogs, antibody conjugates formed with these analogs, pharmaceutical compositions containing the analogs or conjugates, and the use of the analogs, conjugates, and pharmaceutical compositions of the invention for the treatment of oxysterol binding protein (OSBP1)-related diseases or conditions, including, in particular, cancer.

An aspect of the invention is a compound of formula (I) or a pharmaceutically acceptable salt thereof:

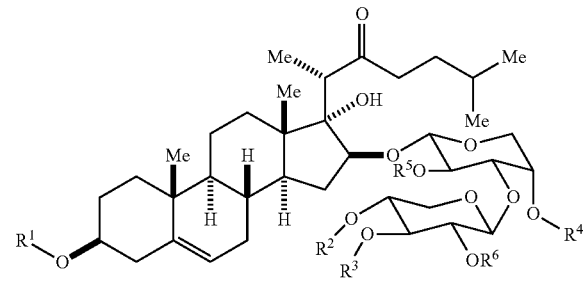

(I)

wherein
$R^1$, $R^2$, $R^3$, and $R^6$ are independently selected from the group consisting of hydrogen, trialkylsilyl, and

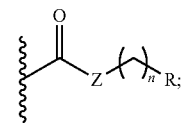

Z is absent or is selected from the group consisting of O and $NR^{10}$;
n is an integer 0-6;
R is selected from the group consisting of substituted or unsubstituted: alkyl, alkenyl, amino, alloc-protected amino, Fmoc-protected amino, aryl, 5- to 13-membered cycloalkyl or cycloalkenyl group, and 5- to 10-membered cyclic heteroaromatic group comprising 1-3 heteroatoms independently selected from the group consisting of N, O, and S;
$R^4$ is selected from the group consisting of hydrogen and C1-C6 alkyl;
$R^5$ is selected from the group consisting of hydrogen and acyl; and
$R^{10}$ is selected from the group consisting of hydrogen and C1-C6 alkyl;
provided that:
(a) at least one of $R^1$, $R^2$, $R^3$, $R^4$, $R^5$, and $R^6$ is not hydrogen;
(b) if each of $R^1$, $R^2$, $R^3$, and $R^4$ is hydrogen and $R^5$ is acetyl, then $R^6$ is not hydrogen, para-methoxybenzoyl, or 3-phenyl-2-propenoyl;
(c) if $R^1$ is tert-butyldimethylsilyl, then $R^5$ is not acetyl or $R^6$ is not para-methoxybenzoyl;
(d) if $R^1$ is 4-(alloc-aminomethyl)benzylaminocarbonyl, then at least one of $R^2$, $R^3$, $R^4$, $R^5$, and $R^6$ is not hydrogen; or
(e) if $R^2$ or $R^3$ is 4-(alloc-aminomethyl)benzylaminocarbonyl, then $R^5$ is not acetyl or $R^6$ is not para-methoxybenzoyl.

In certain embodiments, the present invention relates to any one of the above-referenced compounds, wherein R⁴ is hydrogen. Alternatively, in certain embodiments, the present invention relates to any one of the above-referenced compounds, wherein R⁴ is a C1-C6 alkyl. For example, in certain embodiments, the present invention relates to any one of the above-referenced compounds, wherein R⁴ is methyl.

In certain embodiments, the present invention relates to any one of the above-referenced compounds, wherein R⁵ is hydrogen. Alternatively, in certain embodiments, the present invention relates to any one of the above-referenced compounds, wherein R⁵ is acyl. For example, in certain embodiments, the present invention relates to any one of the above-referenced compounds, wherein R⁵ is acetyl (Ac).

In certain embodiments, the present invention relates to any one of the above-referenced compounds, wherein R¹ is hydrogen. Alternatively, in certain embodiments, the present invention relates to any one of the above-referenced compounds, wherein R¹ is trialkylsilyl. Alternatively, in certain embodiments, the present invention relates to any one of the above-referenced compounds, wherein R¹ is

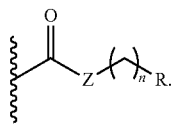

In certain embodiments, the present invention relates to any one of the above-referenced compounds, wherein R² is hydrogen. Alternatively, in certain embodiments, the present invention relates to any one of the above-referenced compounds, wherein R² is trialkylsilyl. Alternatively, in certain embodiments, the present invention relates to any one of the above-referenced compounds, wherein R² is

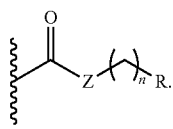

In certain embodiments, the present invention relates to any one of the above-referenced compounds, wherein R³ is hydrogen. Alternatively, in certain embodiments, the present invention relates to any one of the above-referenced compounds, wherein R³ is trialkylsilyl. Alternatively, in certain embodiments, the present invention relates to any one of the above-referenced compounds, wherein R³ is

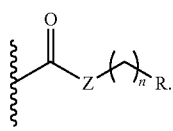

In certain embodiments, the present invention relates to any one of the above-referenced compounds, wherein R⁶ is hydrogen. Alternatively, in certain embodiments, the present invention relates to any one of the above-referenced compounds, wherein R⁶ is trialkylsilyl. Alternatively, in certain embodiments, the present invention relates to any one of the above-referenced compounds, wherein R⁶ is

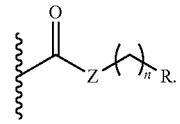

For example, in certain embodiments, the present invention relates to any one of the above-referenced compounds, wherein R⁶ is para-methoxybenzoyl. In another example, in certain embodiments, the present invention relates to any one of the above-referenced compounds, wherein R⁶ is 3-phenylpropanoyl.

In certain embodiments, the present invention relates to any one of the above-referenced compounds, wherein one or more instances of R is alkyl. In certain embodiments, the present invention relates to any one of the above-referenced compounds, wherein one or more instances of R is alkenyl. In certain embodiments, the present invention relates to any one of the above-referenced compounds, wherein one or more instances of R is an amino group. In certain embodiments, the present invention relates to any one of the above-referenced compounds, wherein one or more instances of R is an alloc-protected amino group. In certain embodiments, the present invention relates to any one of the above-referenced compounds, wherein one or more instances of R is an Fmoc-protected amino group. In certain embodiments, the present invention relates to any one of the above-referenced compounds, wherein one or more instances of R is aryl. In certain embodiments, the present invention relates to any one of the above-referenced compounds, wherein one or more instances of R is 5- to 13-membered cycloalkyl group. In certain embodiments, the present invention relates to any one of the above-referenced compounds, wherein one or more instances of R is a 5- to 13-membered cycloalkenyl group. In certain embodiments, the present invention relates to any one of the above-referenced compounds, wherein one or more instances of R is a 5- to 10-membered cyclic heteroaromatic group comprising 1-3 heteroatoms independently selected from the group consisting of N, O, and S.

In certain embodiments, the present invention relates to any one of the above-referenced compounds, wherein one or more instances of Z is oxygen (O).

In certain embodiments, the present invention relates to any one of the above-referenced compounds, wherein in one or more instances Z is O and R is alkyl. Alternatively, in certain embodiments, the present invention relates to any one of the above-referenced compounds, wherein in one or more instances Z is O and R is 4-nitrophenyl.

In certain embodiments, the present invention relates to any one of the above-referenced compounds, wherein in one or more instances Z is O and n is zero (0). Alternatively, in certain embodiments, the present invention relates to any one of the above-referenced compounds, wherein in one or more instances Z is O and n is one (1). Alternatively, in certain embodiments, the present invention relates to any one of the above-referenced compounds, wherein in one or more instances Z is O and n is 2. Alternatively, in certain embodiments, the present invention relates to any one of the above-referenced compounds, wherein in one or more instances Z is O and n is 3. Alternatively, in certain embodiments, the present invention relates to any one of the above-referenced compounds, wherein in one or more instances Z is O and n is 4. Alternatively, in certain embodiments, the present invention relates to any one of the above-referenced compounds, wherein in one or more instances Z is O and n is 5. Alternatively, in certain embodiments, the present invention relates to any one of the above-referenced compounds, wherein in one or more instances Z is O and n is 6.

In certain embodiments, the present invention relates to any one of the above-referenced compounds, wherein one or more instances of Z is $NR^{10}$. For example, in certain embodiments, the present invention relates to any one of the above-referenced compounds, wherein one or more instances of Z is NH. In another example, in certain embodiments, the present invention relates to any one of the above-referenced compounds, wherein in one or more instances Z is $NR^{10}$ and $R^{10}$ is a C1-C6 alkyl.

In certain embodiments, the present invention relates to any one of the above-referenced compounds, wherein in one or more instances Z is NH and R is an amino group.

In certain embodiments, the present invention relates to any one of the above-referenced compounds, wherein in one or more instances Z is NH and R is an alloc- or Fmoc-N'-substituted amino group.

In certain embodiments, the present invention relates to any one of the above-referenced compounds, wherein in one or more instances Z is NH and n is 6. In certain embodiments, the present invention relates to any one of the above-referenced compounds, wherein in one or more instances Z is NH and n is zero (0). In certain embodiments, the present invention relates to any one of the above-referenced compounds, wherein in one or more instances Z is NH and n is one (1). In certain embodiments, the present invention relates to any one of the above-referenced compounds, wherein in one or more instances Z is NH and n is 2. In certain embodiments, the present invention relates to any one of the above-referenced compounds, wherein in one or more instances Z is NH and n is 3. In certain embodiments, the present invention relates to any one of the above-referenced compounds, wherein in one or more instances Z is NH and n is 4. In certain embodiments, the present invention relates to any one of the above-referenced compounds, wherein in one or more instances Z is NH and n is 5.

In certain embodiments, the present invention relates to any one of the above-referenced compounds, wherein in one or more instances Z is NH and R is a para-aminoalkylaryl group. In certain embodiments, the present invention relates to any one of the to above-referenced compounds, wherein in one or more instances Z is NH and R is an alloc- or Fmoc-N'-substituted para-aminomethylphenyl group.

In certain embodiments, the present invention relates to any one of the above-referenced compounds, wherein in one or more instances Z is NH, R is a para-aminoalkylaryl group or an alloc- or Fmoc-N'-substituted para-aminomethylphenyl group, and n is one (1).

In certain embodiments, the present invention relates to any one of the above-referenced compounds, wherein in one or more instances Z is NH, R is phenyl, and n is one (1).

In certain embodiments, the present invention relates to any one of the above-referenced compounds, wherein one or more instances of Z is absent, such that there is a bond between the carbonyl carbon and the methylene group if n is non-zero, or between the carbonyl carbon and R if n is zero (0).

In certain embodiments, the present invention relates to any one of the above-referenced compounds, wherein in one or more instances Z is absent and R is an amino group. In certain embodiments, the present invention relates to any one of the above-referenced compounds, wherein in one or more instances Z is absent and R is an alloc- or Fmoc-N'-substituted amino group.

In certain embodiments, the present invention relates to any one of the above-referenced compounds, wherein in one or more instances Z is absent and n is 2. In certain embodiments, the present invention relates to any one of the above-referenced compounds, wherein in one or more instances Z is absent and n is zero (0). In certain embodiments, the present invention relates to any one of the above-referenced compounds, wherein in one or more instances Z is absent and n is one (1). In certain embodiments, the present invention relates to any one of the above-referenced compounds, wherein in one or more instances Z is absent and n is 3. In certain embodiments, the present invention relates to any one of the above-referenced compounds, wherein in one or more instances Z is absent and n is 4. In certain embodiments, the present invention relates to any one of the above-referenced compounds, wherein in one or more instances Z is absent and n is 5. In certain embodiments, the present invention relates to any one of the above-referenced compounds, wherein in one or more instances Z is absent and n is 6.

In certain embodiments, the present invention relates to any one of the above-referenced compounds, wherein in one or more instances Z is absent and R is a 1-imidazolyl group. In certain embodiments, the present invention relates to any one of the above-referenced compounds, wherein in one or more instances Z is absent, R is a 1-imidazolyl group, and n is zero (0).

In certain embodiments, the present invention relates to any one of the above-referenced compounds, wherein at least one of $R^1$, $R^2$, and $R^3$ is tert-butyldimethylsilyl. For example, in certain embodiments, the present invention relates to any one of the above-referenced compounds, wherein $R^1$ is tert-butyldimethylsilyl. As another example, in certain embodiments, the present invention relates to any one of the above-referenced compounds. wherein $R^2$ is tert-butyldimethylsilyl. As another example, in certain embodiments, the present invention relates to any one of the above-referenced compounds, wherein $R^3$ is tert-butyldimethylsilyl. As yet another example, in certain embodiments, the present invention relates to any one of the above-referenced compounds, wherein each of $R^1$ and $R^2$ is tert-butyldimethylsilyl. As another example, in certain embodiments, the present invention relates to any one of the above-referenced compounds, wherein each of $R^1$ and $R^3$ is tert-butyldimethylsilyl. As another example, in certain embodiments, the present invention relates to any one of the above-referenced compounds, wherein each of $R^2$ and $R^3$ is tert-butyldimethylsilyl. As yet another example, in certain embodiments, the present invention relates to any one of the above-referenced compounds, wherein each of $R^1$, $R^2$, and $R^3$ is tert-butyldimethylsilyl.

An aspect of the invention is a compound selected from the group consisting of:

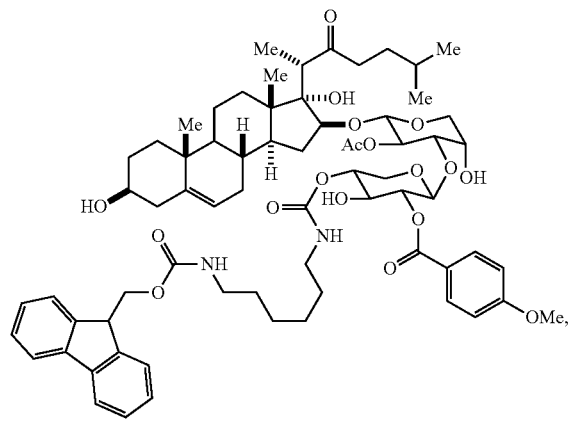
100
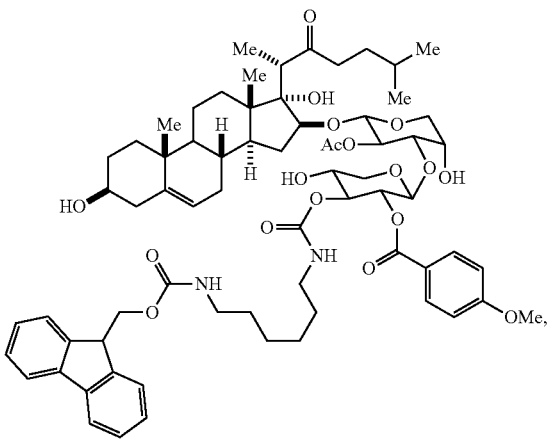
101
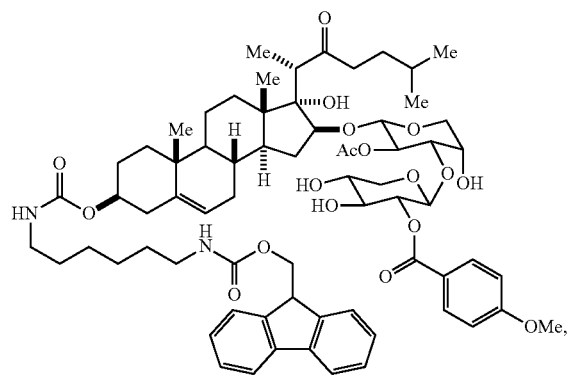
102
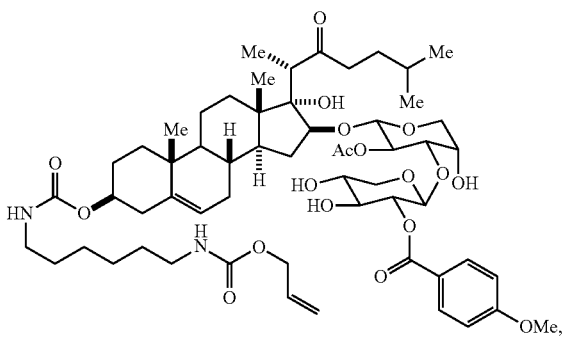
103
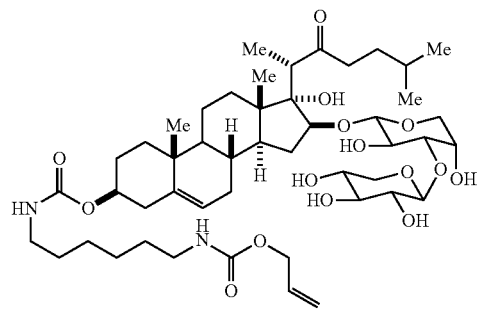
104
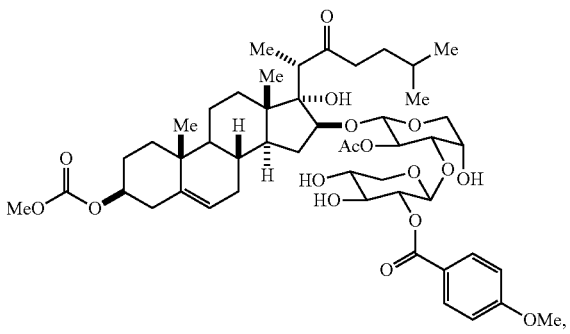
105
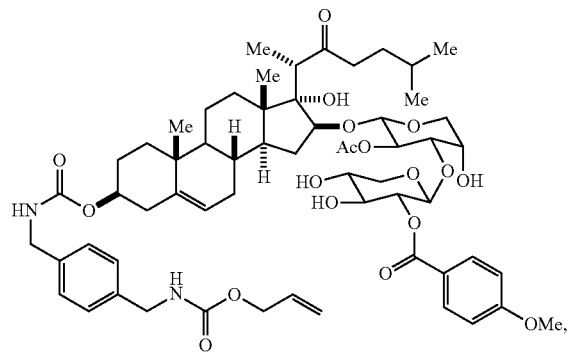
106
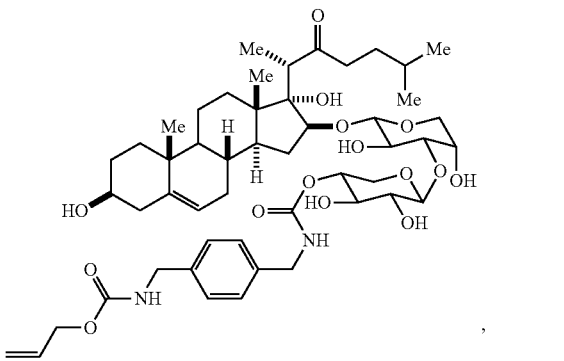
107

-continued
108
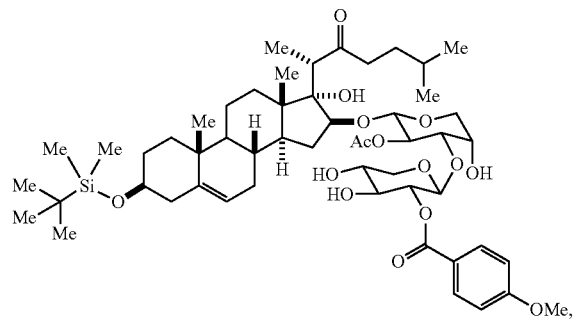
109
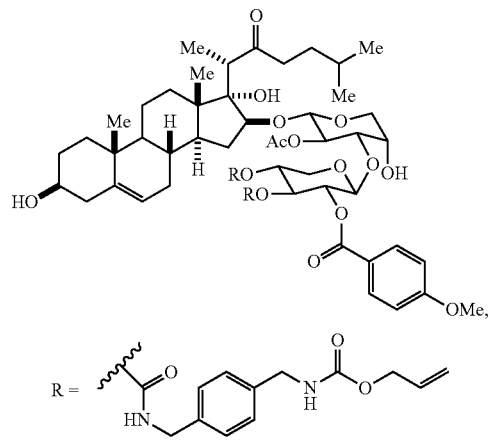
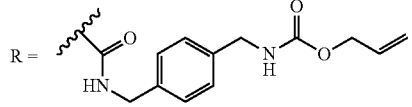
110
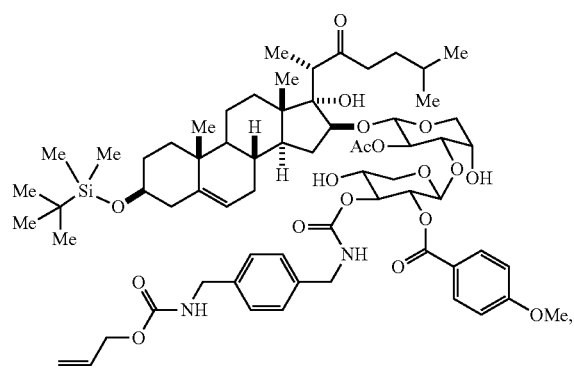
111
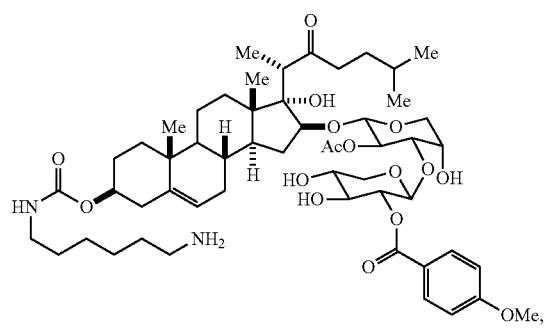
112
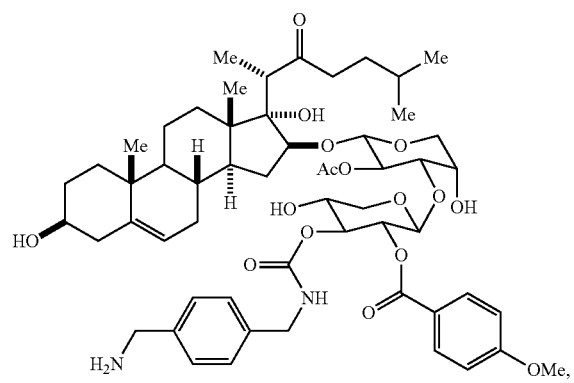
113
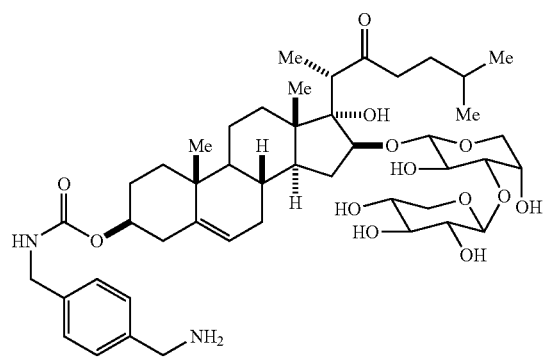
114
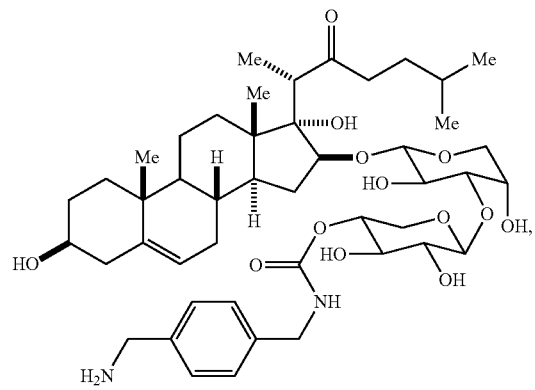

-continued
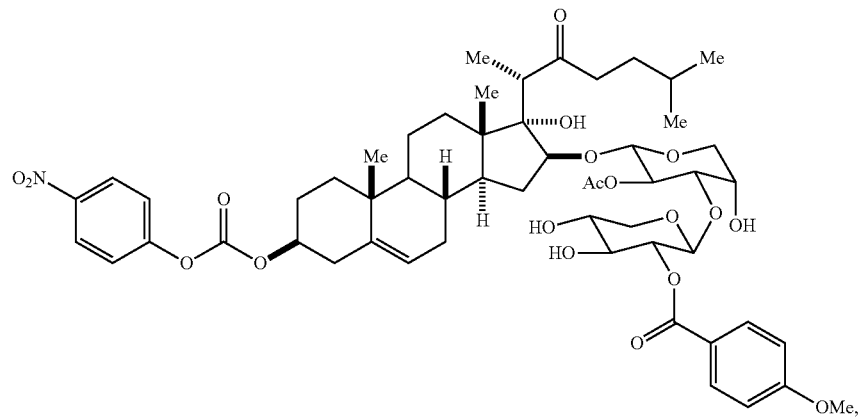
115
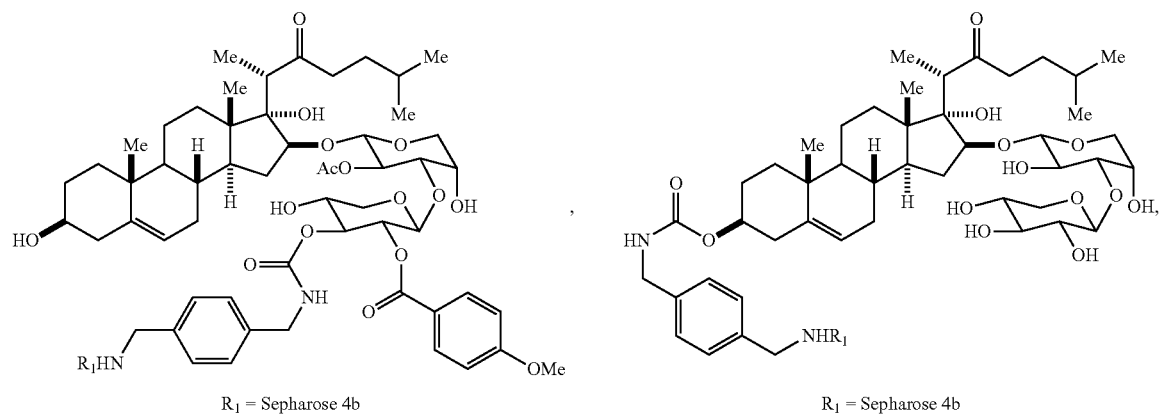
116
R₁ = Sepharose 4b
117
R₁ = Sepharose 4b
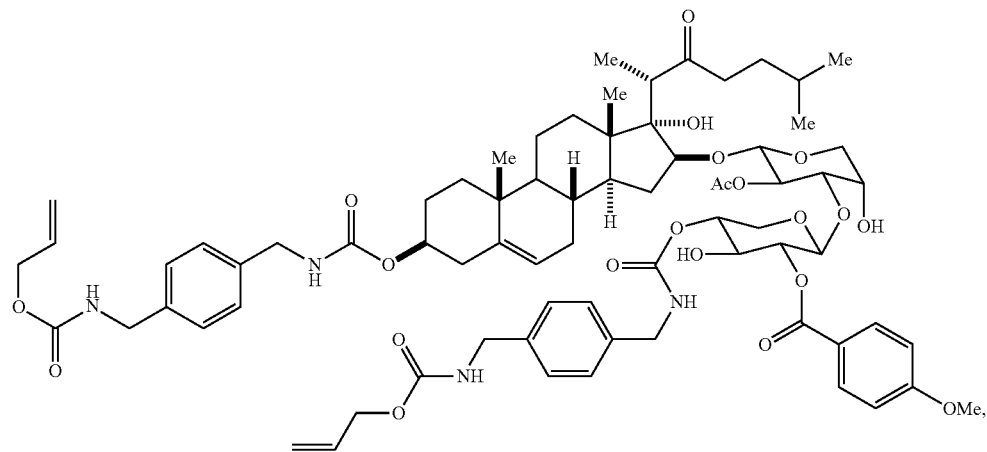
118

119
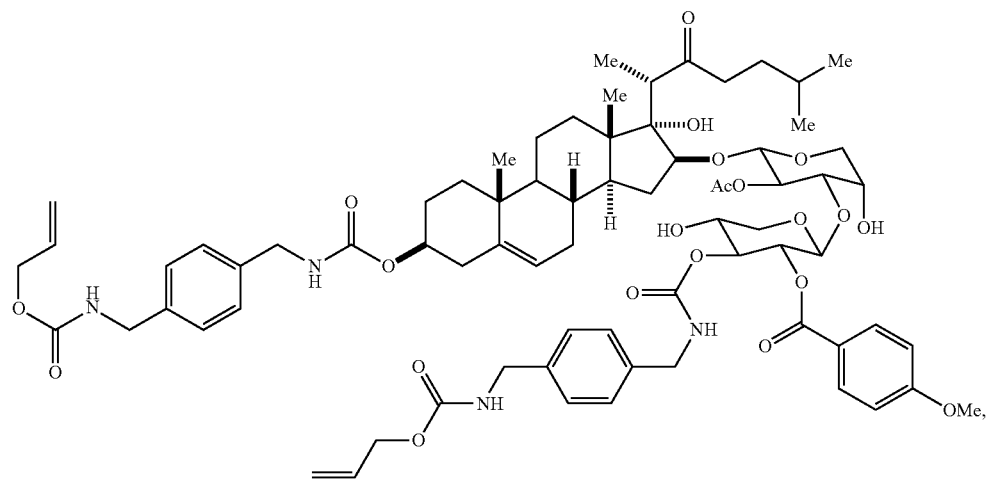
120 121
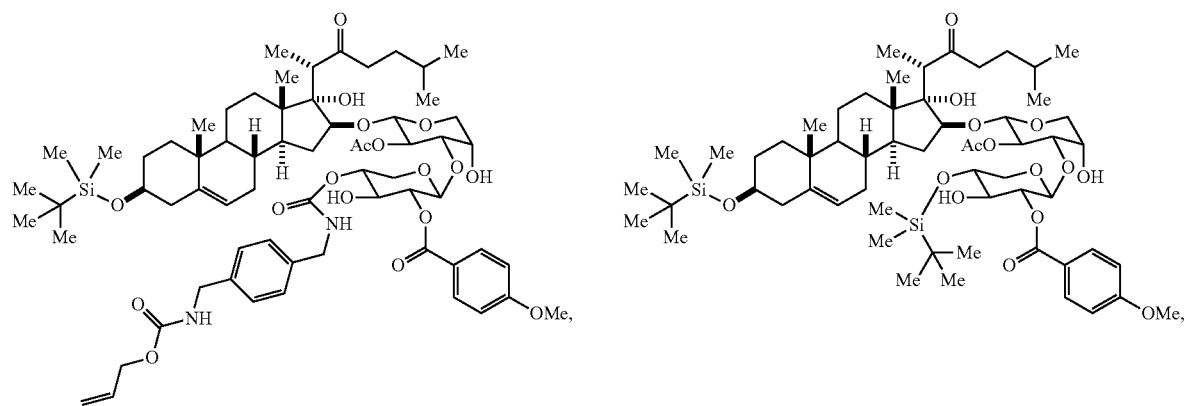
122 123
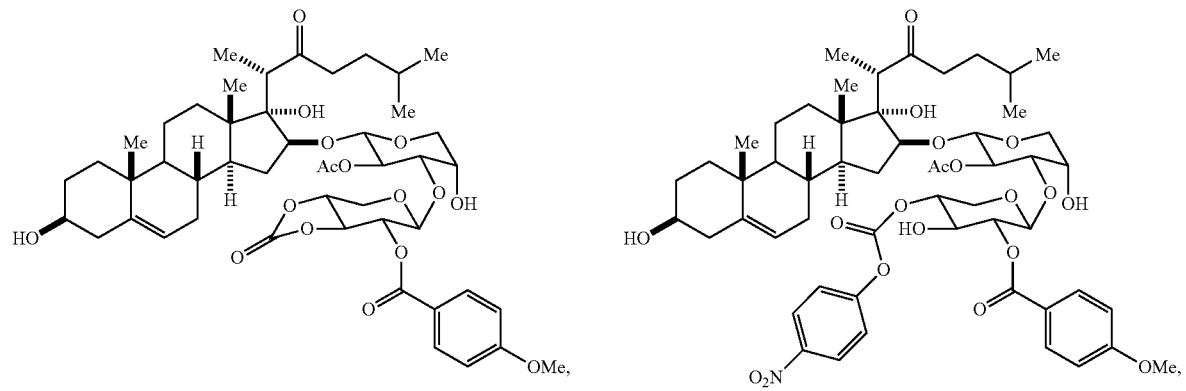

-continued
124
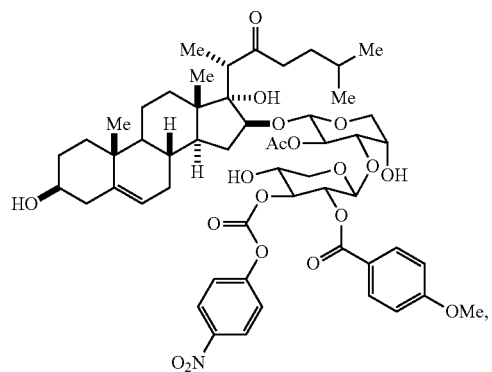
125
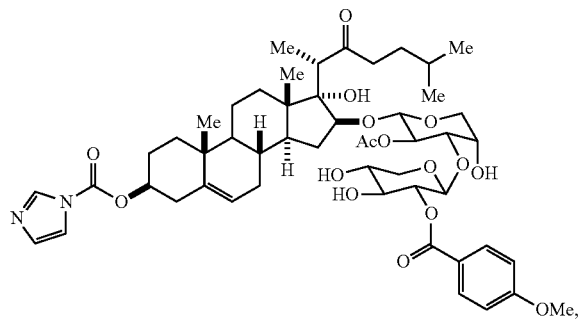
126
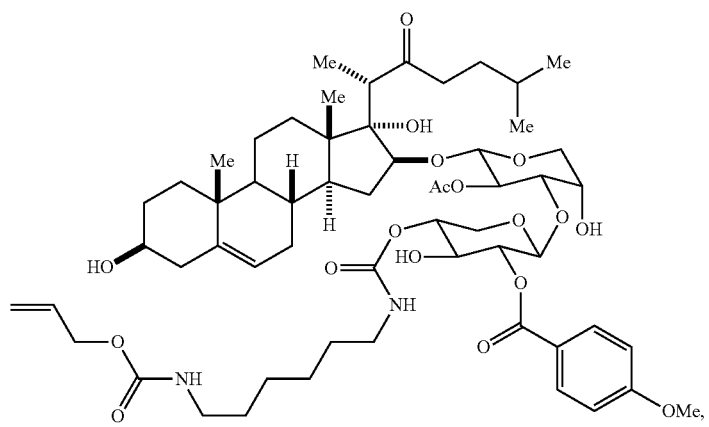
127
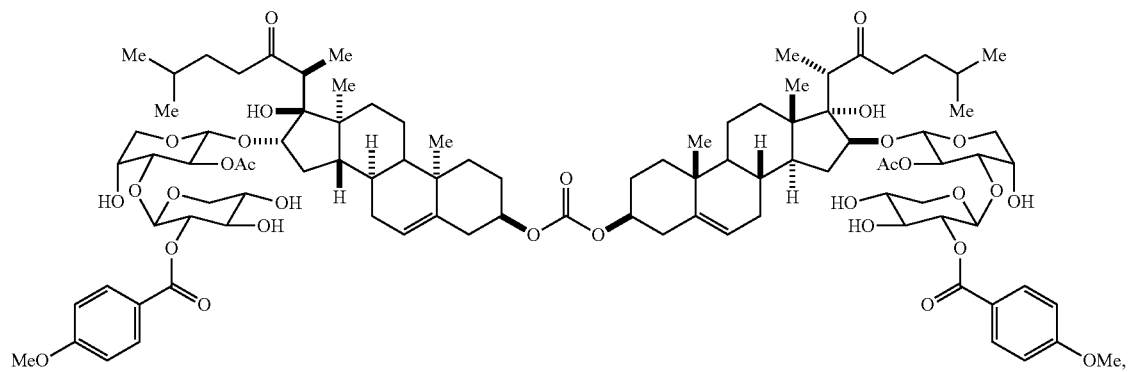
128
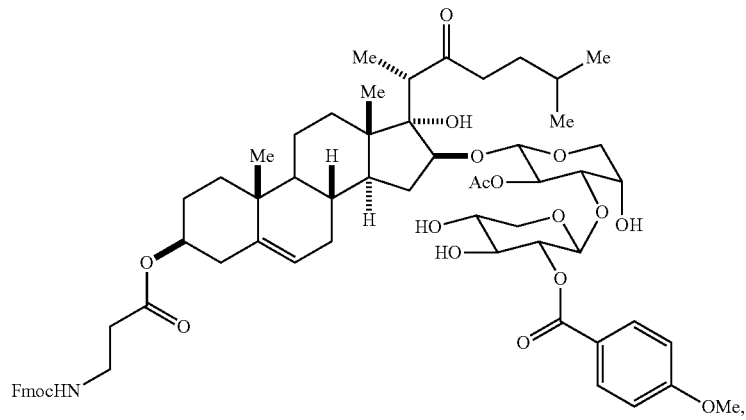

-continued
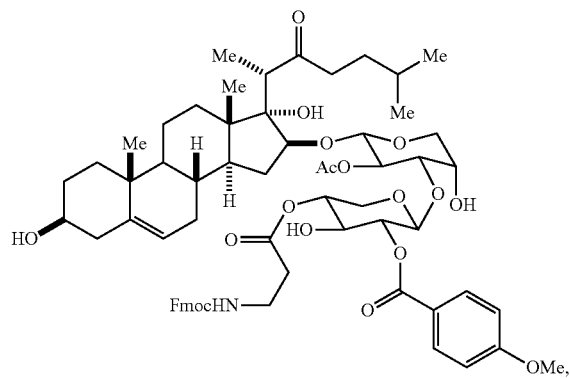
129
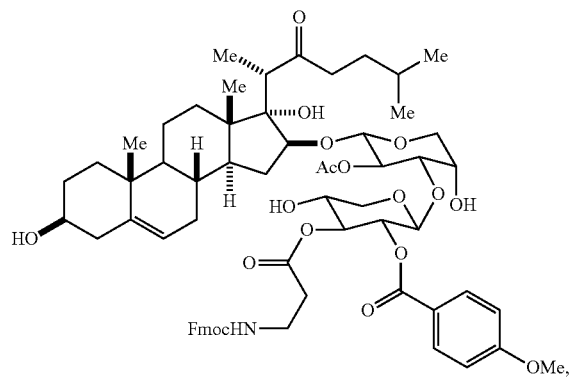
130
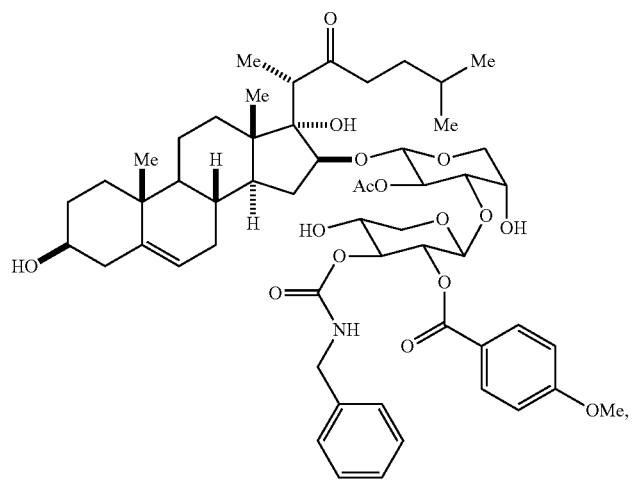
131
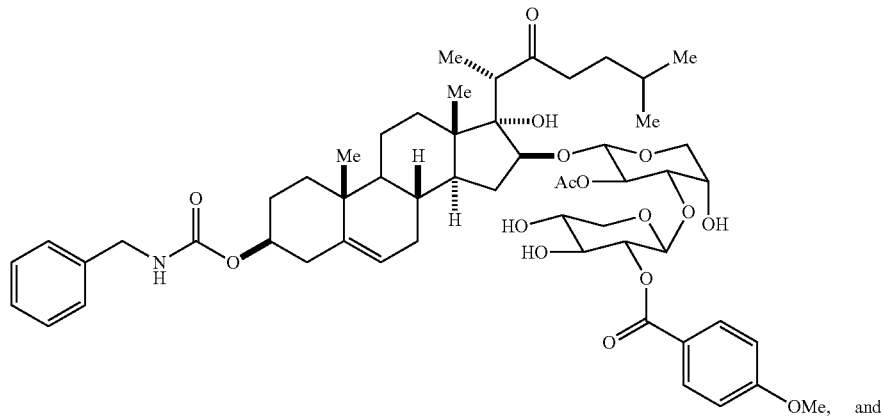
132
and

-continued

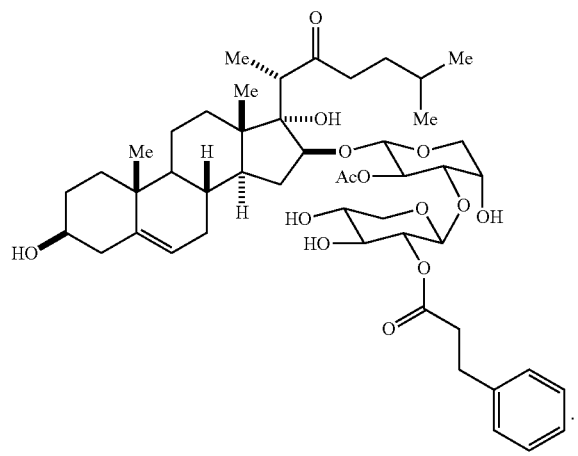

An aspect of the invention is a pharmaceutical composition. The pharmaceutical composition includes any one of the above-referenced compounds and a pharmaceutically acceptable carrier. A pharmaceutical composition according to this aspect of the invention can be prepared by a method that includes the step of combining a therapeutically effective amount of any one of the above-referenced compounds and a pharmaceutically acceptable carrier. Of course the pharmaceutical composition and method for its preparation can include more than one of the above-referenced compounds. Likewise, the pharmaceutical composition and method for its preparation can of course optionally further include at least one additional pharmaceutically active agent other than a compound of the invention.

It should be pointed out that at least certain of the above-referenced compounds of the invention include linker subunits containing functionality capable of bonding OSW-1 analogs to other molecules at specific positions on the OSW-1 framework structure.

An aspect of the invention concerns additional OSW-1 analog compounds including distinct linker subunits containing functionality capable of bonding OSW-1 analogs to other molecules at specific positions on the OSW-1 framework structure. The OSW-1 analogs according to this aspect of the invention may be particularly suited for forming conjugates with proteins, including, for example, antibodies.

An aspect of the invention concerns a compound of formula (II) or a pharmaceutically acceptable salt thereof:

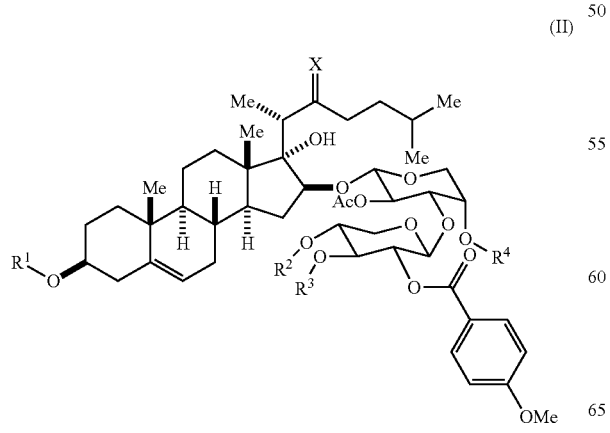

(II)

wherein

X is selected from the group consisting of O and $NOR^{20}$;

$R^1$, $R^2$, and $R^3$ are independently selected from the group consisting of hydrogen, $R^{20}$, trialkylsilyl, and

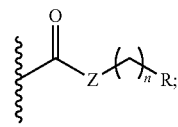

Z is absent or is selected from the group consisting of O and $NR^{10}$;

n is an integer 0-6;

R is selected from the group consisting of substituted or unsubstituted: alkyl, alkenyl, amino, alloc-protected amino, Fmoc-protected amino, aryl, 5- to 13-membered cycloalkyl or cycloalkenyl group, and 5- to 10-membered cyclic heteroaromatic group comprising 1-3 heteroatoms independently selected from the group consisting of N, O, and S;

$R^4$ is selected from the group consisting of hydrogen, C1-C6 alkyl, and $R^{20}$;

$R^{10}$ is selected from the group consisting of hydrogen and C1-C6 alkyl;

$R^{20}$ is selected from the group consisting of

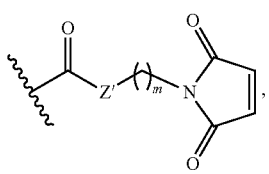

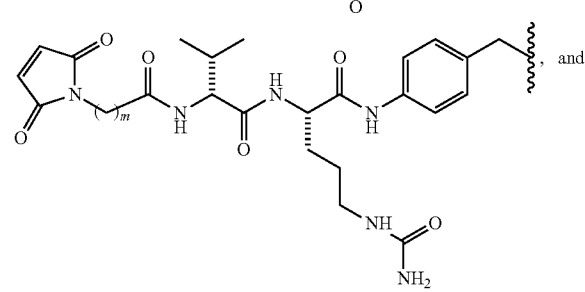

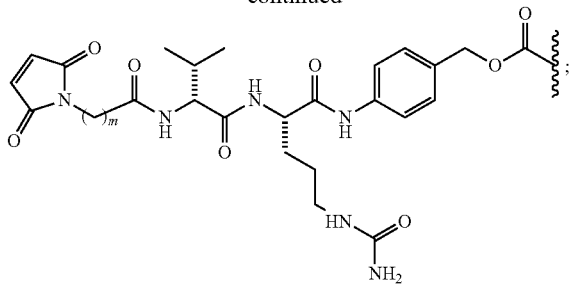

Z' is selected from the group consisting of O and $NR^{10}$; and m is an integer 1-6;

provided that if X is O, then one and only one of $R^1$, $R^2$, $R^3$, and $R^4$ is $R^{20}$; and if X is $NOR^{20}$, then none of $R^1$, $R^2$, $R^3$, and $R^4$ is $R^{20}$. In any case, the compound includes one and only one $R^{20}$.

In certain embodiments, the present invention relates to any one of the above-referenced compounds, wherein $R^1$ is hydrogen. Alternatively, in certain embodiments, the present invention relates to any one of the above-referenced compounds, wherein $R^1$ is $R^{20}$ Alternatively, in certain embodiments, the present invention relates to any one of the above-referenced compounds, wherein $R^1$ is trialkylsilyl. Alternatively, in certain embodiments, the present invention relates to any one of the above-referenced compounds, wherein $R^1$ is

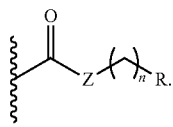

In certain embodiments, the present invention relates to any one of the above-referenced compounds, wherein $R^2$ is hydrogen. Alternatively, in certain embodiments, the present invention relates to any one of the above-referenced compounds, wherein $R^2$ is $R^{20}$. Alternatively, in certain embodiments, the present invention relates to any one of the above-referenced compounds, wherein $R^2$ is trialkylsilyl. Alternatively, in certain embodiments, the present invention relates to any one of the above-referenced compounds, wherein $R^2$ is

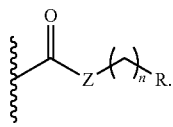

In certain embodiments, the present invention relates to any one of the above-referenced compounds, wherein $R^3$ is hydrogen. Alternatively, in certain embodiments, the present invention relates to any one of the above-referenced compounds, wherein $R^3$ is $R^{20}$. Alternatively, in certain embodiments, the present invention relates to any one of the above-referenced compounds, wherein $R^3$ is trialkylsilyl. Alternatively, in certain embodiments, the present invention relates to any one of the above-referenced compounds, wherein $R^3$ is

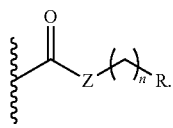

In certain embodiments, the present invention relates to any one of the above-referenced compounds, wherein one or more instances of Z is oxygen (O).

In certain embodiments, the present invention relates to any one of the above-referenced compounds, wherein one or more instances of Z is $NR^{10}$.

In certain embodiments, the present invention relates to any one of the above-referenced compounds, wherein one or more instances of Z is absent, such that there is a bond between the carbonyl carbon and the methylene group if n is non-zero, or between the carbonyl carbon and R if n is zero (0).

In certain embodiments, the present invention relates to any one of the above-referenced compounds, wherein in one or more instances n is zero (0). Alternatively, in certain embodiments, the present invention relates to any one of the above-referenced compounds, wherein in one or more instances n is one (1). Alternatively, in certain embodiments, the present invention relates to any one of the above-referenced compounds, wherein in one or more instances n is 2. Alternatively, in certain embodiments, the present invention relates to any one of the above-referenced compounds, wherein in one or more instances n is 3. Alternatively, in certain embodiments, the present invention relates to any one of the above-referenced compounds, wherein in one or more instances n is 4. Alternatively, in certain embodiments, the present invention relates to any one of the above-referenced compounds, wherein in one or more instances n is 5. Alternatively, in certain embodiments, the present invention relates to any one of the above-referenced compounds, wherein in one or more instances n is 6.

In certain embodiments, the present invention relates to any one of the above-referenced compounds, wherein one or more instances of R is alkyl. In certain embodiments, the present invention relates to any one of the above-referenced compounds, wherein one or more instances of R is alkenyl. In certain embodiments, the present invention relates to any one of the above-referenced compounds, wherein one or more instances of R is an amino group. In certain embodiments, the present invention relates to any one of the above-referenced compounds, wherein one or more instances of R is an alloc-protected amino group. In certain embodiments, the present invention relates to any one of the above-referenced compounds, wherein one or more instances of R is an Fmoc-protected amino group. In certain embodiments, the present invention relates to any one of the above-referenced compounds, wherein one or more instances of R is aryl. In certain embodiments, the present invention relates to any one of the above-referenced compounds, wherein one or more instances of R is 5- to 13-membered cycloalkyl group. In certain embodiments, the present invention relates to any one of the above-referenced compounds, wherein one or more instances of R is a 5- to 13-membered cycloalkenyl group. In certain embodiments, the present invention relates to any one of the above-referenced compounds, wherein one or more instances of R is a 5- to 10-membered cyclic heteroaromatic group comprising 1-3 heteroatoms independently selected from the group consisting of N, O, and S.

In certain embodiments, the present invention relates to any one of the above-referenced compounds, wherein $R^4$ is hydrogen. Alternatively, in certain embodiments, the present invention relates to any one of the above-referenced compounds, wherein $R^4$ is C1-C6 alkyl. Alternatively, in certain embodiments, the present invention relates to any one of the above-referenced compounds, wherein $R^4$ is $R^{20}$.

In certain embodiments, the present invention relates to any one of the above-referenced compounds, wherein X is oxygen (O).

In certain embodiments, the present invention relates to any one of the above-referenced compounds, wherein X is O and each of $R^1$, $R^2$, $R^3$, and $R^4$ is selected from the group consisting of hydrogen and $R^{20}$. Only one of $R^1$, $R^2$, $R^3$, and $R^4$ is $R^{20}$. For example, in certain embodiments, the present invention relates to any one of the above-referenced compounds, wherein X is O, $R^1$ is $R^{20}$, and each of $R^2$, $R^3$, and $R^4$ is hydrogen. As another example, in certain embodiments, the present invention relates to any one of the above-referenced compounds, wherein X is O, $R^2$ is $R^{20}$, and each of $R^1$, $R^3$, and $R^4$ is hydrogen. As another example, in certain embodiments, the present invention relates to any one of the above-referenced compounds, wherein X is O, $R^3$ is $R^{20}$, and each of $R^1$, $R^2$, and $R^4$ is hydrogen. As yet another example, in certain embodiments, the present invention relates to any one of the above-referenced compounds, wherein X is O, $R^4$ is $R^{20}$, and each of $R^1$, $R^2$, and $R^3$ is hydrogen.

Alternatively, in certain embodiments, the present invention relates to any one of the above-referenced compounds, wherein X is $NR^{10}$. In certain embodiments, the present invention relates to any one of the above-referenced compounds, wherein X is $NR^{10}$ and each of $R^1$, $R^2$, $R^3$, and $R^4$ is hydrogen.

In certain embodiments, the present invention relates to any one of the above-referenced compounds, wherein $R^{20}$ is

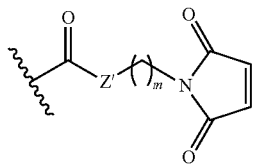

and Z' is oxygen (O). Alternatively, in certain embodiments, the present invention relates to any one of the above-referenced compounds, wherein $R^{20}$ is

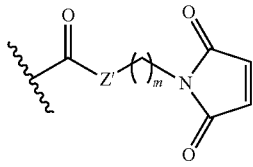

and Z' is $NR^{10}$.

Alternatively, in certain embodiments, the present invention relates to any one of the above-referenced compounds, wherein $R^{20}$ is

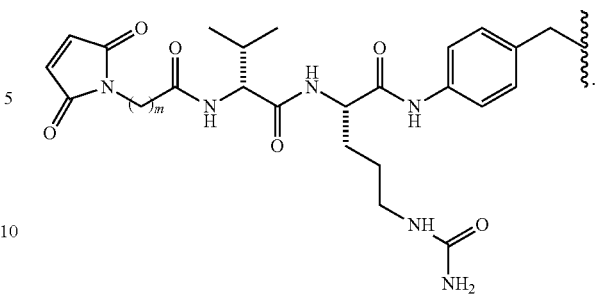

Alternatively, in certain embodiments, the present invention relates to any one of the above-referenced compounds, wherein $R^{20}$ is

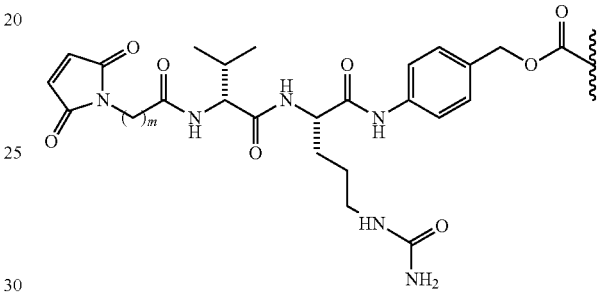

In certain embodiments, the present invention relates to any one of the above-referenced compounds, wherein m is one (1). Alternatively, in certain embodiments, the present invention relates to any one of the above-referenced compounds, wherein m is 2. Alternatively, in certain embodiments, the present invention relates to any one of the above-referenced compounds, wherein m is 3. Alternatively, in certain embodiments, the present invention relates to any one of the above-referenced compounds, wherein m is 4. Alternatively, in certain embodiments, the present invention relates to any one of the above-referenced compounds, wherein m is 5. Alternatively, in certain embodiments, the present invention relates to any one of the above-referenced compounds, wherein m is 6.

In certain embodiments, the present invention relates to any one of the above-referenced compounds, wherein $R^{20}$ is

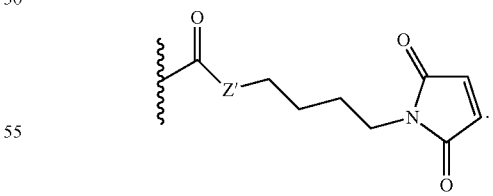

In certain embodiments, the present invention relates to any one of the above-referenced compounds, wherein Z' is oxygen (O). Alternatively, in certain embodiments, the present invention relates to any one of the above-referenced compounds, wherein Z' is $NR^{10}$.

Alternatively, in certain embodiments, the present invention relates to any one of the above-referenced compounds, wherein $R^{20}$ is

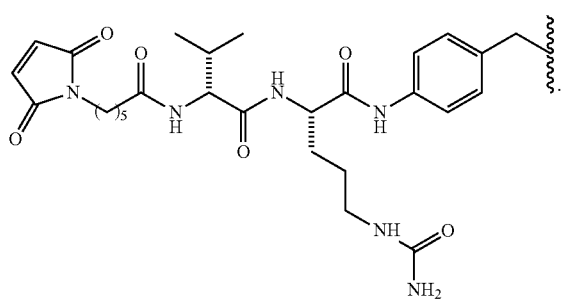

Alternatively, in certain embodiments, the present invention relates to any one of the above-referenced compounds, wherein $R^{20}$ is

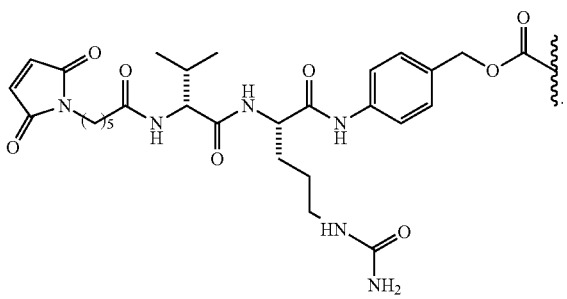

In certain embodiments, the present invention relates to any one of the above-referenced compounds, wherein one or more instances of $R^{10}$ is hydrogen. In certain embodiments, the present invention relates to any one of the above-referenced compounds, wherein one or more instances of $R^{10}$ is C1-C6 alkyl.

An aspect of the invention concerns a compound of formula (III) or a pharmaceutically acceptable salt thereof:

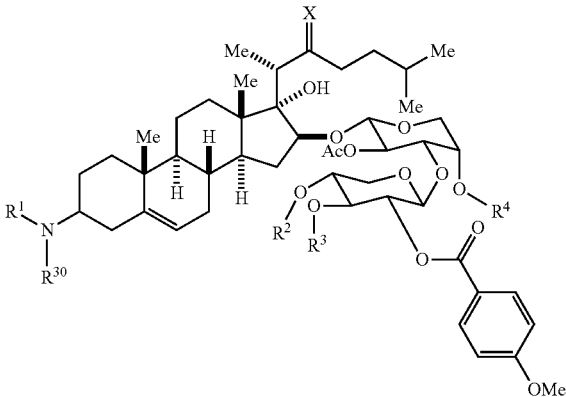

(III)

wherein

X is selected from the group consisting of O and $NOR^{20}$;

$R^1$, $R^2$, and $R^3$ are independently selected from the group consisting of hydrogen, $R^{20}$, trialkylsilyl, and

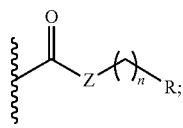

Z is absent or is selected from the group consisting of O and $NR^{10}$;

n is an integer 0-6;

R is selected from the group consisting of substituted or unsubstituted: alkyl, alkenyl, amino, alloc-protected amino, Fmoc-protected amino, aryl, 5- to 13-membered cycloalkyl or cycloalkenyl group, and 5- to 10-membered cyclic heteroaromatic group comprising 1-3 heteroatoms independently selected from the group consisting of N, O, and S;

$R^4$ is selected from the group consisting of hydrogen, C1-C6 alkyl, and $R^{20}$;

$R^{10}$ is selected from the group consisting of hydrogen and C1-C6 alkyl;

$R^{20}$ is selected from the group consisting of

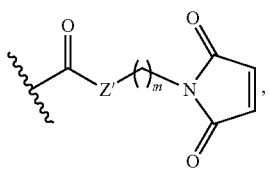

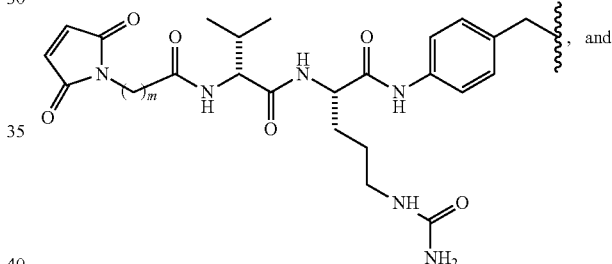

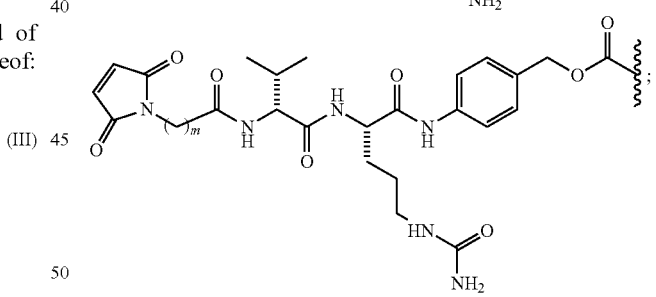

$R^{30}$ is selected from the group consisting of hydrogen, methyl, and C2-C6 alkyl;

$Z'$ is selected from the group consisting of O and $NR^{10}$; and m is an integer 1-6;

provided that if X is O, then one and only one of $R^1$, $R^2$, $R^3$, and $R^4$ is $R^{20}$; and if X is $NOR^{20}$, then none of $R^1$, $R^2$, $R^3$, and $R^4$ is $R^{20}$. In any case, the compound includes one and only one $R^{20}$.

In certain embodiments, the present invention relates to any one of the above-referenced compounds, wherein $R^1$ is hydrogen. Alternatively, in certain embodiments, the present invention relates to any one of the above-referenced compounds, wherein $R^1$ is $R^{20}$. Alternatively, in certain embodiments, the present invention relates to any one of the above-referenced compounds, wherein $R^1$ is trialkylsilyl. Alternatively, in certain embodiments, the present invention relates to any one of the above-referenced compounds, wherein $R^1$ is

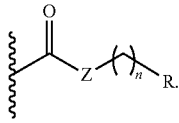

In certain embodiments, the present invention relates to any one of the above-referenced compounds, wherein $R^2$ is hydrogen. Alternatively, in certain embodiments, the present invention relates to any one of the above-referenced compounds, wherein $R^2$ is $R^{20}$. Alternatively, in certain embodiments, the present invention relates to any one of the above-referenced compounds, wherein $R^2$ is trialkylsilyl. Alternatively, in certain embodiments, the present invention relates to any one of the above-referenced compounds, wherein $R^2$ is

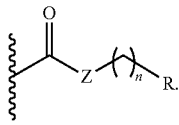

In certain embodiments, the present invention relates to any one of the above-referenced compounds, wherein $R^3$ is hydrogen. Alternatively, in certain embodiments, the present invention relates to any one of the above-referenced compounds, wherein $R^3$ is $R^{20}$. Alternatively, in certain embodiments, the present invention relates to any one of the above-referenced compounds, wherein $R^3$ is trialkylsilyl. Alternatively, in certain embodiments, the present invention relates to any one of the above-referenced compounds, wherein $R^3$ is

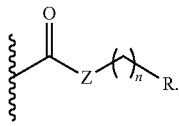

In certain embodiments, the present invention relates to any one of the above-referenced compounds, wherein $R^{30}$ is hydrogen. Alternatively, in certain embodiments, the present invention relates to any one of the above-referenced compounds, wherein $R^{30}$ is methyl. Alternatively, in certain embodiments, the present invention relates to any one of the above-referenced compounds, wherein $R^{30}$ is C2-C6 alkyl.

In certain embodiments, the present invention relates to any one of the above-referenced compounds, wherein one or more instances of Z is oxygen (O).

In certain embodiments, the present invention relates to any one of the above-referenced compounds, wherein one or more instances of Z is $NR^{10}$.

In certain embodiments, the present invention relates to any one of the above-referenced compounds, wherein one or more instances of Z is absent, such that there is a bond between the carbonyl carbon and the methylene group if n is non-zero, or between the carbonyl carbon and R if n is zero (0).

In certain embodiments, the present invention relates to any one of the above-referenced compounds, wherein in one or more instances n is zero (0). Alternatively, in certain embodiments, the present invention relates to any one of the above-referenced compounds, wherein in one or more instances n is one (1). Alternatively, in certain embodiments, the present invention relates to any one of the above-referenced compounds, wherein in one or more instances n is 2. Alternatively, in certain embodiments, the present invention relates to any one of the above-referenced compounds, wherein in one or more instances n is 3. Alternatively, in certain embodiments, the present invention relates to any one of the above-referenced compounds, wherein in one or more instances n is 4. Alternatively, in certain embodiments, the present invention relates to any one of the above-referenced compounds, wherein in one or more instances n is 5. Alternatively, in certain embodiments, the present invention relates to any one of the above-referenced compounds, wherein in one or more instances n is 6.

In certain embodiments, the present invention relates to any one of the above-referenced compounds, wherein one or more instances of R is alkyl. In certain embodiments, the present invention relates to any one of the above-referenced compounds, wherein one or more instances of R is alkenyl. In certain embodiments, the present invention relates to any one of the above-referenced compounds, wherein one or more instances of R is an amino group. In certain embodiments, the present invention relates to any one of the above-referenced compounds, wherein one or more instances of R is an alloc-protected amino group. In certain embodiments, the present invention relates to any one of the above-referenced compounds, wherein one or more instances of R is an Fmoc-protected amino group. In certain embodiments, the present invention relates to any one of the above-referenced compounds, wherein one or more instances of R is aryl. In certain embodiments, the present invention relates to any one of the above-referenced compounds, wherein one or more instances of R is 5- to 13-membered cycloalkyl group. In certain embodiments, the present invention relates to any one of the above-referenced compounds, wherein one or more instances of R is a 5- to 13-membered cycloalkenyl group. In certain embodiments, the present invention relates to any one of the above-referenced compounds, wherein one or more instances of R is a 5- to 10-membered cyclic heteroaromatic group comprising 1-3 heteroatoms independently selected from the group consisting of N, O, and S.

In certain embodiments, the present invention relates to any one of the above-referenced compounds, wherein $R^4$ is hydrogen. Alternatively, in certain embodiments, the present invention relates to any one of the above-referenced compounds, wherein $R^4$ is C1-C6 alkyl. Alternatively, in certain embodiments, the present invention relates to any one of the above-referenced compounds, wherein $R^4$ is $R^{20}$.

In certain embodiments, the present invention relates to any one of the above-referenced compounds, wherein X is oxygen (O).

In certain embodiments, the present invention relates to any one of the above-referenced compounds, wherein X is O and each of $R^1$, $R^2$, $R^3$, and $R^4$ is selected from the group consisting of hydrogen and $R^{20}$. Only one of $R^1$, $R^2$, $R^3$, and $R^4$ is $R^{20}$. For example, in certain embodiments, the present invention relates to any one of the above-referenced compounds, wherein X is O, $R^1$ is $R^{20}$, and each of $R^2$, $R^3$, and $R^4$ is hydrogen. As another example, in certain embodiments, the present invention relates to any one of the above-referenced compounds, wherein X is O, $R^2$ is $R^{20}$, and each of $R^1$, $R^3$, and $R^4$ is hydrogen. As another example, in certain embodiments, the present invention relates to any one of the above-referenced compounds, wherein X is O, $R^3$ is $R^{20}$, and each of $R^1$, $R^2$, and $R^4$ is hydrogen. As yet another example, in certain embodiments, the present invention relates to any one of the above-referenced compounds, wherein X is O, $R^4$ is $R^{20}$, and each of $R^1$, $R^2$, and $R^3$ is hydrogen.

Alternatively, in certain embodiments, the present invention relates to any one of the above-referenced compounds, wherein X is $NR^{10}$. In certain embodiments, the present invention relates to any one of the above-referenced compounds, wherein X is $NR^{10}$ and each of $R^1$, $R^2$, $R^3$, and $R^4$ is hydrogen.

In certain embodiments, the present invention relates to any one of the above-referenced compounds, wherein $R^{20}$ is

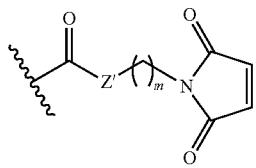

and Z' is oxygen (O).

Alternatively, in certain embodiments, the present invention relates to any one of the above-referenced compounds, wherein $R^{20}$ is

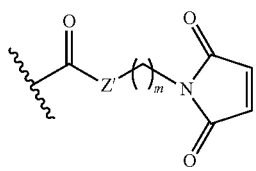

and Z' is $NR^{10}$.

Alternatively, in certain embodiments, the present invention relates to any one of the above-referenced compounds, wherein $R^{20}$ is

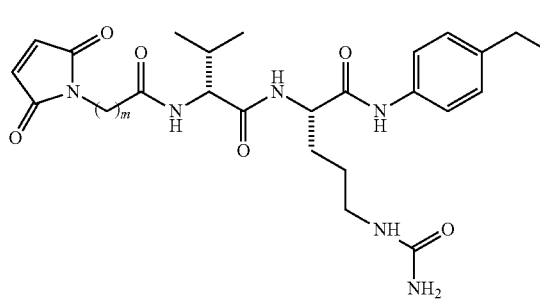

Alternatively, in certain embodiments, the present invention relates to any one of the above-referenced compounds, wherein $R^{20}$ is

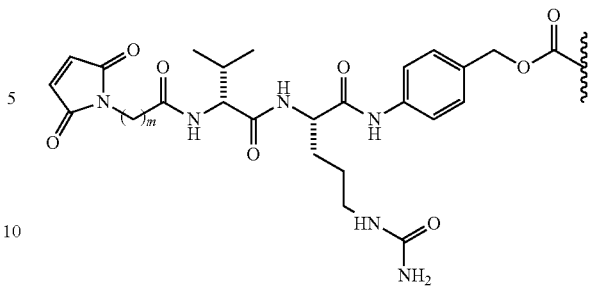

In certain embodiments, the present invention relates to any one of the above-referenced compounds, wherein m is one (1). Alternatively, in certain embodiments, the present invention relates to any one of the above-referenced compounds, wherein m is 2. Alternatively, in certain embodiments, the present invention relates to any one of the above-referenced compounds, wherein m is 3. Alternatively, in certain embodiments, the present invention relates to any one of the above-referenced compounds, wherein m is 4. Alternatively, in certain embodiments, the present invention relates to any one of the above-referenced compounds, wherein m is 5. Alternatively, in certain embodiments, the present invention relates to any one of the above-referenced compounds, wherein m is 6.

In certain embodiments, the present invention relates to any one of the above-referenced compounds, wherein $R^{20}$ is

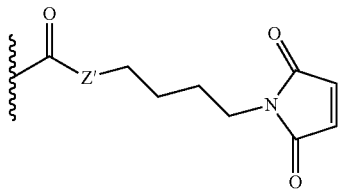

In certain embodiments, the present invention relates to any one of the above-referenced compounds, wherein Z' is oxygen (O). Alternatively, in certain embodiments, the present invention relates to any one of the above-referenced compounds, wherein Z' is $NR^{10}$.

Alternatively, in certain embodiments, the present invention relates to any one of the above-referenced compounds, wherein $R^{20}$ is

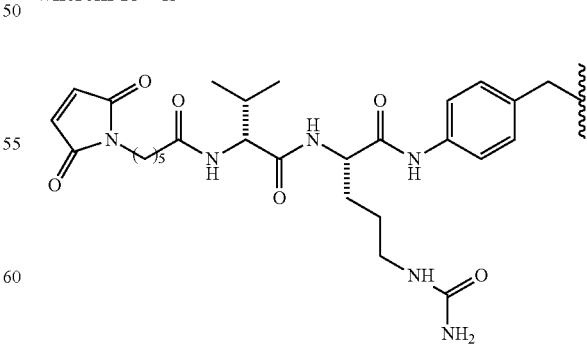

Alternatively, in certain embodiments, the present invention relates to any one of the above-referenced compounds, wherein $R^{20}$ is

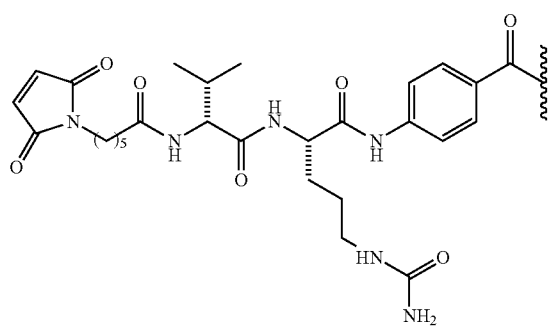

In certain embodiments, the present invention relates to any one of the above-referenced compounds, wherein one or more instances of $R^{10}$ is hydrogen. In certain embodiments, the present invention relates to any one of the above-referenced compounds, is wherein one or more instances of $R^{10}$ is C1-C6 alkyl.

In certain embodiments, the present invention relates to any one of the above-referenced compounds, wherein X is O, $R^1$ is

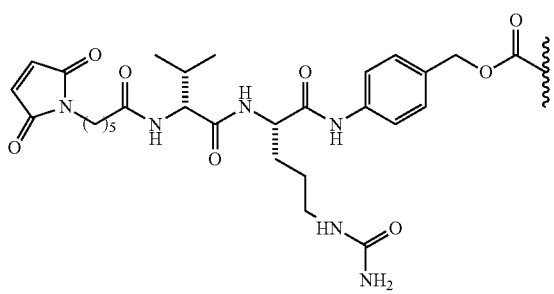

and each of $R^2$, $R^3$, and $R^4$ is hydrogen.

In certain embodiments, the present invention relates to any one of the above-referenced compounds, wherein the compound is present as only a single stereoisomer.

An aspect of the invention is a conjugate comprising a monoclonal antibody covalently linked to any one of the above-referenced compounds. In one embodiment the compound is a compound of formula (II) or a pharmaceutically acceptable salt thereof, which includes an $R^{20}$ moiety as described herein. In one embodiment the compound is a compound of formula (III) or a pharmaceutically acceptable salt thereof, which includes an $R^{20}$ moiety as described herein. In one embodiment the monoclonal antibody and the compound are covalently linked through a cysteine thiol-maleimide Michael addition product, a valine-citrulline p-aminobenzyl linker, or a valine-citrulline p-aminobenzyl-carbamate linker. Such linkage chemistry, in general, is well known in the art and does not require further description here. See, for example, U.S. Pat. No. 7,659,241 to Senter et al., U.S. Pat. No. 7,745,394 to Doronina et al., U.S. Pat. No. 7,829,531 to Senter et al., and U.S. Pat. No. 7,851,437 to Senter et al., the entire contents of which are incorporated herein by reference. The monoclonal antibody preferably retains its cognate antigen-binding specificity and avidity when it is part of the conjugate. The compound preferably retains its activity as an ORPphilin when it is part of the conjugate.

Monoclonal antibodies and methods for their preparation are well known in the art. Monoclonal antibodies can include whole antibodies as well as antigen-binding fragments thereof, e.g., Fab fragments and F(ab')$_2$ fragments of monoclonal antibodies. In various embodiments, monoclonal antibodies also can include chimeric, humanized, and fully human antibodies. In certain embodiments, monoclonal antibodies can include bispecific antibodies.

In one embodiment, the monoclonal antibody binds specifically to an antigen expressed on a cancer cell. In certain embodiments, such antigens may be overexpressed by the cancer cell, characteristically expressed by the cancer cell, or uniquely expressed by the cancer cell. Antigens of these types have been termed cancer antigens or tumor antigens. Some of these antigens may be tumor-specific antigens or tumor-associated antigens. "Tumor-specific antigens" are antigens that are specifically present in tumor cells but not normal cells. Examples of tumor-specific antigens are viral antigens in tumors induced by DNA or RNA viruses. "Tumor-associated antigens" are present in both tumor cells and normal cells but are present in a different quantity or a different form in tumor cells. Examples of such antigens are oncofetal antigens (e.g., carcinoembryonic antigen (CEA)), differentiation antigens (e.g., T and Tn antigens), and oncogene products (e.g., HER/neu).

A number of cancer antigens are known and have been described in the art. A "cancer antigen" as used herein is a compound, such as a peptide or protein, associated with a tumor or cancer cell surface and which is capable of provoking an immune response when expressed on the surface of an antigen-presenting cell (APC) in the context of an MHC molecule. Cancer antigens can be prepared from cancer cells either by preparing crude extracts of cancer cells, for example, as described in Cohen et al. (1994) *Cancer Res* 54:1055, by partially purifying the antigens, by recombinant technology, or by de novo synthesis of known antigens. Cancer antigens include but are not limited to antigens that are recombinantly expressed, an immunogenic portion of, or a whole tumor or cancer. Such antigens can be isolated or prepared recombinantly or by any other means known in the art.

In one embodiment, a cancer antigen is a human cancer antigen, i.e., a cancer antigen associated with or derived from a human cancer.

Non-limiting examples of already-commercialized monoclonal antibodies that bind specifically to an antigen expressed on a human cancer cell include alemtuzumab (Campath; anti-CD52); bevacizumab (Avastin; anti-VEGF); cetuximab (Erbitux; anti-EGFR); gemtuzumab (Mylotarg; anti-CD33); ibritumomab (Zevalin; anti-CD20); panitumumab (Vectibix; anti-EGFR); rituximab (Rituxan; anti-CD20); tositumomab (Bexxar; anti-CD20); and trastuzumab (Herceptin; anti-ErbB2). Many additional monoclonal antibodies that bind specifically to an antigen expressed on a human cancer cell are under development, including those under regulatory review.

In certain embodiments, the cancer cell expressing the antigen recognized by the monoclonal antibody is deficient for expression of p21. A cancer cell of this type is referred to herein as p21-deficient. The level of p21 expression can be assessed using any suitable method, including, for example, binding by a p21-specific monoclonal antibody either to whole cells or cell extracts, reverse transcriptase-polymerase chain reaction (RT-PCR) performed using appropriate sequence-specific oligonucleotide primers, Northern blotting, and the like. Monoclonal anti-p21 antibodies are available from a variety of commercial suppliers. The nucleotide sequence of human p21/WAF1 is publicly available as, for example, GenBank Accession No. S67388.

A cell is said to be p21-deficient when the expressed amount of p21 is objectively and measurably less than the expressed amount of p21 as measured in a suitable positive control cell. In one embodiment, a cell is said to be p21-deficient when the expressed amount of p21 is at least 5 percent less than the expressed amount of p21 as measured in a suitable positive control cell. In various additional or alternative embodiments, a cell is said to be p21-deficient when the expressed amount of p21 is at least 10, 20, 25, 30, 40, 50, 60, 70, 75, 80, 90, 95, 99, or 100 percent less than the expressed amount of p21 as measured in a suitable positive control cell.

An aspect of the invention is a pharmaceutical composition. The pharmaceutical composition includes any one of the above-referenced conjugates and a pharmaceutically acceptable carrier. A pharmaceutical composition according to this aspect of the invention can be prepared by a method that includes the step of combining a therapeutically effective amount of any one of the above-referenced conjugates and a pharmaceutically acceptable carrier. Of course the pharmaceutical composition and method for its preparation can include more than one of the above-referenced conjugates. Likewise, the pharmaceutical composition and method for its preparation can of course optionally further include at least one additional pharmaceutically active agent other than a conjugate of the invention.

An aspect of the invention is a method of killing a mammalian cell. The method includes the step of contacting a mammalian cell with an effective amount of any one of the aforementioned compounds of the invention. In certain embodiments, the method relates to any one of the compounds according to formula (I) or a pharmaceutically acceptable salt thereof:

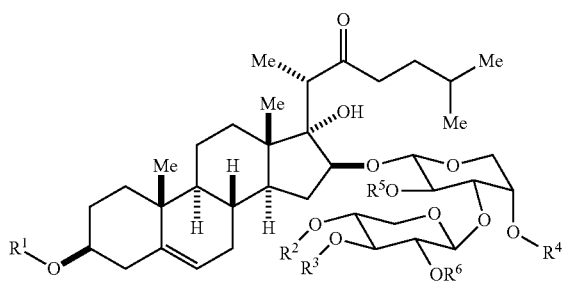

(I)

wherein
$R^1$, $R^2$, $R^3$, and $R^6$ are independently selected from the group consisting of hydrogen, trialkylsilyl, and

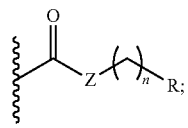

Z is absent or is selected from the group consisting of O and $NR^{10}$;
n is an integer 0-6;
R is selected from the group consisting of substituted or unsubstituted: alkyl, alkenyl, amino, alloc-protected amino, Fmoc-protected amino, aryl, 5- to 13-membered cycloalkyl or cycloalkenyl group, and 5- to 10-membered cyclic heteroaromatic group comprising 1-3 heteroatoms independently selected from the group consisting of N, O, and S;
$R^4$ is selected from the group consisting of hydrogen and C1-C6 alkyl;
$R^5$ is selected from the group consisting of hydrogen and acyl; and
$R^{10}$ is selected from the group consisting of hydrogen and C1-C6 alkyl;
provided that:
(a) at least one of $R^1$, $R^2$, $R^3$, $R^4$, $R^5$, and $R^6$ is not hydrogen;
(b) if each of $R^1$, $R^2$, $R^3$, and $R^4$ is hydrogen and $R^5$ is acetyl, then $R^6$ is not hydrogen, para-methoxybenzoyl, or 3-phenyl-2-propenoyl;
(c) if $R^1$ is tert-butyldimethylsilyl, then $R^S$ is not acetyl or $R^6$ is not para-methoxybenzoyl;
(d) if $R^1$ is 4-(alloc-aminomethyl)benzylaminocarbonyl, then at least one of $R^2$, $R^3$, $R^4$, $R^5$, and $R^6$ is not hydrogen; or
(e) if $R^2$ or $R^3$ is 4-(alloc-aminomethyl)benzylaminocarbonyl, then $R^5$ is not acetyl or $R^6$ is not para-methoxybenzoyl.

In certain embodiments, the method relates to any one of the above-referenced compounds, wherein $R^4$ is hydrogen. Alternatively, in certain embodiments, the method relates to any one of the above-referenced compounds, wherein $R^4$ is a C1-C6 alkyl. For example, in certain embodiments, the method relates to any one of the above-referenced compounds, wherein $R^4$ is methyl.

In certain embodiments, the method relates to any one of the above-referenced compounds, wherein $R^5$ is hydrogen. Alternatively, in certain embodiments, the method relates to any one of the above-referenced compounds, wherein $R^5$ is acyl. For example, in certain embodiments, the method relates to any one of the above-referenced compounds, wherein $R^5$ is acetyl (Ac).

In certain embodiments, the method relates to any one of the above-referenced compounds, wherein $R^1$ is hydrogen. Alternatively, in certain embodiments, the method relates to any one of the above-referenced compounds, wherein $R^1$ is trialkylsilyl. Alternatively, in certain embodiments, the method relates to any one of the above-referenced PS compounds, wherein $R^1$ is

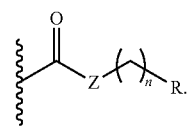

In certain embodiments, the method relates to any one of the above-referenced compounds, wherein $R^2$ is hydrogen. Alternatively, in certain embodiments, the method relates to any one of the above-referenced compounds, wherein $R^2$ is trialkylsilyl. Alternatively, in certain embodiments, the method relates to any one of the above-referenced compounds, wherein $R^2$ is

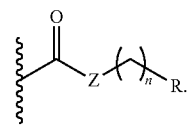

In certain embodiments, the method relates to any one of the above-referenced compounds, wherein $R^3$ is hydrogen. Alternatively, in certain embodiments, the method relates to any one of the above-referenced compounds, wherein $R^3$ is trialkylsilyl. Alternatively, in certain embodiments, the method relates to any one of the above-referenced compounds, wherein $R^3$ is

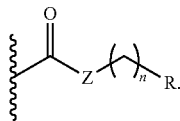

In certain embodiments, the method relates to any one of the above-referenced compounds, wherein $R^6$ is hydrogen. Alternatively, in certain embodiments, the method relates to any one of the above-referenced compounds, wherein $R^6$ is trialkylsilyl. Alternatively, in certain embodiments, the method relates to any one of the above-referenced compounds, wherein $R^6$ is

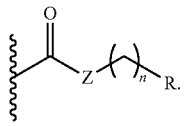

For example, in certain embodiments, the method relates to any one of the above-referenced compounds, wherein $R^6$ is para-methoxybenzoyl. In another example, in certain embodiments, the method relates to any one of the above-referenced compounds, wherein $R^6$ is 3-phenylpropanoyl.

In certain embodiments, the method relates to any one of the above-referenced compounds, wherein one or more instances of R is alkyl. In certain embodiments, the method relates to any one of the above-referenced compounds, wherein one or more instances of R is alkenyl. In certain embodiments, the method relates to any one of the above-referenced compounds, wherein one or more instances of R is an amino group. In certain embodiments, the method relates to any one of the above-referenced compounds, wherein one or more instances of R is an alloc-protected amino group. In certain embodiments, the method relates to any one of the above-referenced compounds, wherein one or more instances of R is an Fmoc-protected amino group. In certain embodiments, the method relates to any one of the above-referenced compounds, wherein one or more instances of R is aryl. In certain embodiments, the method relates to any one of the above-referenced compounds, wherein one or more instances of R is 5- to 13-membered cycloalkyl group. In certain embodiments, the method relates to any one of the above-referenced compounds, wherein one or more instances of R is a 5- to 13-membered cycloalkenyl group. In certain embodiments, the method relates to any one of the above-referenced compounds, wherein one or more instances of R is a 5- to 10-membered cyclic heteroaromatic group comprising 1-3 heteroatoms independently selected from the group consisting of N, O, and S.

In certain embodiments, the method relates to any one of the above-referenced compounds, wherein one or more instances of Z is oxygen (O).

In certain embodiments, the method relates to any one of the above-referenced compounds, wherein one or more instances Z is O and R is alkyl. Alternatively, in certain embodiments, the method relates to any one of the above-referenced compounds, wherein in one or more instances Z is O and R is 4-nitrophenyl.

In certain embodiments, the method relates to any one of the above-referenced compounds, wherein in one or more instances Z is O and n is zero (0). Alternatively, in certain embodiments, the method relates to any one of the above-referenced compounds, wherein in one or more instances Z is O and n is one (1). Alternatively, in certain embodiments, the method relates to any one of the above-referenced compounds, wherein in one or more instances Z is O and n is 2. Alternatively, in certain embodiments, the method relates to any one of the above-referenced compounds, wherein in one or more instances Z is O and n is 3. Alternatively, in certain embodiments, the method relates to any one of the above-referenced compounds, wherein in one or more instances Z is O and n is 4. Alternatively, in certain embodiments, the method relates to any one of the above-referenced compounds, wherein in one or more instances Z is O and n is 5. Alternatively, in certain embodiments, the method relates to any one of the above-referenced compounds, wherein in one or more instances Z is O and n is 6.

In certain embodiments, the method relates to any one of the above-referenced compounds, wherein one or more instances of Z is $NR^{10}$. For example, in certain embodiments, the method relates to any one of the above-referenced compounds, wherein one or more instances of Z is NH. In another example, in certain embodiments, the method relates to any one of the above-referenced compounds, wherein in one or more instances Z is $NR^{10}$ and $R^{10}$ is a C1-C6 alkyl.

In certain embodiments, the method relates to any one of the above-referenced compounds, wherein in one or more instances Z is NH and R is an amino group. In certain embodiments, the method relates to any one of the above-referenced compounds, wherein in one or more instances Z is NH and R is an alloc- or Fmoc-N'-substituted amino group.

In certain embodiments, the method relates to any one of the above-referenced compounds, wherein in one or more instances Z is NH and n is 6. In certain embodiments, the method relates to any one of the above-referenced compounds, wherein in one or more instances Z is NH and n is zero (0). In certain embodiments, the method relates to any one of the above-referenced compounds, wherein in one or more instances Z is NH and n is one (1). In certain embodiments, the method relates to any one of the above-referenced compounds, wherein in one or more instances Z is NH and n is 2. In certain embodiments, the method relates to any one of the above-referenced compounds, wherein in one or more instances Z is NH and n is 3. In certain embodiments, the method relates to any one of the above-referenced compounds, wherein in one or more instances Z is NH and n is 4. In certain embodiments, the method relates to any one of the above-referenced compounds, wherein in one or more instances Z is NH and n is 5.

In certain embodiments, the method relates to any one of the above-referenced compounds, wherein in one or more instances Z is NH and R is a para-aminoalkylaryl group. In certain embodiments, the method relates to any one of the above-referenced compounds, wherein in one or more instances Z is NH and R is an alloc- or Fmoc-N'-substituted para-aminomethylphenyl group.

In certain embodiments, the method relates to any one of the above-referenced compounds, wherein in one or more instances Z is NH, R is apara-aminoalkylaryl group or an alloc- or Fmoc-N'-substituted para-aminomethylphenyl group, and n is one (1).

In certain embodiments, the method relates to any one of the above-referenced compounds, wherein in one or more instances Z is NH, R is phenyl, and n is one (1).

In certain embodiments, the method relates to any one of the above-referenced compounds, wherein one or more instances of Z is absent, such that there is a bond between the carbonyl carbon and the methylene group if n is non-zero, or between the carbonyl carbon and R if n is zero (0).

In certain embodiments, the method relates to any one of the above-referenced compounds, wherein in one or more instances Z is absent and R is an amino group. In certain embodiments, the method relates to any one of the above-referenced compounds, wherein in one or more instances Z is absent and R is an alloc- or Fmoc-N'-substituted amino group.

In certain embodiments, the method relates to any one of the above-referenced compounds, wherein in one or more instances Z is absent and n is 2. In certain embodiments, the method relates to any one of the above-referenced compounds, wherein in one or more instances Z is absent and n is zero (0). In certain embodiments, the method relates to any one of the above-referenced compounds, wherein in one or more instances Z is absent and n is one (1). In certain embodiments, the method relates to any one of the above-referenced compounds, wherein in one or more instances Z is absent and n is 3. In certain embodiments, the method relates to any one of the above-referenced compounds, wherein in one or more instances Z is absent and n is 4. In certain embodiments, the method relates to any one of the above-referenced compounds, wherein in one or more instances Z is absent and n is 5. In certain embodiments, the method relates to any one of the above-referenced compounds, wherein in one or more instances Z is absent and n is 6.

In certain embodiments, the method relates to any one of the above-referenced compounds, wherein in one or more instances Z is absent and R is a 1-imidazolyl group. In certain embodiments, the method relates to any one of the above-referenced compounds, wherein in one or more instances Z is absent, R is a 1-imidazolyl group, and n is zero (0).

In certain embodiments, the method relates to any one of the above-referenced compounds, wherein at least one of $R^1$, $R^2$, and $R^3$ is tert-butyldimethylsilyl. For example, in certain embodiments, the method relates to any one of the above-referenced compounds, wherein $R^1$ is tert-butyldimethylsilyl. As another example, in certain embodiments, the method relates to any one of the above-referenced compounds, wherein $R^2$ is tert-butyldimethylsilyl. As another example, in certain embodiments, the method relates to any one of the above-referenced compounds, wherein $R^3$ is tert-butyldimethylsilyl. As yet another example, in certain embodiments, the method relates to any one of the above-referenced compounds, wherein each of $R^1$ and $R^2$ is tert-butyldimethylsilyl. As another example, in certain embodiments, the method relates to any one of the above-referenced compounds, wherein each of $R^1$ and $R^3$ is tert-butyldimethylsilyl. As another example, in certain embodiments, the method relates to any one of the above-referenced compounds, wherein each of $R^2$ and $R^3$ is tert-butyldimethylsilyl. As yet another example, in certain embodiments, the method relates to any one of the above-referenced compounds, wherein each of $R^1$, $R^2$, and $R^3$ is tert-butyldimethylsilyl.

In certain embodiments, the method relates to a compound selected from the group consisting of:

100

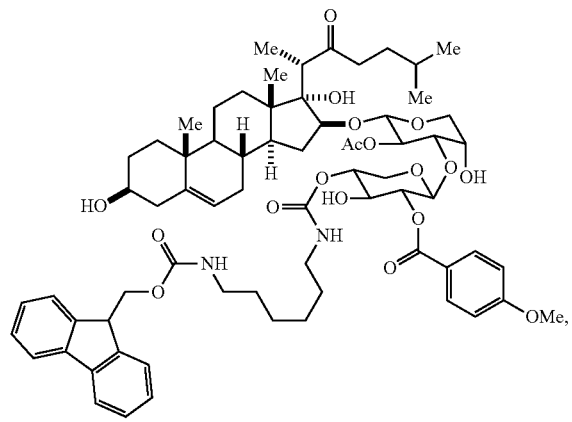

101

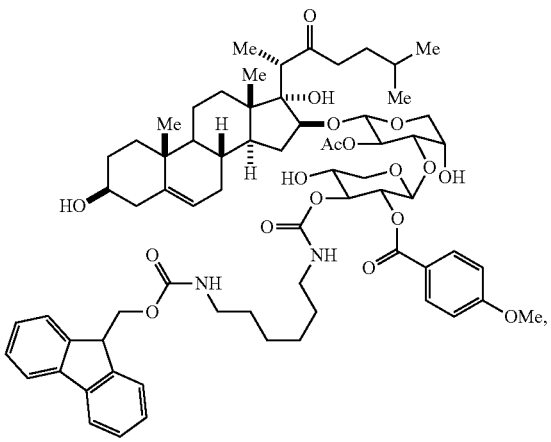

102

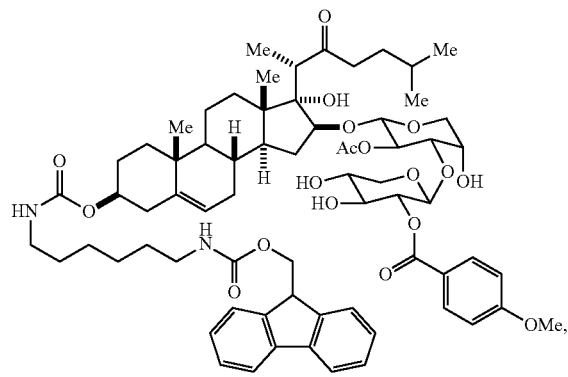

103

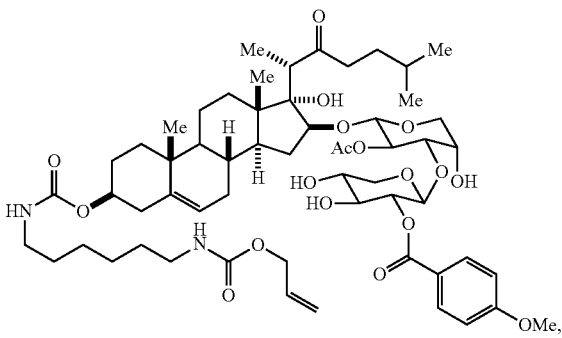

-continued
104
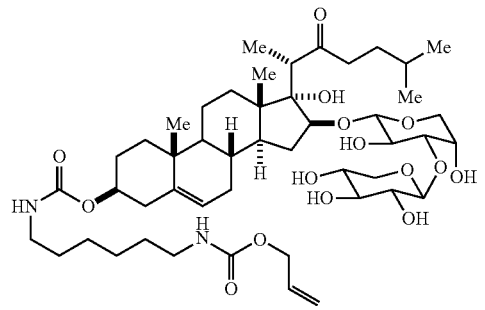
105
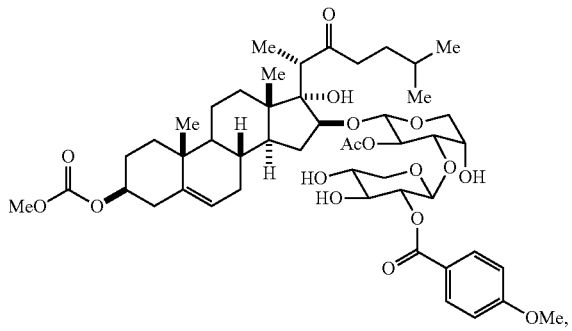
106
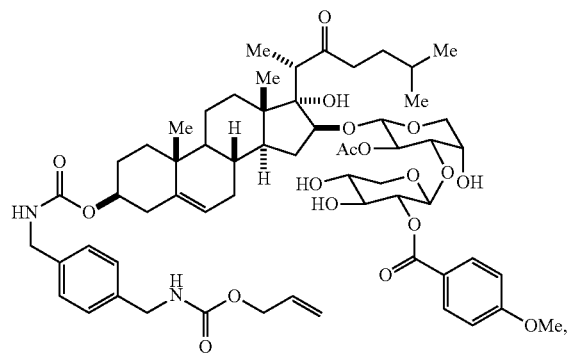
107
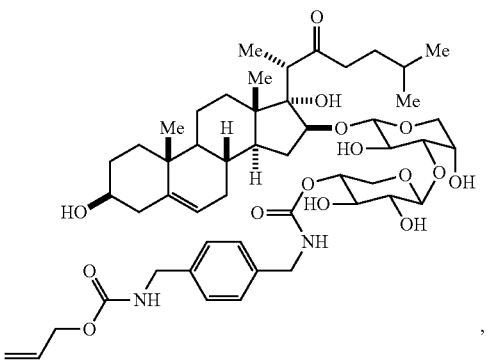
108
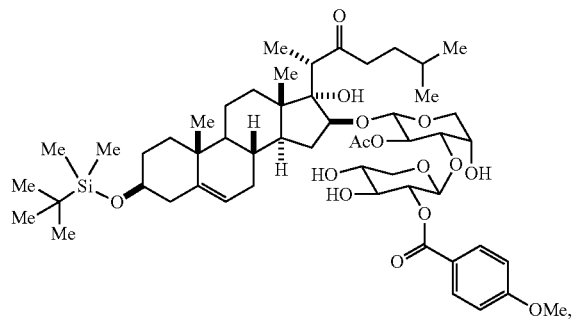
109
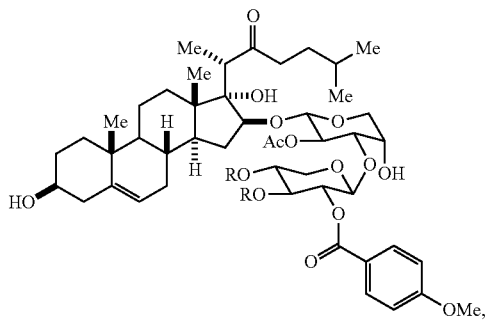
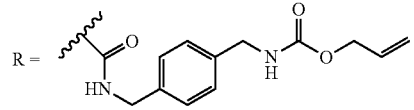
110
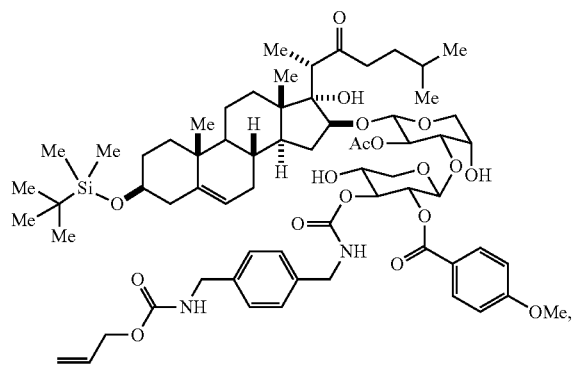
111
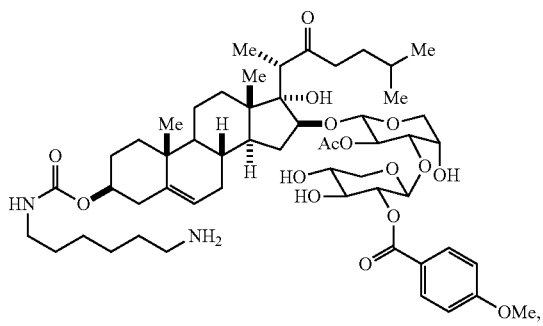

-continued
112
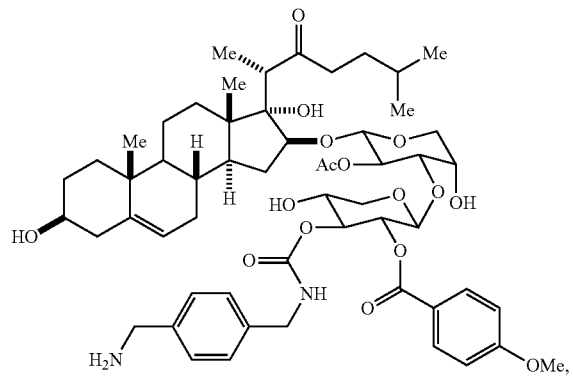
113
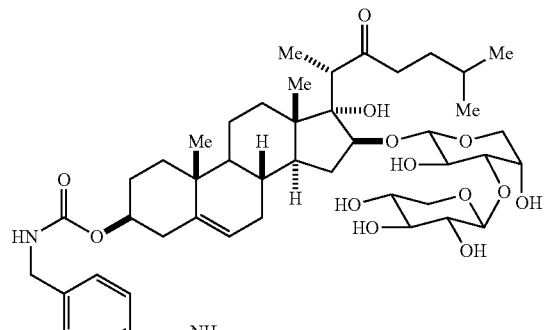
114
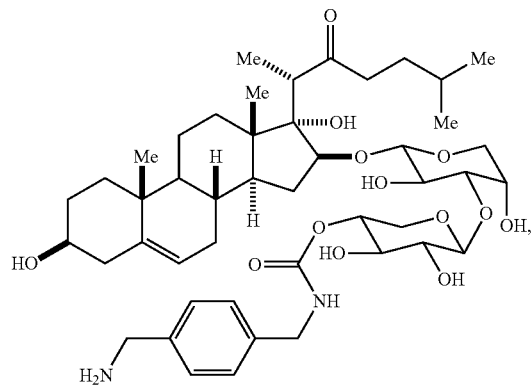
115
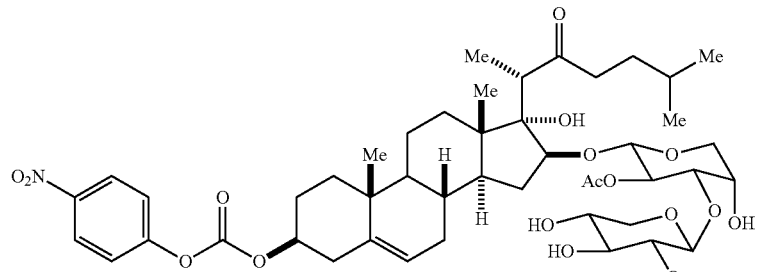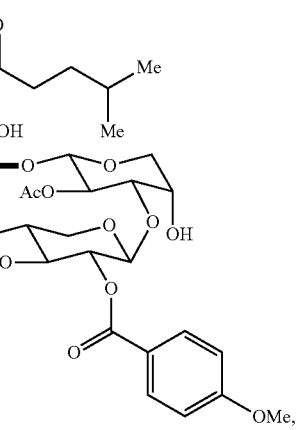
116
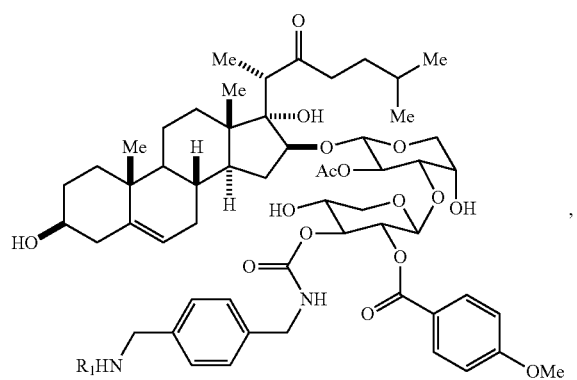
R₁ = Sepharose 4b
117
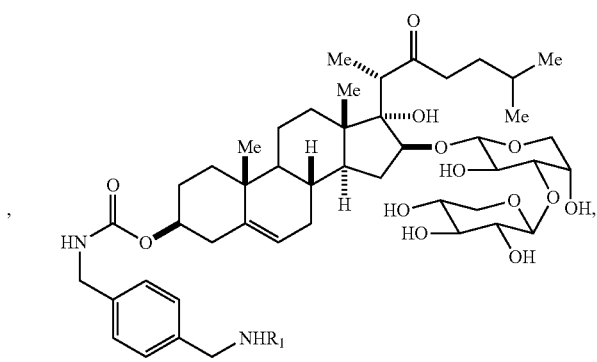
R₁ = Sepharose 4b -continued
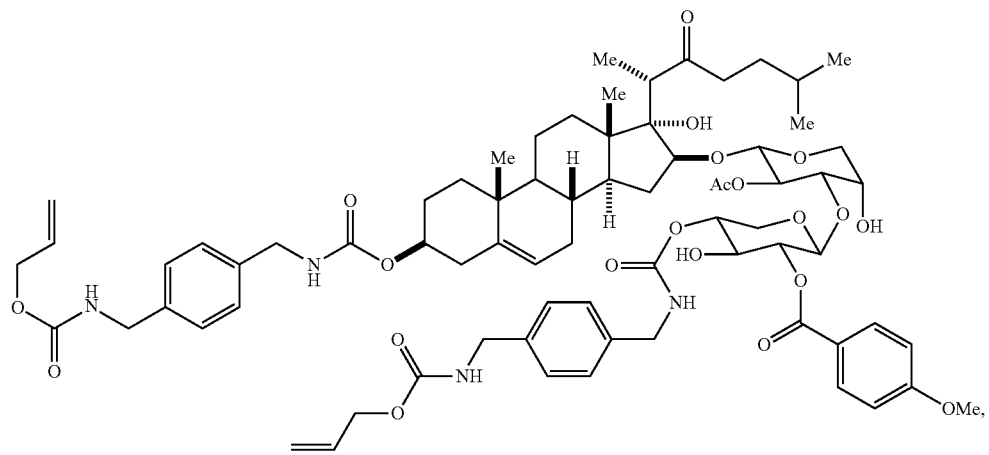
118
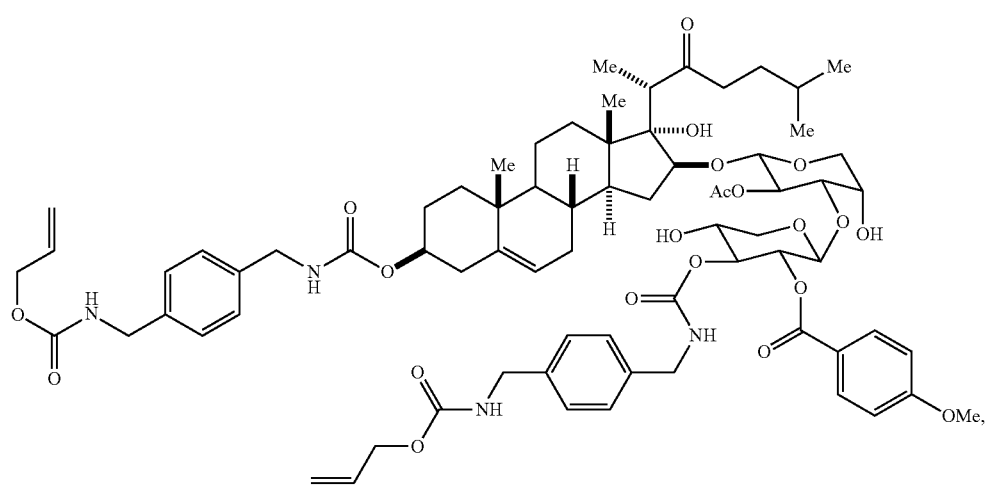
119
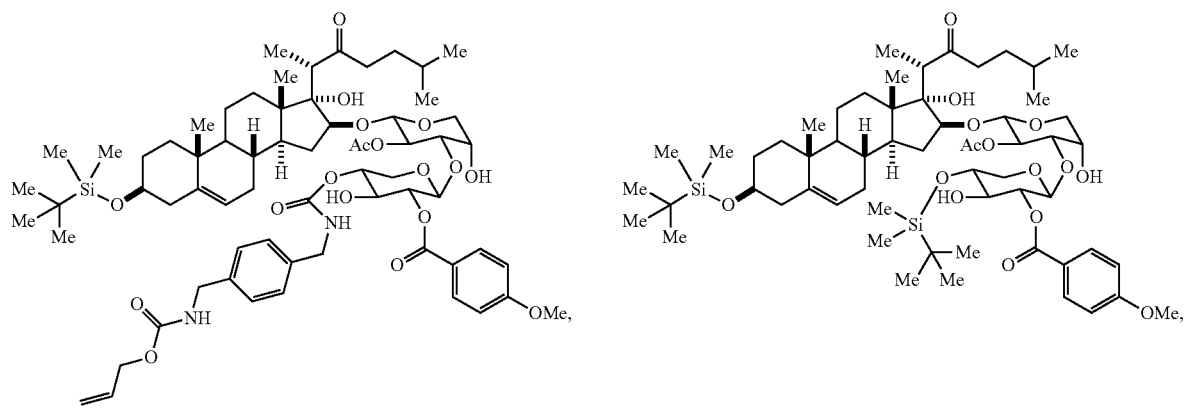

-continued
122
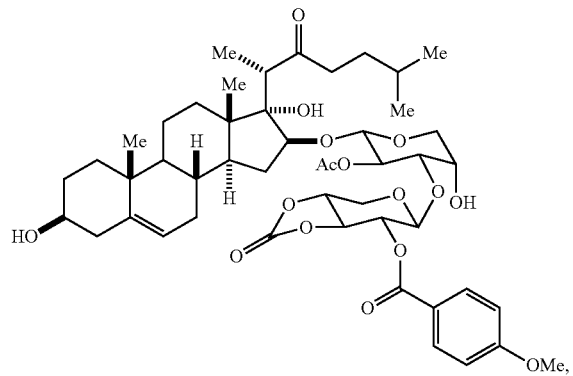
123
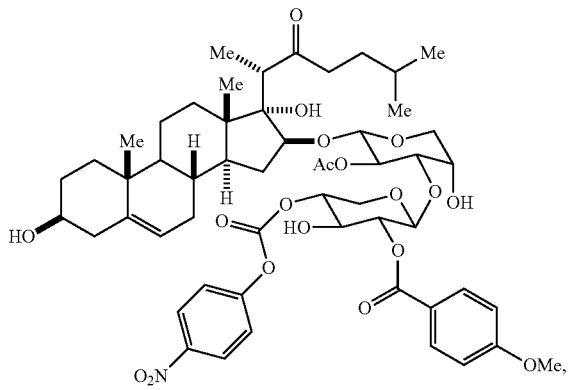
124
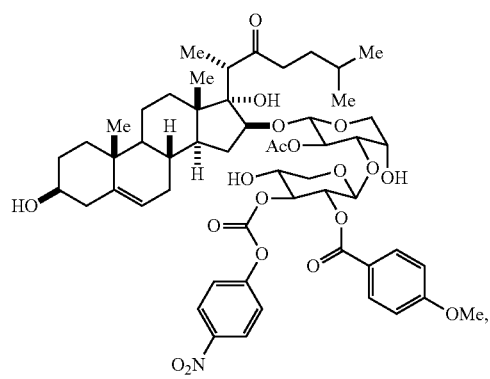
125
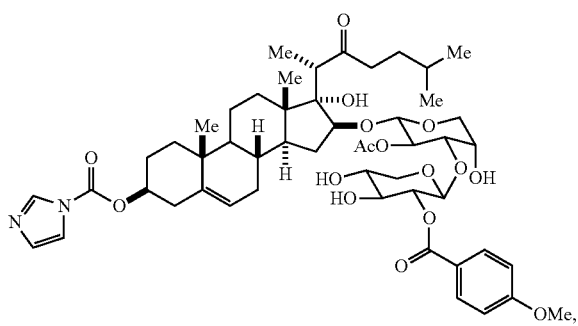
126
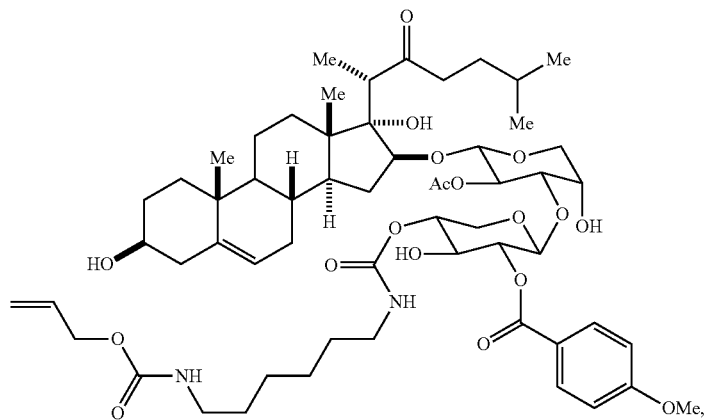
127
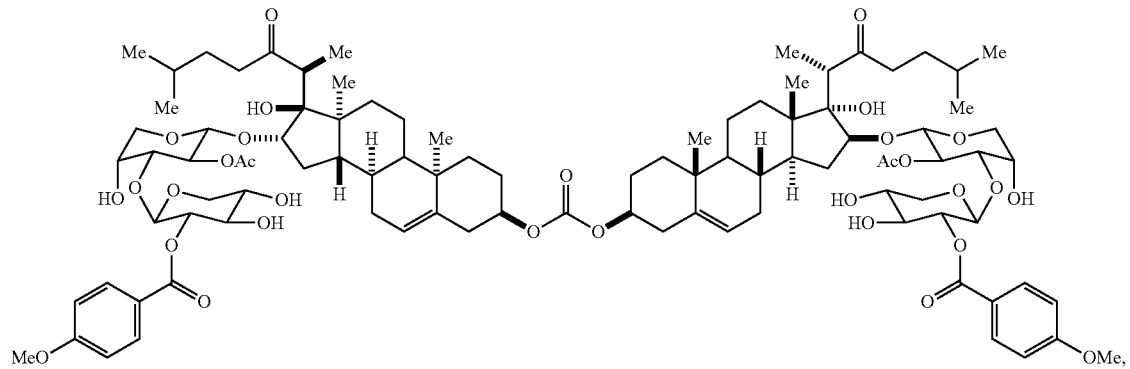

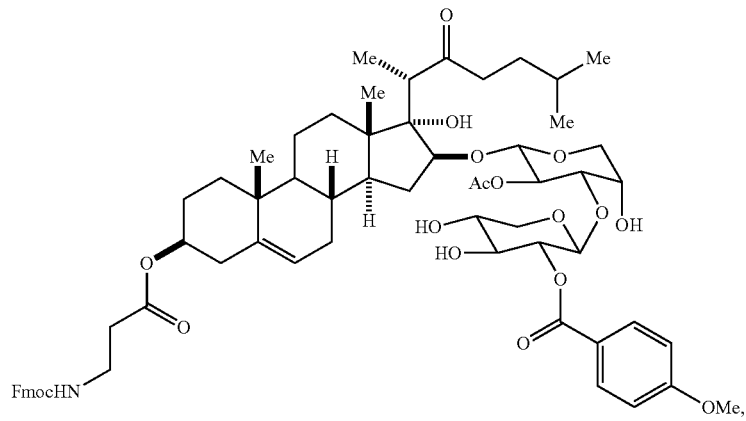
128
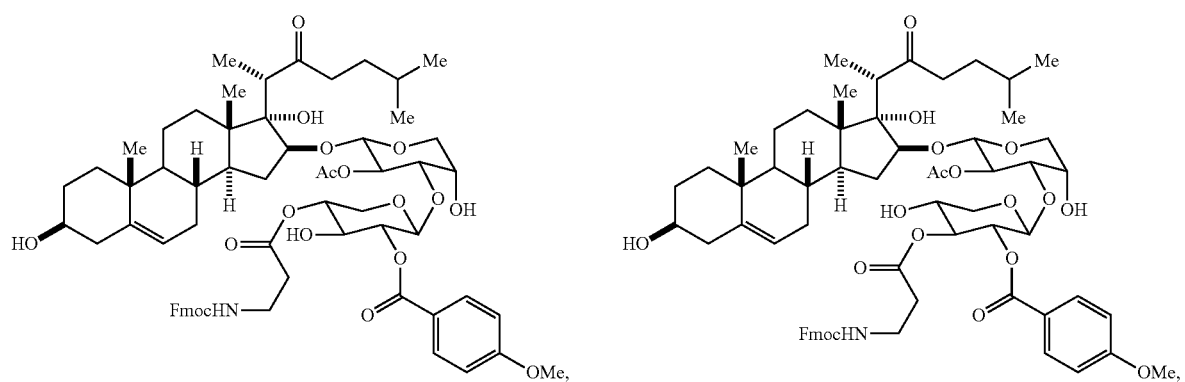
129
130
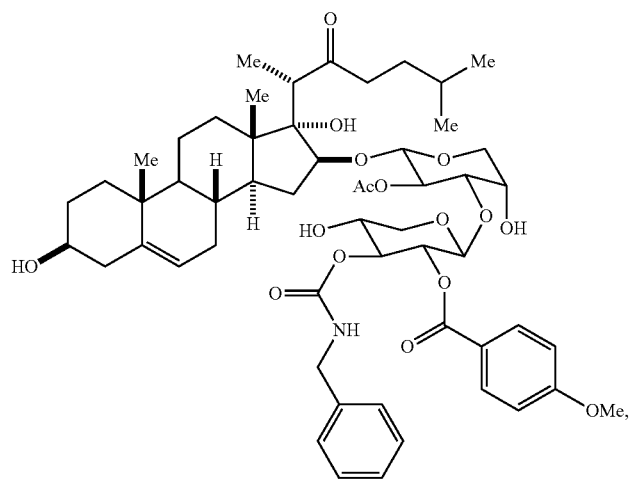
131

-continued

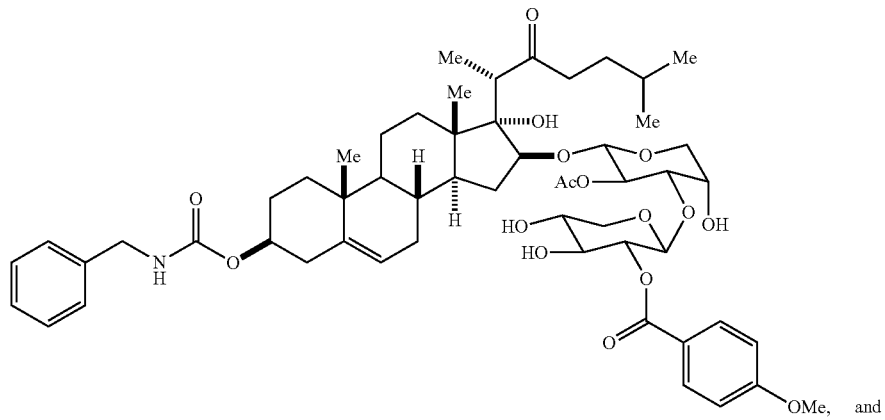

132

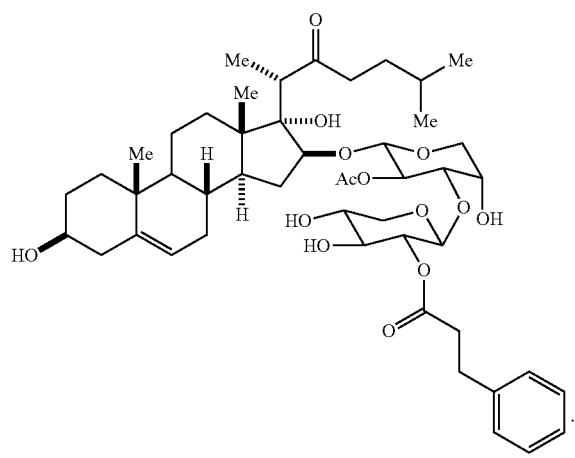

133

Further in accordance with this method of the invention, in one embodiment the mammalian cell is a cancer cell. In one embodiment, the cancer cell is a human cancer cell. In on embodiment, the cancer cell is p21-deficient.

An aspect of the invention is a method of treating an OSBP-related disease or condition. The method includes the step of administering to a subject in need thereof an effective amount of a compound of the invention, thereby to increase apoptosis of OSBP-expressing cells associated with the OSBP-related disease or condition.

As used herein, an "OSBP-related disease or condition" refers to any disease or condition in which an oxysterol binding protein (OSBP) or OSBP-related protein (ORP) has been shown or can be shown to participate in the pathogenesis of the disease or condition. In one embodiment, an OSBP-related disease or condition is cancer. In one embodiment, an OSBP-related disease or condition is atherosclerosis. In one embodiment, an OSBP-related disease or condition is Alzheimer's disease.

As used herein, "treating" refers to reducing or slowing the progression of at least one symptom or objective manifestation of a disease or condition in a subject having the disease or condition. In one embodiment, "treating" refers to eliminating a disease or condition in a subject having the disease or condition.

A "subject" refers to a living mammal. In one embodiment a subject is a human.

An "effective amount" is an amount that is sufficient to achieve a desired result. For example, an effective amount to increase apoptosis of OSBP-expressing cells is an amount sufficient to increase apoptosis of OSBP-expressing cells.

A method that increases apoptosis of OSBP-expressing cells associated with an OSBP-related disease or condition reduces the number (or population) of cells associated with the OSBP-related disease or condition.

Apoptosis refers to programmed cell death. In apoptosis, biochemical events lead to characteristic changes in cell morphology and cell death. These changes include blebbing, loss of cell membrane asymmetry and attachment, cell shrinkage, nuclear fragmentation, chromatin condensation, and chromosomal DNA fragmentation. Unlike necrosis, apoptosis produces cell fragments called apoptotic bodies that surrounding cells are able to engulf and quickly remove before the contents of the cell can spill out onto surrounding cells and cause damage.

The process of apoptosis is controlled by a diverse range of cell signals, which may originate either extracellularly or intracellularly. Extracellular signals may include toxins, hormones, growth factors, nitric oxide, or cytokines, that must either cross the plasma membrane or transduce a signal across the plasma membrane to effect a response.

A cell initiates intracellular apoptotic signaling in response to a stress, which may bring about cell suicide. The binding of nuclear receptors by glucocorticoids, heat, radiation, nutrient deprivation, viral infection, hypoxia, and increased intracellular calcium concentration, for example, by damage to the membrane, can all trigger the release of intracellular apoptotic signals by a damaged cell. A number of cellular components, such as poly ADP ribose polymerase, may also help regulate apoptosis.

Before the actual process of cell death is precipitated by enzymes, apoptotic signals must cause regulatory proteins to initiate the apoptosis pathway. This step allows apoptotic signals to cause cell death, or the process to be stopped, should the cell no longer need to die. Several proteins are involved, but two main methods of regulation have been identified: targeting mitochondria functionality, or directly transducing the signal via adaptor proteins to the apoptotic mechanisms. Another extrinsic pathway for initiation identified in several toxin studies is an increase in calcium concentration within a cell caused by drug activity, which also can cause apoptosis via a calcium-binding protease, calpain.

Apoptotic pathways can be caspase-dependent or caspase-independent. Caspases are a family of cysteine proteases which can proteolytically degrade a host of intracellular proteins to carry out the cell death program.

There are a number of methods known in the art that are useful to measure apoptosis. These include caspase assays, terminal deoxynucleotidyl transferase dUTP nick end labeling (TUNEL) and DNA fragmentation assays, cell permeability assays, and annexin V assay, to name but a few. Any of these assays can be used to detect apoptosis of OSBP-expressing cells associated with an OSBP-related disease or condition. Using such assays, apoptosis is said to be increased when the amount or degree of apoptosis is objectively and measurably greater than suitable negative control amount or degree of apoptosis. For example, in one embodiment the apoptosis is increased if it is at least 5 percent greater than suitable negative control amount or degree of apoptosis. In alternative embodiments, apoptosis is increased if it is at least 10, 20, 25, 30, 40, 50, 60, 70, 75, 80, 90, or 100 percent greater than suitable negative control amount or degree of apoptosis.

In certain embodiments, the invention relates to the any of the above-referenced methods, wherein the OSBP-related disease or condition is cancer, and the OSBP-expressing cells are cancer cells. Because ORPphilins may be highly selective for tumors that have lost p21 expression, an event that often occurs at later stages in the clinical progression of some types of tumors, ORPphilins might play a role as a new last line of defense in the treatment of cancer: as tumors become resistant to standard therapy through loss of p21, these tumors could be become more sensitive to the ORPphilins. Therefore, in certain embodiments, the invention relates to any one of the above-referenced methods, wherein the cancer is a p21-deficient cancer, i.e., the cancer cells are p21-deficient.

Exemplary cancers that may be treated include cancers selected from the group consisting of Acute Lymphoblastic Leukemia (ALL); Acute Myeloid Leukemia (AML); Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma; Bladder Cancer; Bone Cancer; Brain Stem Glioma; Brain Tumor; Breast Cancer; Bronchial Adenomas/Carcinoids; Burkitt's Lymphoma; Carcinoid Tumor; Carcinoma of Unknown Primary Site; Central Nervous System Lymphoma, Primary; Cerebellar Astrocytoma; Cerebral Astrocytoma/Malignant Glioma; Cervical Cancer; Childhood Cancers; Chronic Lymphocytic Leukemia (CLL); Chronic Myelogenous Leukemia (CML); Chronic Myeloproliferative Disorders; Colon Cancer; Colorectal Cancer; Cutaneous T-Cell Lymphoma; Endometrial Cancer; Ependymoma; Esophageal Cancer; Ewing's Family of Tumors; Ewing's Sarcoma; Extracranial Germ Cell Tumor; Extragonadal Germ Cell Tumor; Extrahepatic Bile Duct Cancer; Gallbladder Cancer; Gastric (Stomach) Cancer; Gastrointestinal Carcinoid Tumor; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Glioma, Hypothalamic and Visual Pathway; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hypopharyngeal Cancer; Intraocular Melanoma; Islet Cell Carcinoma; Kaposi's Sarcoma; Kidney (Renal Cell) Cancer; Laryngeal Cancer; Leukemia; Lip and Oral Cavity Cancer; Liver Cancer, Adult (Primary); Liver Cancer, Childhood (Primary); Lung Cancer, Non-Small Cell; Lung Cancer, Small Cell; Malignant Fibrous Histiocytoma; Malignant Fibrous Histiocytoma of Bone/Osteosarcoma; Medulloblastoma; Melanoma; Merkel Cell Carcinoma; Mesothelioma; Mesothelioma, Adult Malignant; Metastatic Squamous Neck Cancer with Occult Primary; Multiple Endocrine Neoplasia (MEN) Syndrome; Multiple Myeloma; Myelodysplastic Syndromes; Myelodysplastic/Myeloproliferative Diseases; Myeloid Leukemia, Adult Acute; Myeloid Leukemia, Childhood Acute; Myeloproliferative Disorders, Chronic; Nasal Cavity and Paranasal Sinus Cancer; Nasopharyngeal Cancer; Neuroblastoma; Non-Hodgkin's Lymphoma; Oral Cancer; Oropharyngeal Cancer; Osteosarcoma; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Paranasal Sinus and Nasal Cavity Cancer; Parathyroid Cancer; Penile Cancer; Pheochromocytoma; Pineoblastoma and Supratentorial Primitive Neuroectodermal Tumors; Pituitary Tumor; Pleuropulmonary Blastoma; Primary Central Nervous System Lymphoma; Prostate Cancer; Rectal Cancer; Retinoblastoma; Rhabdomyosarcoma; Salivary Gland Cancer; Sarcoma, Soft Tissue; Sarcoma, Uterine; Sezary Syndrome; Skin Cancer; Skin Cancer (non-Melanoma); Small Intestine Cancer; Soft Tissue Sarcoma; Squamous Cell Carcinoma; Squamous Neck Cancer with Occult Primary, Metastatic; Supratentorial Primitive Neuroectodermal Tumors; Testicular Cancer, Thymoma; Thymoma and Thymic Carcinoma; Thyroid Cancer; Transitional Cell Cancer of the Renal Pelvis and Ureter; Trophoblastic Tumor, Gestational; Unusual Cancers of Childhood; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; and Wilms' Tumor.

In certain embodiments, the method relates to any one of the compounds according to formula (I) or a pharmaceutically acceptable salt thereof:

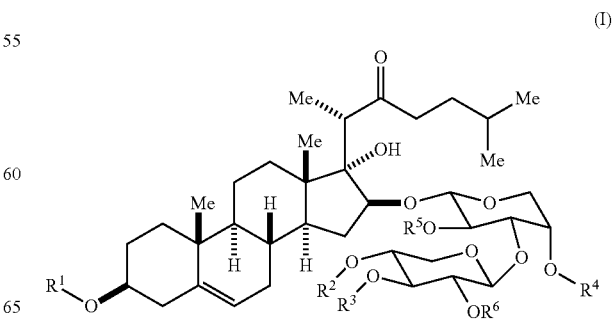

wherein
$R^1$, $R^2$, $R^3$, and $R^6$ are independently selected from the group consisting of hydrogen, trialkylsilyl, and

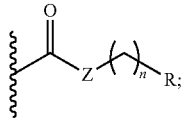

Z is absent or is selected from the group consisting of O and $NR^{10}$;

n is an integer 0-6;

R is selected from the group consisting of substituted or unsubstituted: alkyl, alkenyl, amino, alloc-protected amino, Fmoc-protected amino, aryl, 5- to 13-membered cycloalkyl or cycloalkenyl group, and 5- to 10-membered cyclic heteroaromatic group comprising 1-3 heteroatoms independently selected from the group consisting of N, O, and S;

$R^4$ is selected from the group consisting of hydrogen and C1-C6 alkyl;

$R^5$ is selected from the group consisting of hydrogen and acyl; and $R^{10}$ is selected from the group consisting of hydrogen and C1-C6 alkyl;

provided that:
(a) at least one of $R^1$, $R^2$, $R^3$, $R^4$, $R^5$, and $R^6$ is not hydrogen;
(b) if each of $R^1$, $R^2$, $R^3$, and $R^4$ is hydrogen and $R^5$ is acetyl, then $R^6$ is not S hydrogen, para-methoxybenzoyl, or 3-phenyl-2-propenoyl;
(c) if $R^1$ is tert-butyldimethylsilyl, then $R^5$ is not acetyl or $R^6$ is not para-methoxybenzoyl;
(d) if $R^1$ is 4-(alloc-aminomethyl)benzylaminocarbonyl, then at least one of $R^2$, $R^3$, $R^4$, $R^5$, and $R^6$ is not hydrogen; or
(e) if $R^2$ or $R^3$ is 4-(alloc-aminomethyl)benzylaminocarbonyl, then $R^S$ is not acetyl or $R^6$ is not para-methoxybenzoyl.

In certain embodiments, the method relates to any one of the above-referenced compounds, wherein $R^4$ is hydrogen. Alternatively, in certain embodiments, the method relates to any one of the above-referenced compounds, wherein $R^4$ is a C1-C6 alkyl. For example, in certain embodiments, the method relates to any one of the above-referenced compounds, wherein $R^4$ is methyl.

In certain embodiments, the method relates to any one of the above-referenced compounds, wherein $R^5$ is hydrogen. Alternatively, in certain embodiments, the method relates to any one of the above-referenced compounds, wherein $R^5$ is acyl. For example, in certain embodiments, the method relates to any one of the above-referenced compounds, wherein $R^5$ is acetyl (Ac).

In certain embodiments, the method relates to any one of the above-referenced compounds, wherein $R^1$ is hydrogen. Alternatively, in certain embodiments, the method relates to any one of the above-referenced compounds, wherein $R^1$ is trialkylsilyl. Alternatively, in certain embodiments, the method relates to any one of the above-referenced compounds, wherein $R^1$ is

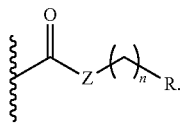

In certain embodiments, the method relates to any one of the above-referenced compounds, wherein $R^2$ is hydrogen. Alternatively, in certain embodiments, the method relates to any one of the above-referenced compounds, wherein $R^2$ is trialkylsilyl. Alternatively, in certain embodiments, the method relates to any one of the above-referenced compounds, wherein $R^2$ is

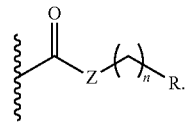

In certain embodiments, the method relates to any one of the above-referenced compounds, wherein $R^3$ is hydrogen. Alternatively, in certain embodiments, the method relates to any one of the above-referenced compounds, wherein $R^3$ is trialkylsilyl. Alternatively, in certain embodiments, the method relates to any one of the above-referenced compounds, wherein $R^3$ is

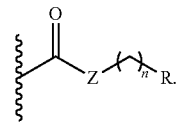

In certain embodiments, the method relates to any one of the above-referenced compounds, wherein $R^6$ is hydrogen. Alternatively, in certain embodiments, the method relates to any one of the above-referenced compounds, wherein $R^6$ is trialkylsilyl. Alternatively, in certain embodiments, the method relates to any one of the above-referenced compounds, wherein $R^6$ is

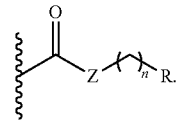

For example, in certain embodiments, the method relates to any one of the above-referenced compounds, wherein $R^6$ is para-methoxybenzoyl. In another example, in certain embodiments, the method relates to any one of the above-referenced compounds, wherein $R^6$ is 3-phenylpropanoyl.

In certain embodiments, the method relates to any one of the above-referenced compounds, wherein one or more instances of R is alkyl. In certain embodiments, the method relates to any one of the above-referenced compounds, wherein one or more instances of R is alkenyl. In certain embodiments, the method relates to any one of the above-referenced compounds, wherein one or more instances of R is an amino group. In certain embodiments, the method relates to any one of the above-referenced compounds, wherein one or more instances of R is an alloc-protected amino group. In certain embodiments, the method relates to any one of the above-referenced compounds, wherein one or more instances of R is an Fmoc-protected amino group. In certain embodiments, the method relates to any one of the above-referenced compounds, wherein one or more instances of R is aryl. In certain embodiments, the method relates to any one of the above-referenced compounds, wherein one or more instances of R is 5- to 13-membered cycloalkyl group. In certain embodiments, the method relates to any one of the above-referenced compounds, wherein one or more instances of R is a 5- to 13-membered cycloalkenyl group. In certain embodiments, the method relates to any one of the above-referenced compounds, wherein one or more instances of R is a 5- to 10-membered cyclic heteroaromatic group comprising 1-3 heteroatoms independently selected from the group consisting of N, O, and S.

In certain embodiments, the method relates to any one of the above-referenced compounds, wherein one or more instances of Z is oxygen (O).

In certain embodiments, the method relates to any one of the above-referenced compounds, wherein in one or more instances Z is O and R is alkyl. Alternatively, in certain embodiments, the method relates to any one of the above-referenced compounds, wherein in one or more instances Z is O and R is 4-nitrophenyl.

In certain embodiments, the method relates to any one of the above-referenced compounds, wherein in one or more instances Z is O and n is zero (0). Alternatively, in certain embodiments, the method relates to any one of the above-referenced compounds, wherein in one or more instances Z is O and n is one (1). Alternatively, in certain embodiments, the method relates to any one of the above-referenced compounds, wherein in one or more instances Z is O and n is 2. Alternatively, in certain embodiments, the method relates to any one of the above-referenced compounds, wherein in one or more instances Z is O and n is 3. Alternatively, in certain embodiments, the method relates to any one of the above-referenced compounds, wherein in one or more instances Z is O and n is 4. Alternatively, in certain embodiments, the method relates to any one of the above-referenced compounds, wherein in one or more instances Z is O and n is 5. Alternatively, in certain embodiments, the method relates to any one of the above-referenced compounds, wherein in one or more instances Z is O and n is 6.

In certain embodiments, the method relates to any one of the above-referenced compounds, wherein one or more instances of Z is $NR^{10}$. For example, in certain embodiments, the method relates to any one of the above-referenced compounds, wherein one or more instances of Z is NH. In another example, in certain embodiments, the method relates to any one of the above-referenced compounds, wherein in one or more instances Z is $NR^{10}$ and $R^{10}$ is a C1-C6 alkyl.

In certain embodiments, the method relates to any one of the above-referenced compounds, wherein in one or more instances Z is NH and R is an amino group. In certain embodiments, the method relates to any one of the above-referenced compounds, wherein in one or more instances Z is NH and R is an alloc- or Fmoc-N'-substituted amino group.

In certain embodiments, the method relates to any one of the above-referenced compounds, wherein in one or more instances Z is NH and n is 6. In certain embodiments, the method relates to any one of the above-referenced compounds, wherein in one or more instances Z is NH and n is zero (0). In certain embodiments, the method relates to any one of the above-referenced compounds, wherein in one or more instances Z is NH and n is one (1). In certain embodiments, the method relates to any one of the above-referenced compounds, wherein in one or more instances Z is NH and n is 2. In certain embodiments, the method relates to any one of the above-referenced compounds, wherein in one or more instances Z is NH and n is 3. In certain embodiments, the method relates to any one of the above-referenced compounds, wherein in one or more instances Z is NH and n is 4. In certain embodiments, the method relates to any one of the above-referenced compounds, wherein in one or more instances Z is NH and n is 5.

In certain embodiments, the method relates to any one of the above-referenced compounds, wherein in one or more instances Z is NH and R is a para-aminoalkylaryl group. In certain embodiments, the method relates to any one of the above-referenced compounds, wherein in one or more instances Z is NH and R is an alloc- or Fmoc-N'-substituted para-aminomethylphenyl group.

In certain embodiments, the method relates to any one of the above-referenced compounds, wherein in one or more instances Z is NH, R is a para-aminoalkylaryl group or an alloc- or Fmoc-N'-substitutedpara-aminomethylphenyl group, and n is one (1).

In certain embodiments, the method relates to any one of the above-referenced compounds, wherein in one or more instances Z is NH, R is phenyl, and n is one (1).

In certain embodiments, the method relates to any one of the above-referenced compounds, wherein one or more instances of Z is absent, such that there is a bond between the carbonyl carbon and the methylene group if n is non-zero, or between the carbonyl carbon and R if n is zero (0).

In certain embodiments, the method relates to any one of the above-referenced compounds, wherein in one or more instances Z is absent and R is an amino group. In certain embodiments, the method relates to any one of the above-referenced compounds, wherein in one or more instances Z is absent and R is an alloc- or Fmoc-N'-substituted amino group.

In certain embodiments, the method relates to any one of the above-referenced compounds, wherein in one or more instances Z is absent and n is 2. In certain embodiments, the method relates to any one of the above-referenced compounds, wherein in one or more instances Z is absent and n is zero (0). In certain embodiments, the method relates to any one of the above-referenced compounds, wherein in one or more instances Z is absent and n is one (1). In certain embodiments, the method relates to any one of the above-referenced compounds, wherein in one or more instances Z is absent and n is 3. In certain embodiments, the method relates to any one of the above-referenced compounds, wherein in one or more instances Z is absent and n is 4. In certain embodiments, the method relates to any one of the above-referenced compounds, wherein in one or more instances Z is absent and n is 5. In certain embodiments, the method relates to any one of the above-referenced compounds, wherein in one or more instances Z is absent and n is 6.

In certain embodiments, the method relates to any one of the above-referenced compounds, wherein in one or more instances Z is absent and R is a 1-imidazolyl group. In certain embodiments, the method relates to any one of the above-referenced compounds, wherein in one or more instances Z is absent, R is a 1-imidazolyl group, and n is zero (0).

In certain embodiments, the method relates to any one of the above-referenced compounds, wherein at least one of $R^1$, $R^2$, and $R^3$ is tert-butyldimethylsilyl. For example, in certain embodiments, the method relates to any one of the above-referenced compounds, wherein $R^1$ is tert-butyldimethylsilyl. As another example, in certain embodiments, the method relates to any one of the above-referenced compounds, wherein $R^2$ is tert-butyldimethylsilyl. As another example, in certain embodiments, the method relates to any one of the above-referenced compounds, wherein $R^3$ is tert-butyldimethylsilyl. As yet another example, in certain embodiments, the method relates to any one of the above-referenced compounds, wherein each of $R^1$ and $R^2$ is tert-butyldimethylsilyl. As another example, in certain embodiments, the method relates to any one of the above-referenced compounds, wherein each of $R^1$ and $R^3$ is tert-butyldimethylsilyl. As another example, in certain embodiments, the method relates to any one of the above-referenced compounds, wherein each of $R^2$ and $R^3$ is tert-butyldimethylsilyl. As yet another example, in certain embodiments, the method relates to any one of the above-referenced compounds, wherein each of $R^1$, $R^2$, and $R^3$ is tert-butyldimethylsilyl.

In certain embodiments, the method relates to a compound selected from the group consisting of:

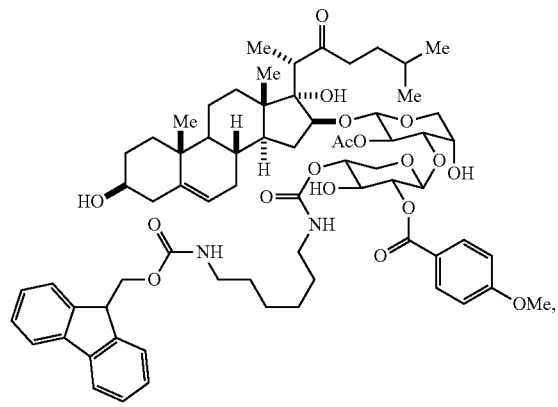

100

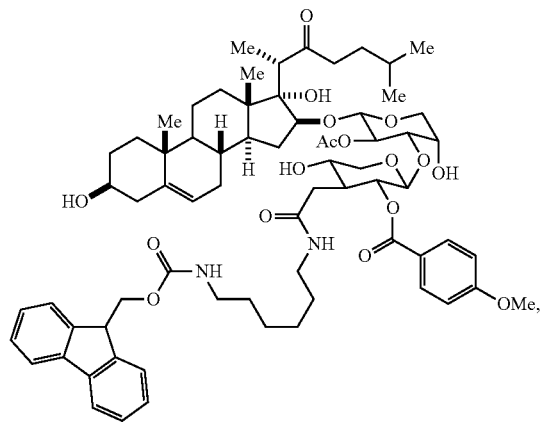

101

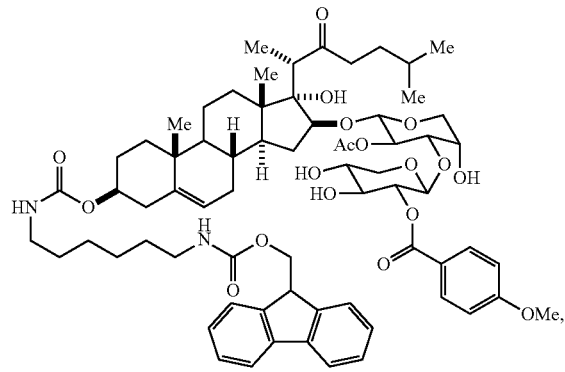

102

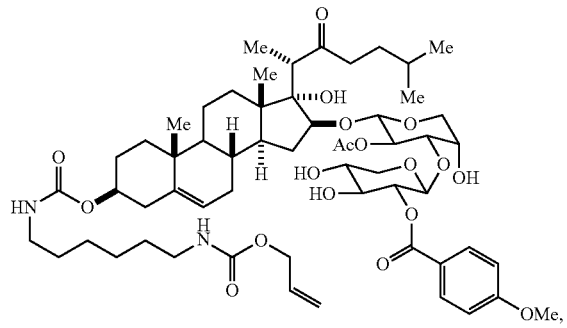

103

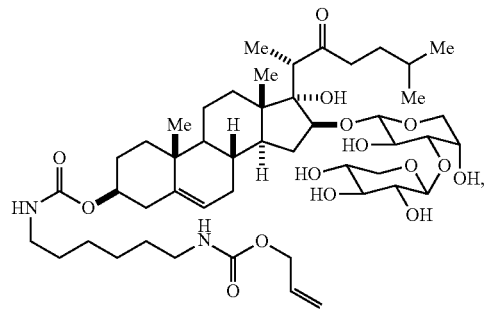

104

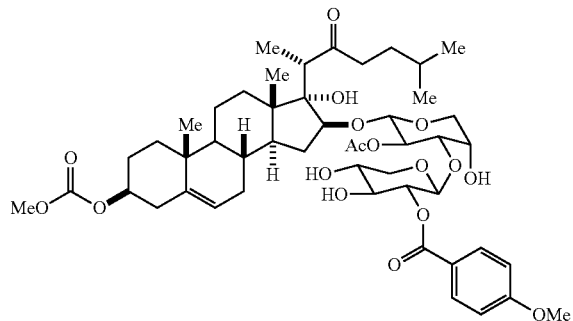

105

106
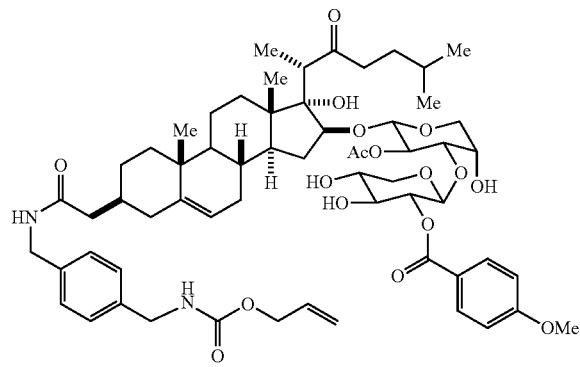
107
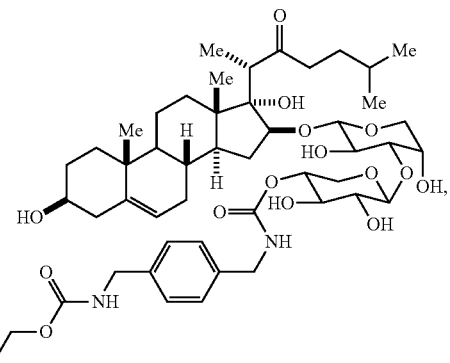
108
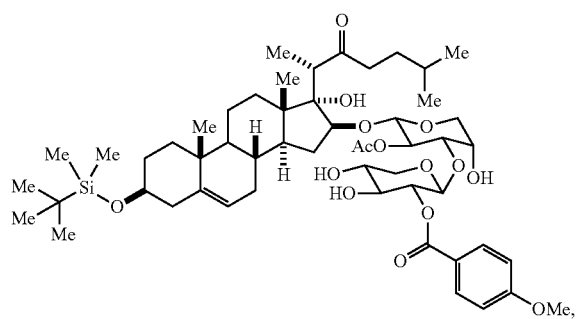
109
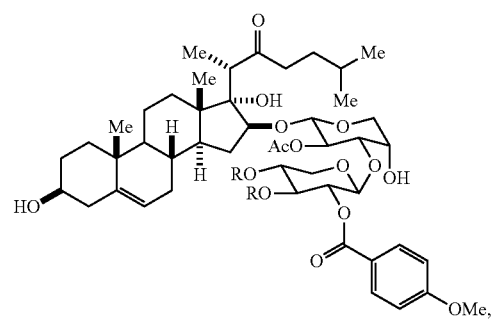
R =
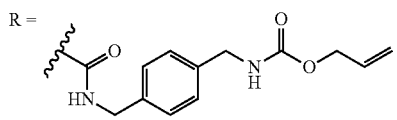
110
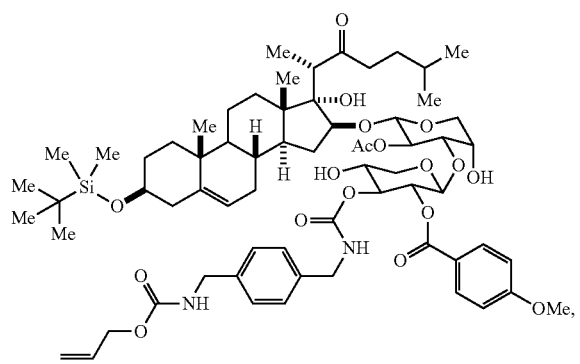
111
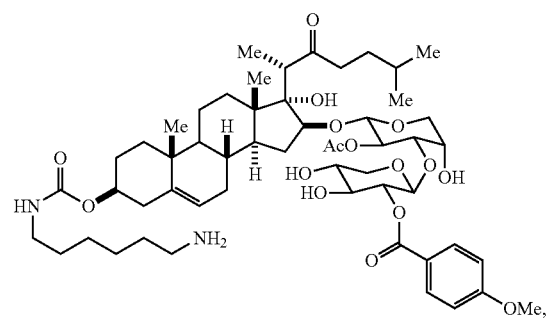
112
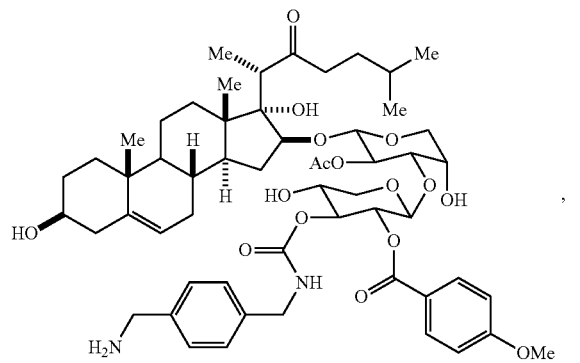
113
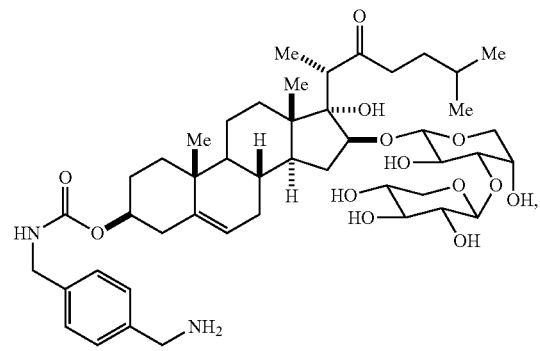

-continued
114
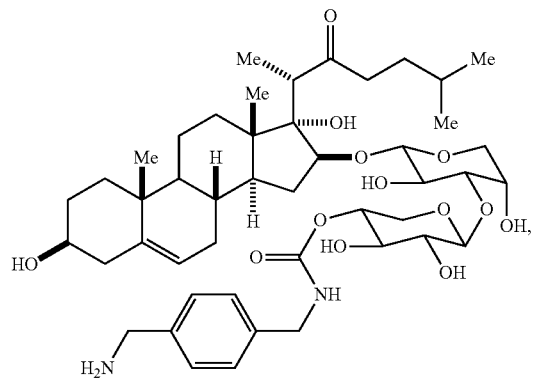
115
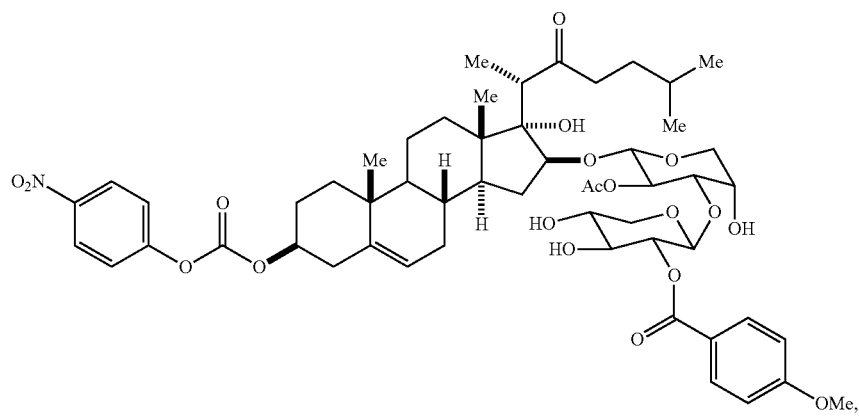
116
117
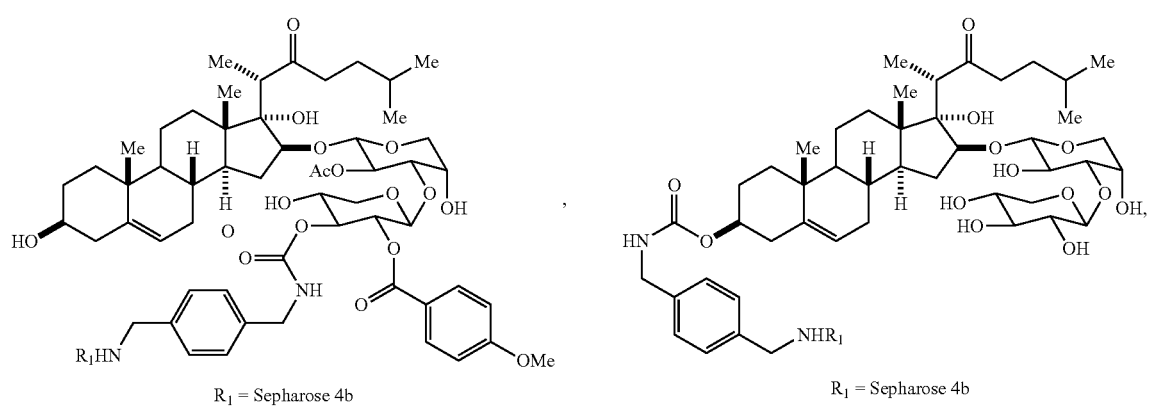
R₁ = Sepharose 4b
R₁ = Sepharose 4b
118
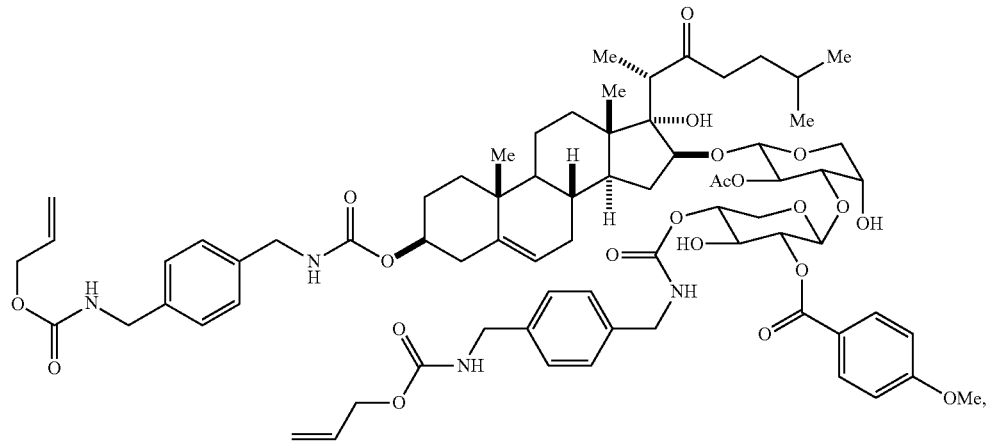

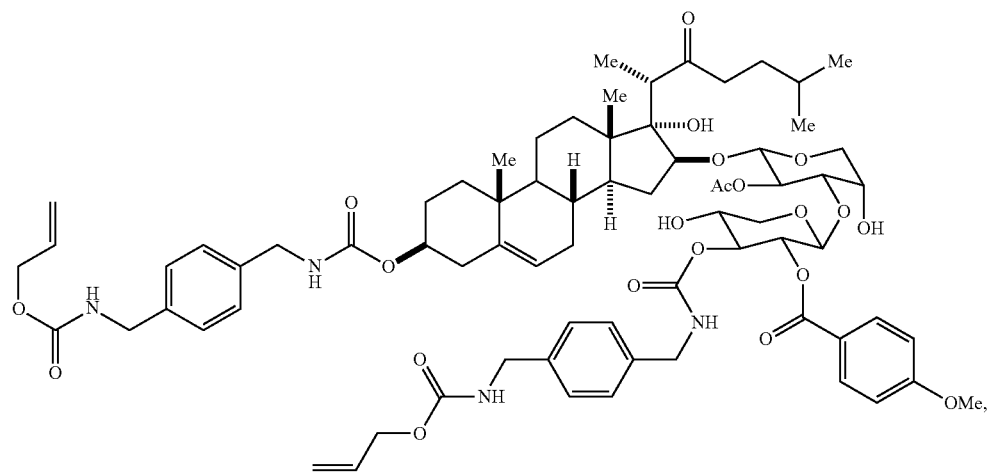
119
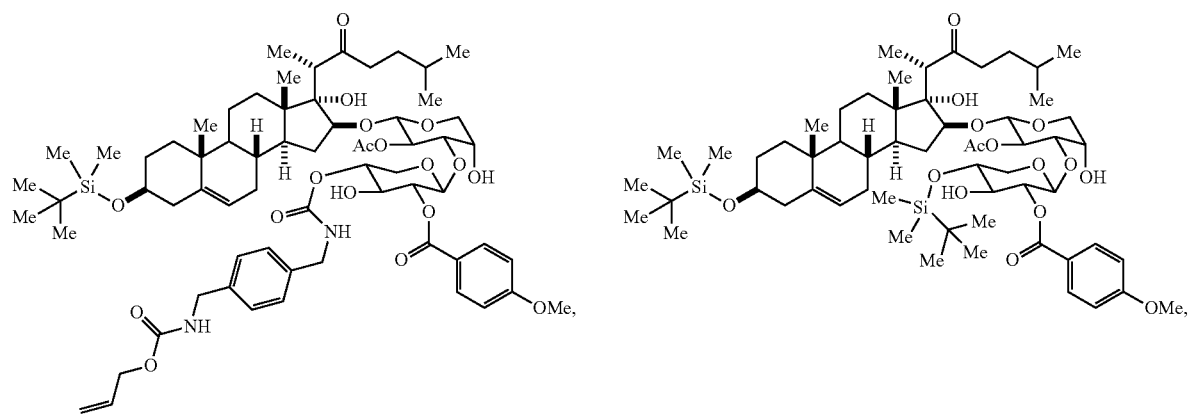
120
121
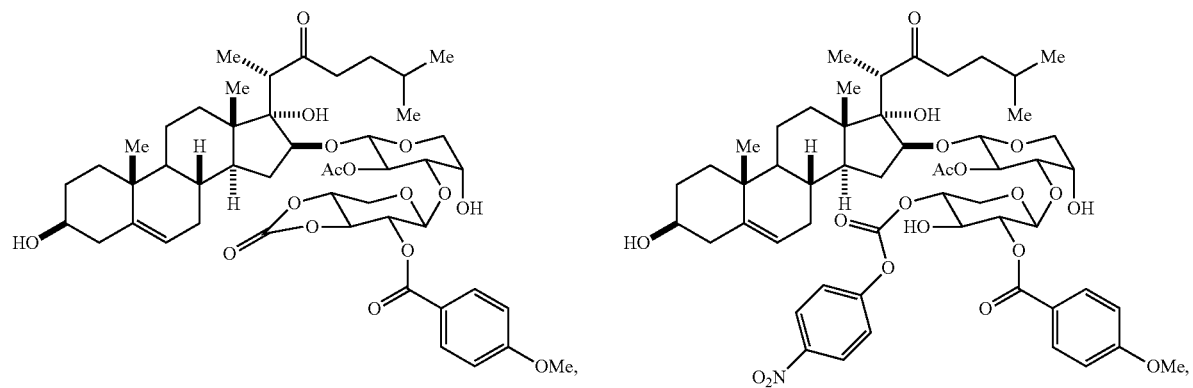
122
123

124
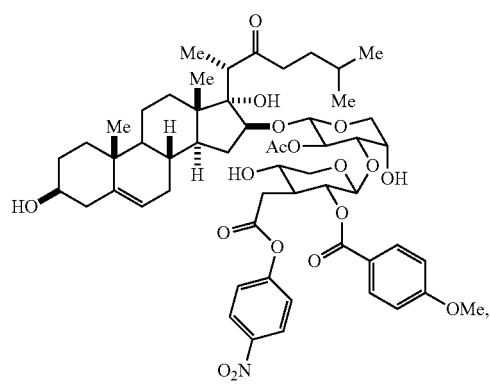
125
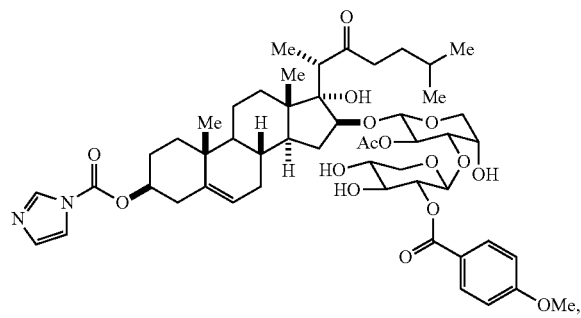
126
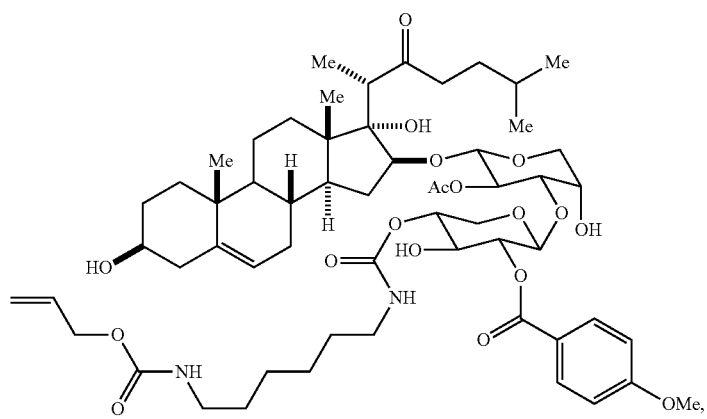
127
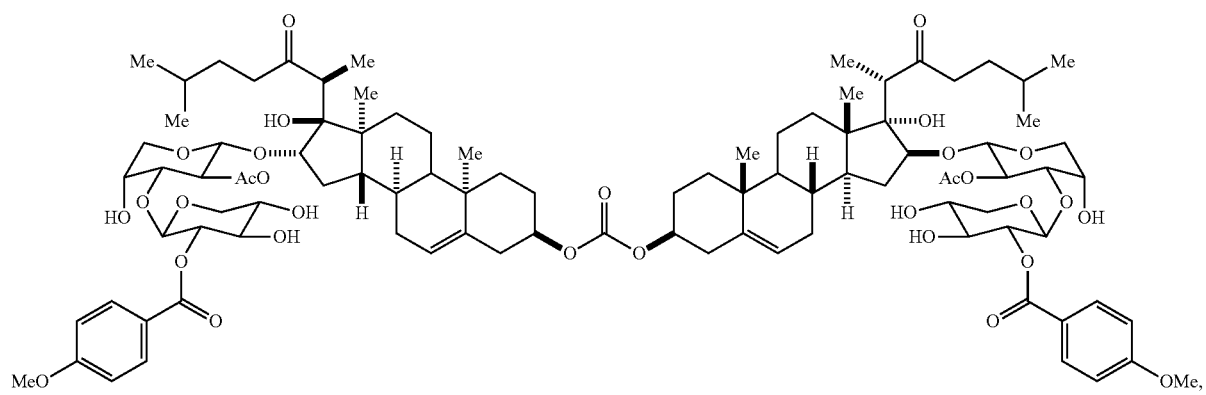
128
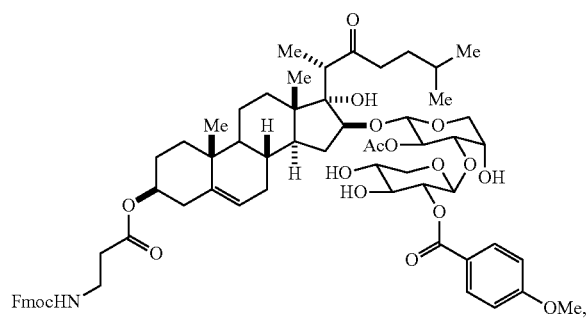
129
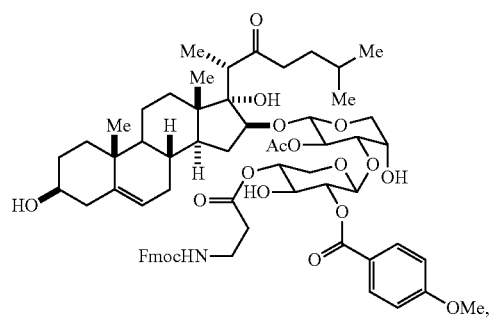

130

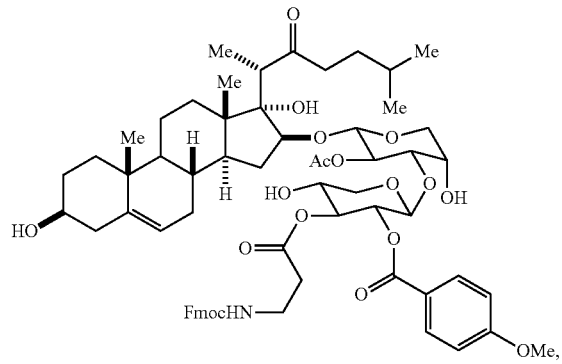

131

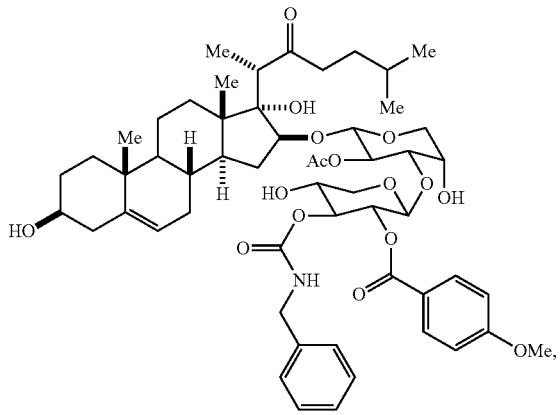

132

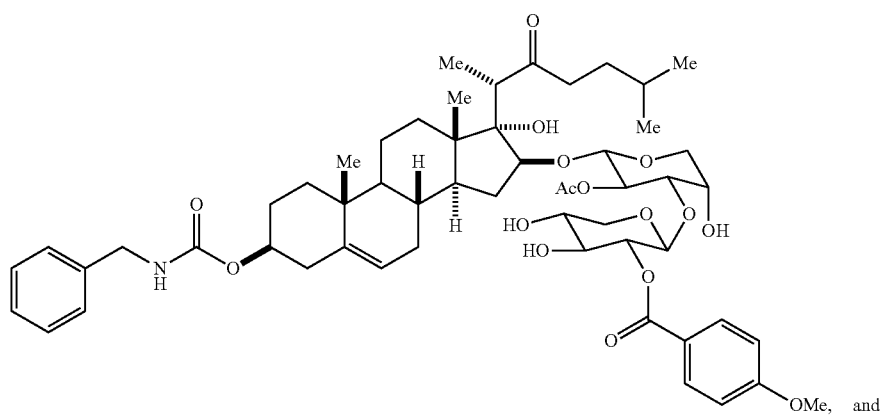

and

133

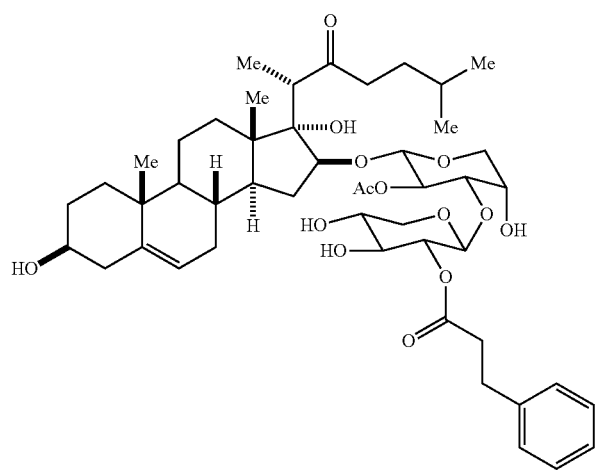

.

An aspect of the invention is a method of killing a cancer cell. The method includes the step of contacting a cancer cell with an effective amount of a conjugate of the invention. In one embodiment, the cancer cell is p21-deficient.

An aspect of the invention is a method of treating a cancer. The method includes the step of administering to a subject in need thereof an effective amount of a conjugate of the invention. In one embodiment, the cells of the cancer are p21-deficient.

Certain compounds of the invention which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of the invention and their salts may exist in more than one crystal form and the present invention includes each crystal form and mixtures thereof.

Certain compounds of the invention and their salts may also exist in the form of solvates, for example hydrates, and the present invention includes each solvate and mixtures thereof.

Certain compounds of the invention may contain one or more chiral centers, and exist in different optically active forms. When compounds of the invention contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of the invention contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of the invention and mixtures thereof.

Certain compounds of the invention may exist in different tautomeric forms or as different geometric isomers, and the present invention includes each tautomer and/or geometric isomer of compounds of the invention and mixtures thereof.

Certain compounds of the invention may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of the invention and mixtures thereof.

Certain compounds of the invention may exist in zwitterionic form and the present invention includes each zwitterionic form of compounds of the invention and mixtures thereof.

Pharmaceutical Compositions

One or more compounds of the invention can be administered alone to a subject or in the form of pharmaceutical compositions where they are mixed with biologically suitable carriers or excipient(s) at doses to treat or ameliorate a disease or condition as described herein. Mixtures of these compounds can also be administered to the subject as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration include, for example, oral, eyedrop, rectal, transmucosal, topical, or intestinal administration; parenteral delivery, including intravenous, intramuscular, intraperitoneal, subcutaneous, intramedullary injections, as well as intrathecal, direct intraventricular, intranasal, or intraocular injections.

Alternatively, one may administer the compound in a local rather than a systemic manner, for example, via injection of the compound directly into a specific site, e.g., a tumor, often in a depot or sustained release formulation.

Furthermore, one may administer the drug in a targeted drug delivery system, for example, in a liposome coated with a cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof, such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and the like salts. Preferred pharmaceutically acceptable acid addition salts include those formed with mineral acids such as hydrochloric acid and hydrobromic acid, and especially those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylaminc; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

Dosage

For any compound or composition used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition). In some cases it is appropriate to determine the $IC_{50}$ in the presence of 3 to 5% serum albumin since such a determination approximates the binding effects of plasma protein on the compound. Such information can be used to more accurately determine useful doses in humans.

A "therapeutically effective dose" refers to that amount of the compound that results in amelioration of symptoms in a subject. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

Exemplary Formulations

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention.

Capsules containing an active compound can be prepared. In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

Tablets can be prepared, for example, from the active compound (10 parts by weight), lactose (190 parts by weight), maize starch (22 parts by weight), polyvinylpyrrolidone (10 parts by weight) and magnesium sterate (3 parts by weight). The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

The tablets can be enteric coated in a conventional manner using a solution of 20% cellulose acetate phthalate and 3% diethyl phthalate in ethanol:dichloromethane (1:1).

Suppositories containing an active compound can be prepared. In the preparation of suppositories, for example, 100 parts by weight of active compound can be incorporated in 1300 parts by weight of triglyceride suppository base and the mixture formed into suppositories each containing a therapeutically effective amount of active ingredient.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "arylalkoxy" and "heteroalkoxy" as used herein, means an aryl group or heteroaryl group, as defined herein, appended to the parent molecular moiety through an alkoxy group, as defined herein. Representative examples of arylalkoxy include, but are not limited to, 2-chlorophenylmethoxy, 3-trifluoromethylethoxy, and 2,3-methylmethoxy.

The term "arylalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkylene," is art-recognized, and as used herein, pertains to a bidentate moiety obtained by removing two hydrogen atoms, either both from the same carbon atom, or one from each of two different carbon atoms, of a hydrocarbon compound, which may be aliphatic or alicyclic, or a combination thereof, and which may be saturated, partially unsaturated, or fully unsaturated. Examples of linear saturated $C_{1-10}$ alkylene groups include, but are not limited to, —$(CH_2)_n$— where n is an integer from 1 to 10, for example, —$CH_2$— (methylene), —$CH_2CH_2$— (ethylene), —$CH_2CH_2CH_2$— (propylene), —$CH_2CH_2CH_2CH_2$— (butylene), —$CH_2CH_2CH_2CH_2CH_2$— (pentylene) and —$CH_2CH_2CH_2CH_2CH_2CH_2$— (hexylene). Examples of branched saturated $C_{1-10}$ alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—. Examples of linear partially unsaturated $C_{1-10}$ alkylene groups include, but are not limited to, —CH=CH— (vinylene), —CH=CH—$CH_2$—, —CH=CH—$CH_2$—$CH_2$—, —CH=CH—$CH_2$—$CH_2$—$CH_2$—, —CH=CH—CH=CH—, —CH=CH—CH=CH—$CH_2$—, —CH=CH—$CH_2$—CH=CH—, and —CH=CH—$CH_2$—$CH_2$—CH=CH—. Examples of branched partially unsaturated $C_{1-10}$ alkylene groups include, but are not limited to, —C($CH_3$)=CH—, —C($CH_3$)=CH$CH_2$—, and —CH=CH—CH($CH_3$)—. Examples of alicyclic saturated $C_{1-10}$ alkylene groups include, but are not limited to, cyclopentylene (e.g., cyclopent-1,3-ylene), and cyclohexylene (e.g., cyclohex-1,4-ylene). Examples of alicyclic partially unsaturated $C_{1-10}$ alkylene groups include, but are not limited to, cyclopentenylene (e.g., 4-cyclopenten-1,3-ylene), and cyclohexenylene (e.g., 2-cyclohexen-1,4-ylene, 3-cyclohexen-1,2-ylene, and 2,5-cyclohexadien-1,4-ylene).

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" and "arylcarbonyloxy" as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio. The terms "arylthio," "alkenylthio" and "arylakylthio," for example, are likewise defined.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein, means —NHC(=O)—, wherein the amido group is bound to the parent molecular moiety through the nitrogen atom. Examples of amido include alkylamido such as $CH_3C$(=O)N(H)— and $CH_3CH_2C$(=O)N(H)—.

The term "amino" as used herein, refers to radicals of both unsubstituted and substituted amines appended to the parent molecular moiety through a nitrogen atom. The two groups are each independently hydrogen, alkyl, alkylcarbonyl, alkylsulfonyl, arylcarbonyl, or formyl. Representative examples include, but are not limited to methylamino, acetylamino, and acetylmethylamino.

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicylic aromatic rings. For example, bicyclic aromatic rings containing heteroatoms in a hydrocarbon ring structure are referred to as bicyclic heteroaryl rings.

The term "aryl," as used herein, means a phenyl group or a naphthyl group. The aryl groups of the present invention can be optionally substituted with one, two, three, four, or five substituents independently selected from the group consisting of deuterium, tritium, is alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, silyl and silyloxy.

The term "arylalkyl" or "aralkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkoxy" or "arylalkyloxy" as used herein, means an arylalkyl group, as defined herein, appended to the parent molecular moiety through an oxygen atom. The term "heteroarylalkoxy" as used herein, means a heteroarylalkyl group, as defined herein, appended to the parent molecular moiety through an oxygen atom.

The term "arylcarbonyl" as used herein, means an aryl group, as defined herein, appended to the parent molecular moiety through a carbonyl group, as defined herein. Representative examples of arylcarbonyl include, but are not limited to, benzoyl and naphthoyl.

The term "aryloxy" as used herein, means an aryl group, as defined herein, appended to the parent molecular moiety through an oxygen atom. The term "heteroaryloxy" as used herein, means a heteroaryl group, as defined herein, appended to the parent molecular moiety through an oxygen atom.

The term "carbonyl" as used herein, means a —C(=O)— group.

The term "carboxy" as used herein, means a —CO$_2$H group.

The term "cycloalkyl" as used herein, means monocyclic or multicyclic (e.g., bicyclic, tricyclic, etc.) hydrocarbons containing from 3 to 12 carbon atoms that is completely saturated or has one or more unsaturated bonds but does not amount to an aromatic group. Examples of a cycloalkyl group include cyclopropyl, cyclobutyl, cyclopentyl, cyclopentenyl, cyclohexyl and cyclohexenyl.

The term "cycloalkoxy" as used herein, means a cycloalkyl group, as defined herein, appended to the parent molecular moiety through an oxygen atom.

The term "cyano" as used herein, means a —CN group.

The term "formyl" as used herein, means a —C(=O)H group.

The term "halo" or "halogen" means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocyclyl", as used herein, include non-aromatic, ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, or 3 substituents independently selected from deuterium, tritium, alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, silyl and silyloxy.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention, representative examples of heteroaryl include: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention may be substituted with 0, 1, 2, or 3 substituents independently selected from deuterium, tritium, alkenyl, alkoxy, alkoxycarbonyl, alkoxysulfonyl, alkyl, alkylcarbonyl, alkylcarbonyloxy, alkylsulfonyl, alkylthio, alkynyl, amido, amino, carboxy, cyano, formyl, halo, haloalkoxy, haloalkyl, hydroxyl, hydroxyalkyl, mercapto, nitro, silyl and silyloxy.

The term "heteroarylalkyl" or "heteroaralkyl" as used herein, means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl)ethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —NO$_2$ group.

The term "prenyl" as used herein dimethylallyl, geranyl, neryl, farnesyl and geranylfarnesyl, as well as partially saturated equivalents thereof.

The term "prenylaryl" or "prenylheteroaryl" means a prenyl, as defined herein, appended to the parent molecular moiety through an aryl or heteroaryl, as defined herein. Representative examples of haloalkoxy include geranylphenyl and geranylpyridinyl.

The term "silyl" as used herein includes hydrocarbyl derivatives of the silyl (H$_3$Si—) group (i.e., (hydrocarbyl)$_3$Si—), wherein a hydrocarbyl groups are univalent groups formed by removing a hydrogen atom from a hydrocarbon, e.g., ethyl, phenyl. The hydrocarbyl groups can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The following examples are provided to illustrate one or more preferred embodiments of the invention. Numerous variations may be made to the following examples that lie within the scope of the invention.

EXAMPLES

General Methods

Natural Product Compounds. Cephalostatin 1 (1) (~2 mg) was supplied via total synthesis in accordance with published method Fortner et al. (2009) *J Am Chem Soc* 132:275-80. OSW-1 (2) was obtained through isolation from nature by Y. Mimaki and co-workers and also through total synthesis. OSW-1 analogs 6-9 (FIG. 1B) were prepared as detailed in WO 2010/068877, the entire contents of which is incorporated herein by reference. Schweinfurthin A (4a) (~3 mg) and ritterazine B (3) (0.2 mg) were obtained from the NCI.

Antibodies. Rabbit anti-OSBP (N-terminus) polyclonal was obtained as a gift from H. Arai; rabbit anti-OSBP (C-terminus) (11096-1-AP) polyclonal was obtained from Proteintech; rabbit anti-actin polyclonal was obtained from Sigma; mouse anti-tubulin monoclonal (DSHB E7) was obtained from Developmental Studies Hybridoma Bank; rabbit anti-c-Myc (N-262) polyclonal was obtained from Santa Cruz Biotechnologies; mouse anti-c-Myc (9E10) monoclonal was obtained from Santa Cruz Biotechnologies; rabbit anti-COL4A3BP/CERT (ab72536) polyclonal was obtained from Abcam; mouse anti-P230 monoclonal was obtained from BD Biosciences.

Cell lines. HCT-116 wild-type and HCT-116 p21$^{-/-}$ cell lines were supplied by the Bert Vogelstein lab (Johns Hopkins). CHO-7 cells were a gift from Michael Brown and Joseph Goldstein (UT-Southwestern). M12 cells were a gift from Daniel Ory (Washington University in St. Louis). All other cell lines were purchased from American Type Culture Collection (ATCC, Manassas, Va.).

Plasmids, Vectors, and OSBP1 shRNAs. The pcDNA™3.1/myc-His vector and the pcDNA™3.1/myc-His lacZ control vector were purchased from Invitrogen. OSBP1 cDNA was purchased from Open Biosystems. ORP4L cDNA was cloned from HeLa total RNA extract using standard molecular biology techniques. The OSBP1 and ORP4L cDNAs were cloned into the pcDNA™3.1/myc-His vector (Invitrogen). OSBP1(M446W), OSBP1 (V582M), ORP4L(M550W), and ORP4L(V686M) mutants were prepared with the QuikChange® II XL Site-directed Mutagenesis Kit (Stratagene) as instructed by the supplier. OSBP1 shRNAs in the pSIREN-RetroQ vector (BD Biosciences) were generously provided by Giulio Romeo (Joslin Diabetes Center).

Affinity chromatography experiment—iTRAQ. 25 mg HeLa-S3 S100 lysate was pre-incubated with DMSO or 10 µM OSW-1, followed by overnight incubation at 4° C. with 30 µL of packed OSW-1 affinity matrix 6b per pulldown. The resin was transferred to a Mobicol 1 mL column (Boca Scientific). The resin was extensively washed with buffer, and the bound protein was eluted via denaturation in NuPage® LDS sample loading buffer under reducing conditions, alkylated with iodoacetamide, and separated on a NuPage® 4-12% Bis-Tris gradient gel (Invitrogen). Gel lanes were excised using a LEAP 2-DiD robot, in-gel digested with trypsin (Tecan Freedom EVO 200) and the resulting 8 samples per lane were labeled with iTRAQ™ reagent (AB/Sciex). Samples were mixed and analyzed using an Eksigent NanoLC 1D+HPLC coupled to a Thermo LTQ-Orbitrap XL mass spectrometer operated in Pulsed-Q Dissociation (PQD) mode. Peptide/protein identification and validation, quantitative data analysis was done via an automated workflow incorporating a forward/reverse version of IPIv3.55, Mascot v2.2 (Matrix Science) and Transproteomic pipeline v3.3sqall (Institute for Systems Biology) Spotfire DXP. Protein fold changes were derived as median peptide fold change, p-values were calculated using a one-way T-test, and data were visualized for further analysis using Spotfire DXP.

Cell viability assay. Cells were plated into 96-well plates in 75 µL of media. After 24 h, a time-zero plate was produced by adding 25 µL of media and 20 µL of CellTiter-Blue® (Promega) to the wells, followed by incubation at 37° C. for 90 min. Fluorescence (544 nm excitation; 590 nm emission) was detected using a SPECTRAmax® Gemini XS to establish cell viability at time of dosing. Then, compounds were serially diluted in media and delivered to the cells as 4× solutions in 25 µL of media. At either 48 h or 72 h, CellTiter-Blue® was added and the fluorescence was recorded as described above. Growth relative to untreated cells was calculated and this data was fitted to a four-parameter dose-response curve using Graphpad Prism 5.

Overexpression-viability assays with wild-type and mutant OSBP/ORP4L constructs were carried out by transfecting HeLa cells with the appropriate plasmids using Lipofectamine™ LTX with PLUS™ reagent (Invitrogen) as instructed, and after 8 h of transfection, the cells were re-plated for the cell viability assay, performed as described above. Expression levels were evaluated by immunoblotting at the time of dosing.

Immunofluorescence microscopy. HCT-116 or A549 (adenocarcinomic human alveolar basal epithelial) cells were plated on coverslips in 6-well plates. After 72 h, the culture media was removed and replaced with media containing either compound or vehicle control. At the indicated timepoints, the cells were fixed for 10 min using 3.7% formaldehyde in PBS. The coverslips were washed with PBS and permeabilized for 5 min with 0.5% Triton X-100 in PBS. Following PBS washing, the coverslips were blocked for 30 min using Image-iT™ FX (Invitrogen), washed with PBS, and then blocked for 30 min at room temperature (RT) with 1% BSA in PBS (BSA/PBS). The coverslips were then incubated overnight at 4° C. with a primary antibody solution in BSA/PBS. The coverslips were washed with BSA/PBS and incubated for 60 min at RT with Alexa Fluor®-conjugated secondary antibodies (Invitrogen) in BSA/PBS, with the final 30 min including incubation with Hoescht 33258. The coverslips were then washed sequentially with BSA/PBS, PBS, and water and finally mounted on microscope slides using Aqua Poly/Mount (Polysciences Inc.). Imaging data was acquired using Zeiss LSM 510 META scanning confocal microscope.

General Synthetic Chemistry Procedures. All reactions were performed in oven- or flame-dried glassware under a positive pressure of argon unless noted otherwise. Flash column chromatography was performed either as described by Still et al. (1978) *J Org Chem* 43:2923-5 employing E. Merck silica gel 60 (230-400 mesh ASTM). Tetrahydrofuran (THF), diethyl ether, methylene chloride ($CH_2Cl_2$), toluene, and dimethylformamide (DMF) were degassed with argon and passed through a solvent purification system (designed by J. C. Meyer of Glass Contour) utilizing alumina columns.

Thin layer chromatography (TLC) analyses and preparative TLC (pTLC) purification was performed on 250 µm Silica Gel 60 $F_{254}$ plates purchased from EM Science (Gibbstown, N.J.).

Instrumentation. Infrared spectra were recorded on a Perkin Elmer Spectrum One FT-IR spectrometer. $^1$H and $^{13}$C NMR spectra were recorded on a Varian INOVA600, INOVA500 or Mercury400 spectrometer. Chemical shifts for proton and carbon resonances are reported in ppm (δ) relative to the residual proton or the specified carbon in chloroform (δ 7.27, proton; 77.23, carbon), $CD_3CN$ (δ 1.94, proton; 118.26, nitrile carbon), pyridine-$d_5$ (δ 8.71, C2-H, proton; 149.9, C2, carbon). Mass spectra were obtained from the Harvard University Mass Spectrometry Laboratory using an Agilent 6210 TOF LC/MS instrument. High pressure liquid chromatography (HPLC) purification was performed on an Agilent 1100. All compounds used for biological experimentation were HPLC purified. The yields reported are following silica gel purification, prior to HPLC purification. Semi-preparative HPLC was performed using a diode-array detector with the indicated columns and solvent conditions.

[$^3$H]-25-Hydroxycholesterol charcoal-dextran binding assay. OSBP1, OSBP1(M446W), OSBP1(V582M), ORP4L, ORP4L(M550W), ORP4L(V686M), and lacZ were cloned into the pcDNA3.1 vector (Invitrogen), which encodes a C-terminal myc-his tag. These vectors were transfected into HEK-293T cells using Lipofectamine™2000 (Invitrogen), and 48 h after transfection, on-plate lysis of the transfected cells with the M-Per®/HALT™ with EDTA (ThermoScientific) reagent was performed, followed by ultracentrifugation at 100,000 g. The S100 lysate was diluted to 0.2 mg/mL, aliquoted and stored at −80° C. until use. The HEK-293T OSBP1-, ORP4L- or lacZ-myc-his lysate was incubated with [$^3$H]-25-hydroxycholesterol at 4° C. for 16 h in 96-well plates. After incubation, charcoal/dextran (C/D) was added to the wells for 30 min of shaking at RT, followed by centrifugation for 15 min at 1900 g to pellet the C/D. The C/D-cleared lysate was added to MicroScint™-20 (PerkinElmer) scintillation fluid, and the remaining protein-bound radiolabel was quantified using a TopCount™ scintillation counter. [$^3$H]-25-hydroxycholesterol binding curves and competition curves were repeated at least three times. Competition binding experiments to generate $K_i$ values for compounds 1, 2, 3, 4a, 6, 7, 8, and 9 were performed with 20 nM of [$^3$H]-25-hydroxycholesterol.

High-throughput $^3$H-25-hydroxycholesterol ($^3$H-25-OHC) Charcoal/Dextran Binding Assay:

Reagents:

Norit A® Charcoal (MP Biomedicals cat.#102489). Dextran 500,000 MW powder (Spectrum Chemicals, cat.#D1004). Poyl(vinyl alcohol) (PVA), 80% hydrolyzed (Sigma-Aldrich cat.#360627). 13.2 µM 97% $^3$H-25-hydroxycholesterol (1 µCi/µL, 77-80 mmol/Ci) solution in ethanol (PerkinElmer cat.#NET674250UC). OptiPlate™ 96-well plates (PerkinElmer cat.#6005290). 'V'-shaped 96-well plates (Costar cat.#3897). Microscint™-scintillation fluid (PerkinElmer cat.#6013621). TopSealA-Films (PerkinElmer cat.#6005185). PlateMax, Aluminum Foil Sealing Film (Axygen cat.#PCR-AS-28). Lipofectamine 2000 (Invitrogen, cat.#11668). Opti-Mem® Reduced Serum Media (Invitrogen cat.#11058).

Binding Buffer: 50 mM HEPES pH 7.4, 50 mM KCl, 5 mM DTT, 1×HALT™ Protease Inhibitor with EDTA (ThermoScientific).

OSBP1, ORP4L and LacZ cDNA were cloned into the pcDNA3.1 vector (Invitrogen) with standard molecular biology methods and verified via sequencing. OSBP1(M446W) and to OSBP1(V582M) mutants were prepared with the QuikChange® II XL Site-directed Mutagenesis Kit (Stratagene) as instructed by the supplier and verified via sequencing.

Charcoal/Dextran (C/D): C/D was prepared as described in Taylor and Kandutsch (1985) *Methods Enzymol* 110:9-19.

The 20% PVA solution was prepared in a 50 mL conical tube, adding water to the solid PVA. The PVA solution was heated in an 80° C. water bath, with frequent sonication and vortexing, until homogeneity was achieved (~1 h). The 20% PVA solution was then kept at room temperature (rt).

Procedures:

A. Preparation of lysates from OSBP1-myc-his or ORP4L-myc-his Cells for Binding Assays:

This procedure is based on the online protocol found at http://www.lipidomicnet.org/index.php/Oxysterol_binding_assay. Importantly, using the cell lysis conditions—multiple passages through a small gauge needle—caused a significant amount of OSBP1 and ORP4L proteolysis. Although the presence of the overexpressed degraded OSBP1 or ORP4L had no measurable effect of 25-OHC binding, the different OSBP1 and ORP4L protein fragments had dramatically different binding affinities for the ORPphilins. This mandated developing cell lysis conditions with no OSBP1 or ORP4L degradation. Also, the binding assay was adapted into a 96-well, high-throughput format.

4×10$^6$ HEK-293T cells were plated in 10 cm$^2$ dishes. After 24 h, the cells were ~90% confluent and ready for transfection. 24 µg of OSBP1-myc-his, OSBP1-M446W-myc-his, OSBP1-V582M-myc-his, or ORP4L-myc-his in the pcDNA3.1 vector was transfected into the 10 cm$^2$ dishes using Lipofectamine 2000 (60 µL per 10 cm$^2$ dish), following the suppliers instructions. Opti-Mem® was used to mix the plasmid and transfection reagent (total of 3 mL of Opti-Mem® for each 10 cm$^2$ plate). Then, 12 mL of HEK-293T media (DMEM/10% FBS) with no antibiotics were added per dish.

After 48 h incubation, the cells were washed once with rt PBS, then 2 mL of the M-Per®/HALT™ with EDTA (ThermoScientific) cell-lysis reagent was added per plate. The plates were rocked for 5 min at 250 rpm at rt. All subsequent steps were performed at 4° C. or with tubes on ice. The lysate was transferred to ultracentrifuge tubes and centrifuged for 1 h at 100,000 g at 4° C. in either a 70 Ti or a 70.1 Ti rotor (Beckman Coulter) in a Beckman Coulter ultracentrifuge. BCA protein determination on the supernatant was performed and the lysates were diluted to 0.2 mg/mL with Binding Buffer. Due to the high level of expression of OSBP1-myc-his and its mutants in the HEK-293T, the 0.2 mg/mL S100 protein lystate was then diluted 1:1 with non-transfected HEK-293T 0.2 mg/mL S100 lysate. The 0.2 mg/mL S100 ORP4L-myc-his lysate was not diluted with non-transfected lysate. Each 10 cm$^2$ dish transfected with OSBP1-myc-his generated ~40 mL of lysate for binding. Each 10 cm$^2$ dish transfected with ORP4L-myc-his generated ~20 mL of lysate for binding. The lysates were aliquoted, snap-frozen in liquid $N_2$ and stored at −80° C. until use.

B. OSBP1-myc-his or ORP4L-myc-his $^3$H-25-OHC Binding Assays

Lysates were thawed on ice, with brief periods of hand warming. Both the $^3$H-25-OHC direct binding assays and the $^3$H-25-OHC competition binding assays were set up similarly, with a large stock of binding assay lysate being prepared, then 73.5 µL of the binding assay mixture dispensed using a multi-channel pipettor into "V"-shaped 96-well plates. For the $^3$H-25-OHC direct binding assay, 1.5 µL of $^3$H-25-OHC and $^3$H-25-OHC/40×25-OHC added to the wells in dilutions in 100% ethanol. For the $^3$H-25-OHC competition binding assays, $^3$H-25-OHC was added to the large stock of binding assay lysate to a final concentration of 20 nM. This $^3$H-25-OHC-containing binding lysate was then dispensed using a multi-channel pipettor into the 96-well plates. Then, 1.5 µL of a serial dilution of the inhibitors in either 100% ethanol (25-OHC) or DMSO (the ORPphilins) was added to each well.

The binding lysate used in each well of the 96-well plate consisted of 60 µL of 0.2 mg/mL S100 lysate, 7.5 µL 20% PVA, and 5.6 µL 2M KCl. For $^3$H-25-OHC binding curve experiments, 0.4 µL of buffer was then added (total volume per well: 73.5 µL). For the $^3$H-25-OHC inhibition competition assays, 0.11 µL of 13.2 µM $^3$H-25-OHC and 0.29 µL binding buffer was added for each well (total volume per well: 73.5 µL).

New serial dilutions were made for each experiment. Compound dilutions were performed in 0.2 mL polypropylene 96-well plates (VWR cat#82006-636). All 25-OHC dilutions were performed in the cold room with cold ethanol. ORPphilin dilutions in DMSO were performed at rt. Compound was added to triplicate wells, in the cold room for 25-OHC. The lysate-containing plates were taken out of the cold room briefly to allow addition of the DMSO compounds.

Binding assays were incubated, standing, for 16 h at 4° C. Then 30 µL of the rt C/D solution was multichannel pipetted into new "V" shaped 96-well plates, and 60 µL of the binding lysate mixture was then added. The plates were briefly, lightly vortexed (~10 sec), 10 and then rocked at 250 rpm for 30 min at rt. The plates were then centrifuged at 1900 g for 15 min at 4° C. in Microplate Carriers (Sorvall cat. #75006449S) in a Sorvall Legend RT centrifuge. Carefully so as to not disturb the C/D pellet, 30 µL of the supernatant was transferred to 170 µL of Microscint-20 in the OptiPlates. The plates were sealed with the TopSealA-Films, and vigorously vortexed (max speed, >1 min). $^3$H-25-OHC detection in the wells was then performed using a TopCount Scintillation detector, counting each well for 2 min. Data was graphed and analyzed using GraphPad PrismS, using non-linear regression to determine $K_D$ and $K_1$ values.

Example 1

OSBP1 and ORP4L Are Receptors of ORPphilins

Figure 2A:
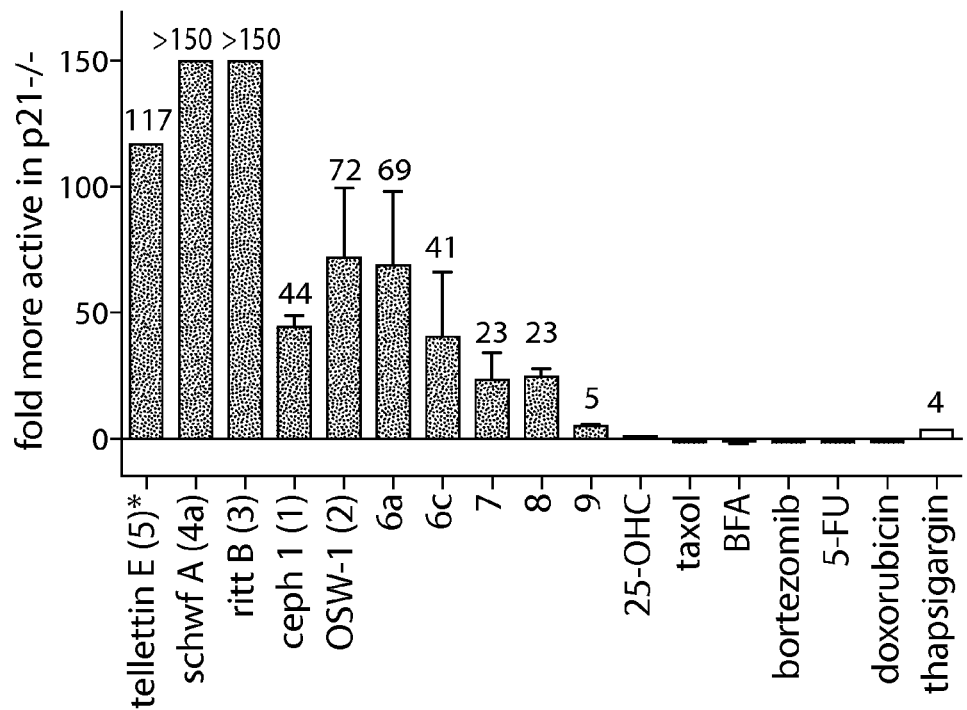
FIG. 2A is graph depicting selective growth inhibitory effects of compounds 1-5 and OSW-1 analogs 6-8 toward HCT-116 (human colorectal carcinoma) cells lacking p21. BFA: brefeldin A.

Since similar NCI-60 cytotoxicity profiles can only indicate the possibility that compounds share a mechanism of action, additional experimental support that compounds 1-5 form a new class of mechanistically related antiproliferative agents was sought. Stellettin E (5) was previously reported to be 117-times more growth inhibitory to HCT-116 p21$^{-/-}$ cells than HCT-116 wild-type (wt) cells. Tasdemir et al. (2002) J Nat Prod 65:210-4. GI$_{50}$-values of the compounds were determined in HCT-116 p21$^{+/+}$ (wt) and p21$^{-/-}$ cells after 48 h using a resazurin redox dye to measure cell viability. The growth inhibitory activities of compounds 1-4a were also significantly enhanced in HCT-116 p21$^{-/-}$ cells versus HCT-116 wt cells (FIG. 2A). The high degree of p21$^{-/-}$ selectivity of compounds 1-5 was a unique characteristic of these compounds since many other antiproliferative small molecules tested did not exhibit this selectivity (FIG. 2A). The p21$^{-/-}$ selectivity of compounds 1-5 provided evidence beyond the NCI-60 COMPARE analysis that these compounds were mechanistically related. Moreover, this p21$^{-/-}$ selectivity could be used as a defining feature for this class of compounds, allowing analogs of 1-5 to be identified that shared the same characteristic mechanism of action.

Figure 1B:
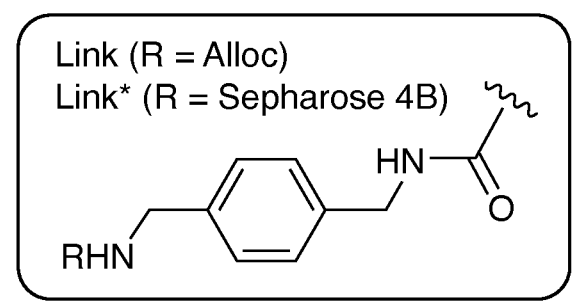
FIG. 1B depicts selected OSW-1 analogs.

Affinity purification was used to identify putative targets of compounds 1-4a. With access to sufficient quantities of OSW-1 (2), OSW-1 (2) analogs were prepared with the goal of maintaining the potency and the p21$^{-/-}$ selectivity of 2; these same analogs were also used to prepare an OSW-1 affinity matrix (FIG. 1B). It was discovered that Alloc-protected amine 6a, prepared through formation of a carbamate with the C3-hydroxyl of the xylosyl saccharide, maintained the antiproliferative potency of 2 and, critically, also exhibited p21$^{-/-}$ selectivity commensurate with that of 2 (FIG. 2A).

Figure 2B:
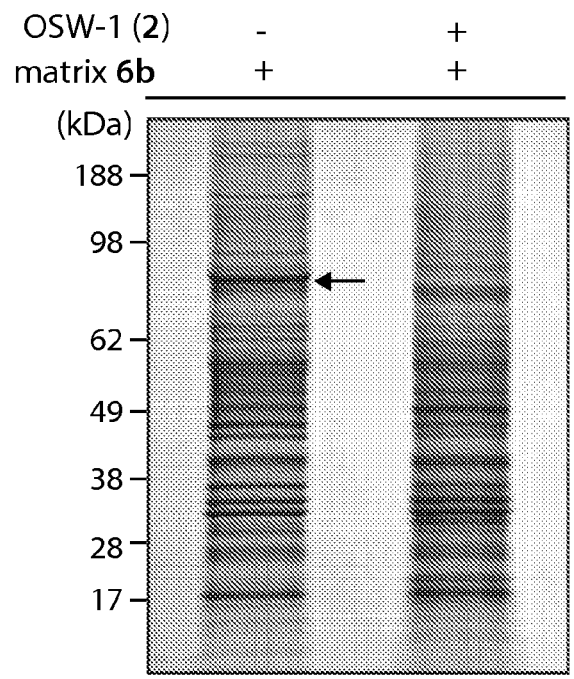
FIG. 2B is an image of a Coomassie-stained polyacrylamide gel electrophoresis (PAGE) chromatograph of HeLa cell lysates using 6b in the absence (left lane) and presence (right lane) of excess OSW-1. Arrow: band identified as OSBP1.

Analog 6a was then loaded on resin to prepare sepharose-linked reagent 6b (FIG. 1B). The affinity matrix was incubated overnight with HeLa S-100 lysate at 4° C. Following washing, the bound proteins were eluted by denaturation. Samples were separated on a protein gel and stained with Coomassie. Affinity chromatography of HeLa-S3 cell lysate with 6b followed by protein gel electrophoresis afforded a significantly enriched band at ~90 kD (FIG. 2B, see arrow). The band indicated with the arrow was excised from the gel and, following trypsin digestion and mass spectrometry analysis, was identified as OSBP1. Significantly, pretreatment of the HeLa-S3 lysate with 10 µM of OSW-1 (2) competed away this band, indicating that this protein specifically bound OSW-1. Analysis of the full gel lane by iTRAQ-based quantitative mass spectrometry revealed that this band corresponded to oxysterol binding protein 1 (OSBP1).

Figure 2C:
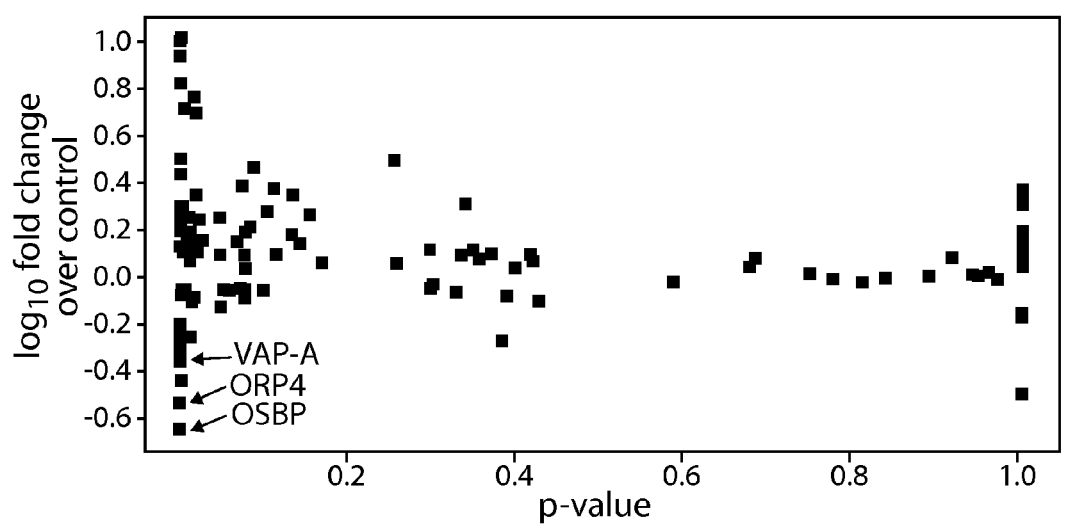
FIG. 2C is a scatter plot depicting 121 proteins identified and quantified by iTRAQ-based quantitative proteomics. Competition is plotted on the y-axis as $\log_{10}$ fold change for 10 μM OSW-1 over dimethylsulfoxide (DMSO) control and p value representing statistical significance is plotted on x-axis. P-values are arbitrarily set to 1 for non-significant single peptide quantitations. VAP-A: vesicle-associated membrane protein-associated protein A.

Amongst the 121 identified proteins, OSBP1 and OSBP-paralog ORP4L showed the most significant competition by soluble 2 (FIG. 2C). Additionally, VAP-A (vesicle-associated membrane protein-associated protein A) showed a >50% competition by 2. VAP-A is known to interact with both OSBP1 and ORP4L. Furthermore, OSBP1 and ORP4L are believed to physically interact. Wyles et al. (2007) Exp Cell Res 313:1426-37. Therefore, any of these three proteins could have been the direct binding partner of affinity reagent 6b, with the other two proteins being co-purified. However, since OSBP1 and ORP4L are high-affinity receptors of oxysterols, and 2 comprises an oxysterol moiety, OSBP1 and ORP4L were chosen for investigation as putative targets for compounds 1-4.

Figure 2D:
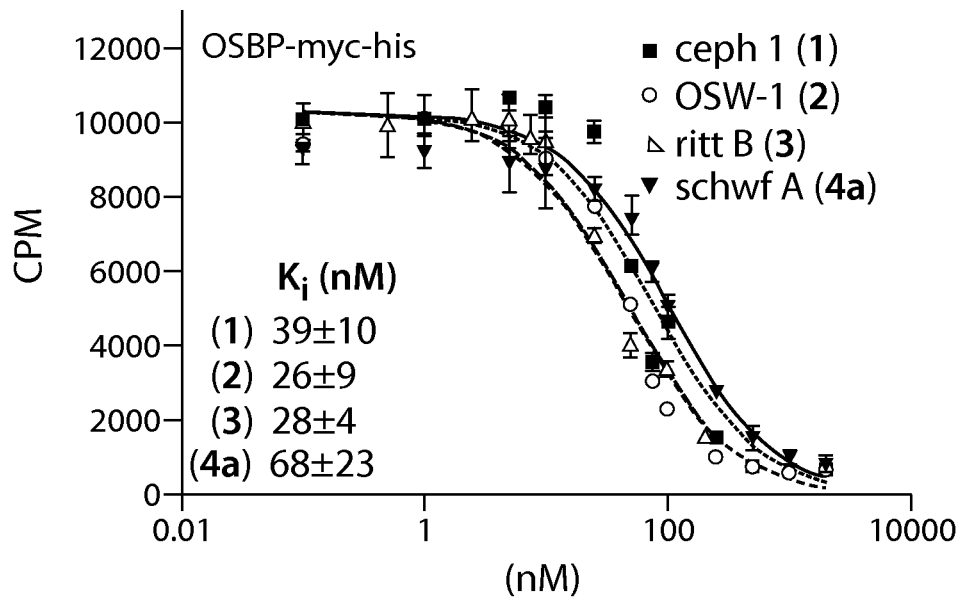
FIG. 2D is a graph depicting competition binding experiments of [$^3$H]-25-OHC (20 nM) with compounds 1-4a in S100 lysate made from HEK-293T cells overexpressing OSBP1-myc-his. CPM: counts per minute.
Figure 2E:
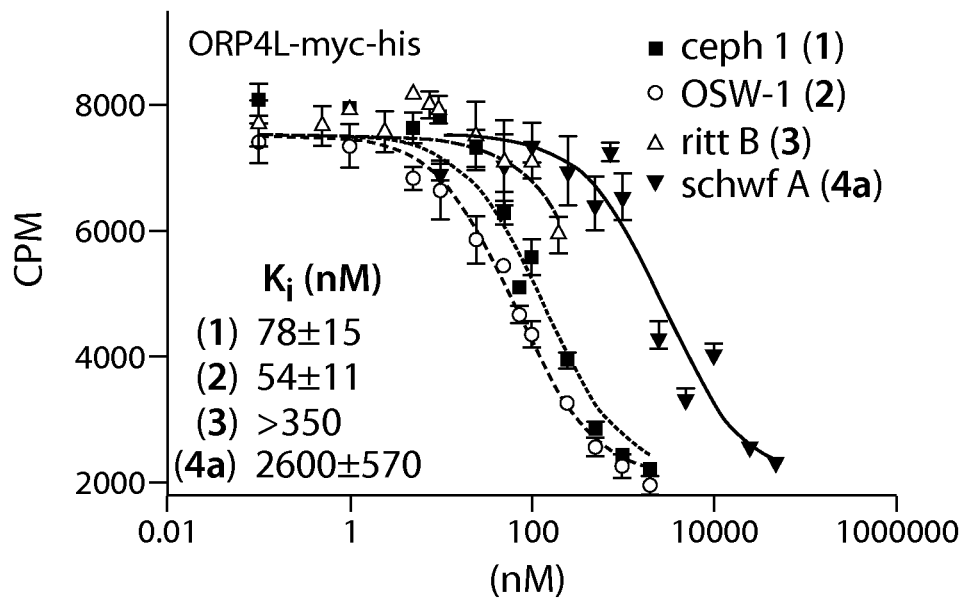
FIG. 2E is a graph depicting competition binding experiments of [$^3$H]-25-OHC (20 nM) with compounds 1-4a in S100 lysate made from HEK-293T cells overexpressing ORP4L-myc-his. CPM: counts per minute.

To determine if 1-4 bind OSBP1 or ORP4L, competition-binding assays with OSBP1-myc-his or ORP4L-myc-his were performed, using [$^3$H]-25-hydroxycholesterol (25-OHC, 11), a high-affinity ligand of both proteins (OSBP1 $K_d$=32±14 nM; ORP4L, $K_d$=54±23 nM). Binding experiments were performed at 4° C. for 16 h. Unbound sterol was removed using dextran-coated charcoal, and protein-bound sterol left in the supernatant was quantified by scintillation counting. $K_i$-values were determined as mean±s.d. from at least three independent experiments. As shown in FIG. 2D and FIG. 2E, it was found that 1, 2, 3 and 4a each bind OSBP1-myc-his ($K_i$=39±10 nM, 26±9 nM, 28±4 nM, and 68±23 nM, respectively) and that 1, 2, 3 and 4a also bind ORP4L-myc-his ($K_i$=78±15 nM, 54±11 nM, >360 nM, and 2600±570 nM respectively). Compound 4a is an outlier compared to the other ORPphilins, since its affinity for ORP4L is significantly (~40 fold) lower than for OSBP1.

Example 2

Cellular Levels of OSBP1 and ORP4L Affect the Antiproliferative Activities of ORPphilins To ascertain if the antiproliferative activity of the ORPphilins depended on the levels of OSBP1 and ORP4L in cells, short hairpin RNA (shRNA) knockdown of OSBP1 expression was performed and then its effect on the growth inhibitory activity of 1, 2, and 4a measured. Cells were treated with compounds for 72 h and $GI_{50}s$ were determined as described in connection with FIG. 2. While reduction of OSBP1 levels by 85% (FIG. 3B) did not affect HCT-116 $p21^{-/-}$ cell growth, it did sensitize cells to 1, 2, and 4a by 4-, 6-, and 9-fold, respectively (FIG. 3A). However, shRNA knockdown of OSBP1 did not sensitize cells to taxol, revealing that OSBP1 knockdown does not non-specifically sensitize cells to cytotoxic small molecules. Similar results were obtained in HeLa cells. Overexpression of OSBP1-myc-his or ORP4L-myc-his (FIG. 3C) for 48 h desensitized HeLa cells to the antiproliferative activity of 1, 2, or 4a by ~2-5-fold (FIG. 3D). However, taxol-induced growth inhibition was not affected by overexpression of OSBP1-myc-his or ORP4L-myc-his (FIG. 3D).

Example 3

Correlating ORPphilins' Antiproliferative Activity and Binding to OSBP1 and ORP4L If OSBP1 and/or ORP4L mediate the antiproliferative activity of the ORPphilins, a positive correlation between their affinity for OSBP1 and ORP4L and their antiproliferative activity should exist. Indeed, plotting the OSBP1 $K_i$ values versus the HCT-116 $GI_{50}$ values of 1-4a and four OSW-1 analogs (6a, 6c, 7 and 8) revealed a strong, positive correlation (r=0.9644) (FIG. 3E). The same analysis with the ORP4L $K_i$ values also revealed a strong, positive correlation (r=0.9069), but only if schweinfurthin A (4a) was excluded (FIG. 3F). Similar SAR correlation results were obtained for both OSBP1 and ORP4L in the A549 and HCT-116 $p21^{-/-}$ cell lines.

The contention that binding to OSBP1 and/or ORP4L is required for the antiproliferative activity of the ORPphilins is further supported by the activity of OSW-1 analog 9, which bears a tert-butyldimethylsilyl group on the C3 carbinol (FIG. 1B). Compound 9 is ca. 1,400-fold less active than OSW-1 (2) in HCT-116 cells ($GI_{50}$=2300 nM). Similarly, 9 is 700-fold less cytotoxic than 2 in A549 cells and 2100-fold less cytotoxic than 2 in HCT-116 $p21^{-/-}$ cells. Notably, compound 9 did not compete with $[^3H]$-25-OHC for binding to OSBP1 or ORP4L.

Example 4

25-Hydroxycholesterol Suppresses the Antiproliferative Activities of ORPphilins

25-OHC (11) is a high-affinity ligand of OSBP1 and ORP4L that is not cytotoxic at concentrations up to 10 µM. Example 1 established that the ORPphilins compete with 25-OHC for binding to OSBP1 and ORP4L (FIG. 2D,E). Therefore, if OSBP1 and ORP4L mediate the biological activities of these compounds, co-administration of sublethal doses of 25-OHC with the ORPphilins should inhibit binding of the ORPphilins to OSBP1 and ORP4L, thereby desensitizing cells to the cytotoxic effects of the ORPphilins.

Addition of 25-OHC was found to cause a significant dose-dependent suppression of the antiproliferative activity of 1, 2 and 4a in the HCT-116 (FIG. 4A) and HeLa cell lines. Co-administration of 10 µM 25-OHC provided a nearly complete desensitization of HCT-116 cells treated with 250 nM of cephalostatin 1 (1) or 10 nM OSW-1 (2)—doses of 1 and 2 that alone caused >75% growth inhibition. 25-OHC also desensitized cells to schweinfurthin A (4a), although to a lesser degree than for 1 and 2. Importantly, 25-OHC did not affect the antiproliferative activity of brefeldin A or taxol, demonstrating that 25-OHC did not non-specifically desensitize cells to cytotoxic small molecules.

In addition to OSBP1 and ORP4L, NPC1 and Insig are also cellular receptors of 25-OHC. NPC1 is involved in the egress of lipoprotein-derived cholesterol from lysosomes.

Figure 4B:
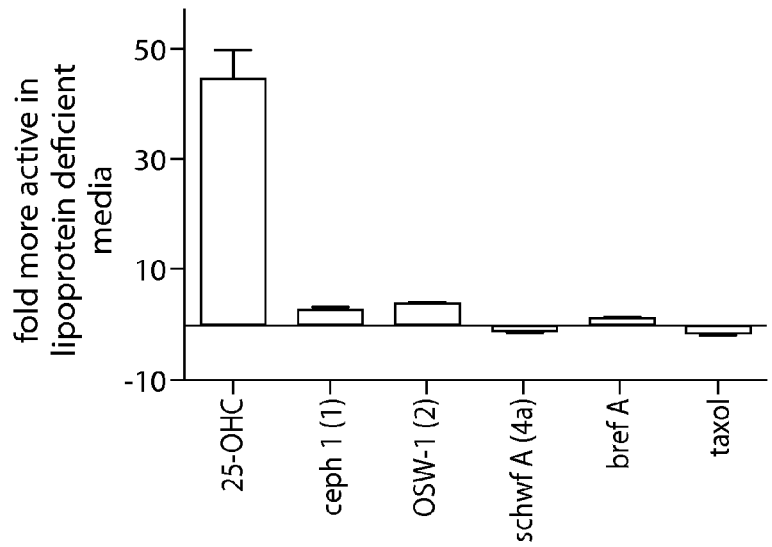
FIG. 4B is a bar graph depicting how removal of lipoproteins from the growth medium sensitizes CHO-7 cells to 25-OHC but not 1, 2, or 4a. Mean±s.d. of two individual experiments. Bref A, brefeldin A.

Insig is a chief regulator of SREBP-dependent cholesterol homeostasis, and 25-OHC exerts much of its ability to inhibit cholesterol biosynthesis through its binding to Insig. The possibility that suppression of the antiproliferative activity of the ORPphilins by 25-OHC could be due to displacement of these compounds from NPC1 or Insig was considered. However, no change was observed in the antiproliferative activity of 1, 2 or 4a in $NPC1^{-/-}$ (M12) CHO cells compared to wt CHO cells, demonstrating that the activity of ORPphilins does not depend upon NPC1. In addition, the antiproliferative activity of 1-4a was evaluated in the CHO-7 cell line, which is a cell line adapted to grow in lipoprotein-deficient media. In lipoprotein-deficient media, CHO-7 cells are dependent on Insig-mediated cholesterol biosynthesis for survival, and are therefore sensitive to 25-OHC binding to Insig. Unlike 25-OHC, the antiproliferative activity of 1, 2, and 4a in CHO-7 cells was not enhanced in lipoprotein-deficient media. This indicates the ORPphilins do not affect cholesterol biosynthesis and are therefore not ligands for Insig (FIG. 4B).

Example 5

Identification of Mutant Alleles of OSBP1 That Desensitize Cells to ORPphilins

Figures 4C, 4D:
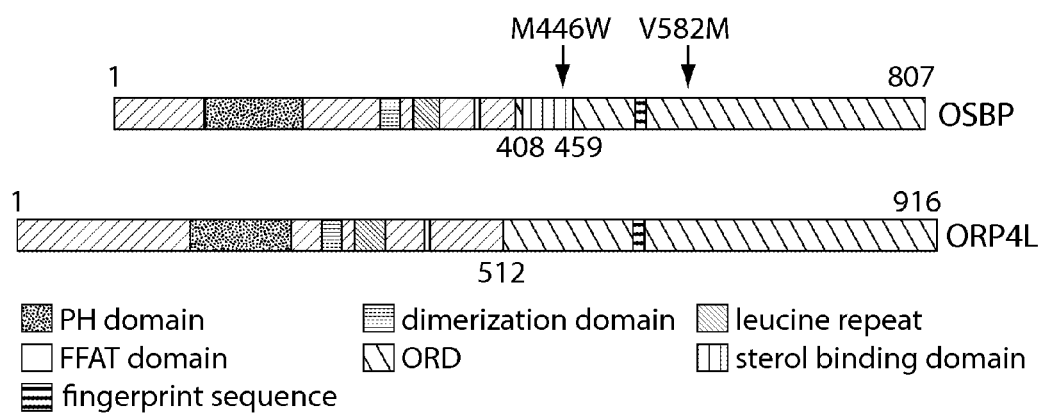
FIG. 4C is a schematic depiction of the human OSBP1 and ORP4L domains. OSBP1 point mutations M446W and V582M are indicated.
FIG. 4D is a table listing the binding coefficients ($K_D$) of $^3$H-25-hydroxycholesterol for OSBP, ORP4L, and two OSBP point mutants: OSBP(M446W) and OSBP(V582M). It also lists the inhibition binding coefficient ($K_i$) values for cephalostatin 1, OSW-1 and schweinfurthin A inhibiting the binding of 20 nM $^3$H-25-hydroxycholesterol to OSBP, ORP4L, OSBP(M446W), and OSBP(V582M).

For additional support that OSBP1 and ORP4L are targets of the ORPphilins, dominant drug-resistant alleles of these proteins were sought. 15 OSBP1 residues inside and outside the region of the protein previously reported to mediate sterol binding were mutated (FIG. 4C). The growth inhibition induced by the ORPphilins was determined in HeLa cells overexpressing either wild-type or mutant OSBP1-myc-his proteins. Expression of wt OSBP1-myc-his and mutant OSBP1-myc-his were nearly equivalent as measured by western blot.

Figure 4E:
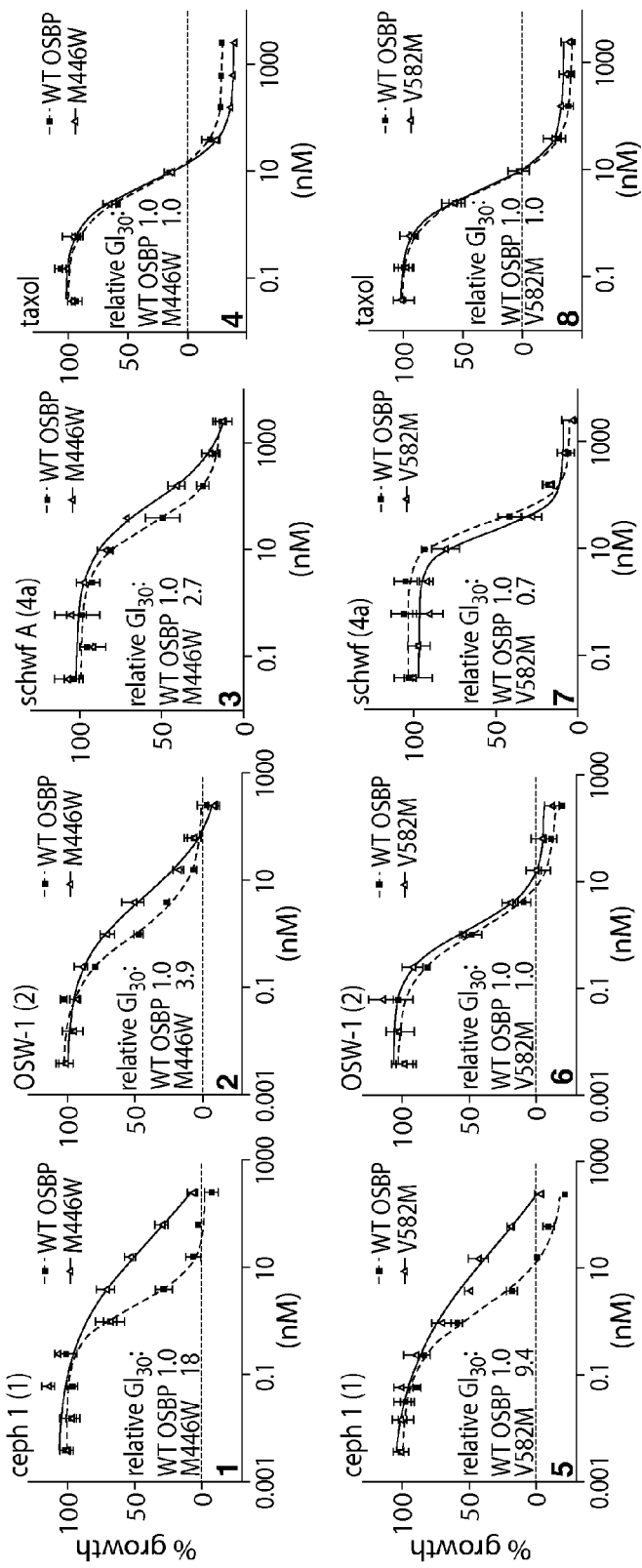
FIG. 4E is a panel of 8 graphs depicting effect of overexpression of wild-type (WT) OSBP1 or point mutants M446W (upper row) and V582M (lower row) on the growth inhibitory activity of 1, 2, 4a, and Taxol® in HeLa cells after 48 h. Relative $GI_{50}$ values are averages from two individual experiments.

Two mutations in OSBP1-myc-his were revealed to confer ORPphilin resistance. Expression of OSBP1(M446W)-myc-his caused an 18-fold reduction in the antiproliferative activity of cephalostatin 1 (1) at the $GI_{50}$ level compared to expression of wt OSBP1-myc-his (FIG. 4E1). The same mutant caused a 3.9-fold reduction in the antiproliferative activity of OSW-1 (2) (FIG. 4E2) and a 2.7-fold reduction in the activity of schweinfurthin A (4a) (FIG. 4E3). A second OSBP1 mutant, V582M, reduced the antiproliferative activity of 1 by 9.4-fold when compared to wt OSBP1-myc-his, yet this mutant did not affect the antiproliferative activity of 2 or 4a (FIG. 4E5-7). The antiproliferative activity of taxol was unaffected by expression of these two OSBP1 mutant proteins (FIGS. 4E4, 4E8).

The binding affinity of 1, 2 and 4a to the OSBP1(M446W) and OSBP1(V582M) mutants were then determined using $[^3H]$-25-OHC competition binding. The binding affinity of 25-OHC for OSBP1(M446W) was identical to wt. The OSBP1(V582M) mutant had a slightly higher 25-OHC $K_D$ as compared to wt. Within error limits, the binding affinity of 1, 2 and 4a for these two OSBP1 mutants were unchanged compared to wt OSBP1-myc-his (FIG. 4D). This suggests that these mutations provide resistance to the ORPphilins not by affecting compound binding but by altering the cellular function of OSBP1.

Based on the sequence alignment of OSBP1 and ORP4L, mutations in ORP4L were then made at positions equivalent to OSBP1(M446W) and OSBP1(V582M). Unlike expression of the two aforementioned OSBP1 mutants, expression of ORP4L(M550W) and ORP4L(V686M) did not reduce cell sensitivity to the ORPphilins when compared to wt ORP4L-myc-his.

Example 6

ORPphilins Perturb Cellular Localization of OSBP1

Although the function of OSBP1 is not yet fully elucidated, several cellular activities have been observed. For instance, OSBP1 translocates from cytoplasmic sites to the trans-Golgi network (TGN) upon addition of 25-OHC to cells. HCT-116 cells were treated with ORPphilins for short time periods (4 h) and the effects on OSBP1 localization monitored using immunofluorescence microscopy.

OSBP1 (green) and trans-Golgi protein P230 (red) were visualized in HCT-116 cells using indirect immunofluorescence microscopy. Cells were treated with compound for 4 h, fixed with 3.7% formaldehyde/PBS, washed, and permeabilized using 0.5% Triton X-100 in PBS. Proteins were labelled using specific primary antibodies against OSBP1 and P230 overnight at 4° C. After washing, cells were treated with Alexa Fluor 488 and Alexa Fluor 546 secondary antibodies for 1 h at RT.

Similar to the effect of 25-OHC (FIG. 5B), schweinfurthin A (4a) treatment caused OSBP1 to accumulate at perinuclear positions with a large degree of co-localization with the trans-Golgi marker p230, suggesting that 4a causes OSBP1 to translocate to the trans-Golgi network (FIG. 5C). OSW-1 (2) caused OSBP1 to localize to a perinuclear position that did not co-localize with p230 (FIG. 5D). Instead, OSW-1 treatment caused the p230 marker to appear as small, dispersed vesicles, which is indicative of trans-Golgi dismemberment. Similar to 2, cells treated with cephalostatin 1 (1) also resulted in OSBP1 occupying a perinuclear position with little co-localization of the dispersed p230 marker (FIG. 5E). However, unlike 25-OHC, 2 or 4a, 1 also caused OSBP1 to partially localize to the plasma membrane (FIG. 5E). This effect was also observed with ritterazine B (3), although there appeared to be greater co-localization of OSBP1 and p230 with 3 than with 1. Perturbations of OSBP1 localization by 1, 2, and 4b in A549 cells were also observed. Schweinfurthin B (4b) treatment resulted in perinuclear OSBP1-staining similar to 25-OHC, whereas 1 and 2 in this cell line induced dispersal or vesiculation of OSBP1.

Example 7

Cephalostatin 1 and OSW-1 Cause a Reduction in Cellular OSBP1 Levels

In the course of the immunofluorescence studies in Example 6, a significantly lower fluorescent OSBP1 signal was noticed in cells treated for more than 8 hours with cephalostatin 1 (1) and OSW-1 (2). A possible explanation for this observation was that treatment with 1 and 2 caused a decrease in OSBP1 levels. Treatment of HCT-116 cells with vehicle (DMSO) or 25-OHC (10 μM) had no effect on OSBP1 levels, as assessed by western blotting (FIG. 6A). However, treatment with 1 or 2 induced a dramatic, time-dependent reduction of OSBP1 levels (FIG. 6A). For example, 50 nM of 1 or 10 nM of 2 caused an approximately 75% reduction in OSBP1 protein levels at 24 h in HCT-116 cells (FIG. 6A), with a similar effect recorded in A549 cells. Interestingly, there was no effect on OSBP1 levels with schweinfurthin A (4a) (FIG. 6C). OSBP1 levels were determined using both an antibody recognizing the far N-terminus of OSBP1 (FIG. 6) and also an antibody recognizing the C-terminus of OSBP1. Both antibodies showed the OSBP1 reduction induced by 1 and 2, indicating degradation of the entire protein, as opposed to proteolysis or modification to one terminal region of OSBP1.

One possible explanation for the reduction in OSBP1 levels upon treatment with 1 and 2 was proteasome-dependent degradation. To determine whether degradation of OSBP1 was proteasome dependent, proteasome inhibitors MG-132 or lactacystin were co-administered with 1 and 2. While MG-132 or lactacystin alone did not affect OSBP1 levels, these inhibitors completely blocked degradation of OSBP1 by 1 and 2 (FIG. 6B) in HCT-116 cells. Similar results were obtained in A549 cells.

Interestingly, as stated, 25-OHC dosed at 10 μM did not reduce OSBP1 levels (FIGS. 6A and 6C). Since it was determined that co-administration of 25-OHC blocks the antiproliferative activity of cephalostatin 1 (1) and OSW-1 (2) (FIG. 4A), addition of 25-OHC was tested to determine whether would it block the reduction of OSBP1 levels caused by treatment with 1 or 2. Indeed, co-administration of 25-OHC (10 M or 20 M) with 2 (1 nM) significantly suppressed OSBP1 level reduction (FIG. 6C). This result further indicates that 25-OHC is capable of blocking the activities of the ORPphilins in cells by competing for binding to OSBP 1. Since 25-OHC suppressed the antiproliferative activity and the OSBP1 degradation caused by 2, it suggests that these events could be linked.

Finally, since 4a does not induce a reduction of OSBP1 levels, the potential of 4a to block the reduction of OSBP1 levels caused by 2 was tested. Remarkably, addition of 5 μM schweinfurthin A (4a) to cells treated with 10 nM of 2 completely suppressed the reduction of OSBP1 levels (FIG. 6C). These results reveal that although 2 and 4a both bind and perturb OSBP1 in cells, they have dramatically different effects on its activity.

Example 8

ORPphilins Affect Sphingomyelin Biosynthesis

Sphingomyelin is biosynthesized from ceramide at the Golgi apparatus. Ceramide is primarily transported from the ER to the Golgi by ceramide transport protein (CERT), and the transport activity of CERT is both OSBP1- and VAP-A dependent. In CHO-K1 cells, 25-OHC has been shown to induce an increase in sphingomyclin biosynthesis in an OSBP1-dependent fashion. To determine whether the ORPphilins affect sphingomyelin synthesis, pulse-labeling with [$^3$H]-serine was performed in CHO-K1 and HCT-116 cells and the amount of tritium incorporated into sphingomyelin and other lipids then measured. Cells were treated with vehicle or compound for 6 h, and in the last 2 h the cells were pulsed with 10 µCi [$^3$H]-serine. Lipids were extracted and isolated by TLC, and label incorporation into sphingomyelin was measured by scintillation counting.

As reported, treatment of CHO-K1 cells with 25-OHC (5 µM) induced a ca. 4-fold increase in the biosynthesis of sphingomyelin (SM) (FIG. 7). Treatment of CHO-K1 cells with low doses ($GI_{10}$) of ORPphilins 1-4 (with schweinfurthin B (4b) in place of schweinfurthin A (4a)) all induced an increase in SM biosynthesis, similar to, but not to the extent of, 25-OHC. Incorporation of radiolabel into phosphatidylethanolamine, a control lipid, was not significantly perturbed by the ORPphilins. In HCT-116 cells, treatment with a range of OSW-1 (2) concentrations had no effect on ceramide labeling. This result is consistent with the ORPphilins altering the conversion of ceramide into SM, a process that 25-OHC binding to OSBP1 is known to affect.

However, unlike 25-OHC, exposure of CHO-K1 cells to high doses ($GI_{90}$) of ORPphilins caused a significant reduction in the biosynthesis of SM (FIG. 7). Treatment of CHO-K1 cells with a $GI_{90}$ dose of 25-OHC (15 µM) caused a robust stimulation of SM biosynthesis, which is contrary to the reduction that was observed with 1. Inhibition of SM biosynthesis did not occur upon exposure of cells to taxol or the ER stress-inducing small molecule thapsigargin, demonstrating that 1, 2 and 4a do not inhibit SM biosynthesis due to induction of general cytotoxicity or ER stress.

Suppression of CERT expression is reported to cause a significant reduction in basal SM biosynthesis. Therefore, 1 and 2 were tested for their ability to induce a reduction in CERT levels, akin to the effects of 1 and 2 on OSBP1 levels. Treatment of HCT-116 cells or A549 cells with high dose ($GI_{90}$) 1 or 2 did not affect CERT protein levels.

Example 9

Preparation of OSW-1 Carbamates 100, 101, and 102

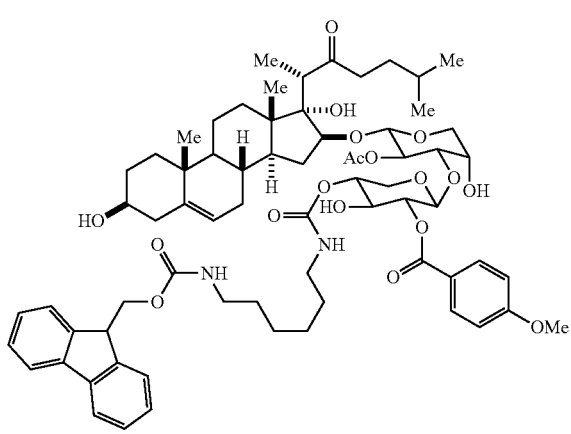

100

Chemical Formula: $C_{69}H_{92}N_2O_{18}$
Exact Mass: 1236.63451

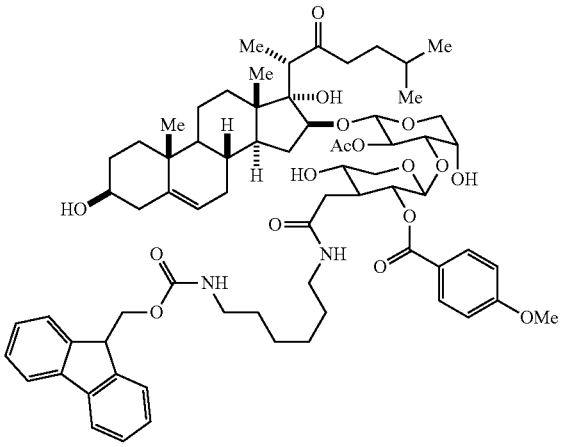

101

Chemical Formula: $C_{69}H_{92}N_2O_{18}$
Exact Mass: 1236.63451

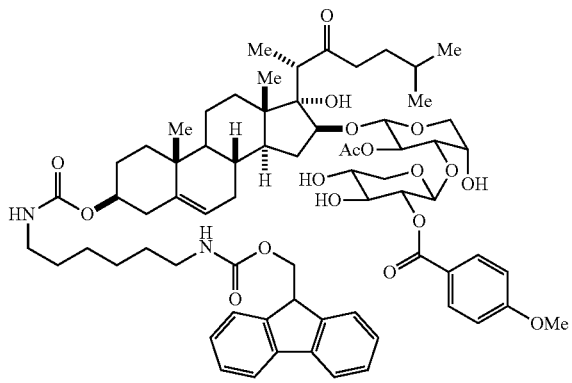

102

Chemical Formula: $C_{69}H_{92}N_2O_{18}$
Exact Mass: 1236.63451

Under argon, 1.0 mL of $CH_2Cl_2$ and 1.0 mL of $CH_3CN$ were added to mono-Fmoc-1,6-diaminohexane hydrochloride (36 mg, 0.096 mmol) to give a suspension containing white solid material. DIPEA (36 µL, 0.18 mmol) was added drop-wise and the reaction was stirred for 10 min; the solution never became completely homogenous. Concurrently, triphosgene (10.1 mg, 0.033 mmol) was charged to a flask in the atmosphere, argon purged and then dissolved in 0.5 mL $CH_2Cl_2$. The mono-Fmoc-1,6-diaminohexane solution was added slowly drop-wise through a large-gauge needle to the triphosgene solution, over 15 min. With washing of the reaction flask, a total of 2.3 mL of $CH_2Cl_2$/$CH_3CN$ was used to transfer the mono-Fmoc-1,6-diaminohexane. Upon addition of the mono-Fmoc-1,6-diaminohexane to the triphosgene, the solution became close to homogeneous. After 10 min stirring, argon was bubbled for 5 min directly into the reaction to remove excess phosgene. Concurrently, OSW-1 (9.4 mg, 0.01 mmol), under argon, was dissolved in 0.5 mL of $CH_2Cl_2$. 0.3 mL (~0.01 mol, ~1 eq.) of the isocyanate solution was added to the OSW-1 solution. After ~10 h, 0.15 mL more of the isocyanate solution was added (~0.005 mmol, ~0.5 eq.). After a further 16 h, the reaction had progressed considerably by TLC analysis.

The reaction was stopped by addition of 1.5 mL MeOH. Following stirring for 15 min, the reaction was diluted in CHCl₃ and washed with aq. NH₄Cl. White precipitate formed, which partitioned into the aqueous layer. The organic phase was then washed with H₂O, followed by brine. The aqueous phases were combined and back-extracted once with CHCl₃. The combined organic phases were the dried over Na₂SO₄. The reaction was purified with pTLC, using 8% MeOH/CH₂Cl₂ as an eluent, and two major product bands were isolated. The upper band ($R_f$=0.52) is ~85% pure 100. The other band is a ~2:3 mixture of 101:102 ($R_f$=0.42). OSW-1 was also recovered. 100, 101, and 102 were fully purified using semi-preparative reverse-phase HPLC with a Zorbax C-18SB column (I.D. 9.4 mm, 3.9 mL/min) using isocratic elution with 90% MeOH/H₂O. 100 (elution time 15.3 min) was obtained as a white solid (1.2 mg, 9%, 25% borsm). 101 (elution time 17.4 min) was obtained as a white solid (1.4 mg, 11%, 29% borsm). 102 (elution time 20.8 min) was obtained as a white solid (1.8 mg, 14%, 38% borsm).

Carbamate 100: $R_f$ (8% MeOH/CH₂Cl₂)=0.52. ¹H NMR (500 Hz, D₃CN) δ=8.01 (d, J=8.7 Hz, 2 H), 7.83 (d, J=7.8 Hz, 2 H), 7.65 (d, J=7.3 Hz, 2 H), 7.42 (t, J=7.3 Hz, 2 H), 7.37-7.30 (m, J=7.3 Hz, 2 H), 7.01 (d, J=8.7 Hz, 2 H), 5.67-5.59 (m, 1 H), 5.59-5.52 (m, 1 H), 5.31 (d, J=5.5 Hz, 1 H), 4.97-4.90 (m, J=7.8 Hz, 1 H), 4.75 (dd, J=6.0, 7.8 Hz, 1 H), 4.69 (d, J=6.9 Hz, 1 H), 4.64-4.56 (m, 1 H), 4.36-4.26 (m, 2 H), 4.25-4.17 (m, 2 H), 4.13-4.00 (m, 2 H), 3.93-3.81 (m, 4 H), 3.81-3.72 (m, 2 H), 3.72-3.64 (m, 2 H), 3.47-3.20 (m, 6 H), 3.12-2.99 (m, 4 H), 2.95-2.87 (m, 1 H), 2.68 (d, J=4.6 Hz, 1 H), 2.56-2.42 (m, 2 H), 1.85-1.76 (m, 2 H), 1.76-1.15 (m, 24 H), 1.14-0.85 (m, 10 H), 0.94-0.84 (m, 2 H), 0.78 (m, 9 H). LRMS (+TOF): calculated for $C_{69}H_{96}N_3O_{18}$ [M+NH₄⁺]=1254.6683; found: 1254.9.

Carbamate 101: $R_f$ (8% MeOH/CH₂Cl₂)=0.46. ¹H NMR (500 Hz, CD₃CN) δ=7.93 (d, J=8.7 Hz, 1 H), 7.83 (d, J=7.3 Hz, 1 H), 7.65 (d, J=7.3 Hz, 1 H), 7.41 (t, J=7.3 Hz, 2 H), 7.33 (t, J=7.3 Hz, 2 H), 6.98 (d, J=8.7 Hz, 1 H), 5.62-5.54 (m, 1 H), 5.51-5.45 (m, 1 H), 5.32-5.28 (m, 1 H), 4.97-4.86 (m, 2 H), 4.75-4.66 (m, 3 H), 4.32 (d, J=6.9 Hz, 1 H), 4.26-4.17 (m, 3 H), 4.00 (d, J=6.4 Hz, 1 H), 3.95 (dd, J=5.5, 11.4 Hz, 1 H), 3.91-3.70 (m, 8 H), 3.70-3.60 (m, 4 H), 3.59-3.52 (m, 3 H), 3.46-3.24 (m, 7 H), 3.21-3.17 (m, 1 H), 3.06-2.95 (m, 3 H), 2.95-2.72 (m, 6 H), 2.70-2.64 (m, 2 H), 2.51-2.39 (m, 3 H), 1.85-1.75 (m, 2 H), 1.75-0.96 (m, 34 H), 0.95-0.82 (m, 2 H), 0.83-0.71 (m, 9 H). LRMS (+TOF): calculated for $C_{69}H_{96}N_3O_{18}$ [M+NH₄⁺]=1254.6683; found: 1255.0.

Carbamate 102: $R_f$ (8% MeOH/CH₂Cl₂)=0.46. ¹H NMR (500 MHz, CD₃CN) δ=8.01 (d, J=9.2 Hz, 2 H), 7.83 (d, J=7.8 Hz, 2 H), 7.65 (d, J=7.3 Hz, 2 H), 7.42 (t, J=7.6 Hz, 2 H), 7.33 (t, J=7.3 Hz, 2 H), 7.02 (d, J=9.2 Hz, 2 H), 5.69-5.61 (m, 1 H), 5.41-5.34 (m, 1 H), 5.32 (d, J=4.6 Hz, 1 H), 4.88-4.82 (m, J=7.8 Hz, 1 H), 4.73 (dd, J=6.4, 8.2 Hz, 1 H), 4.61 (d, J=7.3 Hz, 1 H), 4.36-4.26 (m, 3 H), 4.25-4.17 (m, 2 H), 4.00 (d, J=6.0 Hz, 1 H), 3.96-3.84 (m, 5 H), 3.77 (dd, J=4.1, 12.4 Hz, 1 H), 3.72-3.64 (m, 2 H), 3.63-3.51 (m, 2 H), 3.42 (dd, J=1.8, 12.4 Hz, 1 H), 3.31-3.23 (m, 2 H), 3.12-3.00 (m, 4 H), 2.86 (q, J=7.3 Hz, 1 H), 2.46 (ddd, J=6.6, 9.0, 18.2 Hz, 1 H), 2.34-2.22 (m, 2 H), 1.88-1.75 (m, 2 H), 1.67 (s, 4 H), 1.64-1.37 (m, 9 H), 1.36-1.14 (m, 9 H), 1.12-1.05 (m, 4 H), 1.03-0.96 (m, 3 H), 0.96-0.86 (m, 2 H), 0.79 (d, J=6.9 Hz, 9 H). LRMS (+TOF): calculated for $C_{69}H_{96}N_3O_{18}$ [M+NH₄⁺]=1254.6683; found: 1255.0.

Example 10

OSW-1 Analogs 7 and 8

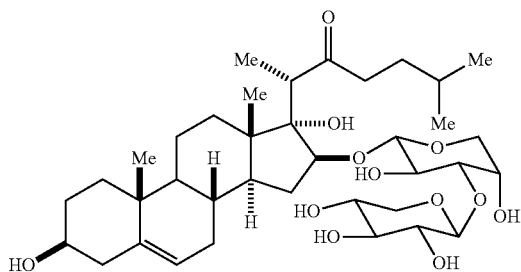

8

Chemical Formula: $C_{37}H_{60}O_{12}$
Exact Mass: 696.40848

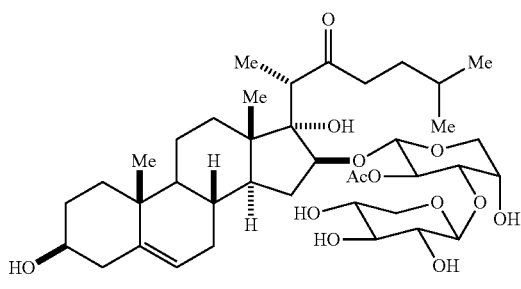

7

Chemical Formula: $C_{39}H_{62}O_{13}$
Exact Mass: 738.41904

OSW-1 analogs 7 and 8 were prepared as previously described. Kubo et al. (1992) *Phytochemistry* 31(11):3969-73. HPLC purification of 7: Zorbax C 8SB column, isocratic 82% MeOH/HO₂O. HPLC purification of 8: Eclipse C8 column, isocratic 60% CH₃CN/H₂O.

Example 11

Preparation of OSW-1 O-Methylcarbonate 105

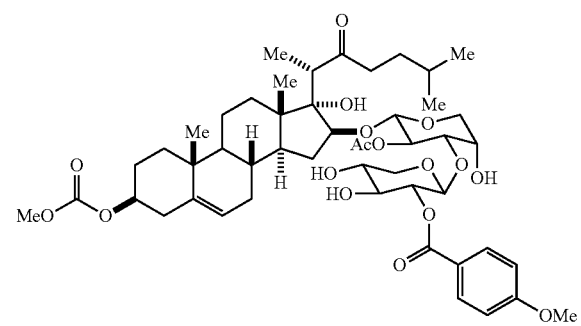

105

Chemical Formula: $C_{49}H_{70}O_{17}$
Exact Mass: 930.46130

Methyl ester 105 was isolated from the reaction of mono-Fmoc-1,6-diaminohexane isocyanate and OSW-1; this is the same reaction that produced 100-102. 105 is a minor product of this reaction discovered when HPLC purification was used to purify the remaining products of this reaction. Presumably, 105 arises from attack of MeOH on an activated ester form of OSW-1. The activated ester of OSW-1 could be the OSW-1 acid chloride, formed from OSW-1 reacting with phosgene in the reaction. Apparently this activated OSW-1 ester then reacted with MeOH upon pTLC purification. This is a trace product of the reaction (yield <10%).

OSW-1 O-Methylcarbonate 105: $^1$H NMR (500 MHz, CD$_3$CN) δ=8.01 (d, J=9.2 Hz, 2 H), 7.02 (d, J=9.2 Hz, 2 H), 5.42-5.32 (m, 1 H), 4.90-4.78 (m, 1 H), 4.73 (dd, J=6.4, 8.2 Hz, 1 H), 4.61 (d, J=7.8 Hz, 1 H), 4.39-4.26 (m, 1 H), 4.23-4.15 (m, 1 H), 4.01 (d, J=6.0 Hz, 1 H), 3.95-3.80 (m, 5 H), 3.76 (dd, J=4.6, 12.4 Hz, 1 H), 3.72-3.63 (m, 5 H), 3.63-3.49 (m, 2 H), 3.47-3.35 (m, 2 H), 3.33-3.21 (m, 2 H), 2.86 (q, J=7.3 Hz, 1 H), 1.78-1.39 (m, 13 H), 1.40-1.16 (m, 10 H), 1.15-0.98 (m, 8 H), 0.98-0.83 (m, 2 H), 0.83-0.72 (m, 9 H). LRMS (+TOF): calculated for C$_{49}$H$_{70}$O$_{71}$ [M+Na$^+$]: 946.4505; found: 946.6.

Example 12

Preparation of OSW-1 Carbonate 122

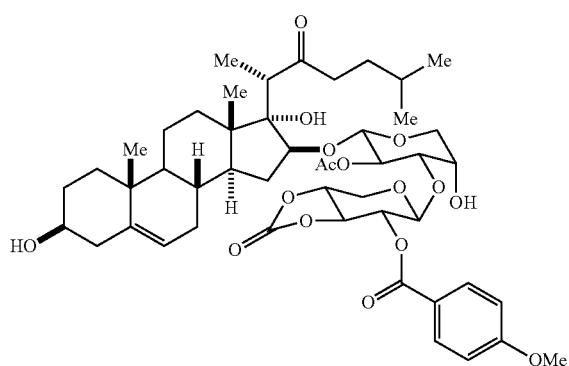

122

Chemical Formula: C$_{48}$H$_{66}$O$_{16}$
Exact Mass: 898.43509

40 mg ofp-Nitrophenyl chloroformate (97%) was dissolved in 2.0 mL CH$_2$Cl$_2$ to create a reagent stock solution. OSW-1 (5.0 mg, 0.006 mmol) was dissolved in 0.1 mL CH$_2$Cl$_2$ was added to OSW-1. To the OSW-1 solution, 0.1 mL of the p-Nitrophenyl chloroformate stock solution (2.0 mg, 0.01 mmol) was added, followed by ~1 µL of DIPEA.

The reaction was sealed and stirred for ~12 h. ~60% of the starting material remain, with three major product spots. Another ~1 µL of DIPEA was added, and the reaction was stirred for a further 7 h. The TLC became much more complex. Then 3 mL of CH$_3$CN was added, and the reaction concentrated in vacuo. The reaction was purified by pTLC, loaded 2/3 a plate and eluted with 8% MeOH/CH$_2$Cl$_2$. A very complex mixture of products was obtained, that could not be readily purified and identified. The only product identified was cyclic carbonate 122, isolated as a yellowish film/solid (<1 mg, ~15%).

Cyclic Carbonate 122: R$_f$ (8% MeOH/CH$_2$C2)=0.56. $^1$H NMR (500 MHz, CD$_3$CN) δ=8.05 (d, J=8.7 Hz, 2 H), 7.04 (d, J=8.7 Hz, 2 H), 5.35-5.25 (m, 2 H), 4.97 (d, J=3.7 Hz, 1 H), 4.81-4.71 (m, 2 H), 4.65-4.55 (m, 1 H), 4.38 (dd, J=5.7, 9.8 Hz, 1 H), 4.16 (s, 1 H), 4.10 (d, J=5.0 Hz, 1 H), 3.95-3.83 (m, 5 H), 3.83-3.73 (m, 3 H), 3.72-3.64 (m, 2 H), 3.48-3.40 (m, 2 H), 3.37-3.26 (m, 2 H), 2.98-2.90 (m, 1 H), 2.72-2.65 (m, 1 H), 2.55-2.44 (m, 1 H), 1.89-1.65 (m, 7 H), 1.63-0.96 (m, 17 H), 0.95-0.84 (m, 2 H), 0.83-0.72 (m, 9 H). LRMS (+TOF): calculated for C$_{49}$H$_{66}$NaO$_{16}$ [M+Na$^+$]: 921.4243; found: 921.7.

Example 13

Preparation of OSW-1 Carbonates 115, 123, 124, and 127

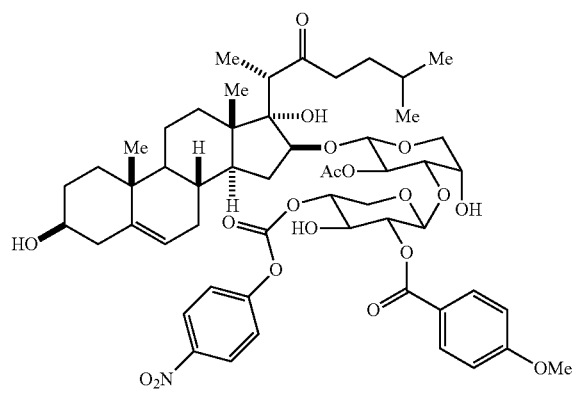

123

Chemical Formula: C$_{54}$H$_{71}$NO$_{19}$
Exact Mass: 1037.46203

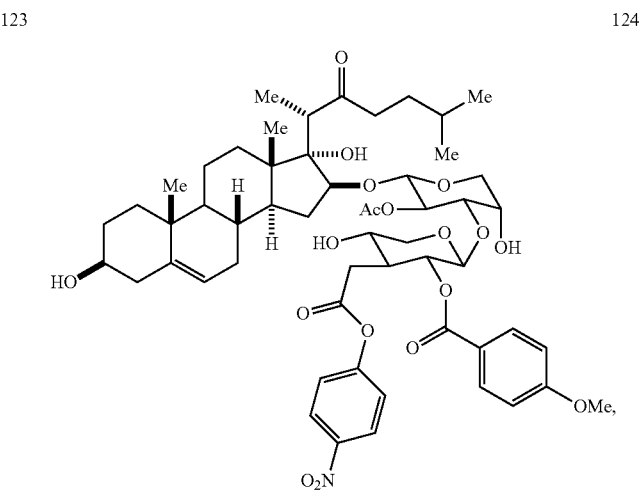

124

Chemical Formula: C$_{54}$H$_{71}$NO$_{19}$
Exact Mass: 1037.46203

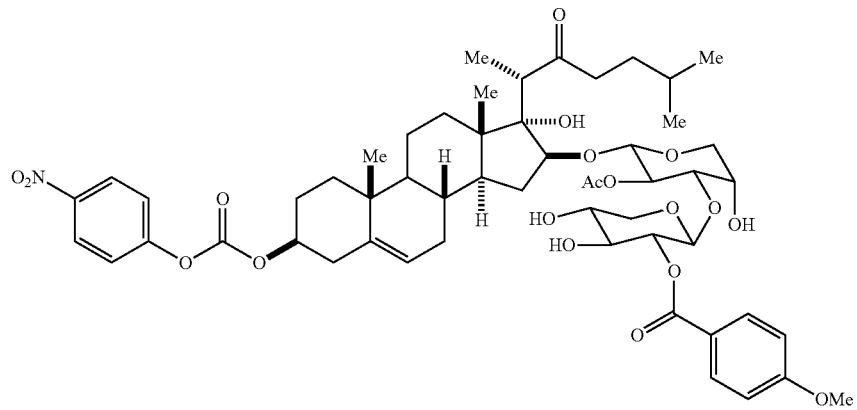

Chemical Formula: $C_{54}H_{71}NO_{19}$
Exact Mass: 1037.46203

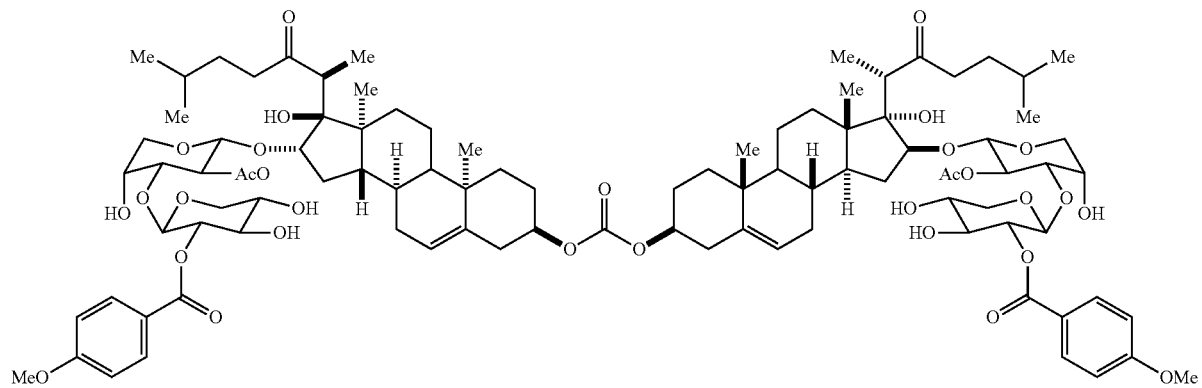

Chemical Formula: $C_{95}H_{134}O_{31}$
Exact Mass: 1770.89091

91 mg of p-Nitrophenyl chloroformate (97%) was dissolved in 0.86 mL $CH_2Cl_2$ to create a reagent stock solution. OSW-1 (15.0 mg, 0.017 mmol) was dissolved in 0.1 mL $CH_2Cl_2$ was added to OSW-1. To the OSW-1 solution, ~50 µL of DIPEA was added, followed by 0.05 mL of the p-Nitrophenyl chloroformate stock solution (5.3 mg, 0.025 mmol). The reaction was sealed and stirred for ~16 h. Then 3 mL of $CH_3CN$ was added, and the reaction concentrated in vacuo. The reaction was purified by pTLC, loaded on 2 plates and eluted with 8% $MeOH/CH_2Cl_2$. Several products were isolated and identified via $^1H$ NMR and LRMS.~1-2 mg of >80% 115, 123, and 124 were produced (~10% yield), with less than 1 mg of 127 produced (~10% yield). The carbonate products showed some instability on TLC, suggesting a significant portion was degraded during purification. Also, carbonate 123 and 124 are contaminated with each other, which could be due to incomplete purification, but there are also suggestions that the compounds can interconvert in solution, transferring the p-nitrophenyl carbonyl group between the 3" and 4" xylosyl hydroxyls.

Carbonate 123: $^1H$ NMR (500 MHz, $CD_3CN$) δ=8.27 (d, J=8.7 Hz, 2 H), 8.02 (d, J=9.2 Hz, 2 H), 7.43 (d, J=9.2 Hz, 2 H), 7.02 (d, J=8.7 Hz, 2 H), 5.42 (d, J=4.6 Hz, 1 H), 4.89-4.79 (m, 1 H), 4.77-4.68 (m, 1 H), 4.65-4.57 (m, 1 H), 4.55-4.43 (m, 1 H), 4.21 (s, 1 H), 4.09-3.97 (m, 2 H), 3.96-3.86 (m, 5 H), 3.82-3.71 (m, 2 H), 3.72-3.64 (m, 2 H), 3.64-3.51 (m, 2 H), 3.51-3.38 (m, 2 H), 3.36-3.14 (m, 2 H), 2.91-2.82 (m, 1 H), 2.53-2.37 (m, 2 H), 1.67 (s, 5 H), 1.64-1.13 (m, 12 H), 1.06 (s, 6 H), 1.03-0.83 (m, 3 H), 0.83-0.70 (m, 9 H).

Carbonate 124: $^1H$ NMR (500 MHz, $D_3CN$). Significantly impure with 123.

Carbonate 115: $^1H$ NMR (600 MHz, $CD_3CN$) δ=8.29-8.26 (m, 2 H), 8.03-8.00 (m, 2 H), 7.46-7.38 (m, 2 H), 7.06-6.98 (m, 2 H), 5.44-5.41 (m, 1 H), 4.87-4.82 (m, 1 H), 4.75-4.71 (m, 1 H), 4.61 (d, J=7.6 Hz, 1 H), 4.54-4.46 (m, 1 H), 4.21 (s, 1 H), 4.01 (d, J=6.2 Hz, 1 H), 3.96-3.84 (m, 6 H), 3.76 (dd, J=4.0, 12.4 Hz, 1 H), 3.71-3.65 (m, 2 H), 3.64-3.51 (m, 3 H), 3.47-3.38 (m, 2 H), 3.31-3.23 (m, 2 H), 2.91-2.83 (m, 1 H), 2.52-2.41 (m, 3 H), 1.79-1.45 (m, 9 H), 1.36-1.11 (m, 7 H), 1.10-1.03 (m, 6 H), 1.02-0.85 (m, 2 H), 0.84-0.72 (m, 9 H).

OSW-1 Dimer 127: $^1H$ NMR (500 MHz, $CD_3CN$) δ=7.99 (d, J=8.7 Hz, 4 H), 6.99 (d, J=8.7 Hz, 4 H), 5.28 (d, J=5.0 Hz, 2 H), 4.85-4.80 (m, 2 H), 4.73-4.68 (m, 2 H), 4.59 (d, J=7.8 Hz, 2 H), 4.18 (s, 2 H), 3.98 (d, J=6.4 Hz, 2 H), 3.90

(dd, J=4.6, 11.4 Hz, 2 H), 3.87-3.81 (m, 10 H), 3.80-3.70 (m, 4 H), 3.69-3.49 (m, 12 H), 3.43-3.36 (m, 2 H), 3.34-3.20 (m, 6 H), 3.06 (q, J=7.3 Hz, 2 H), 2.89-2.79 (m, J=7.3 Hz, 2 H), 2.73 (d, J=4.6 Hz, 2 H), 2.48-2.38 (m, 2 H), 1.85-1.11 (m, 28 H), 1.09-1.01 (m, 6 H), 1.01-0.93 (m, 8 H). 0.91-0.82 (m, 4 H), 0.80-0.70 (m, 18 H) LRMS (+TOF): calculated for $C_5H_{136}NaO_{31}$ [M+2H$^+$+Na$^+$]: 1795.8947; found: 1795.6.

Example 14

Preparation of Carbamate 126

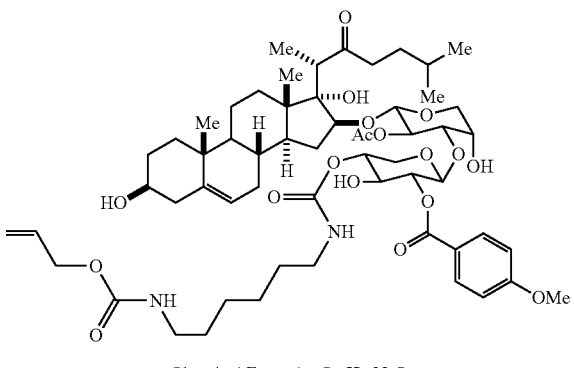

Chemical Formula: $C_{58}H_{86}N_2O_{18}$
Exact Mass: 1098.58756

Method 1: Using Carbonate 123 as substrate: Carbonate 123 (~1 mg, 0.001 mmol) was dissolved in 0.2 mL CH$_2$Cl$_2$. A stock solution of mono-Alloc-1,6-hexanediamine was prepared in CH$_2$Cl$_2$ and added (0.6 mg, 0.003 mmol) to the 123 solution. A catalytic amount of DMAP solid was added (<0.5 mg) to the reaction, which was sealed and stirred overnight. The yellow solution was concentrated and purified using pTLC (½ plate) using 8% MeOH/CH$_2$Cl$_2$ to develop the plate. Two products were purified. The higher R$_f$ product was identified as being cyclic carbonate 122. The lower R$_f$ product was the desired carbamate 126 (~0.4 mg, ~35%).

Method 2: Using Carbonate 124 as substrate: Performed identically as Method 1. Unexpectedly, instead of giving the desired carbamate on the 3"-xylosyl position, 4"-xylosyl carbamate 126 (~0.4 mg, ~35%) was obtained, in addition to some cyclic carbonate 122. This outcome suggests that either 1) DMAP initially catalyzes the formation of cyclic carbonate 122, which then proceeds to form the carbamate product; or 2) DMAP catalyzes the acyl transfer from the 3-xylose hydroxyl to the 4-xylose, which then proceeds to form the carbamate product.

Carbamate 126: $^1$H NMR (600 MHz, CD$_3$CN) δ=8.02 (d, J=8.9 Hz, 2 H), 7.02 (d, J=8.9 Hz, 2 H), 5.97-5.87 (m, 1 H), 5.62-5.52 (m, 2 H), 5.34-5.29 (m, 1 H), 5.27 (d, J=17.0 Hz, 1 H), 5.16 (d, J=10.4 Hz, 1 H), 4.98-4.89 (m, 1 H), 4.79-4.67 (m, 2 H), 4.65-4.54 (m, 1 H), 4.52-4.41 (m, 2 H), 4.20 (s, 1 H), 4.08 (dd, J=5.1, 11.9 Hz, 1 H), 4.04 (d, J=6.0 Hz, 1 H), 3.92-3.85 (m, 5 H), 3.82-3.73 (m, 3 H), 3.72-3.65 (m, 2 H), 3.46-3.22 (m, 6 H), 3.11-3.01 (m, 4 H), 2.95-2.87 (m, 1 H), 2.71 (d, J=4.5 Hz, 1 H), 2.57-2.45 (m, 1 H), 1.90-1.64 (m, 8 H), 1.64-1.15 (m, 17 H), 1.08 (d, J=7.5 Hz, 3 H), 1.05-0.97 (m, 4 H), 0.95-0.83 (m, 2 H), 0.83-0.74 (m, 9 H).

Example 15

Preparation of Carbamate 103

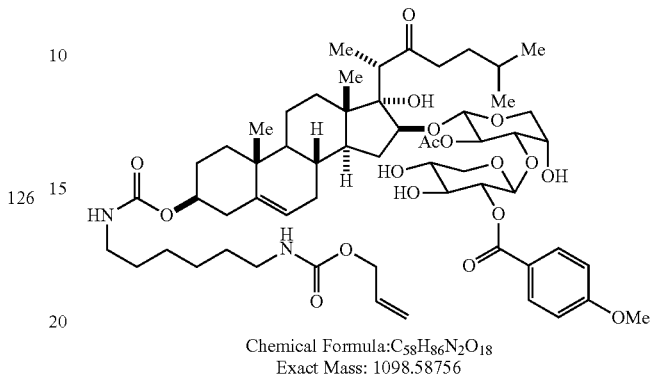

Chemical Formula: $C_{58}H_{86}N_2O_{18}$
Exact Mass: 1098.58756

Method 1: Mono-Alloc-1,6-hexanediamine hydrochloride (Sigma-Aldrich) (23.5 mg, 0.118 mmol) was azeotroped from benzene and subjected to a high vacuum to ensure complete removal of solvent. It was then dissolved in CH$_2$Cl$_2$ 0.5 mL to give a homogenous, weakly yellow solution. DIPEA (22 µL, 0.126 mmol) was added and the solution stirred for ~15 min. Meanwhile, 32 mg of triphosgene (98%, Sigma-Aldrich) was charged to reaction flask in the atmosphere, placed under an argon atmosphere, and dissolved in 0.5 mL CH$_2$Cl$_2$. 0.25 mL of this triphosgene stock solution (16.0 mg, 0.054 mmol) was syringe transferred to a new flask, under argon. To the 0.25 mL triphosgene solution, the mono-Alloc-1,6-hexanediamine solution was added slowly drop-wise over 30 min. After 5 min stirring, post-addition, argon was bubbled through the reaction to remove excess phosgene. OSW-1 (8.8 mg, 0.010 mmol) was charged to a separate reaction flask, under argon, and dissolved to give a clear, homogenous solution in 0.2 mL CH$_2$Cl$_2$ To the OSW-1 solution, 75 µL of the isocyanate solution was added (approx. 2.4 mg isocyante, 0.012 mmol). TLC monitoring at 5, 35. and 60 min showed slight conversion of the starting material that had stalled. After 1 h, the remaining totality of the isocyanate solution was added (an addition 21.4 mg, 0.11 mmol). TLC showed a renewed conversion of OSW-1, stalling again after 60 min (~40% OSW-1 remaining).

The reaction was diluted in ~15 mL CHCl$_3$ and washed with H$_2$O, to give a cloudy organic layer. Washing with aq. NH$_4$Cl clarified the organic phase, which then washed with H$_2$O, brine and dried over Na$_2$SO$_4$. The reaction was purified via pTLC (two plates 8% MeOH/CH$_2$Cl$_2$), yielding 103 in approximate 90% purity. Semi-preparative HPLC with a Zorbax C-18SB column (I.D. 9.4 mm, 3.9 mL/min) using isocratic elution with 90% MeOH/H$_2$O yielded pure 103 (3.5 mg, 34%, 58% borsm) (elution peak at 8.9 min) as a white solid. 3.7 mg of OSW-1 was also recovered (42%), with the rest of the mass balance accounted for by a complex mixture of other OSW-1 carbamate products.

Method 2: 115 (3-(4-Nitrophenyl)-OSW-1 carbonate) (~1 mg, 0.001 mmol), under argon, was dissolved in 0.2 mL of CH$_2$Cl$_2$. A reagent stock solution of mono-Alloc-1,6-hexanediamine was prepared by dissolving 4.0 mg in 0.5 mL of $CH_2Cl_2$. 75 μL of the reagent solution (0.6 mg, 0.003 mmol) was added. The reaction was sealed, and quickly became yellow. After 16 h, little desired formed, added more mono-Alloc-1,6-hexanediamine (1 mg, 0.005 mmol) as a solid to the reaction. Clear desired began to form, seemed to stall after 6 hr. More solid mono-Alloc-1,6-hexanediamine (1.6 mg. 0.008 mmol) was then added. The reaction was then stirred for a further 19 h. By TLC, ~90% of the starting material (sm) looked consumed, but due to hydrolysis of the sm, TLC analysis of conversion was difficult to ascertain. More solid mono-Alloc-1,6-hexanediamine (1.6 mg. 0.008 mmol) was then added, and the reaction was stirred for a further 2 h. Then, the brightly yellow reaction was directly concentrated in vacuo. To remove the large excess of mono-Alloc-1,6-hexanediamine, the reaction was dissolved in $CHCl_3$, and extracted with aq. $NH_4C$ twice, followed by washing the organic layer with $H_2O$ and brine, and drying over $Na_2SO_4$. The reaction was pTLC purified with 5% $MeOH/CH_2Cl_2$, to yield slightly impure 103 (estimated yield ~50-70%).

Carbamate 103: $R_f$ (8% $MeOH/CH_2Cl_2$)=0.30. $^1H$ NMR (500 MHz, $CD_3CN$) δ=8.00 (d, J=8.7 Hz, 2 H), 7.01 (d, J=8.7 Hz, 2 H), 5.96-5.84 (m, 1 H), 5.60-5.47 (m, 1 H), 5.42-5.30 (m, 2 H), 5.25 (d, J=17.4 Hz, 1 H), 5.14 (d, J=10.1 Hz, 1 H), 4.87-4.79 (m, 1 H), 4.76-4.68 (m, 1 H), 4.61-4.59 (m, 1 H), 4.51-4.42 (m, 1 H), 4.35-4.25 (m, 1 H), 4.19 (s, 1 H), 4.03-3.96 (m, 1 H), 3.85 (s, 5 H), 3.78-3.72 (m, 1 H), 3.69-3.64 (m, 2 H), 3.61-3.49 (m, 2 H), 3.44-3.36 (m, 1 H), 3.30-3.21 (m, 1 H), 3.09-2.99 (m, 4 H), 2.89-2.81 (m, 1 H), 2.50-2.38 (m, 1 H), 2.33-2.17 (m, 3 H), 1.89-1.64 (m, 10 H), 1.27 (td, J=3.3, 6.8 Hz, 10 H), 1.11-0.95 (m, 8 H), 0.96-0.86 (m, 1 H), 0.80-0.71 (m, 9 H). LRMS (+TOF): calculated for $C_{58}H_{88}N_2O_{18}$ [M+2H$^+$]: 1100.6021. found: 1100.1; calculated for $C_{58}H_{87}N_2NaO_{18}$ [M+H$^+$+Na$^+$]: 1122.5840; found: 1122.1.

Example 16

Preparation of OSW-1 Carbamate 104

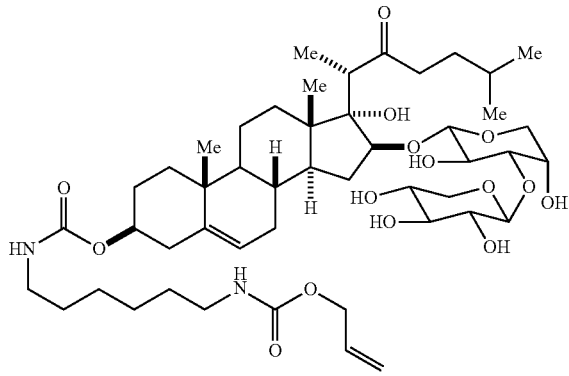

Chemical Formula: $C_{48}H_{78}N_2O_{15}$
Exact Mass: 922.54022

OSW-1 carbamate 103 (6.0 mg, 0.0054 mmol) was dissolved in 0.20 mL of a 4% KOH/EtOH solution. The lightly yellow colored solution was stirred for 40 min. The reaction was carefully neutralized to neutral pH with 10% HCl, then diluted with $CHCl_3$. Extracting with $H_2O$ gave a cloudy, poorly separated extraction, to which aq. sat. $NaHCO_3$ was then added. The organic layer was separated, the aqueous fraction back-extracted with $CHCl_3$, and the combined organic phases dried over $Na_2SO_4$. 104 was purified with silica gel chromatography, using a 5-15% $MeOH/CH_2Cl_2$ gradient eluent. 104 was obtained as white solid (3.3 mg, 68%).

OSW-1 Carbamate 104: $^1H$ NMR (500 MHz, $CD_3OD$) δ=6.03-5.84 (m, 1 H), 5.50-5.36 (m, 1 H), 5.29 (d, J=17.1 Hz, 1 H), 5.17 (d, J=10.3 Hz, 1 H), 4.57-4.45 (m, 3 H), 4.43-4.32 (m, 1 H), 4.00 (d, J=7.3 Hz, 1 H), 3.97-3.91 (m, 1 H), 3.91-3.79 (m, 3 H), 3.67-3.60 (m, 1 H), 3.59-3.44 (m, 3 H), 3.25-3.16 (m, 2 H), 3.16-3.01 (m, 4 H), 2.93-2.81 (m, 1 H), 2.77-2.64 (m, 1 H), 2.39-2.12 (m, 3 H), 2.05-1.74 (m, 3 H), 1.72-1.27 (m, 21 H), 1.26-1.18 (m, 3 H), 1.18-1.00 (m, 4 H), 0.90 (s, 9 H). LRMS (+TOF): calculated for $C_{48}H_{83}N_3O_{15}$ [M+Na$^+$+H$^+$]: 941.5818; found: 941.5.

Example 17

Preparation of 1-(N-Alloc-aminomethyl)-4-(N-Boc-aminomethyl)benzene

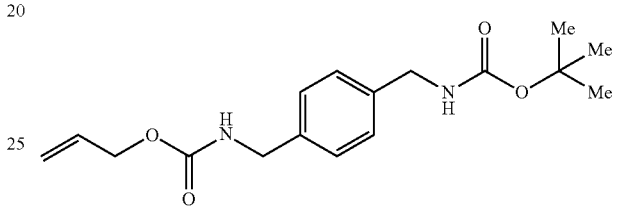

1-(N-Boc-Aminomethyl)-4-(amino-methyl)benzene (2.01 g, 8.47 mmol) charged into a dry reaction flask was dissolved in THF (30 mL, 0.28 M). Pyridine (0.673 g, 0.686 mL, 8.51 mmol) was added via syringe, and then the reaction was cooled to −78° C. Allyl chloroformate (1.02 g, 8.51 mmol) was added drop-wise. After 10 min, the reaction was allowed to warm to room temperature and stirred for ~2.5 h. The reaction was stopped via addition of 10 mL methanol and then concentrated in vacuo. The crude reaction mixture was directly chromatographed with a 5% methanol/$CH_2Cl_2$ mixture to yield the desired product as an off-white solid (2.15 g, 76%).

1-(N-Alloc-aminomethyl)-4-(N-Boc-aminomethyl)benzene: $^1H$ NMR (500 MHz, $CDCl_3$): δ 7.25 (m, 4 H), 5.92 (m, 1 H), 5.32 (d, J=17.0 Hz, 1 H), 5.21 (d, J=10.8 Hz, 1 H), 5.13 (br s, 1 H), 4.90 (br s, 1 H), 4.59 (d, J=4.9 Hz, 2 H), 4.35 (d, J=5.9 Hz, 2 H), 4.29 (d, J=4.9 Hz, 2 H), 1.46 (s, 9 H). $^{13}C$ NMR (500 MHz, pyridine-$d_5$): 157.3, 156.9, 139.5, 139.0, 134.2, 128.0, 116.9, 78.3, 65.3, 44.9, 44.6, 28.6. FTIR (film): 3323, 1682, 1530, 1253 cm$^{-1}$. HRMS (+TOF): calculated for $C_{17}H_{24}N_2NaO_4$ [M+Na$^+$]: 343.1628. found: 343.1648. Δ=5.8 ppm.

Example 18

Preparation of 1-(N-Alloc-aminomethyl)-4-(aminomethyl)benzene

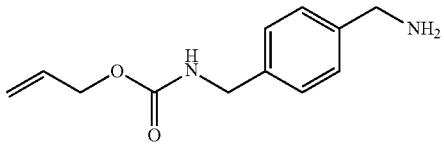 [SMILES: C=CCOC(=O)NCc1ccc(CN)cc1]

At room temperature, 1-(N-Alloc-aminomethyl)-4-(N-Boc-aminomethyl)benzene (0.325 g, 1.01 mmol) was partially dissolved in $CH_2Cl_2$ (4.0 mL). TFA (1.54 mL, 20.0 mmol) was added fast drop-wise to produce a yellow/orange-colored homogenous solution. After 1 h, the solution was directly concentrated in vacuo and placed on a high vacuum pump for 2 h. To liberate the free amine from the amine salt, the crude reaction mixture was dissolved in 30 mL chloroform and washed twice with a 0.2 M NaOH solution. The aqueous layer was back-extracted once with chloroform, and the combined organic layers were washed with water and dried over $Na_2SO_4$. No purification was performed of the resultant to thick yellow oil (76 mg, 43%).

1-(N-Alloc-aminomethyl)-4-(aminomethyl)benzene: $^1$H NMR (500 MHz, $CDCl_3$): δ 7.28 (m, 4 H), 5.93 (m, 1 H), 5.32 (d, J=17.1 Hz, 1 H), 5.21 (dd, J=1.0, 10.4 Hz, 1 H), 4.59 (d, J=4.6 Hz, 2 H), 4.35 (d, J=5.7 Hz, 2 H), 3.85 (s, 2 H). $^{13}$C NMR (500 MHz, pyridine-$d_5$): 157.7, 143.5, 136.2, 128.3, 128.1, 124.1, 117.2, 65.6, 46.7, 45.4. FTIR (film): 3311, 1692, 1531, 1255 $cm^{-1}$. HRMS (+TOF): calculated for $C_{12}H_{17}N_2O_2[M+H^+]$: 221.1285; found: 221.1283. Δ=−0.90 ppm.

Example 19

Preparation of Alloc-(N)-diaminomethyl benzene isocyanate

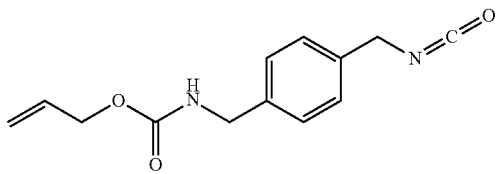 [SMILES: C=CCOC(=O)NCc1ccc(CN=C=O)cc1]

Alloc-(N)-diaminomethyl benzene (105 mg, 0.4 mmol) under argon, was dissolved in dry EtOAc (3.3 mL). Solid triphosgene (74 mg, 0.25 mmol) was added, and the reaction was heated to 90° C. under reflux conditions for 5 h: the reaction never became homogeneous. After cooling, the solvent was removed in vacuo and the reaction was subjected to high vacuum pumping overnight producing a yellow solid (118 mg, ~quantitative yield). IR analysis of the product clearly showed a peak consistent with isocyanate formation at 2265 $cm^{-1}$ (expected range 2230-2280 $cm^{-1}$). The product was used immediately without purification. $^1$H NMR (500 MHz, $CDCl_3$): δ=7.32-7.22 (m, 4 H), 6.05 (br s, 1 H), 5.92 (m, 1 H), 5.27 (d, J=17.0 Hz, 1 H), 5.16 (d, J=10.5 Hz, 1 H), 4.51 (m, 2 H), 4.41 (d, J=6.0 Hz, 2 H), 4.23 (m, 2 H). FTIR (film): 3328, 2940, 2265, 1698, 1516, 1250 $cm^{-1}$.

Example 20

Preparation of OSW-1 Carbamates 6c, 6a, and 109

6c

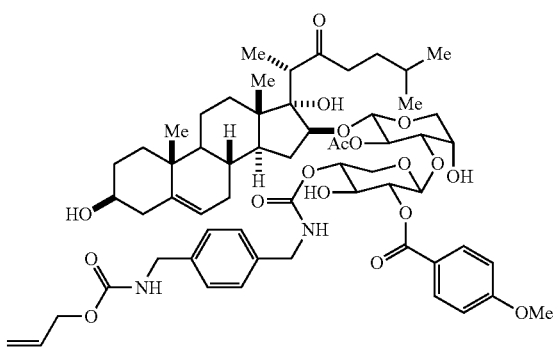

Chemical Formula: $C_{60}H_{82}N_2O_{18}$
Exact Mass: 1118.55626

6a

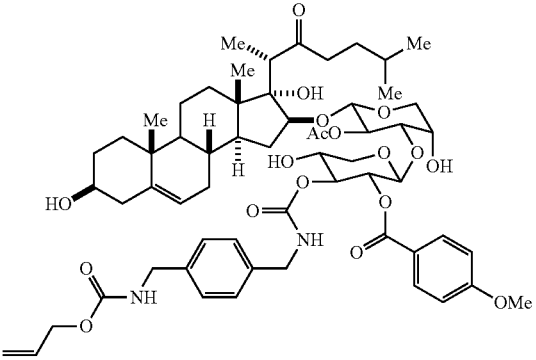

Chemical Formula: $C_{60}H_{82}N_2O_{18}$
Exact Mass: 1118.55626

109

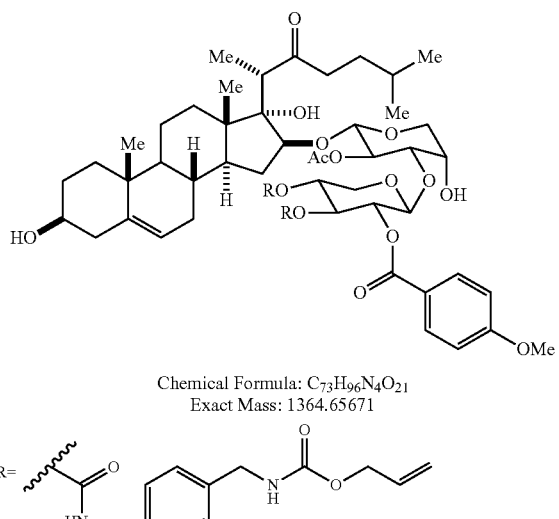

Chemical Formula: $C_{73}H_{96}N_4O_{21}$
Exact Mass: 1364.65671

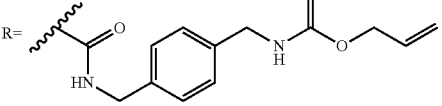

OSW-1 (22 mg, 0.025 mmol) under argon was dissolved in DMF (0.4 mL). In a nitrogen glove bag, copper (I) chloride (10 mg, 0.10 mmol) and Alloc-(N)-diaminomethyl benzene isocyanate (25 mg, 0.10 mmol) were charged into a dry vial and dissolved in DMF (1.0 mL) to make a reagent stock solution. 0.5 mL of the reagent stock solution (copper (I) chloride 5 mg, (0.05 mmol) Alloc-(N)-diaminomethyl benzene isocyanate 12.5 mg (0.05 mmol)) was added to the OSW-1 solution via syringe at ambient temperature and stirred for 5 h. The reaction was diluted with ~15 mL of chloroform and washed twice with saturated aq. $NaHCO_3$. The blue aqueous layer was back-extracted once, and the combined brown/yellow organic layer was washed with brine. The organic layer was dried over $Na_2SO_4$ and reduced in vacuo to produce a yellow crude solution in residual DMF, which was evaporated to a crude solid mixture with an overnight period on the high vacuum pump. A mixture of OSW-1-mono-carbamate compounds 6c and 6a was produced, as well as bis-carbamate compound to 109. Interestingly, no 106 was identified in this reaction. 6c, 6a, and 109 were purified via pTLC (two plates) eluted with 7.5% MeOH/$CH_2Cl_2$ to ~90% purity. Carbamate 6c was obtained as a white solid (6.3 mg, 23%, 27% borsm). 6a was obtained as a white solid (7.4 mg, 26%, 31% borsm). Bis-carbamate 109 was obtained as a white solid (6.7 mg, 19%, 24% borsm). Both carbamate 6c and 6a were purified to analytical purity via HPLC (Eclipse C8 column, isocratic 83% MeOH/$H_2O$) for biological experimentation.

Carbamate 6c: $R_f$ (7.5% MeOH/CH$_2$Cl$_2$)=0.35. $^1$H NMR (500 MHz, CD$_3$CN): δ 7.95 (d, J=8.8 Hz, 2 H), 7.05-6.89 (m, 6 H), 6.00-5.93 (m, 5 H), 5.32-5.17 (m, 3 H), 4.99-4.92 (m, 2 H), 4.75-4.70 (m, 2 H), 4.56-4.52 (m, 2 H), 4.24-4.15 (m, 5 H), 4.03-3.94 (m, 2 H), 3.91-3.86 (m, 4 H), 3.79-3.74 (m, 1 H), 3.71-3.66 (m, 1 H), 3.64 (m, 1 H), 3.46-3.18 (m, 4 H), 2.86 (dd, J=7.0, 14.3 Hz, 1 H), 2.68 (d, J=4.6 Hz, 1 H), 2.48 (m, 1 H), 2.25-2.15 (m, 5 H), 1.87-1.78 (m, 1 H), 1.75-1.63 (m, 5 H), 1.62-1.16 (m, 9 H), 1.08-0.98 (m, 7 H), 0.88 (m, 1 H), 0.94-0.75 (m, 9 H). $^{13}$C NMR (500 MHz, pyridine-d$_5$): 218.9, 169.2, 165.4, 164.0, 159.3, 157.3, 141.9, 138.7, 134.3, 132.7, 128.0, 127.9, 127.8, 127.6, 121.1, 116.9, 116.8, 114.2, 103.5, 100.9, 88.2, 85.6, 81.5, 77.1, 73.0, 71.9, 71.3, 68.7, 68.5, 66.9, 66.3, 65.3, 55.5, 50.2, 48.5, 46.6, 46.3, 45.0, 44.9, 44.7, 44.2, 43.5, 39.3, 37.8, 36.9, 34.5, 32.7, 32.6, 32.3, 32.1, 27.8, 22.8, 22.5, 20.9, 20.8, 19.6, 13.5, 11.8. FTIR (film, cm$^{-1}$); HRMS (+TOF): calculated for C$_{60}$H$_{86}$N$_3$O$_{18}$ [M+NH$_4^+$]: 1136.5901; found: 1136.5896. Δ=−0.43 ppm.

Carbamate 6a: $R_f$ (7.5% MeOH/CH$_2$Cl$_2$)=0.28. $^1$H NMR (600 MHz, CD$_3$CN): δ 8.02 (d, J=8.8 Hz, 2 H), 7.22 (m, 4 H), 7.00 (d, J=8.8 Hz, 2 H), 6.09-6.02 (m, 2 H), 5.92 (m, 1 H), 5.32-5.25 (m, 2 H), 5.17 (d, J=10.8 Hz, 1 H), 4.94 (dd, J=6.7, 8.2 Hz, 1 H), 4.75 (dd, J=6.0, 8.1 Hz, 1 H), 4.72 (d, J=6.7 Hz, 1 H), 4.64 (m, 1 H), 4.51 (dt, 1.5, 5.5 Hz, 2 H), 4.29-4.16 (m, 5 H), 4.11 (dd, J=4.7, 11.7 Hz, 1 H), 4.05 (d, J=6.1 Hz, 1 H), 3.93-3.65 (m, 7 H), 3.45-3.21 (m, 4 H), 2.91 (m, 1 H), 2.69 (d, J=4.4 Hz, 1 H), 2.51 (m, 1 H), 2.26-2.03 (m, 5 H), 1.85-1.78 (m, 1 H), 1.75-1.68 (m, 5 H), 1.63-1.19 (m, 9 H), 1.09 (d, J=7.3 Hz, 3 H), 1.06-0.98 (m, 5 H), 0.92-0.85 (m, 2 H), 0.81-0.77 (m, 9 H). $^{13}$C NMR (500 MHz, pyridine-d$_5$): 218.9, 169.3, 165.4, 164.0, 157.3, 157.0, 141.9, 138.8, 134.2, 132.5, 128.1, 128.0, 128.0, 127.9, 121.1, 116.9, 114.1, 110.6, 100.8, 88.8, 85.8, 74.0, 72.2, 71.3, 65.3, 55.5, 50.2, 48.5, 46.5, 46.4, 45.0, 44.9, 44.2, 43.2, 39.4, 37.8, 36.9, 34.6, 32.7, 32.3, 32.1, 29.6, 27.8, 22.8, 22.4, 20.9, 19.6, 13.6, 11.9. HRMS (+TOF): calculated for C$_{60}$H$_{82}$N$_2$NaO$_{18}$ [M+Na$^+$]: 1141.5455; found: 1141.5444. Δ=0.96 ppm.

Bis-carbamate 109: $R_f$ (7.5% MeOH/CH$_2$Cl$_2$)=0.45. $^1$H NMR (500 MHz, CD$_3$CN) δ=7.96 (d, J=8.9 Hz, 2 H), 7.32-7.12 (m, 4 H), 7.09-6.85 (m, 6 H), 6.19-5.81 (m, 6 H), 5.35-5.22 (m, 3 H), 5.17 (d, J=5.3 Hz, 2 H), 5.07 (dd, J=7.1, 8.9 Hz, 1 H), 4.89-4.67 (m, 3 H), 4.59-4.42 (m, 4 H), 4.32-4.08 (m, 8 H), 4.08-3.96 (m, 2 H), 3.96-3.73 (m, 6 H), 3.73-3.58 (m, 3 H), 3.55-3.39 (m, 3 H), 3.39-3.28 (m, 2 H), 3.16 (m, 1 H), 2.49 (br. s., 2 H), 2.37-2.15 (m, 4 H), 1.88-1.75 (m, 2 H), 1.74-1.14 (m, 15 H), 1.12-0.95 (m, 7 H), 0.95-0.84 (m, 2 H), 0.84-0.64 (m, 9 H).

Example 21

Preparation of OSW-1 Free Amine 112

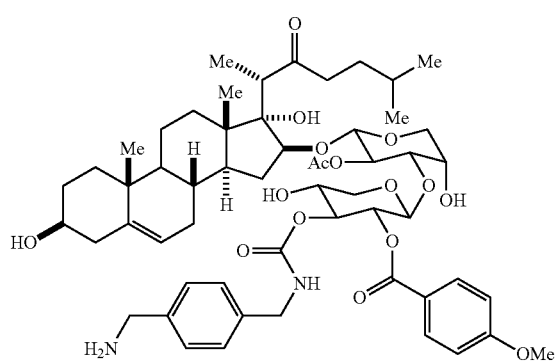

112

Chemical Formula: C$_{56}$H$_{78}$N$_2$O$_{16}$
Exact Mass: 1034.53513

Carbamate 6a (5.7 mg, 0.0051 mmol) was dissolved in THF (0.4 mL) under argon.

Morpholine (3 μL, 0.035 mmol) was added via syringe. The reaction flask was taken into the nitrogen glove bag. Tetrakis(triphenylphosphine)palladium (0) (~0.3 mg, 5 mol %) was added to the reaction as a solid. The light yellow reaction was stirred under argon at ambient temperature for 80 min. A drop of water was added, and the reaction was concentrated in vacuo. NMR and low resolution mass spectroscopic analysis indicated complete Alloc-deprotection was achieved, yielding 112. The free amine compound (112) was carried forward into the coupling with the Sepharose 4B resin without purification due to poor compound solubility. The yield was estimated to be quantitative.

OSW-1 Amine 112: $^1$H NMR (500 MHz, CD$_3$CN) δ=7.99-7.90 (m, 2 H), 7.21-7.14 (m, 2 H), 7.07-6.94 (m, 4 H), 6.07-5.97 (m, 1 H), 5.33-5.26 (m, 1 H), 5.01-4.89 (m, 2 H), 4.77-4.67 (m, 2 H), 4.30-4.22 (m, 1 H), 4.22-4.13 (m, 3 H), 4.09-3.93 (m, 5 H), 3.93-3.82 (m, 6 H), 3.81-3.72 (m, 2 H), 3.71-3.63 (m, 2 H), 3.46-3.27 (m, 3 H), 3.13-3.05 (m, 2 H), 2.91-2.80 (m, 1 H), 2.54-2.39 (m, 2 H), 1.85-1.76 (m, 1 H), 1.76-1.11 (m, 14 H), 1.11-0.95 (m, 8 H), 0.92-0.82 (m, 2 H), 0.82-0.70 (m, 9 H). HRMS (+TOF): calculated for C$_{56}$H$_{79}$N$_2$NaO$_{16}$ [M+H$^+$]: 1035.5429; found: 1035.5409. Δ=−1.9 ppm.

Example 22

Preparation of OSW-1 Solid Phase Resin 116

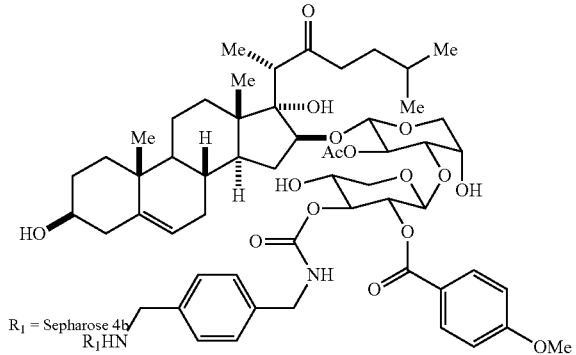

116

0.3 mL of NHS-activated Sepharose 4 Fast Flow™ (16-23 μmol/drained mL resin, GE Healthcare) was charged into an Eppendorf™ tube Filter Cup via a wide-mouth 1000 μL pipet tip. The resin was washed three times with 0.3 mL of d$_6$-DMSO via low speed centrifugation. The amine compound 112 was then dissolved in 0.3 mL of d$_6$-DMSO and transferred to the washed resin. Triethylamine (11 μL, 0.079 mmol, 15.8 eq) was added, and the reaction was incubated shaking at ambient temperature. The reaction was monitored at 0, 1, 2, and ~16 h with LCMS to follow the loss of soluble amine compound. After ~16 h no detectable soluble compound remained. The reaction was centrifuged to separate the solution from the resin. NMR analysis of the d$_6$-DMSO flow-through revealed no amine compound (112). To the resin, 0.3 mL of a 5% ethanolamine in DMSO solution was added and incubated for 4 h at ambient temperature. The resin was then centrifuged to remove the 5% ethanolamine solution and washed three times with 0.5 mL DMSO. The resin was stored dry at −20° C. until use.

Example 23
Preparation of OSW-1 Carbamates 106, 118, and 119
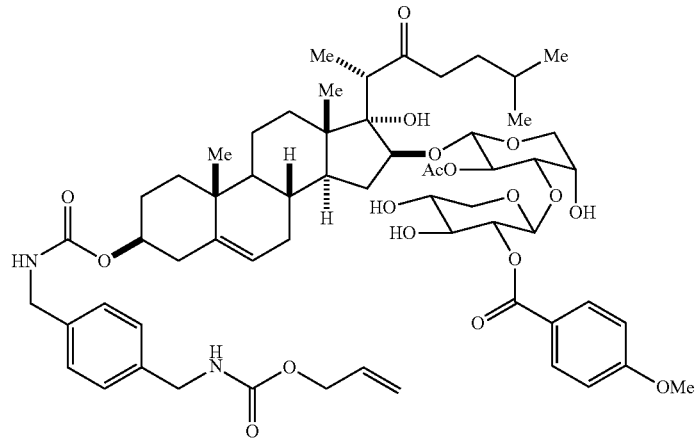
Chemical Formula: C$_{60}$H$_{82}$N$_2$O$_{18}$
Exact Mass: 1118.55626
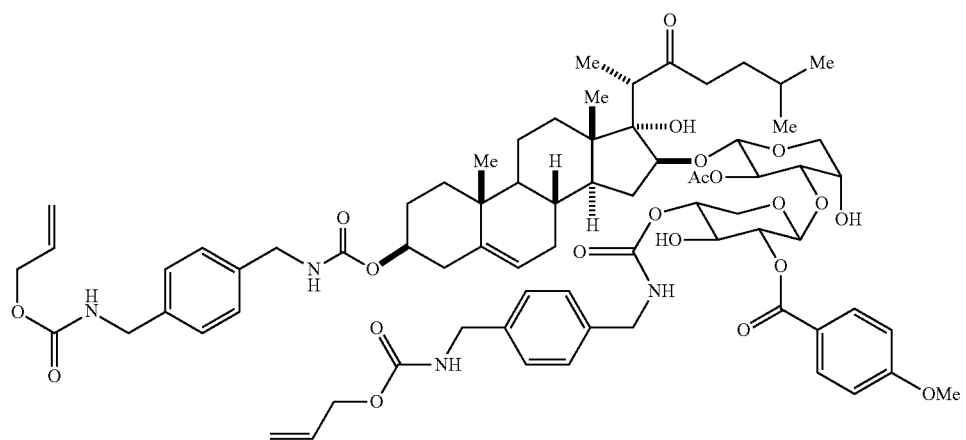
Chemical Formula: C$_{73}$H$_{96}$N$_4$O$_{21}$
Exact Mass: 1364.65671
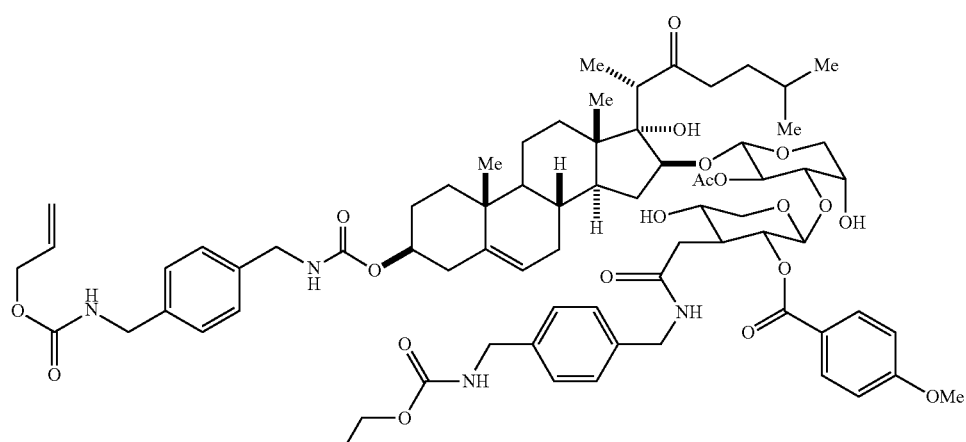
Chemical Formula: C$_{73}$H$_{96}$N$_4$O$_{21}$
Exact Mass: 1364.65671

OSW-1 (5.6 mg, 0.006 mmol) was dissolved in 0.1 mL of $CH_2Cl_2$ while under argon. In a separate conical shaped flask, 15 mg of Alloc-(N)-diaminomethyl benzene isocyanate was azeotroped from benzene followed by $CHCl_3$. 0.3 mL of $CH_2Cl_2$ was then added to the isocyanate to produce a cloudy, brownish reagent stock solution. Under argon, 0.2 mL of the isocyanate solution (10 mg, 0.04 mmol) was added to OSW-1 via syringe at ambient temperature. The reaction was slightly cloudy and yellow in color. The reaction was sealed and stirred for 12 h, followed by addition of 2 mL of MeOH. The solvent was removed in vacuo, and the product mixture was then separated via pTLC (~⅔ plate), developed in 7.5% $MeOH/CH_2Cl_2$. The three carbamates were obtained in ~90% purity, as well as some recovered OSW-1: 118 (1.6 mg, 18%, 24% borsm); 119 (1.8 mg, 20%, 27% borsm); and 106 (3.3 mg, 50%, 61% borsm).

Carbamate 106: $R_f$ (7.5% $MeOH/CH_2Cl_2$)=0.17. $^1$H NMR (500 MHz $CD_3CN$) δ=8.02 (d, J=8.8 Hz, 2 H), 7.23 (s, 4 H), 7.02 (d, J=8.8 Hz, 2 H), 6.09-5.99 (m, 1 H), 5.99-5.84 (m, 2 H), 5.36 (d, J=4.4 Hz, 1 H), 5.28 (d, J=17.6 Hz, 1 H), 5.17 (d, J=11.2 Hz, 1 H), 4.87-4.82 (m, 1 H), 4.73 (dd, J=6.3, 8.3 Hz, 1 H), 4.61 (d, J=7.3 Hz, 1 H), 4.53-4.49 (m, 2 H), 4.39-4.30 (m, 1 H), 4.27-4.18 (m, 9 H), 4.00 (d, J=6.3 Hz, 1 H), 3.92 (dd, J=5.1, 11.5 Hz, 1 H), 3.90-3.84 (m, 5 H), 3.76 (dd, J=4.2, 12.5 Hz, 1 H), 3.70-3.64 (m, 2 H), 3.64-3.51 (m, 2 H), 3.46-3.39 (m, 1 H), 3.30-3.23 (m, 2 H), 2.91-2.82 (m, 1 H), 2.51-2.41 (m, 1 H), 2.35-2.18 (m, 2 H), 2.10-2.05 (m, 1 H), 1.8-1.77 (m, 2 H), 1.76-1.40 (m, 10 H), 1.36-1.15 (m, 4 H), 1.14-1.04 (m, 4 H), 1.04-0.97 (m, 3 H), 0.97-0.87 (m, 1 H), 0.82-0.73 (m, 9 H).

Bis-carbamate 118: $R_f$ (7.5% $MeOH/CH_2Cl_2$)=0.35. $^1$H NMR (500 MHz, $CD_3CN$) δ=8.01 (d, J=8.8 Hz, 2 H), 7.29-7.19 (m, 8 H), 7.00 (d, J=8.8 Hz, 2 H), 6.10-6.00 (m, 3 H), 6.00-5.86 (m, 2 H), 5.36 (d, J=4.4 Hz, 1 H), 5.28 (d, J=17.6 Hz, 1 H), 5.17 (d, J=10.7 Hz, 1 H), 4.93 (t, J=7.6 Hz, 1 H), 4.78-4.70 (m, 2 H), 4.66-4.61 (m, 1 H), 4.51 (s, 3 H), 4.38-4.31 (m, 1 H), 4.29-4.17 (m, 10 H), 4.13-4.01 (m, 2 H), 3.92-3.83 (m, 3 H), 3.83-3.66 (m, 5 H), 3.45-3.36 (m, 2 H), 3.26 (s, 1 H), 3.12 (s, 1 H), 2.94-2.89 (m, 1 H), 2.53-2.48 (m, 1 H), 2.34-2.19 (m, 3 H), 2.08-1.98 (m, 2 H), 1.88-1.75 (m, 2 H), 1.71 (s, 5 H), 1.62-1.43 (m, 4 H), 1.38-1.18 (m, 7 H), 1.15-1.04 (m, 4 H), 1.04-0.99 (m, 3 H), 0.99-0.84 (m, 1 H), 0.84-0.76 (m, 9 H).

Bis-carbamate 119: $R_f$ (7.5% $MeOH/CH_2Cl_2$)=0.28. $^1$H NMR (500 MHz, $CD_3CN$) δ=7.95 (d, J=8.8 Hz, 2 H), 7.25-7.19 (m, 4 H), 7.05-6.89 (m, 6 H), 6.04 (br. s., 1 H), 6.00-5.85 (m, 4 H), 5.36 (br. s., 1 H), 5.28 (m, 2 H), 5.17 (m, 2 H), 4.99-4.92 (m, 2 H), 4.76-4.70 (m, 2 H), 4.54-4.49 (m, 4 H), 4.38-4.31 (m, 1 H), 4.29-4.14 (m, 9 H), 4.07-3.95 (m, 2 H), 3.91-3.82 (m, 4 H), 3.76 (m, 1 H), 3.72-3.65 (m, 1 H), 3.62-3.56 (m, 1 H), 3.45-3.34 (m, 2 H), 3.21 (m, 1 H), 3.11 (s, 1 H), 2.91-2.83 (m, 2 H), 2.51-2.44 (m, 1 H), 2.30-2.14 (m., 2 H), 2.10-2.06 (m, 4 H), 1.87-1.77 (m, 3 H), 1.72-1.17 (m, 14 H), 1.14-0.98 (m, 6 H), 0.96-0.73 (m, 11 H).

Example 24

Preparation of OSW-1 Carbamate 20

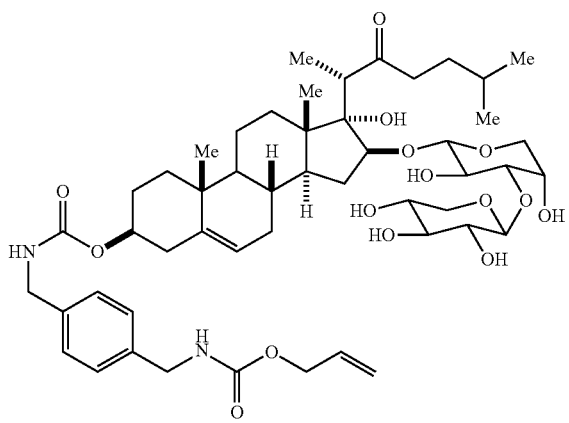

Chemical Formula: $C_{50}H_{74}N_2O_{15}$
Exact Mass: 942.50892

OSW-1 carbamate 106 (4.0 mg, 0.0036 mmol) was dissolved in 0.25 mL of a 4% KOH/EtOH solution. The lightly yellow colored solution was stirred for 70 min. The reaction was carefully neutralized to neutral pH with 10% HCl, then diluted with $CHCl_3$. Extracting with $H_2O$ gave a cloudy, poorly separated extraction. Aq. sat. $NaHCO_3$ was then added. The organic layer was separated, the aqueous fraction back-extracted with $CHCl_3$, and the combined organic phases dried over $Na_2SO_4$. 20 was purified with silica gel chromatography, using a 5-15% $MeOH/CH_2Cl_2$ gradient eluent. 20 was obtained as white solid (2.3 mg, 68%).

Carbamate 20: $^1$H NMR (500 MHz, $CD_3OD$) δ=7.31-7.17 (m, 4 H), 6.02-5.84 (m, 1 H), 5.45-5.25 (m, 2 H), 5.18 (d, J=11.0 Hz, 1 H), 4.54 (d, J=5.3 Hz, 1 H), 4.48 (d, J=7.1 Hz, 1 H), 4.44-4.35 (m, 1 H), 4.30-4.18 (m, 3 H), 4.00 (d, J=7.1 Hz, 1 H), 3.96-3.90 (m, 1 H), 3.89-3.79 (m, 2 H), 3.67-3.60 (m, 1 H), 3.55 (dd, J=3.4, 8.9 Hz, 1 H), 3.53-3.41 (m, 2 H), 3.25-3.13 (m, 2 H), 2.93-2.80 (m, 1 H), 2.76-2.62 (m, 1 H), 2.40-2.28 (m, 2 H), 2.27-2.15 (m, 2 H), 2.04-1.73 (m, 4 H), 1.73-1.46 (m, 8 H), 1.47-1.36 (m, 3 H), 1.36-1.25 (m, 2 H), 1.21 (d, J=7.3 Hz, 4 H), 1.18-1.08 (m, 2 H), 1.08-1.00 (m, 7 H), 1.00-0.78 (m, 9 H).

Example 25

Preparation of OSW-1 Carbamate 107

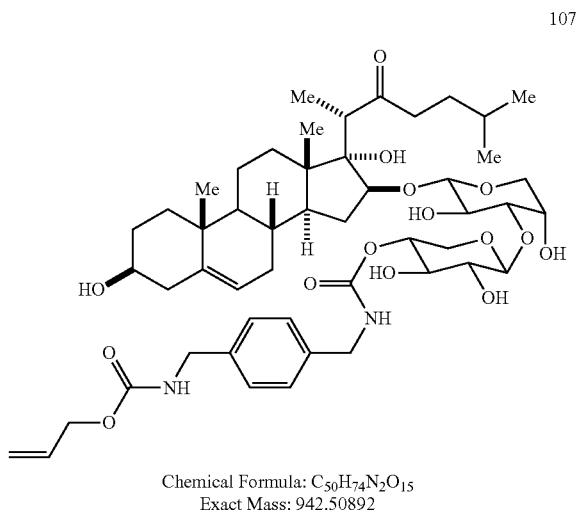

Chemical Formula: $C_{50}H_{74}N_2O_{15}$
Exact Mass: 942.50892

OSW-1 carbamate 6c (5.5 mg, 0.005 mmol) was dissolved in 0.30 mL of a 4% KOH/EtOH solution. The lightly yellow colored solution was stirred for 70 min. The reaction was carefully neutralized to neutral pH with 10% HCl, then diluted with CHCl$_3$. Extracting with H$_2$O gave a cloudy, poorly separated extraction. Aq. sat. NaHCO$_3$ was then added. The organic layer was separated, the aqueous fraction back-extracted with CHCl$_3$, and the combined organic phases dried over Na$_2$SO$_4$. 107 was purified with silica gel chromatography, using a 5-12% MeOH/CH$_2$Cl$_2$ gradient eluent, which only produced a portion of the desired compound pure (1.1 mg, 23%), as a white solid. The remaining 107 was in mixed fractions with impurities (estimated total amount of product from the reaction was 50-70%).

Carbamate 107: $^1$H NMR (500 MHz, cd$_3$od) δ=7.35-7.17 (m, 4 H), 5.99-5.86 (m, 1 H), 5.39-5.26 (m, 2 H), 5.18 (d, J=10.3 Hz, 1 H), 4.64-4.43 (m, 4 H), 4.37-4.19 (m, 3 H), 4.08-3.96 (m, 2 H), 3.96-3.79 (m, 3 H), 3.69-3.37 (m, 5 H), 3.27-3.12 (m, 2 H), 2.95-2.80 (m, 1 H), 2.77-2.61 (m, 1 H), 2.31-2.14 (m, 3 H), 2.05-1.90 (m, 2 H), 1.90-1.73 (m, 3 H), 1.71-1.27 (m, 8 H), 1.20 (d, J=7.3 Hz, 2 H), 1.16-1.00 (m, 6 H), 0.99-0.84 (m, 9 H). HRMS (+TOF): calculated for C$_{50}$H$_{74}$N$_2$NaO$_{15}$ [M+Na$^+$]: 965.4981; found: 965.4986. Δ=0.5 ppm.

Example 26

Preparation of 3-(tert-Butyldimethylsilyl)-OSW-1 (108) 108 Mee

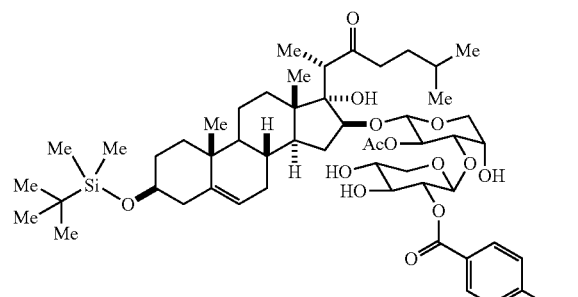

Chemical Formula: $C_{53}H_{82}O_{15}Si$
Exact Mass: 986.54230

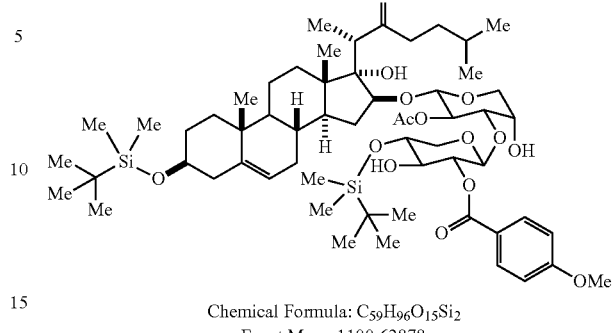

Chemical Formula: $C_{59}H_{96}O_{15}Si_2$
Exact Mass: 1100.62878

Under argon, OSW-1 (18 mg, 0.021 mmol) was dissolved in 0.4 mL dry CH$_2$Cl$_2$. The solution was cooled in an ice bath. 2,6-lutidine (2.5 µL, 0.021 mmol) was added via syringe. tert-Butyldimethylsilyltrifluoromethane sulfonate (6.5 µL, 0.028 mmol) was then added via syringe. After 5 min, the ice bath was removed, and the reaction was allowed to warm to ambient temperature: total reaction time was 15 min. The reaction was diluted in chloroform and extracted with water followed by sat. aq. NaHCO$_3$, then brine. The organic layer was dried over Na$_2$SO$_4$. Purification was accomplished via pTLC, eluted with 5% MeOH/CH$_2$Cl$_2$, yielding compounds 121 (2.5 mg, 10%, 12% borsm) and 108 (12.0 mg, 60%, 65% borsm) as white solids. At least two other unidentified TBS-OSW-1 products were formed in this reaction, but they were inseparable by pTLC. For biological testing, 108 subjected to semi-preparative HPLC with an Eclipse C8 column (I.D. 9.4 mm, 3.9 mL/min) using isocratic elution with 95% MeOH/H$_2$O (108 elution peak at 8.7 min).

Bis-TBS Protected OSW-1 121: R$_f$ (7.5% MeOH/CH$_2$C2)-0.93. $^1$H NMR (500 MHz, CD$_3$CN) δ=8.01 (d, J=9.2 Hz, 2 H), 7.02 (d, J=8.9 Hz, 2 H), 5.31 (d, J=4.8 Hz, 1 H), 4.85 (dd, J=7.8, 9.2 Hz, 1 H), 4.72 (dd, J=6.2, 8.2 Hz, 1 H), 4.62 (d, J=7.8 Hz, 1 H), 4.20 (s, 1 H), 4.01 (d, J=6.2 Hz, 1 H), 3.86 (s, 5 H), 3.79-3.64 (m, 4 H), 3.30-3.22 (m, 2 H), 2.86 (q, J=7.3 Hz, 1 H), 2.49-2.40 (m, 1 H), 2.24-2.16 (m, 3 H), 1.84-1.76 (m, 2 H), 1.67 (s, 5 H), 1.61-1.39 (m, 9 H), 1.35-1.15 (m, 7 H), 1.11-1.04 (m, 3 H), 1.04-1.02 (m, 1 H), 1.00 (s, 4 H), 0.88 (d, J=2.1 Hz, 18 H), 0.81-0.72 (m, 9 H), 0.14-0.05 (m, 12 H).

TBS Protected OSW-1 108: R$_f$ (7.5% MeOH/CH$_2$Cl$_2$) =0.27. $^1$H NMR (500 MHz, CD$_3$CN) δ=8.01 (d, J=9.2 Hz, 2H), 7.02 (d, J=9.2 Hz, 2 H), 5.32 (m, 1 H), 4.84 (m, 1 H), 4.73 (dd, J=1.0 Hz, 1.0 Hz, 1 H), 4.61 (d, J=7.8 Hz, 1 H), 4.20 (s, 1 H), 4.00 (d, J=6.4 Hz, 2 H), 3.92 (dd, J=5.0, 11.5 Hz, 1 H), 3.90-3.84 (m, 4 H), 3.76 (dd, J=12.4, 4.1 Hz, 1 H), 3.72-3.66 (m, 2 H), 3.63-3.51 (m, 2 H), 3.50-3.38 (m, 2 H), 3.33-3.24 (m, 1 H), 2.86 (m, 1 H), 2.46 (m, 2 H), 2.15-2.05 (m, 2 H), 1.85-1.75 (m, 3 H), 1.75-1.64 (m, 6 H), 1.64-1.36 (m, 4 H), 1.36-1.15 (m, 5 H), 1.15-0.95 (m, 8 H), 0.87 (s, 9 H), 0.84-0.69 (m, 9 H), 0.05 (s, 6 H).

δ $^{13}$C NMR (500 MHz, pyridine-d$_5$): 218.9, 169.3, 165.5, 163.9, 141.4, 132.4, 121.5, 114.1, 110.6, 103.7, 100.8, 88.3, 85.7, 81.0, 76.4, 75.1, 72.9, 72.0, 70.7, 67.0, 65.6, 55.5, 50.1, 48.5, 46.5, 46.3, 43.3, 39.3, 37.4, 36.8, 34.6, 32.7, 32.6, 32.3, 32.0, 30.0, 27.7, 26.1, 22.8, 22.5, 20.9, 19.5, 18.3, 13.6, 11.9, −4.4. HRMS (+TOF): calculated for C$_{53}$H$_{82}$NaO$_{15}$Si [M+Na$^+$]: 1009.5315; found: 1009.5304. Δ=−1.1 ppm.

Example 27

Preparation of OSW-1 Amine 111

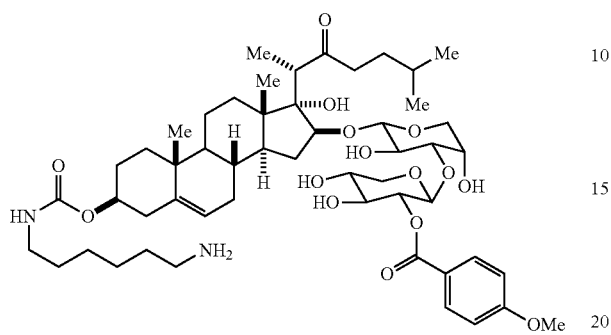

Chemical Formula: C$_{54}$H$_{82}$N$_2$O$_{16}$
Exact Mass: 1014.56643

OSW-1 carbamate 101 (1.3 mg, 0.0011 mmol) was dissolved, under argon, in 0.2 mL THF. Piperidine (8 µL, 0.08 mmol) was added. The reaction was monitored by TLC, and more piperidine was added until deprotection was complete (total piperidine ~40 µL, requiring ~1 hr of time). The piperidine was removed by azeotroping the reaction with toluene twice, followed by three times with CHCl$_3$. The crude NMR should the desired product, with the expected dibenzylfulvene by-product. The product was poorly soluble in several solvents, so purification was very difficult. The product was used crude.

OSW-1 Amine 111: LRMS (+TOF): calculated for C$_{54}$H$_{83}$O$_{16}$ [M+2H$^+$]: 1016.5664; found: 1016.3.

Example 28

Preparation of OSW-1 Amine 113

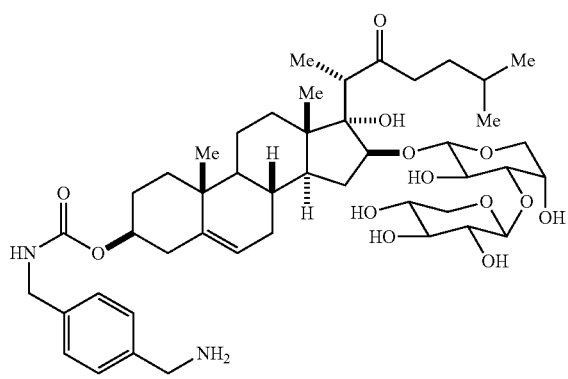

Chemical Formula: C$_{48}$H$_{70}$N$_2$O$_{13}$
Exact Mass: 858.48779

Carbamate 20 (2.1 mg, 0.0022 mmol) was dissolved in THF (0.2 mL) under argon. Morpholine (1.5 µL, 0.018 mmol) was added via syringe. The reaction flask was taken into the nitrogen glove bag. Tetrakis(triphenylphosphine) palladium (0) (~1.0 mg, 39 mol %) was added to the reaction as a solid. The light yellow reaction was stirred under argon at ambient temperature for 75 min. A drop of water was added, and the reaction was concentrated in vacuo. Crude NMR was taken in pyridine, since the compound had no solubility in DMSO. NMR and LCMS analysis showed the amine product as the major product in crude mixture. The free amine compound (113) was carried forward into the coupling with the Sepharose 4B is resin without purification due to poor compound solubility. The yield was estimated to be quantitative.

OSW-1 Amine 113: LRMS (-TOF): calculated for C$_{47}$H$_{71}$N$_2$O$_{15}$ [M+CH$_2$O$_2^-$]: 903.4859; found: 903.55.

Example 29

Preparation of ORW-1 Solid Phase Resin 117

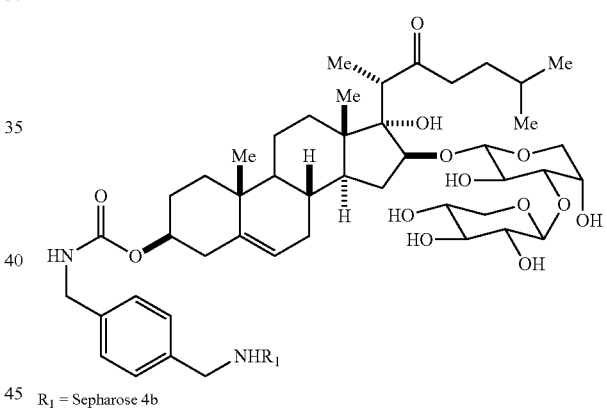

R$_1$ = Sepharose 4b 0.12 mL of NHS-activated Sepharose 4 Fast Flow™ (16-23 mmol/drained mL resin, GE Healthcare) was charged into an EppendorfrM tube Filter Cup via a wide-mouth 1000 µL pipet tip. The resin was washed three times with 0.3 mL of d$_5$-pyridine via low speed centrifugation. The amine compound 117 was then dissolved in 0.3 mL of d$_6$-DMSO and transferred to the washed resin. The reaction was incubated shaking at ambient temperature for ~16 h. After ~16 h no detectable soluble compound remained by LCMS. The reaction was centrifuged to separate the solution from the resin. NMR analysis of the d$_5$-pyridine flow-through revealed no amine compound (117). To the resin, 0.3 mL of a 5% ethanolamine in DMSO solution was added and incubated for 4 h at ambient temperature. The resin was then centrifuged to remove the 5% ethanolamine solution and washed three times with 0.5 mL DMSO. The resin was stored dry at −20° C. until use.

Example 30

Preparation of OSW-1 Amine 114

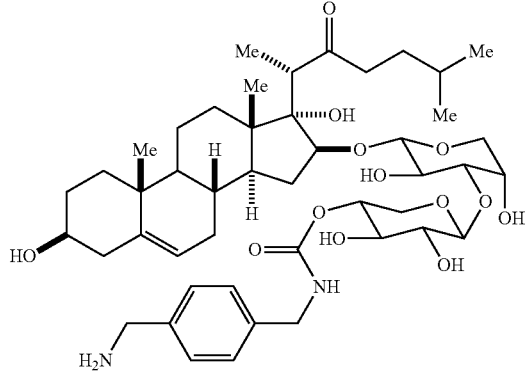

Chemical Formula: C$_{46}$H$_{70}$N$_{2}$O$_{13}$
Exact Mass: 858.48779

Carbamate 6c (2.4 mg, 0.0021 mmol) was dissolved in THF (0.2 mL) under argon. Morpholine (2.0 µL, 0.023 mmol) was added via syringe. The reaction flask was taken into the nitrogen glove bag. Tetrakis(triphenylphosphine)palladium (0) (~0.4 mg, 16 mol %) was added to the reaction as a solid. The light yellow reaction was stirred under argon at ambient temperature for 70 min. A drop of water was added, and the reaction was concentrated in vacuo. Silica gel pipet chromatography with a 3-15% MeOH/CH$_2$Cl$_2$ gradient yielded slightly impure free amine compound 114 (2.0 mg, ~95%) as a whitish solid.

OSW-1 Amine 114: $^1$H NMR (500 MHz, CD$_3$CN) δ=8.01 (d, J=8.8 Hz, 2 H), 7.37 (d, J=7.9 Hz, 2 H), 7.29 (d, J=7.9 Hz, 2 H), 7.01 (d, J=8.8 Hz, 2 H), 6.17-6.09 (m, 1 H), 5.39-5.27 (m, 2 H), 4.97-4.88 (m, J=7.6, 7.6 Hz, 1 H), 4.81-4.67 (m, 2 H), 4.64 (d, J=4.9 Hz, 1 H), 4.37-4.16 (m, 3 H), 4.10 (s, 1 H), 4.07-3.97 (m, 2 H), 3.94-3.63 (m, 8 H), 3.62-3.50 (m, 2 H), 3.49-3.26 (m, 3 H), 2.91 (d, J=7.8 Hz, 1 H), 2.50 (d, J=7.8 Hz, 1 H), 1.87-0.70 (m, 34 H).

Example 31

Preparation of 3-(tert-Butyldimethylsilyl)-OSW-1 Carbamates 110 and 120

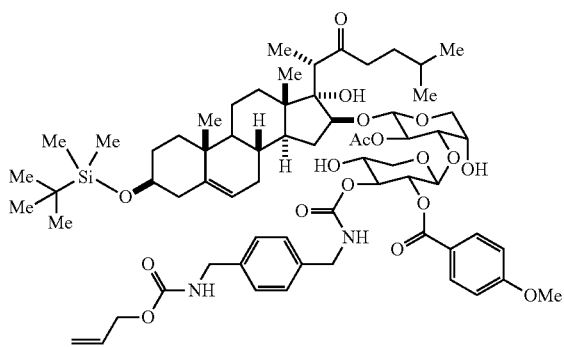

Chemical Formula: C$_{66}$H$_{96}$N$_{2}$O$_{18}$Si
Exact Mass: 1232.64274

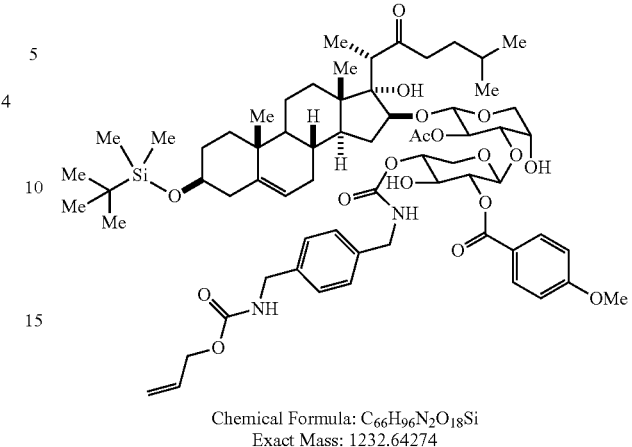

Chemical Formula: C$_{66}$H$_{96}$N$_{2}$O$_{18}$Si
Exact Mass: 1232.64274

OSW-1 (5 mg, 0.005 mmol) under argon was taken into a nitrogen glove bag. Copper (I) chloride (~1 mg, 0.01 mmol) was added to the OSW-1, and under argon, the reaction was dissolved in DMF (0.1 mL). Alloc-(N)-diaminomethyl benzene isocyanate (7 mg) was charged into a dry vial and dissolved in DMF (0.29 mL) to make a reagent stock solution. 0.1 mL of the Alloc-(N)-diaminomethyl benzene isocyanate reagent stock solution (2.4 mg, 0.01 mmol) was added to the OSW-1 solution via syringe at ambient temperature and stirred for 15 h. The initial reaction was weakly green in color, which upon ~40 min after addition of the isocyanate, changed to a yellow and slightly opaque appearance. The reaction was diluted with ~10 mL of chloroform and washed with water, followed by brine. The slightly brown, cloudy organic layer was dried over Na$_2$SO$_4$. The TLC before workup was unclear, with several spots co-eluting. After workup the TLC resolved to three clear spots: sm and two new upper R$_f$ spots. The reaction was purified via pTLC with 5% MeOH/CH$_2$Cl$_2$ (½ plate). Further purification with semi-preparative reverse-phase HPLC with a Zorbax C-18SB column (I.D. 9.4 mm, 3.9 mL/min) using isocratic elution with 95% MeOH/H$_2$O was performed, yielding 120 (1.1 mg, 17%, 35% borsm) and 110 (1.1 mg, 17%, 35% borsm) as white solids.

3-TBS-OSW-1 Carbamate 120: R$_f$ (5% MeOH/CH$_2$Cl$_2$)=0.39. $^1$H NMR (600 MHz, CD$_3$CN) δ=7.95 (d, J=8.8 Hz, 2 H), 7.02 (d, J=8.8 Hz, 2 H), 6.98 (d, J=7.9 Hz, 2 H), 6.91 (d, J=−7.9 Hz, 2 H), 6.00-5.90 (m, 3 H), 5.34-5.26 (m, 2 H), 5.19 (d, J=9.1 Hz, 1 H), 5.01-4.91 (m, 2 H), 4.77-4.68 (m, 2 H), 4.56-4.51 (m, 2 H), 4.24-4.13 (m, 4 H), 4.01 (d, J=6.3 Hz, 1 H), 3.97 (dd, J=5.4, 12.4 Hz, 1 H), 3.93-3.85 (m, 4 H), 3.80-3.73 (m, 2 H), 3.71-3.65 (m, 2 H), 3.61 (d, J=5.0 Hz, 1 H), 3.52-3.33 (m, 4 H), 3.20 (d, J=5.1 Hz, 1 H), 2.90-2.82 (m, 1 H), 2.52-2.42 (m, 1 H), 2.08-2.02 (m, 2 H), 1.86-1.76 (m, 3 H), 1.76-1.67 (m, 3 H), 1.67-1.62 (m, 3 H), 1.62-1.40 (m, 8 H), 1.40-1.15 (m, 7 H), 1.11-1.05 (m, 3 H), 1.02-0.96 (m, 3 H), 0.92-0.84 (m, 9 H), 0.82-0.72 (m, 9 H), 0.07-0.00 (m, 6 H).

3-TBS-OSW-1 Carbamate 110: R$_f$(5% MeOH/CH$_2$Cl$_2$)=0.32. $^1$H NMR (600 MHz, CD$_3$CN) δ=7.95 (d, J=8.9 Hz, 2 H), 7.02 (d, J=8.9 Hz, 2 H), 6.98 (d, J=7.9 Hz, 2 H), 6.91 (d, J=−7.9 Hz, 2 H), 5.99-5.93 (m, 2 H), 5.33-5.27 (m, 2 H), 5.21-5.16 (m, 1 H), 4.99-4.92 (m, 2 H), 4.75-4.69 (m, 2 H), 4.53 (td, J=1.6, 5.4 Hz, 2 H), 4.26-4.12 (m, 2 H), 4.01 (d, J=6.3 Hz, 1 H), 3.97 (dd, J=5.6, 11.9 Hz, 1 H), 3.92-3.86 (m, 4 H), 3.80-3.73 (m, 1 H), 3.71-3.65 (m, 1 H), 3.61 (d, J=4.8 Hz, 1 H), 3.50-3.42 (m, 2 H), 3.37 (dd, J=10.3, 11.7 Hz, 1 H), 3.20 (d, J=3.8 Hz, 1 H), 2.89-2.83 (m, 1 H), 2.51-2.43 (m, 1 H), 1.85-1.77 (m, 4 H), 1.76-1.67 (m, 3 H), 1.67-1.62 (m, 3 H), 1.62-1.41 (m, 4 H), 1.38-1.15 (m, 4 H), 1.07 (d, J=7.5 Hz, 1 H), 1.06-1.01 (m, 1 H), 1.01-0.97 (m, 3 H), 0.91-0.84 (m, 9 H), 0.82-0.78 (m, 6 H), 0.77-0.73 (m, 3 H), 0.06-0.02 (m, 6 H).

Example 32

Preparation of OSW-1 Carbonyl-Imidazole 125

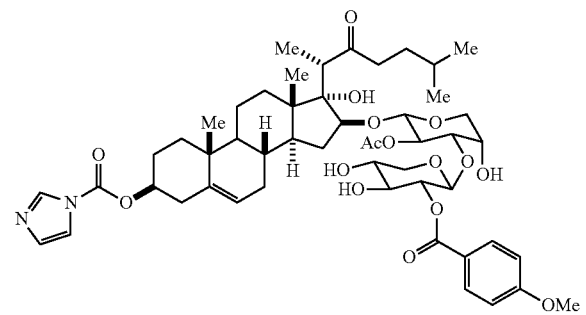

Chemical Formula: $C_{51}H_{70}N_2O_{16}$
Exact Mass: 966.47253

OSW-1 Nitrophenyl carbonate 115 (3.0 mg, 0.0029 mmol) was dissolved in a 9:1 mixture of dioxane:$H_2O$. A catalytic amount of imidazole was added. The reaction was stirred for ~1 hr. Reaction was diluted in $CHCl_3$, and washed with $H_2O$, then brine, and finally dried over $Na_2SO_4$. pTLC (8% MeOH/$CH_2C2$). In addition to OSW-1, which was the intended product of this reaction, 125 was also produced (~1 mg, ~30%).

3-Carbonyl-imidazolyl-OSW-1 125: $^1$H NMR (500 MHz, $CD_3CN$) δ=8.13-8.08 (m, 1 H), 8.02 (d, J=8.7 Hz, 2 H), 7.46 (t, J=1.4 Hz, 1 H), 7.02 (d, J=8.7 Hz, 2 H), 7.01-6.99 (m, 1 H), 5.43 (d, J=4.6 Hz, 1 H), 4.87-4.82 (m, 1 H), 4.77-4.67 (m, 2 H), 4.61 (d, J=7.8 Hz, 1 H), 4.21 (s, 1 H), 4.01 (d, J=6.4 Hz, 1 H), 3.92 (dd, J=5.0, 11.4 Hz, 1 H), 3.90-3.85 (m, 5 H), 3.77 (dd, J=4.1, 12.4 Hz, 1 H), 3.69-3.64 (m, 3 H), 3.64-3.51 (m, 2 H), 3.47-3.38 (m, 2 H), 3.32-3.23 (m, 2 H), 2.92-2.79 (m, J=7.8 Hz, 1 H), 2.55-2.41 (m, 3 H), 1.86-1.65 (m, 6 H), 1.65-1.43 (m, 4 H), 1.39-1.14 (m, 7 H), 1.13-1.02 (m, 7 H), 1.02-0.85 (m, 2 H), 0.84-0.74 (m, 9 H).

Example 33

Preparation of 128, 129, and 130

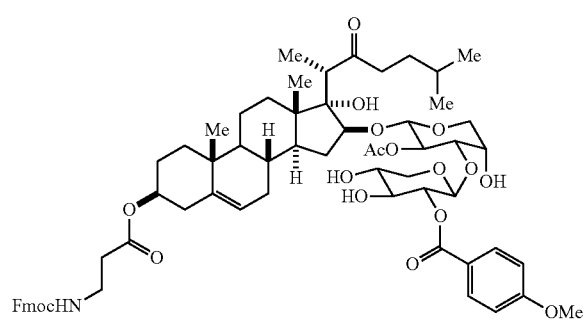

Chemical Formula: $C_{65}H_{83}NO_{18}$
Exact Mass: 1165.56101

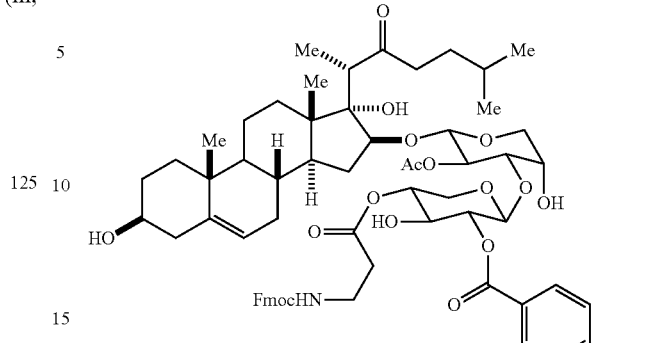

Chemical Formula: $C_{65}H_{83}NO_{18}$
Exact Mass: 1165.56101

Fmoc-β-alanine acid chloride (3.56 mg, 0.011 mmol) was dried in vacuo for 30 minutes. A solution of OSW-1 (10 mg, 0.011 mmol) and triethylamine (1.16 mg, 0.011 mmol) in 4 mL $CH_2Cl_2$ was cooled to 0° C. 9 was dissolved in 0.5 mL $CH_2Cl_2$ and injected into OSW-1 solution. TLC in 7% MeOH/$CH_2Cl_2$ showed the reaction was not done and another 0.8 equivalents of 9 was added. Products purified by pipette column chromatography in 5% MeOH/$CH_2Cl_2$. Dissolved silica gel gave inflated yields of 128, 5.4 mg (40%), 129, 4.7 mg (35%), and 130, 6.7 mg (50%). Products further purified semi-preparative reverse-phase HPLC with a Zorbax C-18SB column (I.D. 9.4 mm, 3.9 mL/min) using isocratic elution with 80% $CH_3CN/H_2O$.

OSW-1 Ester 128: $^1$H NMR (500 MHz, $CDCl_3$): δ=8.10 (d, J=9.5 Hz, 2H), 7.76 (d, J=8 Hz, 2H), 7.59 (d, J=7.5, 2H), 7.40 (t, J=7.5 Hz, 2H), 7.32 (t, J=8 Hz, 2H), 6.99 (d, J=8.5 Hz, 2H), 5.38 (br s, 1H), 5.29 (br s, 1H), 4.93 (t, J=8 Hz, 1H), 4.73 (d, J=6.5 Hz, 2H), 4.72 (br s, 1H), 4.64 (br s, 1H), 4.38 (d, J=6.5 Hz, 2H), 4.17 (m, 4H), 3.88-3.67 (m, 11H), 3.47-3.37 (m, 8H), 2.96 (d, J=5.5 Hz, 1H), 2.70 (q, J=7.5, 1H), 2.53 (br s, 2H), 2.49 (d, J=4 Hz, 2H), 2.33 (d, J=8.5 Hz, 4H), 2.20 (m, 3H), 2.10-2.07 (m, 2H), 1.88-1.75 (m, 8H), 1.53 (s, 35H), 1.25 (s, 18H), 1.04-1.02 (m, 17H), 0.80-0.75 (m, 23H).

OSW-1 Ester 129: $^1$H NMR (500 MHz, CDCl$_3$): δ=8.08 (d, J=9 Hz, 2H), 7.74 (d, J=7 Hz, 2H), 7.54 (d, J=8 Hz, 2H), 7.37 (t, J=7 Hz, 2H), 7.28 (t, J=7.5 Hz, 2H), 6.98 (d, J=9 Hz, 2H), 5.33 (d, J=5 Hz, 2H), 5.02-4.97 (m, 2H), 4.77 (d, J=6 Hz, 1H), 4.71 (t, J=4.5 Hz, 1H), 4.34 (d, J=6.5 Hz, 2H), 4.17 (m, 4H), 3.92-3.68 (m, 9H), 3.54-3.44 (m, 6H), 3.27 (d, J=5.5 Hz, 1H), 3.19 (q, J=7.5, 1H), 2.77 (q, J=7 Hz, 1H), 2.58 (br s, 2H), 2.29-2.11 (m, 8H), 1.85-1.82 (m, 5H), 1.06-1.03 (m, 11H), 0.83 (s, 3H), 0.75 (t, J=6.5 Hz, 7H).

OSW-1 Ester 130: $^1$H NMR (500 MHz, CDCl$_3$): δ=8.02 (d, J=4 Hz, 2H), 7.75 (d, J=7.5 Hz, 2H), 7.55 (t, J=7 Hz, 2H), 7.39 (t, J=7.5 Hz, 2H), 7.31 (t, J=7 Hz, 2H), 6.93 (d, J=9 Hz, 2H), 5.31 (br s, 1H), 5.23 (br s, 1H), 5.12 (br s, 2H), 4.69 (br s, 2H), 4.34 (d, J=6.5 Hz, 2H), 4.18-4.14 (m, 3H), 3.88-3.30 (m, 15H), 2.72 (d, J=6.5 Hz, 1H), 2.46-1.42 (m, 20H), 1.06-0.74 (m, 17H).

Example 34

Preparation of OSW-1 Carbamates 131 and 132

OSW-1 (25 mg, 0.029 mmol) was charged to a dried 5 mL flask under argon atmosphere. Benzylisocyanate (4.6 mg, 0.034 mmol) was weighed out into a separate dried flask and dissolved in 0.5 mL dry pyridine. The pyridine solution was added to the flask containing OSW-1 via syringe and stirred at rt for 20 h. TLC in 100% EtOAc showed multiple spots. Solvent was removed in vacuo. Product was purified via column chromatography in a pipette using 4×10 mL washes of a gradient of 2% to 4% MeOH in CH$_2$Cl$_2$. Column was run three times to yield pure product.

Carbamate 131: $^1$H NMR (500 MHz, CDCl$_3$): δ=8.08 (d, J=9.0 Hz, 2H), 7.34-7.24 (m, 5H), 6.91 (d, J=9 Hz, 2H), 5.33 (d, J=5 Hz, 1H), 5.06-5.01 (m, 2H), 4.83 (m, 1H), 4.78 (d, J=5.5 Hz, 1H), 4.70 (br s, 1H), 4.36 (br s, 2H), 4.27 (dd, J=11.5, 4.5 Hz, 1H), 4.20 (s, 2H), 3.92-3.8 (m, 6H), 3.77 (t, J=11 Hz, 1H), 3.69 (t, J=6 Hz, 1H), 3.53-3.45 (m, 3H), 3.28 (d, J=8 Hz, 1H), 2.79 (q, J=8 Hz, 1H), 2.28-2.12 (m, 4H), 1.98 (s, 4H), 1.83 (m, 4H), 1.76-1.72 (m, 1H), 1.64-1.46 (m, 14H), 1.31-1.20 (m, 6H), 1.08-1.03 (m, 9H), 0.95 (m, 1H), 0.84 (s, 4H), 0.74 (t, J=6.5 Hz, 7H).

131

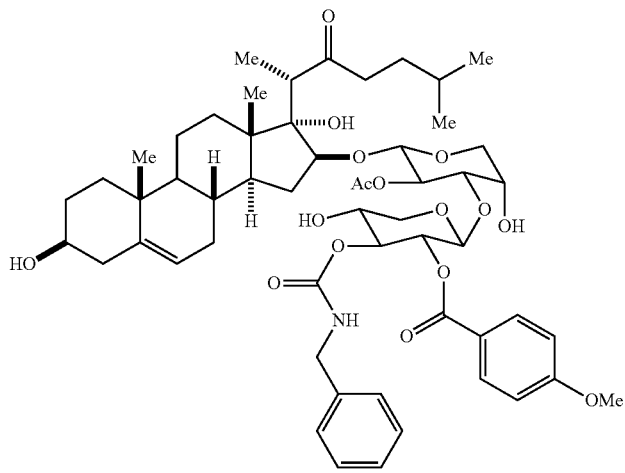

Chemical Formula: C$_{55}$H$_{75}$NO$_{16}$
Exact Mass: 1005.50859

132

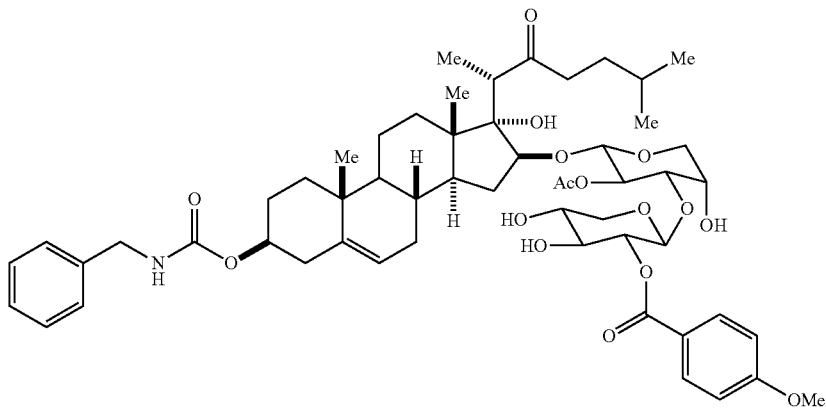

Chemical Formula: C$_{55}$H$_{75}$NO$_{16}$
Exact Mass: 1005.50859

Example 35

Preparation of Hydrogenated Product 133

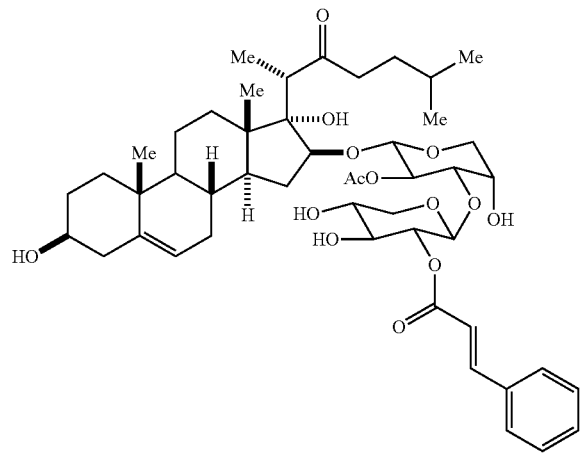

OSW-3

Chemical Formula: C₄₈H₆₈O₁₄
Exact Mass: 868.46

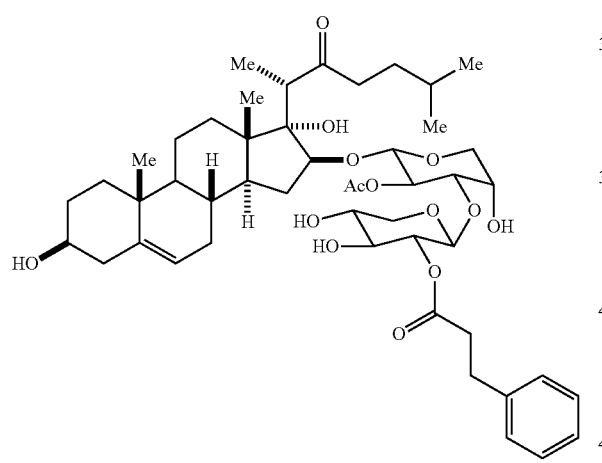

133

Chemical Formula: C₄₈H₇₀O₁₄
Exact Mass: 870.47656

OSW-3 (2.0 mg, 0.0023 mmol) was dissolved in 0.5 mL MeOH. Hydrogen gas was bubbled through the reaction, then the atmosphere of the reaction was flushed with argon. 10% Palladium on carbon (~0.2 mg, ~0.0002 mmol) was added, and the reaction was placed under a hydrogen atmosphere. The reaction was stirred for 45 min. The reaction was filtered through a pad of Celite to remove the Pd/C, with MeOH washing. The reaction was condensed, and purification with a silica gel pipette column was performed using a 4-12% MeOH/CHCl₃ gradient. 133 (~1.0 mg, ~50% yield) was obtained as a white solid.

Example 36

Binding of OSW-1 Analogs

OSW-1 and OSW-1 analogs presented in Examples 9-35 were characterized in vitro in direct and competition binding assays, respectively, with tritiated 25-OHC and either OSBP1-myc-his or ORP4L-myc-his. Methods are described above in the General Methods section. Results are shown in Table 1. Items for which no data is available are reported as "—".

TABLE 1

| | [$^3$H]-25-OHC $K_i$ (nM) | |
|---|---|---|
| Compound | OSBP1-myc-his | ORP4L-myc-his |
| OSW-1 | 26 ± 9 | 54 ± 11 |
| 100 | — | — |
| 101 | — | — |
| 102 | — | — |
| 8 | 170 ± 7 | 760 ± 200 |
| 103 | — | — |
| 104 | — | — |
| 105 | — | — |
| 6c | 46 ± 11 | 150 ± 50 |
| 6a | 18 ± 5 | 43 ± 9 |
| 106 | — | — |
| 20 | — | — |
| 107 | — | — |
| 108 | None detected | None detected |
| 7 | 63 ± 12 | 120 ± 31 |
| 109 | — | — |
| 110 | — | — |
| 111 | — | — |
| 112 | — | — |
| 113 | — | — |
| 114 | — | — |
| 115 | — | — |
| 116 | — | — |
| 117 | — | — |
| 118 | — | — |
| 119 | — | — |
| 120 | — | — |
| 121 | — | — |
| 122 | — | — |
| 123 | — | — |
| 124 | — | — |
| 125 | — | — |
| 126 | — | — |
| 127 | — | — |
| 128 | — | — |
| 129 | — | — |
| 130 | — | — |
| 131 | — | — |
| 132 | — | — |
| 133 | — | — |

Example 37

Growth Inhibition by OSW-1 Analogs

OSW-1 and OSW-1 analogs presented in Examples 9-35 were characterized in vitro in growth inhibition assays with wild-type (p21$^{+/+}$) and p21-deficient (p21$^{-/-}$) HCT-116 cells. Methods are described above in the General Methods section. Results are shown in Table 2. Items for which no data is available are reported as "—".

TABLE 2

| | Growth inhibition of HCT-116 cells | | | |
|---|---|---|---|---|
| | GI$_{50}$ (nM) 48 h | | GI$_{50}$ (nM) 72 h | |
| Compound | p21$^{+/+}$ | p21$^{-/-}$ | p21$^{+/+}$ | p21$^{-/-}$ |
| OSW-1 | 28 | 0.20 ± 0.03 | 1.6 ± 0.6 | 0.04 ± 0 |
| 100 | — | — | — | — |
| 101 | 28 ± 5 | 1.3 ± 0 | — | — |

TABLE 2-continued

Growth inhibition of HCT-116 cells

| Compound | GI$_{50}$ (nM) 48 h | | GI$_{50}$ (nM) 72 h | |
|---|---|---|---|---|
| | p21$^{+/+}$ | p21$^{-/-}$ | p21$^{+/+}$ | p21$^{-/-}$ |
| 102 | 85 | 97 | — | — |
| 8 | 1400 ± 400 | 220 ± 60 | — | — |
| 103 | 172 ± 2 | 138 ± 16 | — | — |
| 104 | >2700 | 525 ± 4 | — | — |
| 105 | — | — | — | — |
| 6c | 17 ± 4 | 2.2 ± 0.5 | — | — |
| 6a | 0.60 ± 0.13 | 0.08 ± 0.02 | — | — |
| 106 | 91 ± 10 | 5 ± 3 | — | — |
| 20 | 6500 ± 3600 | 550 ± 300 | — | — |
| 107 | — | — | — | — |
| 108 | 2300 ± 200 | 720 ± 90 | — | — |
| 7 | 120 ± 40 | 17 ± 2 | — | — |
| 109 | — | — | — | — |
| 110 | — | — | — | — |
| 111 | — | — | — | — |
| 112 | — | — | — | — |
| 113 | — | — | — | — |
| 114 | — | — | — | — |
| 115 | — | — | — | — |
| 116 | — | — | — | — |
| 117 | — | — | — | — |
| 118 | — | — | — | — |
| 119 | — | — | — | — |
| 120 | — | — | — | — |
| 121 | — | — | — | — |
| 122 | — | — | — | — |
| 123 | — | — | — | — |
| 124 | — | — | — | — |
| 125 | — | — | — | — |
| 126 | — | — | — | — |
| 127 | — | — | — | — |
| 128 | — | — | — | — |
| 129 | — | — | — | — |
| 130 | — | — | — | — |
| 131 | — | — | — | — |
| 132 | — | — | — | — |
| 133 | — | — | — | — |

Example 38

Growth Inhibition by OSW-1 Analogs

OSW-1 and OSW-1 analogs presented in Examples 9-35 were characterized in vitro in growth inhibition assays with wild-type A549 cells. Methods are essentially as described above in the General Methods section in connection with assays using HCT-116 cells. Results are shown in Table 3. Items for which no data is available are reported as "—".

TABLE 3

Growth inhibition of A549 cells

| Compound | GI$_{50}$ (nM) 48 h |
|---|---|
| OSW-1 | 0.50 ± 0.24 |
| 100 | — |
| 101 | — |
| 102 | — |
| 8 | 570 ± 250 |
| 103 | — |
| 104 | — |
| 105 | — |
| 6c | 2.9 ± 0.9 |
| 6a | 0.10 ± 0.04 |
| 106 | — |
| 20 | — |
| 107 | — |
| 108 | 1600 ± 500 |

TABLE 3-continued

Growth inhibition of A549 cells

| Compound | GI$_{50}$ (nM) 48 h |
|---|---|
| 7 | 41 ± 25 |
| 109 | — |
| 110 | — |
| 111 | — |
| 112 | — |
| 113 | — |
| 114 | — |
| 115 | — |
| 116 | — |
| 117 | — |
| 118 | — |
| 119 | — |
| 120 | — |
| 121 | — |
| 122 | — |
| 123 | — |
| 124 | — |
| 125 | — |
| 126 | — |
| 127 | — |
| 128 | — |
| 129 | — |
| 130 | — |
| 131 | — |
| 132 | — |
| 133 | — |

EQUIVALENTS

While various embodiments of the invention have been described, it will be apparent to those of ordinary skill in the art that other embodiments and implementations are possible within the scope of the invention. Accordingly, the invention is not to be restricted except in light of the attached claims and their equivalents.

INCORPORATION BY REFERENCE

Except as may be specified otherwise herein, all patents and published patent applications cited herein are hereby incorporated by reference in their entirety.

We claim:

1. A conjugate comprising an antibody, or antigen-binding fragment thereof, covalently linked to a compound of formula (I):

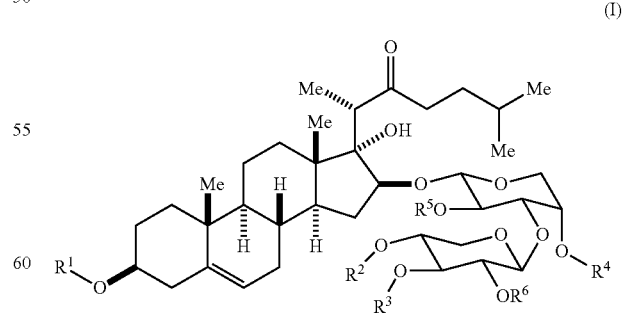

or a pharmaceutically acceptable salt thereof;
wherein:
$R^1$, $R^2$, $R^3$, and $R^6$ are independently selected from the group consisting of hydrogen, trialkylsilyl, and

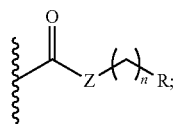

Z is absent or is selected from the group consisting of O and $R^{10}$;
n is an integer 0-6;
R is selected from the group consisting of substituted or unsubstituted: alkyl, alkenyl, amino, alloc-protected amino, Fmoc-protected amino, aryl, 5- to 13-membered cycloalkyl or cycloalkenyl group, and 5- to 10-membered cyclic heteroaromatic group comprising 1-3 heteroatoms independently selected from the group consisting of N, O, and S;
$R^4$ is selected from the group consisting of hydrogen and $C_1$-$C_6$ alkyl;
$R^5$ is selected from the group consisting of hydrogen and acyl; and
$R^{10}$ is selected from the group consisting of hydrogen and $C_1$-$C_6$ alkyl;
provided that at least one of $R^1$, $R^2$, $R^3$, $R^4$, $R^5$, and $R^6$ is not hydrogen.

2. The conjugate of claim 1, wherein $R^4$ is hydrogen.
3. The conjugate of claim 1, wherein $R^5$ is acetyl.
4. The conjugate of claim 1, wherein $R^6$ is para-methoxybenzoyl or 3-phenylpropanoyl.
5. The conjugate of claim 1, wherein Z is O.
6. The conjugate of claim 5, wherein R is selected from the group consisting of alkyl and 4-nitrophenyl.
7. The conjugate of claim 5, wherein n is 0.
8. The conjugate of claim 1, wherein Z is NH.
9. The conjugate of claim 8, wherein R is an amino group.
10. The conjugate of claim 9, wherein n is 6.
11. The conjugate of claim 8, wherein R is a para-aminoalkylaryl group.
12. The conjugate of claim 11, wherein n is 1.
13. The conjugate of claim 8, wherein n is 1; and R is phenyl.
14. The conjugate of claim 1, wherein Z is absent.
15. The conjugate of claim 14, wherein R is an amino group.
16. The conjugate of claim 15, wherein n is 2.
17. The conjugate of claim 14, wherein R is a 1-imidazolyl group.
18. The conjugate of claim 17, wherein n is 0.
19. The conjugate of claim 1, wherein at least one of $R^1$, $R^2$, and $R^3$ is tert-butyldimethylsilyl.
20. A conjugate of claim 1, wherein the antibody, or antigen-binding fragment thereof, and the compound are covalently linked through a cysteine thiol-maleimide Michael addition product, a valine-citrulline p-aminobenzyl linker, or a valine-citrulline p-aminobenzylcarbamate linker.
21. The conjugate of claim 1, wherein the antibody, or antigen-binding fragment thereof, binds specifically to an antigen expressed on a cancer cell.
22. The conjugate of claim 21, wherein the cancer cell is p21-deficient.
23. The conjugate of claim 1, wherein $R^1$ is

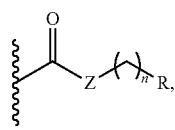

wherein Z is absent or is selected from the group consisting of O and $NR^{10}$.

24. The conjugate of claim 1, wherein $R^2$ is

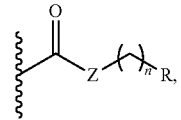

wherein Z is absent or is selected from the group consisting of O and $NR^{10}$.

25. The conjugate of claim 1, wherein $R^3$ is

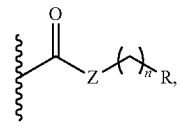

wherein Z is absent or is selected from the group consisting of O and $NR^{10}$.

26. The conjugate of claim 1, wherein:
$R^1$, $R^2$, and $R^3$ are independently selected from the group consisting of hydrogen, trialkylsilyl, and

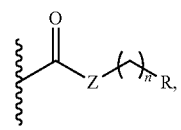

provided that at least one of $R^2$ and $R^3$ is not hydrogen;
$R^6$ is

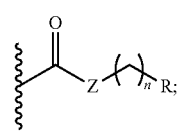

Z is absent or is selected from the group consisting of O and $NR^{10}$;
n is an integer 0-6;
R is selected from the group consisting of substituted or unsubstituted: alkyl, alkenyl, amino, alloc-protected amino, Fmoc-protected amino, aryl, 5- to 13-membered cycloalkyl or cycloalkenyl group, and 5- to 10-membered cyclic heteroaromatic group comprising 1-3 heteroatoms independently selected from the group consisting of N, O, and S;
$R^4$ is hydrogen;
$R^5$ is acyl; and
$R^{10}$ is selected from the group consisting of hydrogen and $C_1$-$C_6$ alkyl.

27. The conjugate of claim 1 comprising an antibody, or antigen-binding fragment thereof, covalently linked to a compound selected from the group consisting of:

135
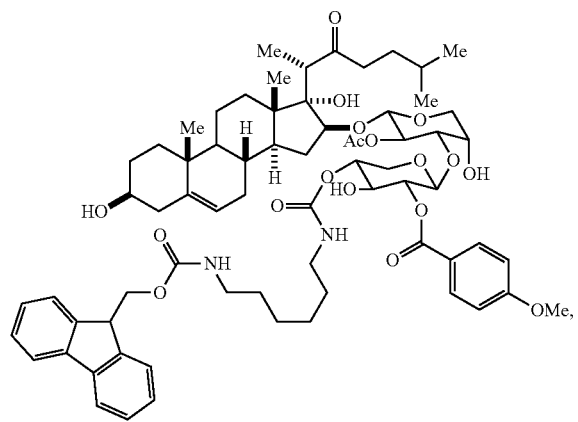
100
136
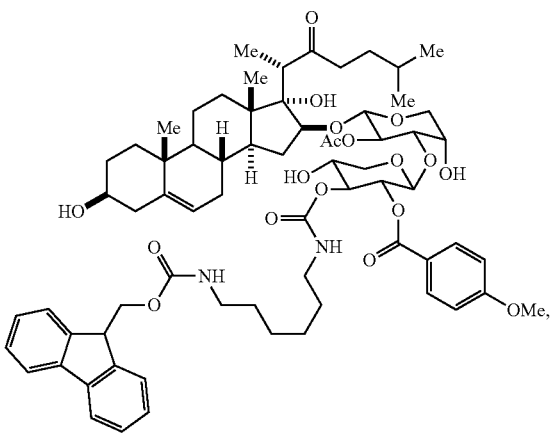
101
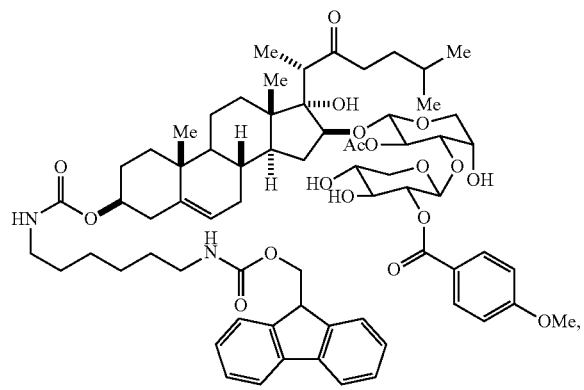
102
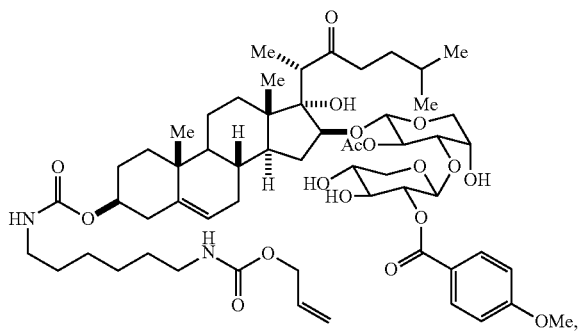
103
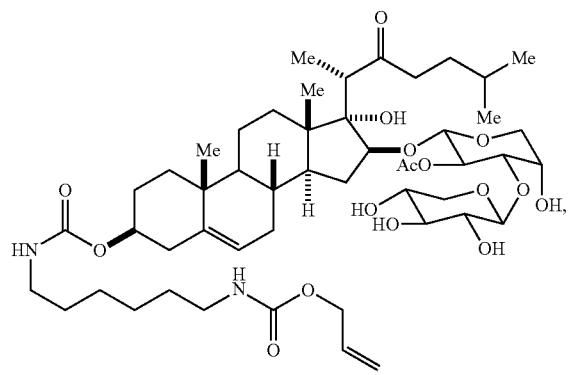
104
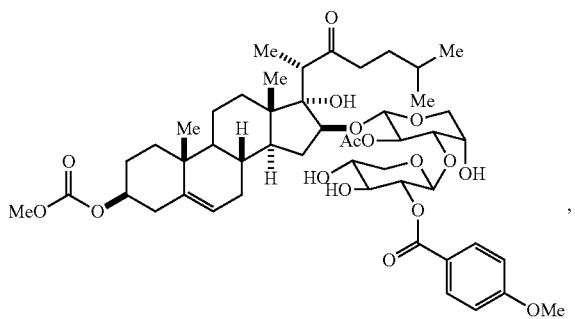
105

-continued
106
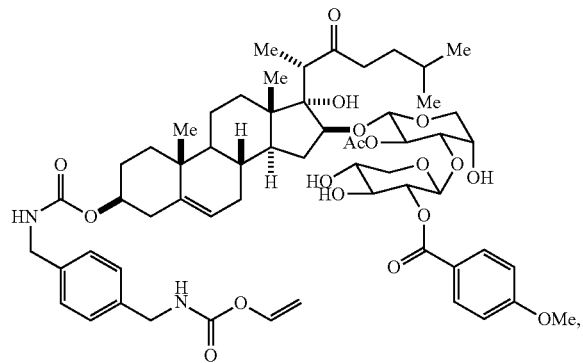
107
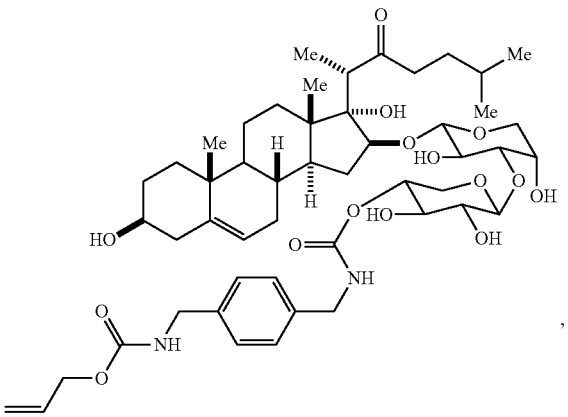
108
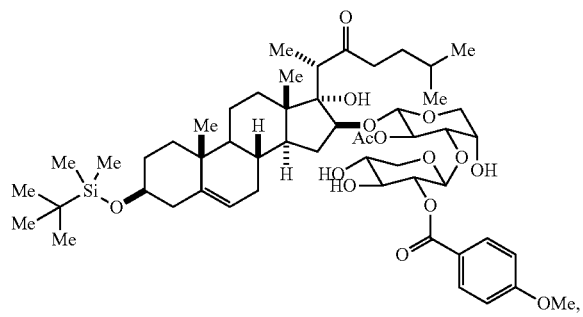
109
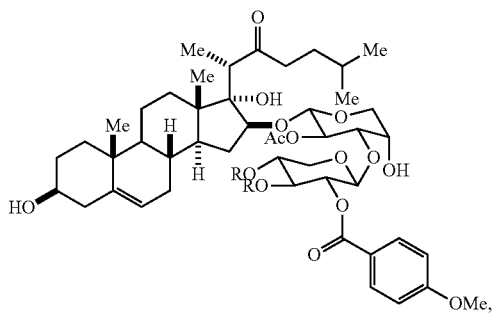
110
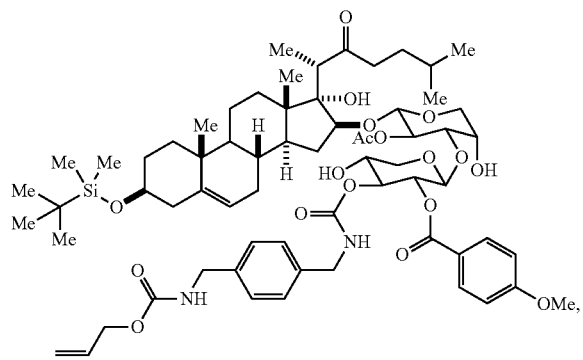
111
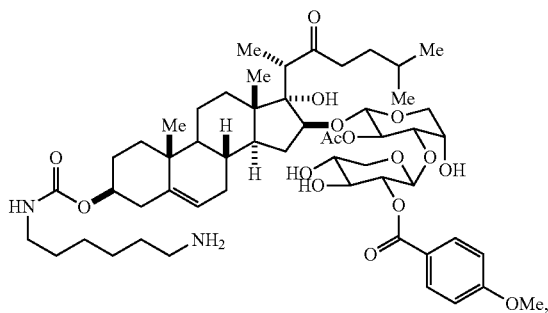
112
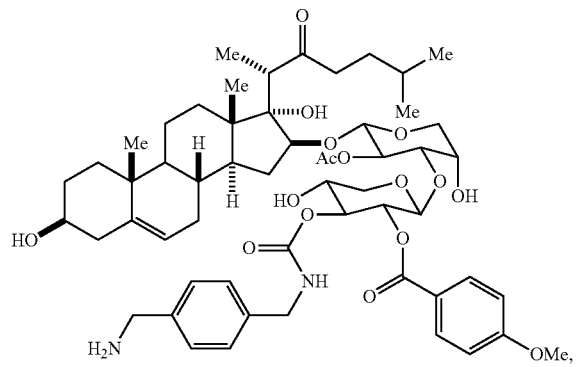
113
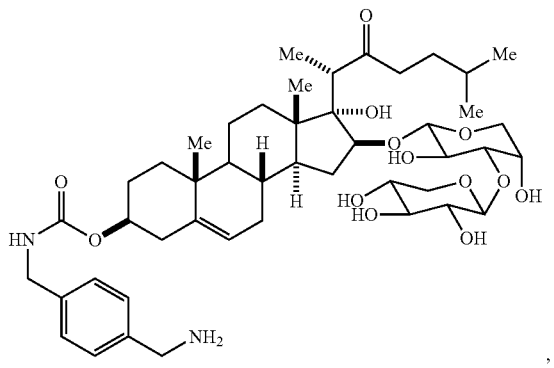

-continued
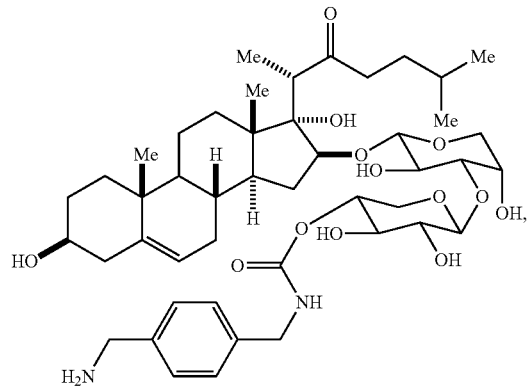
114
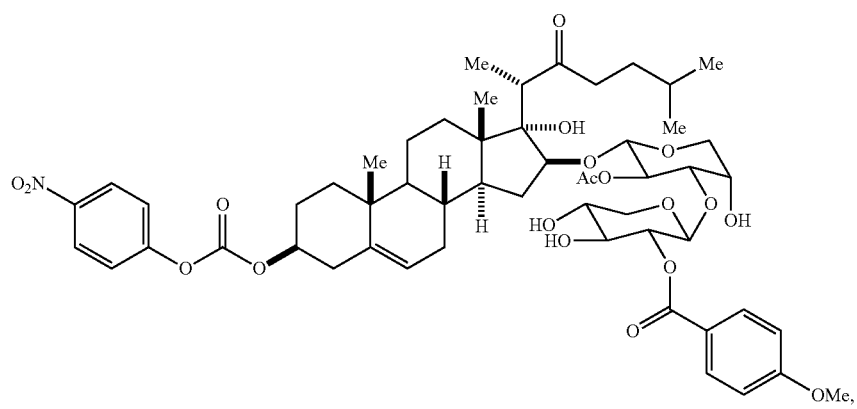
115
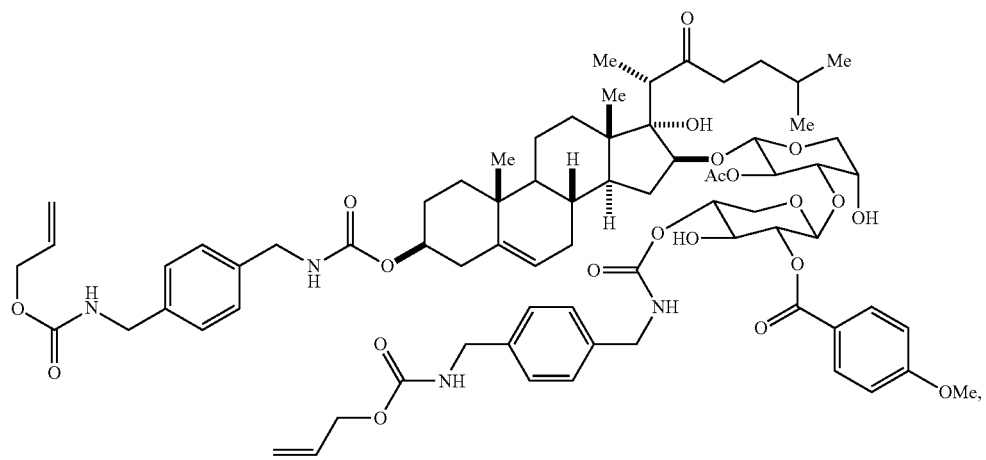
118

-continued
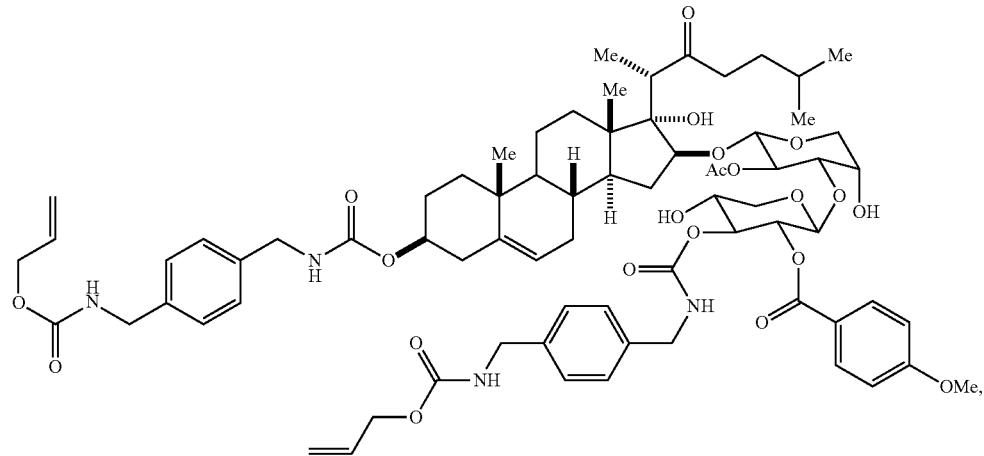
119
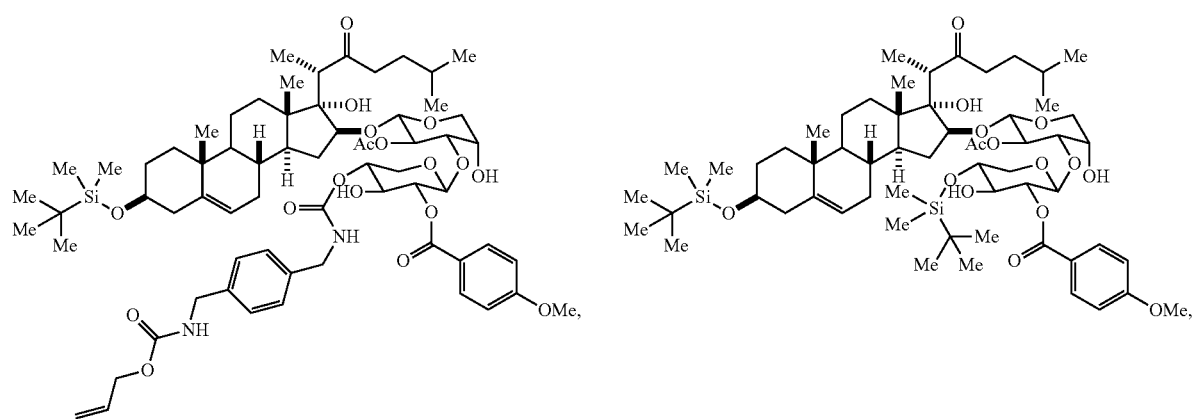
120
121
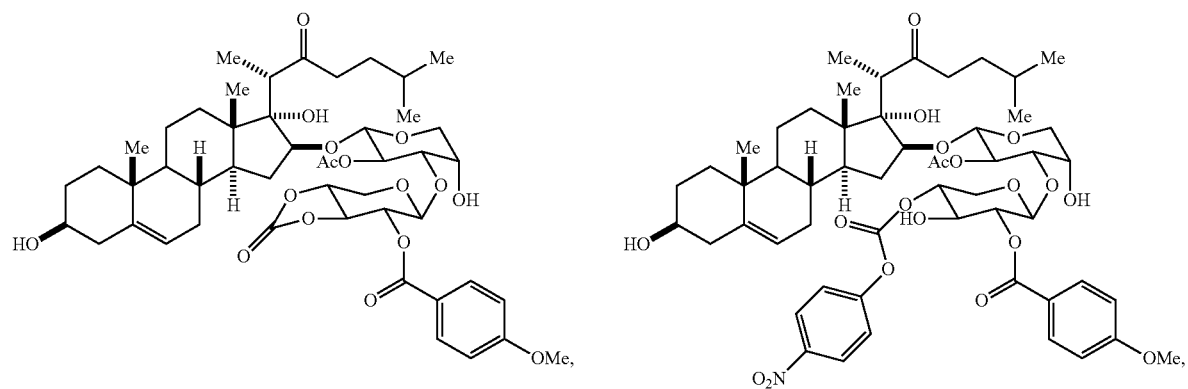
122
123

-continued
124
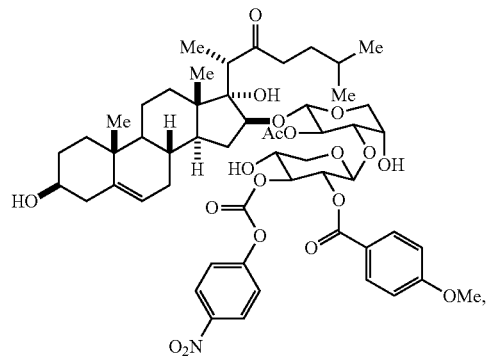
125
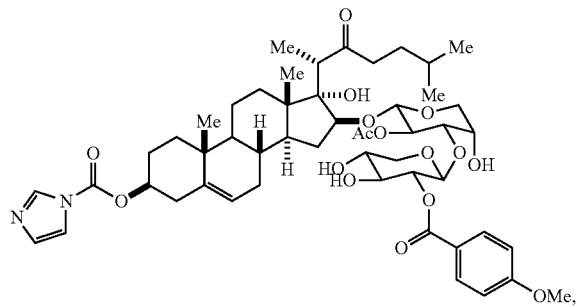
126
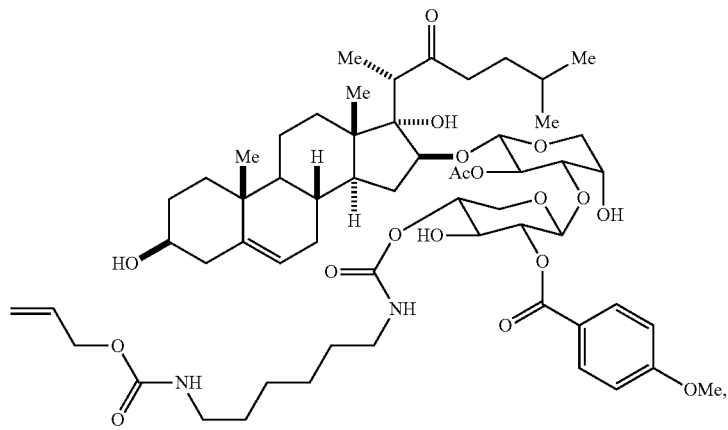
127
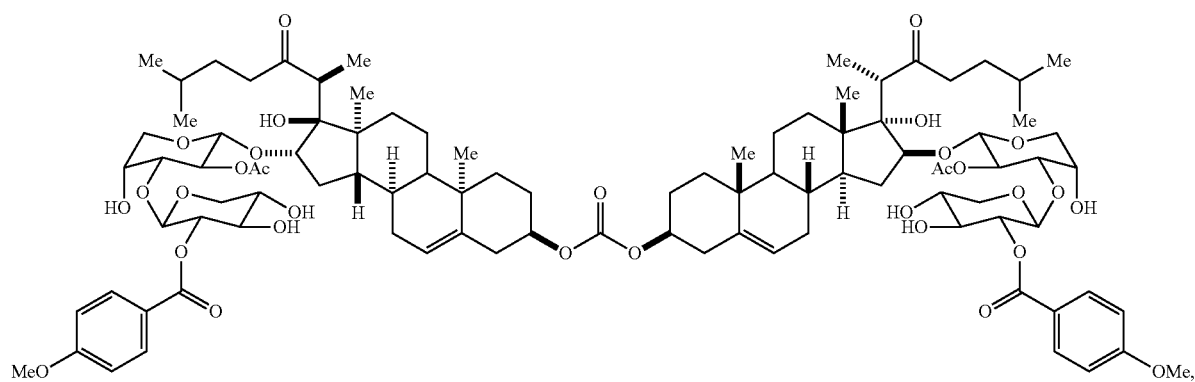
128
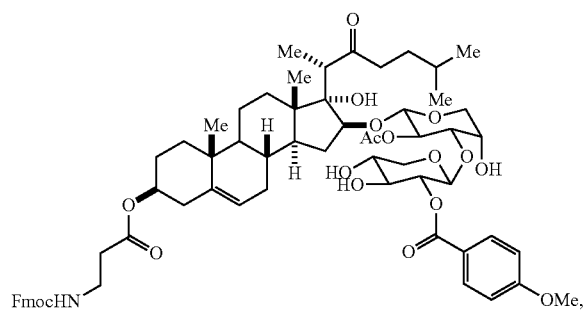
129
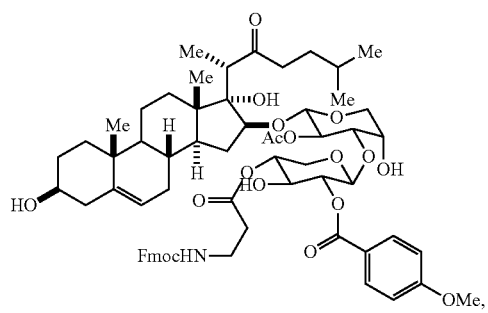

130
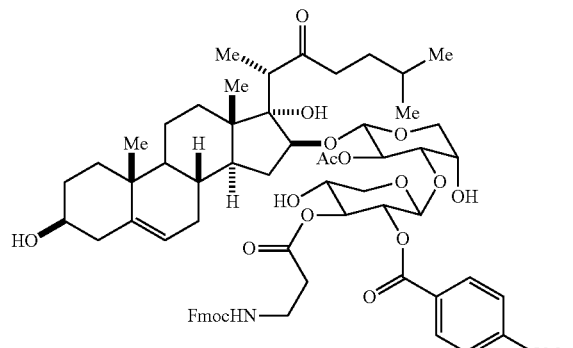
131
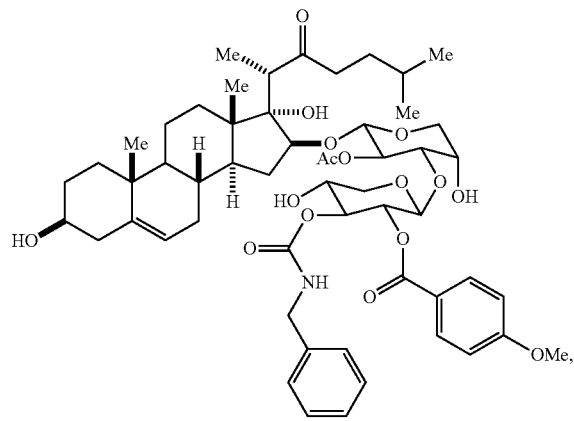
132
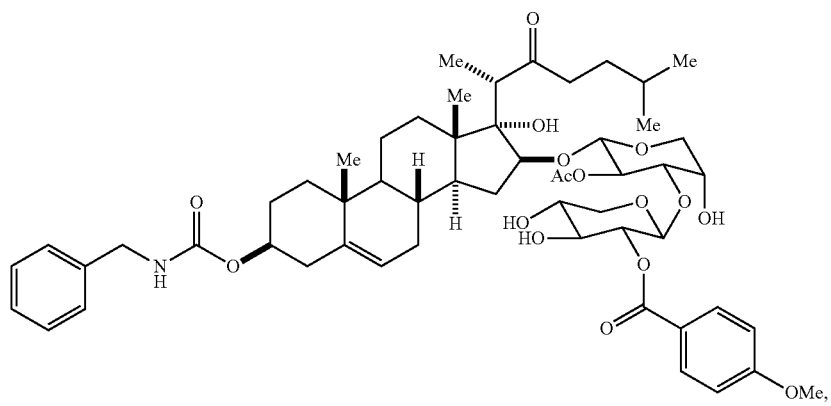
133
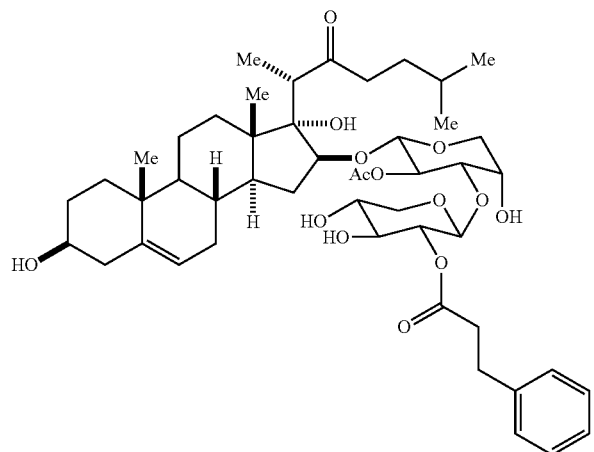
R =
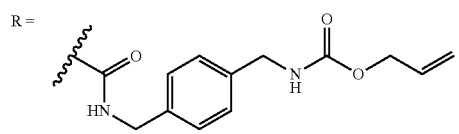
and pharmaceutically acceptable salts thereof.

28. A pharmaceutical composition, comprising a conjugate of claim 1; or a pharmaceutically acceptable salt thereof; and a pharmaceutically acceptable carrier.

29. A method of killing a mammalian cell, comprising contacting a mammalian cell with an effective amount of a conjugate of claim 1 or a pharmaceutically acceptable salt thereof.

30. A compound selected from the group consisting of:

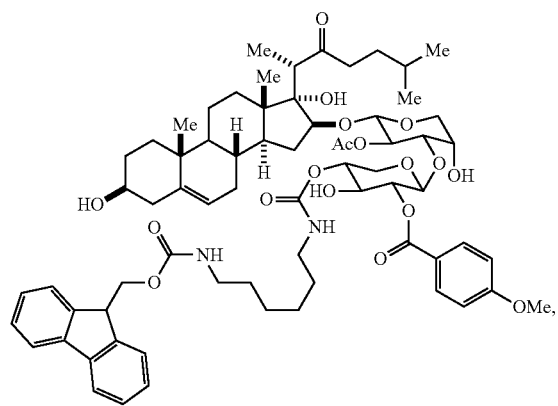

100

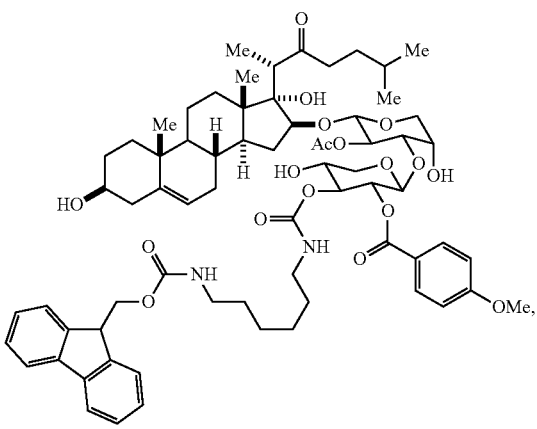

101

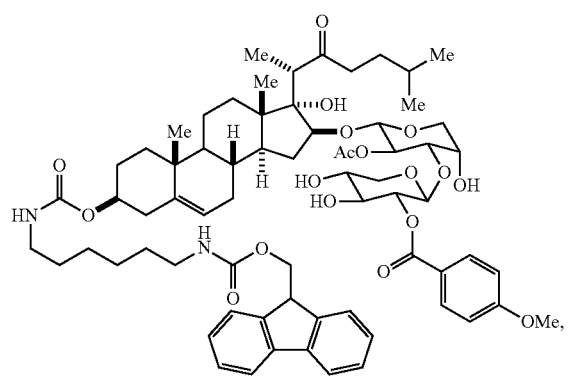

102

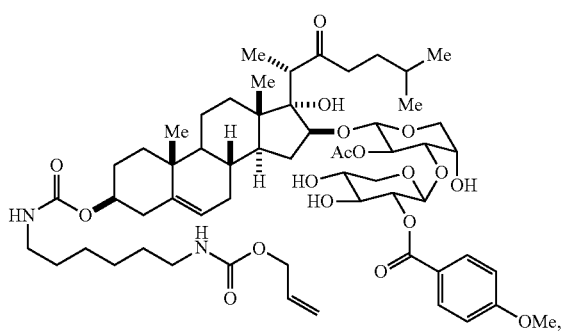

103

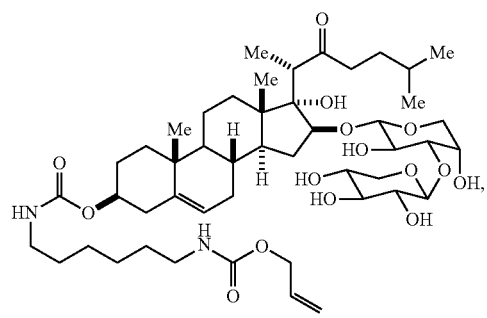

104

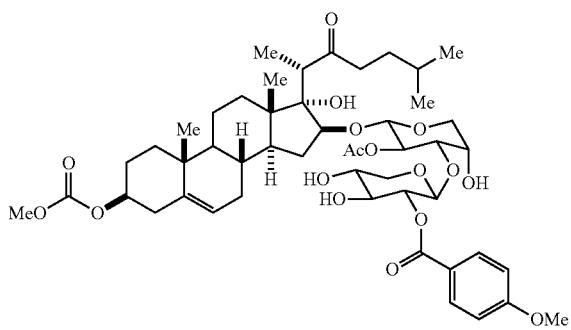

105

-continued
107
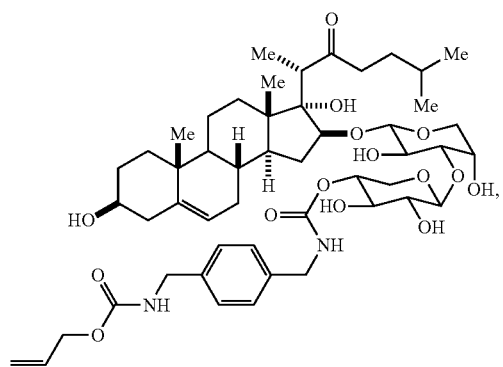
108
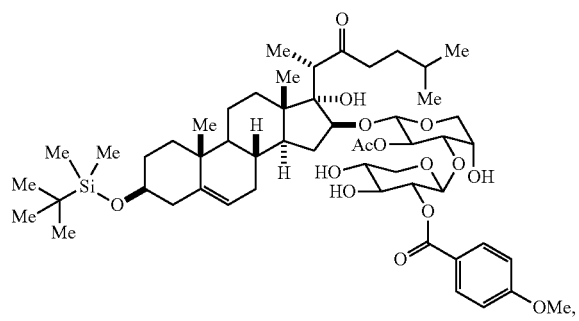
109
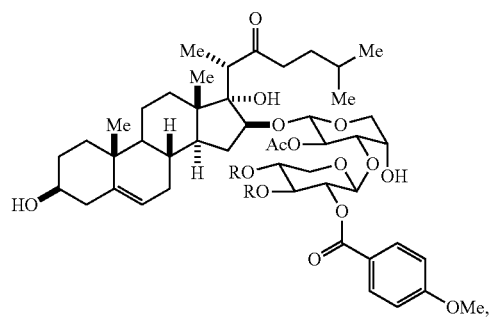
110
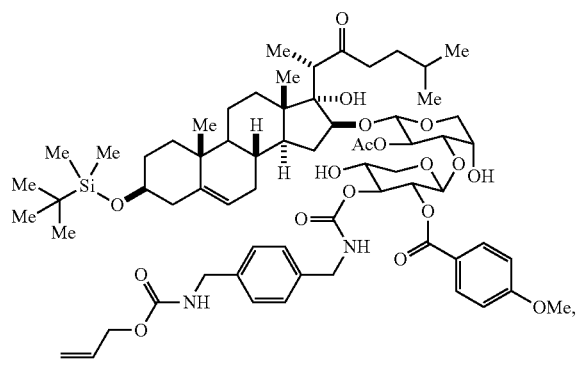
111
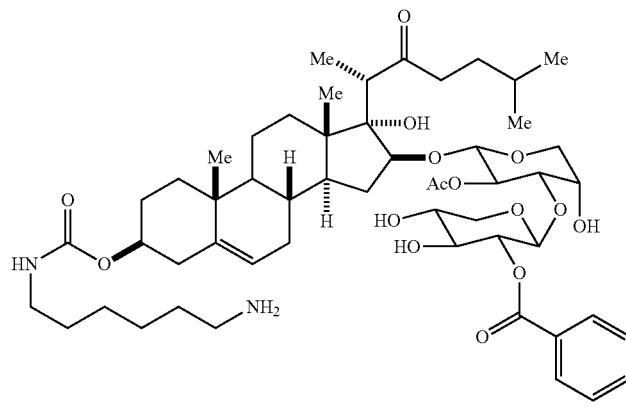
114
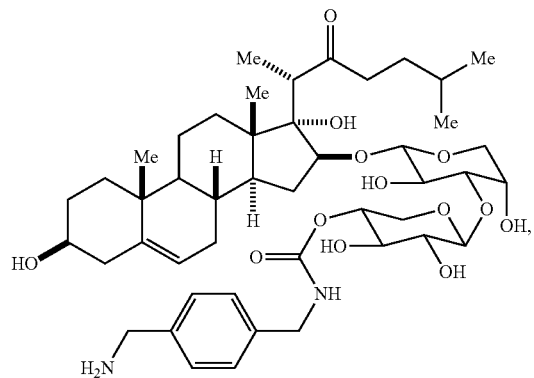

-continued
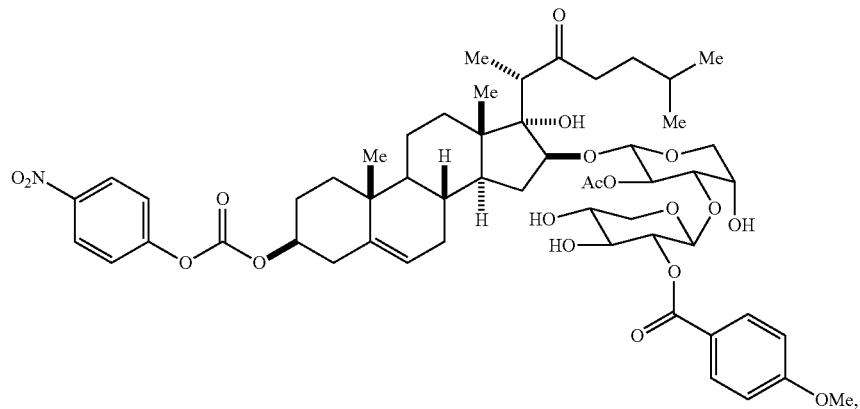
115
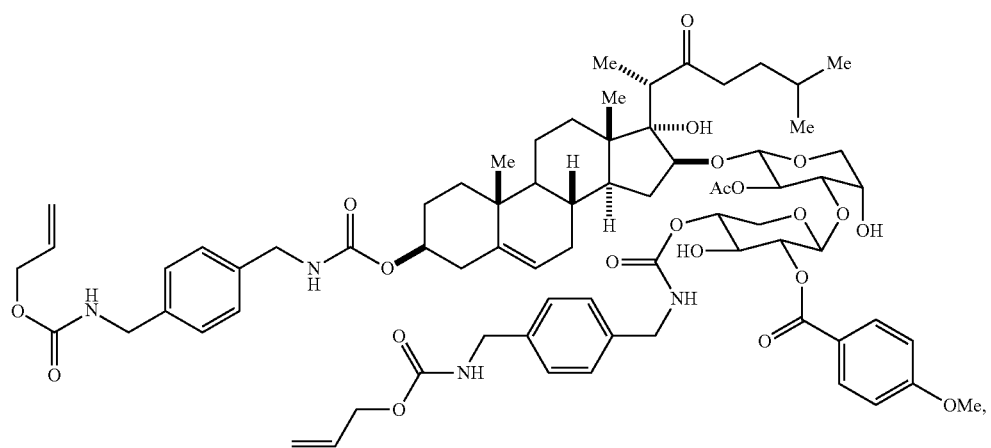
118
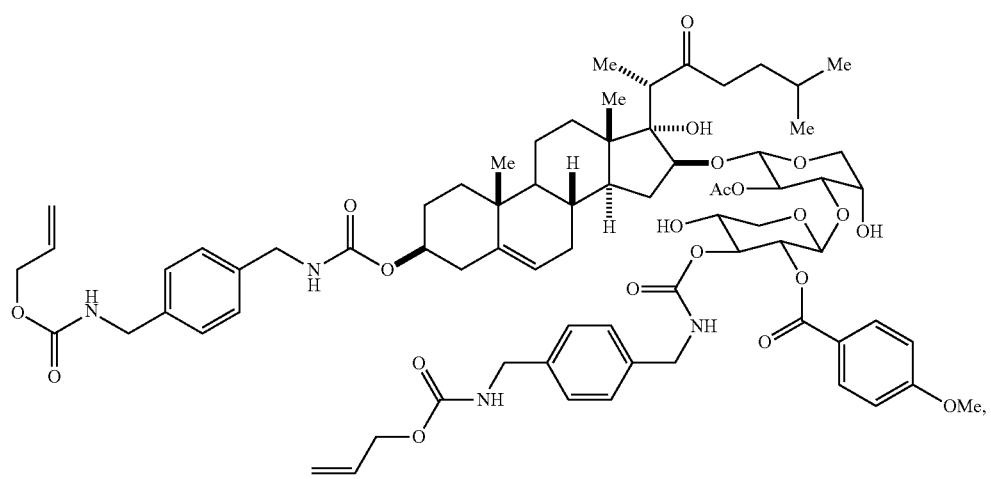
119

-continued
120
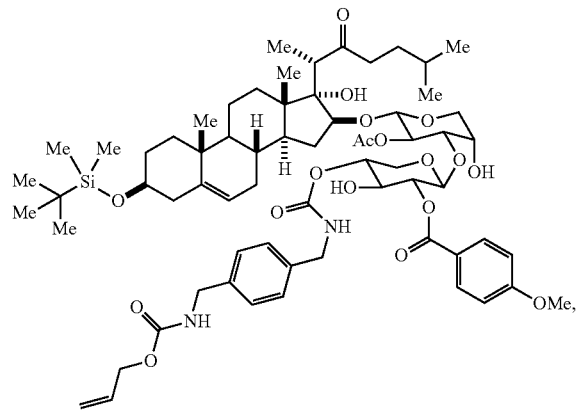
121
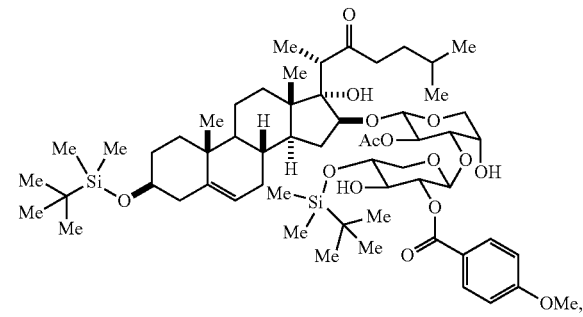
122
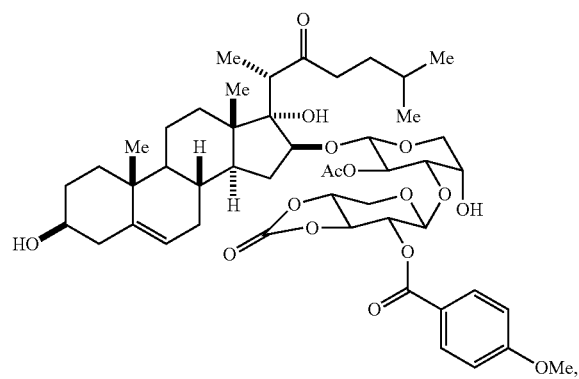
123
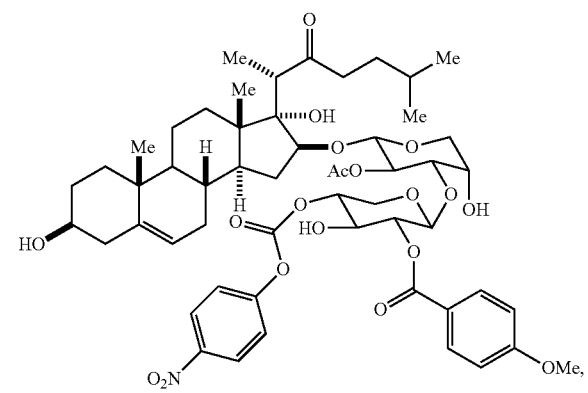
124
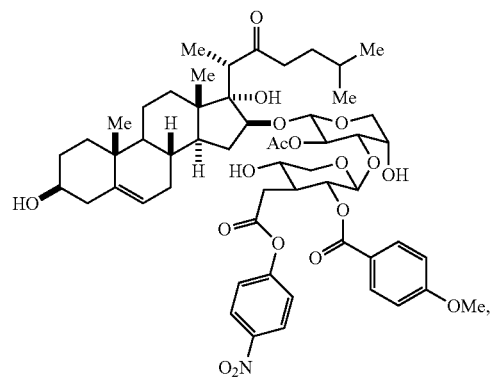
125
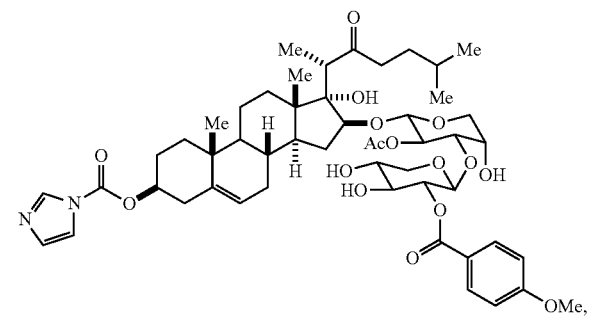
126
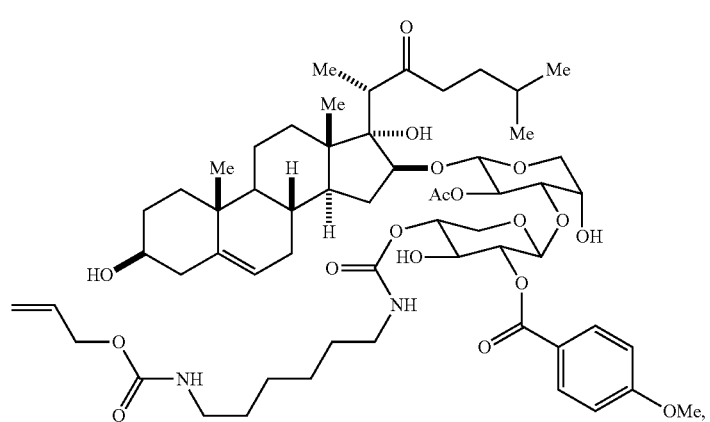

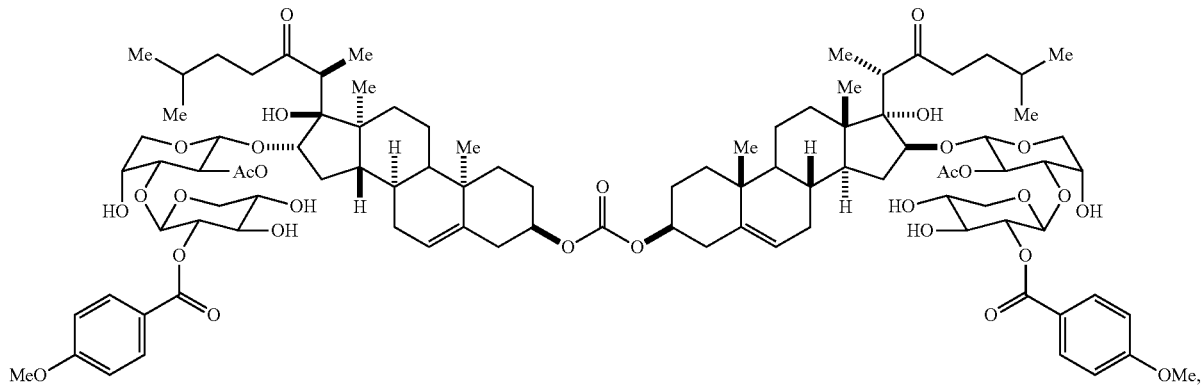

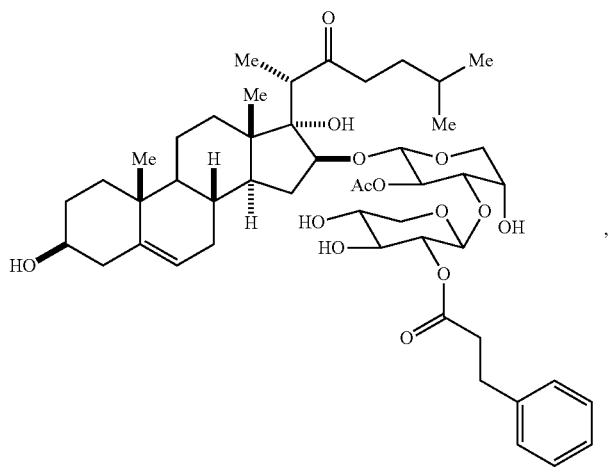

and pharmaceutically acceptable salts thereof.

31. A pharmaceutical composition, comprising a compound of claim 30 or a pharmaceutically acceptable salt thereof; and a pharmaceutically acceptable carrier.

32. A method of killing a mammalian cell, comprising contacting a mammalian cell with an effective amount of a compound of claim 30 or a pharmaceutically acceptable salt thereof.

33. A conjugate comprising an antibody, or antigen-binding fragment thereof, covalently linked to a compound of claim 30 or a pharmaceutically acceptable salt thereof.

34. A method of killing a mammalian cell, comprising contacting a mammalian cell with an effective amount of a conjugate comprising an antibody, or antigen-binding fragment thereof, covalently linked to a compound of claim 30 or a pharmaceutically acceptable salt thereof.

35. A pharmaceutical composition comprising an antibody, or antigen-binding fragment thereof, covalently linked to a compound of claim 30 or a pharmaceutically acceptable salt thereof, and a pharmaceutically acceptable carrier.

36. A compound of formula (II):

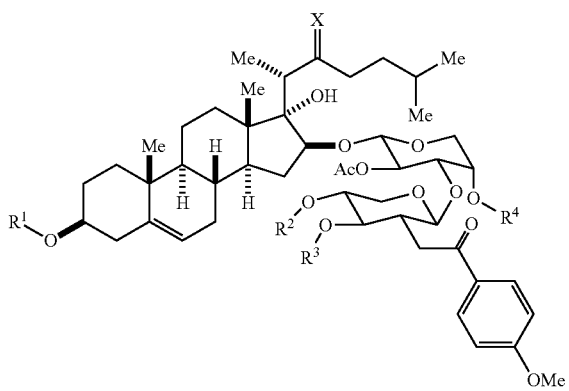

or a pharmaceutically acceptable salt thereof;
wherein:
X is selected from the group consisting of O and $NOR^{20}$;
$R^1$, $R^2$, and $R^3$ are independently selected from the group consisting of hydrogen, $R^{20}$, trialkylsilyl, and

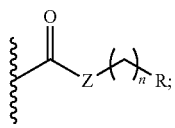

Z is absent or is selected from the group consisting of O and NR$^{10}$;

n is an integer 0-6;

R is selected from the group consisting of substituted or unsubstituted: alkyl, alkenyl, amino, alloc-protected amino, Fmoc-protected amino, aryl, 5- to 13-membered cycloalkyl or cycloalkenyl group, and 5- to 10-membered cyclic heteroaromatic group comprising 1-3 heteroatoms independently selected from the group consisting of N, O, and S;

R$^4$ is selected from the group consisting of hydrogen, C$_1$-C$_6$ alkyl, and R$^{20}$;

R$^{10}$ is selected from the group consisting of hydrogen and C$_1$-C$_6$ alkyl;

R$^{20}$ is selected from the group consisting of

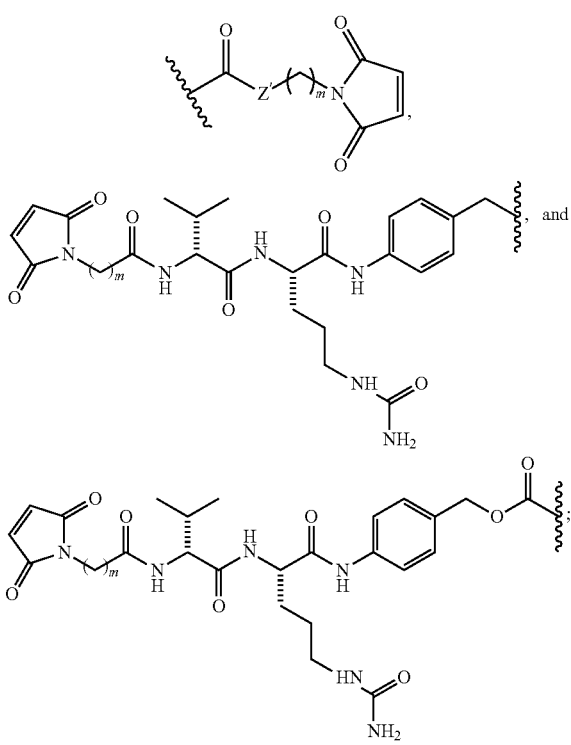

Z' is selected from the group consisting of O and NR$^{10}$; and m is an integer 1-6;

provided that if X is O, then one and only one of R$^1$, R$^2$, R$^3$, and R$^4$ is R$^{20}$; and if X is NOR$^{20}$, then none of R$^1$, R$^2$, R$^3$, and R$^4$ is R$^{20}$.

37. A pharmaceutical composition, comprising a compound of claim 36 or a pharmaceutically acceptable salt thereof; and a pharmaceutically acceptable carrier.

38. A method of killing a mammalian cell, comprising contacting a mammalian cell with an effective amount of a compound of claim 36 or a pharmaceutically acceptable salt thereof.

39. A conjugate comprising an antibody, or antigen-binding fragment thereof, covalently linked to a compound of claim 36 or a pharmaceutically acceptable salt thereof.

40. The compound of claim 36, wherein X is O.

41. The compound of claim 40, wherein each of R$^1$, R$^2$, R$^3$, and R$^4$ is selected from the group consisting of hydrogen and R$^{20}$.

42. The compound of claim 36, wherein X is NOR$^{20}$.

43. The compound of claim 42, wherein each of R$^1$, R$^2$, R$^3$, and R$^4$ is hydrogen.

44. A method of killing a mammalian cell, comprising contacting a mammalian cell with an effective amount of a conjugate comprising an antibody, or antigen-binding fragment thereof, covalently linked to a compound of claim 36 or a pharmaceutically acceptable salt thereof.

45. A pharmaceutical composition comprising an antibody, or antigen-binding fragment thereof, covalently linked to a compound of claim 36 or a pharmaceutically acceptable salt thereof, and a pharmaceutically acceptable carrier.

46. A compound of formula (I):

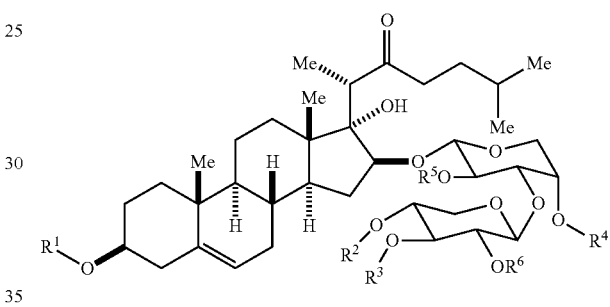

(I)

or a pharmaceutically acceptable salt thereof;
wherein:
R$^1$, R$^2$, and R$^3$ are independently selected from the group consisting of hydrogen, trialkylsilyl, and

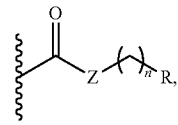

provided at least one instance of R$^1$, R$^2$, or R$^3$ is

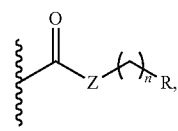

wherein Z is O;
R$^6$ is

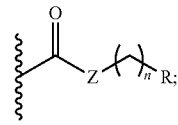

Z is absent or is selected from the group consisting of O and $NR^{10}$;

n is an integer 0-6;

R is selected from the group consisting of substituted or unsubstituted: alkyl, alkenyl, amino, alloc-protected amino, Fmoc-protected amino, aryl, 5- to 13-membered cycloalkyl or cycloalkenyl group, and 5- to 10-membered cyclic heteroaromatic group comprising 1-3 heteroatoms independently selected from the group consisting of N, O, and S;

$R^4$ is selected from the group consisting of hydrogen and $C_1$-$C_6$ alkyl;

$R^5$ is acyl; and $R^{10}$ is selected from the group consisting of hydrogen and $C_1$-$C_6$ alkyl.

47. The compound of claim 46, wherein the compound is selected from the group consisting of:

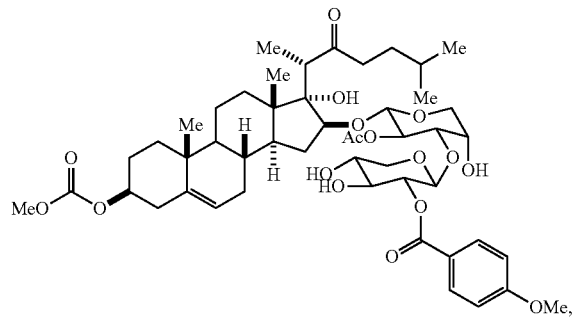

105

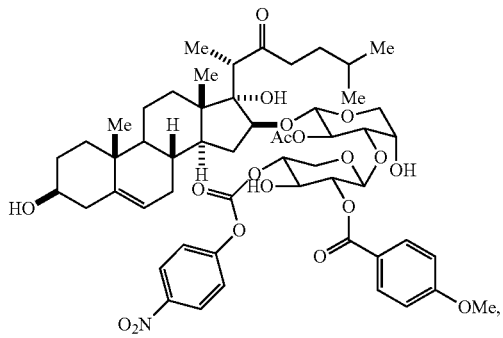

123

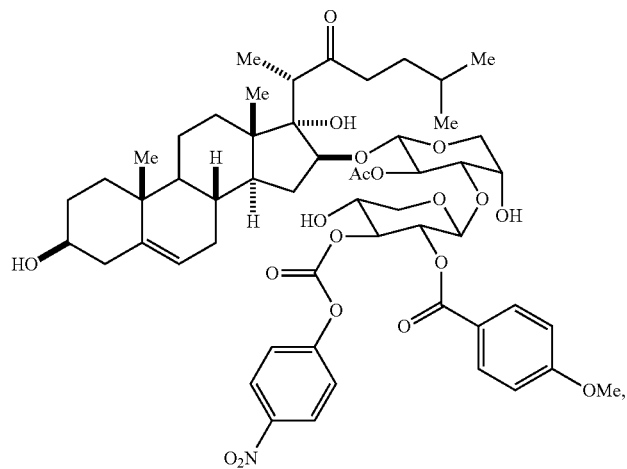

124

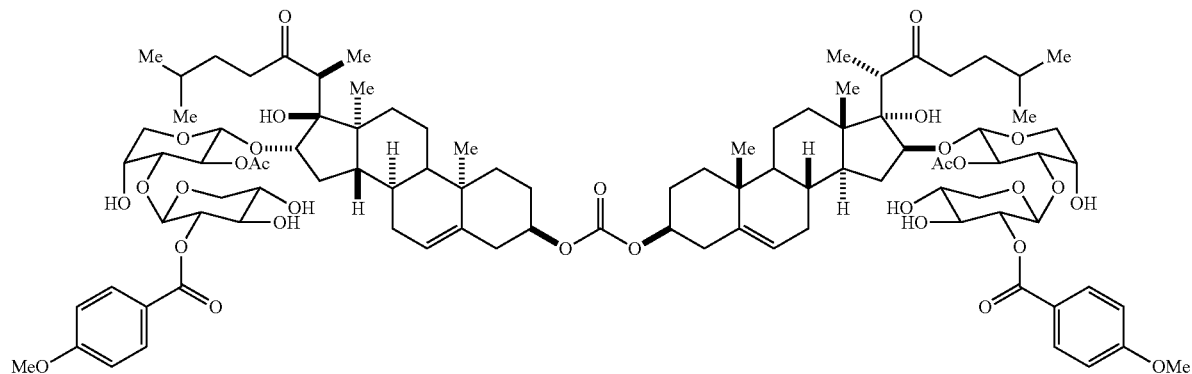

127 and pharmaceutically acceptable salts thereof.

48. A pharmaceutical composition, comprising a compound of claim 46 or a pharmaceutically acceptable salt thereof; and a pharmaceutically acceptable carrier.

49. A method of killing a mammalian cell, comprising contacting a mammalian cell with an effective amount of a compound of claim 46 or a pharmaceutically acceptable salt thereof.

50. A conjugate comprising an antibody, or antigen-binding fragment thereof, covalently linked to a compound of claim 46 or a pharmaceutically acceptable salt thereof.

51. A method of killing a mammalian cell, comprising contacting a mammalian cell with an effective amount of a conjugate comprising an antibody, or antigen-binding fragment thereof, covalently linked to a compound of claim 46 or a pharmaceutically acceptable salt thereof.

52. A pharmaceutical composition comprising an antibody, or antigen-binding fragment thereof, covalently linked to a compound of claim 46 or a pharmaceutically acceptable salt thereof, and a pharmaceutically acceptable carrier.

53. A compound of formula (I):

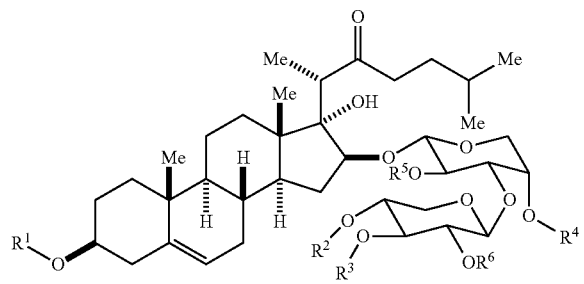

(I)

or a pharmaceutically acceptable salt thereof; wherein:

$R^1$, $R^2$, and $R^3$ are independently selected from the group consisting of hydrogen, trialkylsilyl, and

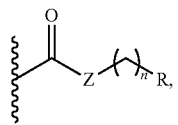

provided that $R^2$ and $R^3$ not hydrogen, or $R^1$ and $R^3$ are not hydrogen, or $R^1$ and $R^2$ are not hydrogen;

$R^6$ is

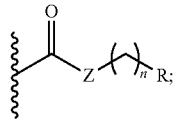

Z is absent or is selected from the group consisting of O and $NR^{10}$;

n is an integer 0-6;

R is selected from the group consisting of substituted or unsubstituted: alkyl, alkenyl, amino, alloc-protected amino, Fmoc-protected amino, aryl, 5- to 13-membered cycloalkyl or cycloalkenyl group, and 5- to 10-membered cyclic heteroaromatic group comprising 1-3 heteroatoms independently selected from the group consisting of N, O, and S;

$R^4$ is selected from the group consisting of hydrogen and $C_1$-$C_6$ alkyl;

$R^5$ is acyl; and $R^{10}$ is selected from the group consisting of hydrogen and $C_1$-$C_6$ alkyl.

54. The compound of claim 53, wherein the compound is selected from the group consisting of:

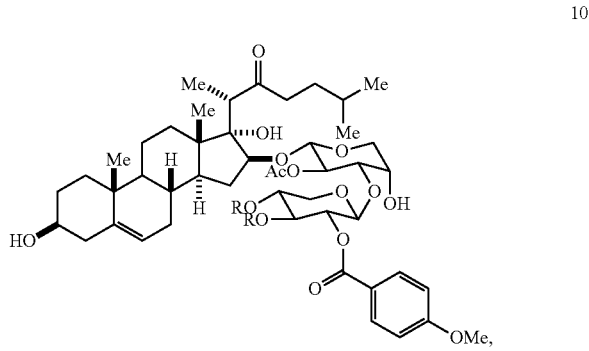

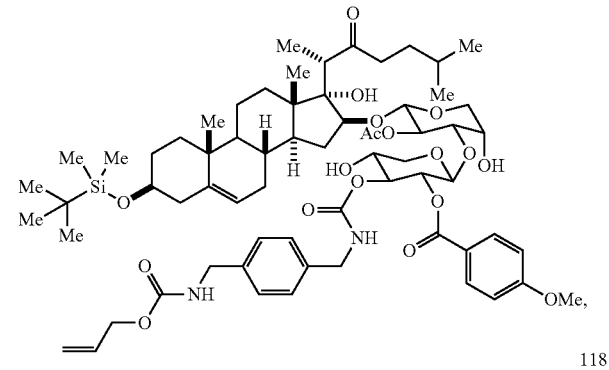

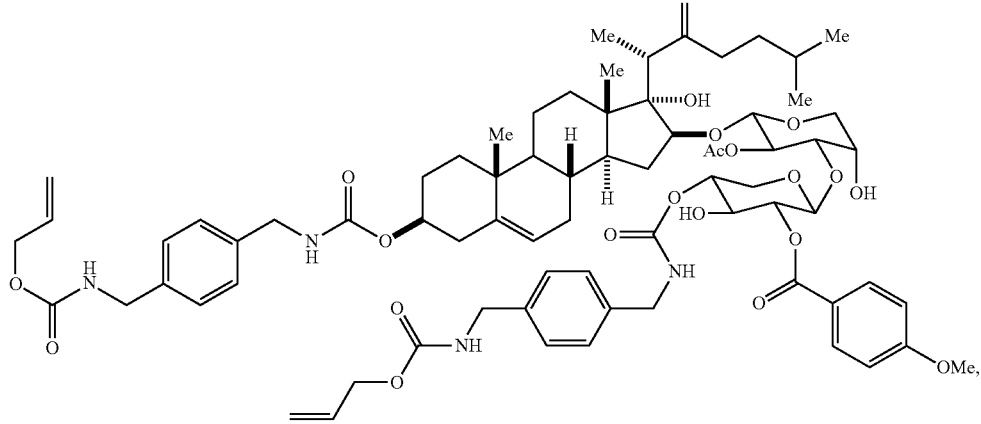

-continued

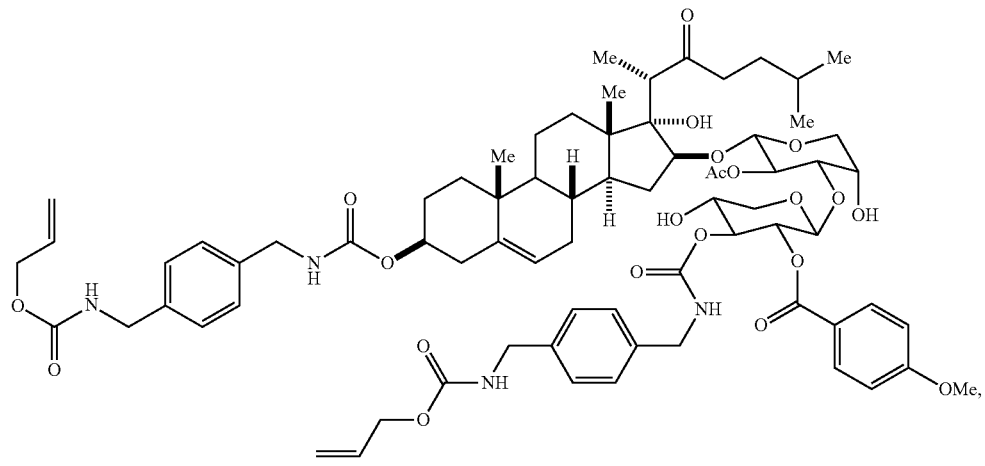
119

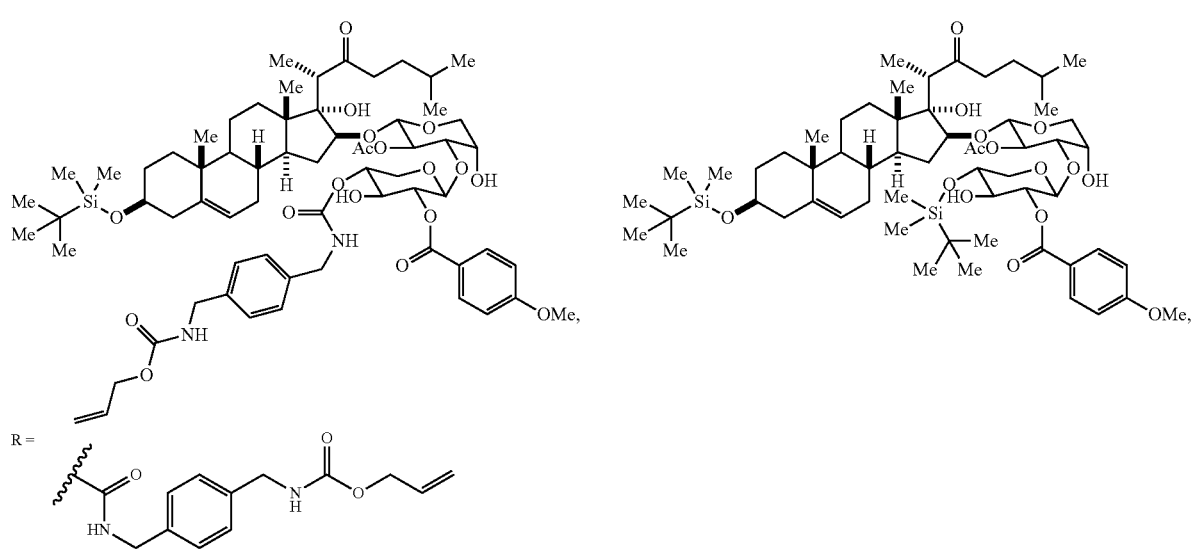
120
121

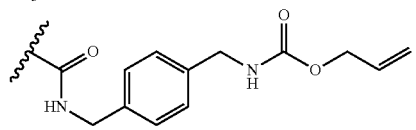
R = and pharmaceutically acceptable salts thereof.

55. A pharmaceutical composition, comprising a compound of claim 53 or a pharmaceutically acceptable salt thereof; and a pharmaceutically acceptable carrier.

56. A method of killing a mammalian cell, comprising contacting a mammalian cell with an effective amount of a compound of claim 53 or a pharmaceutically acceptable salt thereof.

57. A conjugate comprising an antibody, or antigen-binding fragment thereof, covalently linked to a compound of claim 53 or a pharmaceutically acceptable salt thereof.

58. A method of killing a mammalian cell, comprising contacting a mammalian cell with an effective amount of a conjugate comprising an antibody, or antigen-binding fragment thereof, covalently linked to a compound of claim 53 or a pharmaceutically acceptable salt thereof.

59. A pharmaceutical composition comprising an antibody, or antigen-binding fragment thereof, covalently linked to a compound of claim 53 or a pharmaceutically acceptable salt thereof, and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 9,790,253 B2 | Page 1 of 3 |
| APPLICATION NO. | : 14/118589 | |
| DATED | : October 17, 2017 | |
| INVENTOR(S) | : Matthew D. Shair et al. | |

It is certified that error appears in the above-identified patent and that said Letters Patent is hereby corrected as shown below:

In the Claims

In Claim 20, at Column 133, Line 49, the text:
"A conjugate of claim 1"
Should be replaced with the text:
--The conjugate of claim 1--.

In Claim 27, at Column 135, the structure:

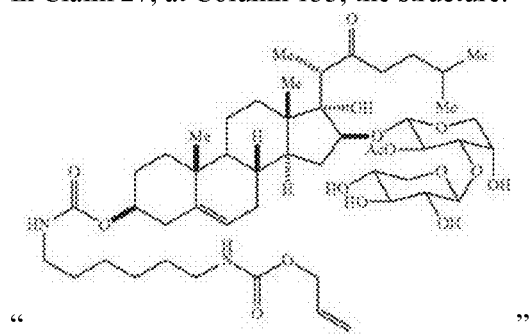

Should be replaced with the structure:

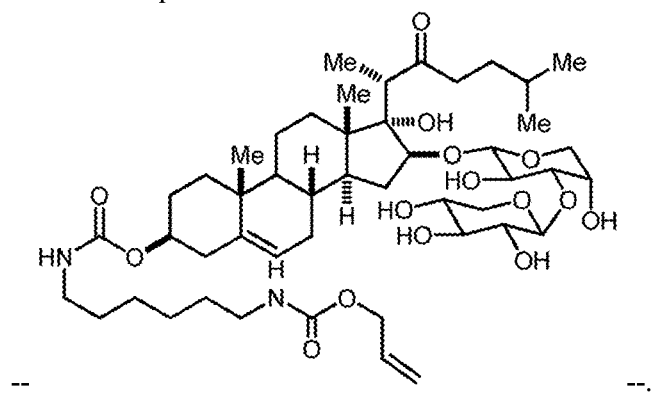

--.

Signed and Sealed this
First Day of May, 2018

Andrei Iancu
*Director of the United States Patent and Trademark Office*

CERTIFICATE OF CORRECTION (continued)
U.S. Pat. No. 9,790,253 B2

In Claim 27, at Column 137, the structure:

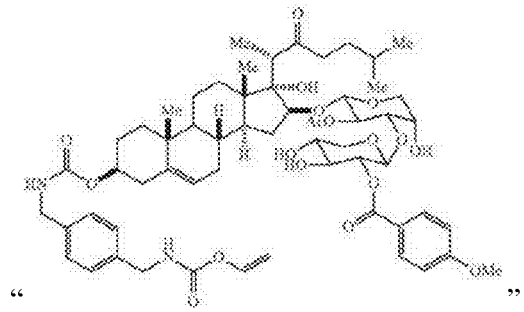

"  "

Should be replaced with the structure:

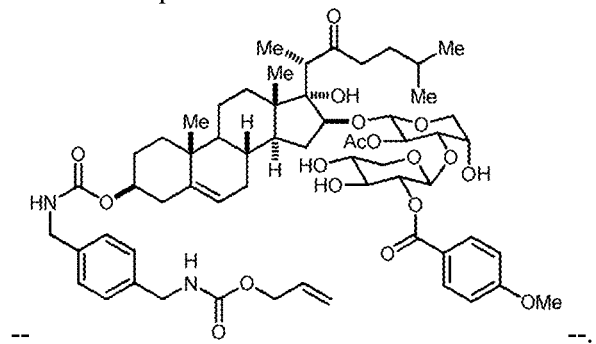

-- --.

In Claim 30, at Column 153, the structure:

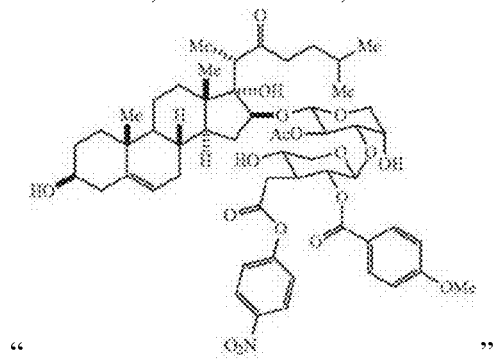

"  "

Should be replaced with the structure:

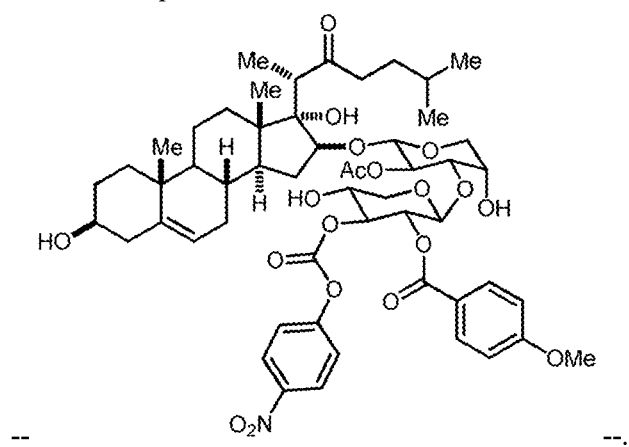

-- --.

CERTIFICATE OF CORRECTION (continued)
U.S. Pat. No. 9,790,253 B2

In Claim 36, at Column 156, Lines 46-63, the structure:

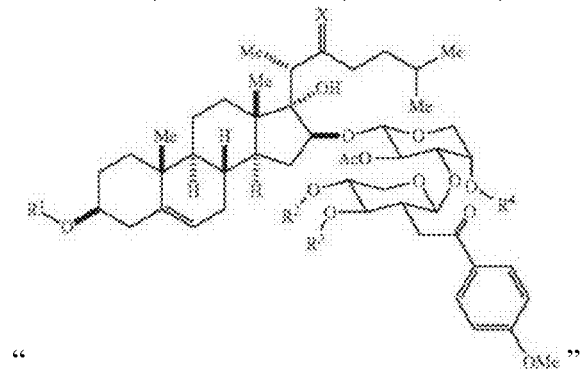

"

Should be replaced with the structure:

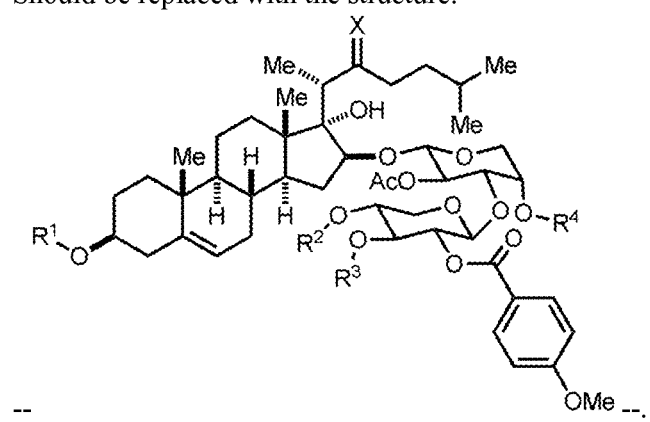

--  --.